US009023874B2

(12) United States Patent
Soergel et al.

(10) Patent No.: US 9,023,874 B2
(45) Date of Patent: May 5, 2015

(54) FLUORINATED OXA OR THIA HETEROARYLALKYLSULFIDE DERIVATIVES FOR COMBATING INVERTEBRATE PESTS

(75) Inventors: Sebastian Soergel, Ludwigshafen (DE); Ralph Paulini, Bad Durkheim (DE); Steffen Gross, Ludwigshafen (DE); Carsten Beyer, Mainz (DE); Matthias Pohlman, Freinsheim (DE); Henricus Maria Martinus Bastiaans, Chapel Hill, NC (US); Michael Rack, Eppelheim (DE); Deborah L. Culbertson, Fuquay Varina, NC (US); Douglas D. Anspaugh, Apex, NC (US); Sarah Thompson, Raleigh, NC (US); Vincent Salgado, Durham, NC (US)

(73) Assignee: Merial, Inc., Duluth, GA (US)

( * ) Notice: Subject to any disclaimer, the term of this patent is extended or adjusted under 35 U.S.C. 154(b) by 170 days.

(21) Appl. No.: 13/510,197

(22) PCT Filed: Nov. 11, 2010

(86) PCT No.: PCT/EP2010/067248
§ 371 (c)(1),
(2), (4) Date: Jul. 30, 2012

(87) PCT Pub. No.: WO2011/061110
PCT Pub. Date: May 26, 2011

(65) Prior Publication Data

US 2012/0289403 A1 Nov. 15, 2012

Related U.S. Application Data

(60) Provisional application No. 61/261,830, filed on Nov. 17, 2009.

(51) Int. Cl.
*A01N 43/824* (2006.01)
*A01N 43/08* (2006.01)
(Continued)

(52) U.S. Cl.
CPC ............ *C07D 285/12* (2013.01); *C07D 251/16* (2013.01); *C07D 333/18* (2013.01); *C07D 307/79* (2013.01); *C07D 209/10* (2013.01); *C07D 213/34* (2013.01); *C07D 213/32* (2013.01); *C07D 207/325* (2013.01); *C07D 261/08* (2013.01); *C07D 307/80* (2013.01); *C07D 209/12* (2013.01); *C07D 263/32* (2013.01); *C07D 307/38* (2013.01); *C07D 249/08* (2013.01); *C07D 271/06* (2013.01);
(Continued)

(58) Field of Classification Search
CPC ..... A61K 31/53; A61K 31/505; A61K 31/50; A61K 31/4402; A61K 31/4406; A61K 31/4409; A61K 31/433; A61K 31/426; A61K 31/4245; A61K 31/4192; A61K 31/4196; A61K 31/4164; A61K 31/415; A61K 31/381; A61K 31/343; A61K 31/341; C07D 207/325; C07D 209/12; C07D 209/10; C07D 213/32; C07D 213/34; C07D 231/12; C07D 233/66; C07D 235/12; C07D 237/08; C07D 239/20; C07D 249/08; C07D 251/16; C07D 257/04; C07D 261/08; C07D 263/32; C07D 271/06; C07D 277/26; C07D 285/12; C07D 307/40; C07D 307/38; C07D 307/79; C07D 307/80; C07D 333/18; C07D 333/54; C07D 333/56; A01N 43/08; A01N 43/10; A01N 43/22; A01N 43/40; A01N 43/46; A01N 43/50; A01N 43/54; A01N 43/56; A01N 43/58; A01N 43/60; A01N 43/62; A01N 43/647; A01N 43/66; A01N 43/713; A01N 43/72; A01N 43/78; A01N 43/80; A01N 43/82
USPC ......... 514/277, 357, 256, 248, 241, 406, 383, 514/365, 363, 399, 381, 374, 378, 438, 461, 514/469, 443, 427, 415; 544/215, 238, 335; 546/339; 548/136, 202, 205, 235, 247, 548/252, 342.1, 376.1, 516, 562, 268.2; 549/58, 78, 471, 497
See application file for complete search history.

(56) References Cited

U.S. PATENT DOCUMENTS 7,229,987 B2 * 6/2007 Ammenn et al. .......... 514/217.1

FOREIGN PATENT DOCUMENTS

WO 2009/025397 A1 2/2009
WO 2009/028727 A1 3/2009
WO 2009/075080 A1 6/2009

*Primary Examiner* — Joseph Kosack
*Assistant Examiner* — Matthew Coughlin
(74) *Attorney, Agent, or Firm* — Judy Jarecki-Black; John Ezcurra; Merial, Inc.

(57) ABSTRACT

The invention relates to alkylsulfide derivatives compounds of formula I as hereunder depicted or the enantiomers or veterinarily acceptable salts thereof which are useful for combating or controlling invertebrate pests, in particular arthropod pests and nematodes. The invention also relates to methods for controlling invertebrate pests by using these compounds and to plant propagation material and to agricultural and veterinary compositions comprising said compounds. wherein U, $R^1$, $R^2$, $R^{3U}$, X, n and p are defined as in the description.

(I)

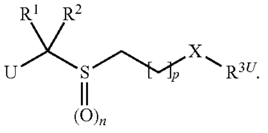

25 Claims, No Drawings

(51) Int. Cl.

| | |
|---|---|
| ***A01N 43/22*** | (2006.01) |
| ***A01N 43/40*** | (2006.01) |
| ***A01N 43/46*** | (2006.01) |
| ***A01N 43/50*** | (2006.01) |
| ***A01N 43/54*** | (2006.01) |
| ***A01N 43/56*** | (2006.01) |
| ***A01N 43/58*** | (2006.01) |
| ***A01N 43/60*** | (2006.01) |
| ***A01N 43/62*** | (2006.01) |
| ***A01N 43/647*** | (2006.01) |
| ***A01N 43/66*** | (2006.01) |
| ***A01N 43/713*** | (2006.01) |
| ***A01N 43/72*** | (2006.01) |
| ***A01N 43/78*** | (2006.01) |
| ***A01N 43/80*** | (2006.01) |
| ***A01N 43/82*** | (2006.01) |
| ***C07D 207/325*** | (2006.01) |
| ***C07D 209/12*** | (2006.01) |
| ***C07D 209/10*** | (2006.01) |
| ***C07D 213/32*** | (2006.01) |
| ***C07D 231/12*** | (2006.01) |
| ***C07D 233/66*** | (2006.01) |
| ***C07D 235/12*** | (2006.01) |
| ***C07D 237/08*** | (2006.01) |
| ***C07D 239/20*** | (2006.01) |
| ***C07D 249/08*** | (2006.01) |
| ***C07D 251/16*** | (2006.01) |
| ***C07D 257/04*** | (2006.01) |
| ***C07D 261/08*** | (2006.01) |
| ***C07D 263/32*** | (2006.01) |
| ***C07D 271/06*** | (2006.01) |
| ***C07D 277/26*** | (2006.01) |
| ***C07D 285/12*** | (2006.01) |
| ***C07D 307/40*** | (2006.01) |
| ***C07D 307/38*** | (2006.01) |
| ***C07D 307/79*** | (2006.01) |
| ***C07D 307/80*** | (2006.01) |
| ***C07D 333/18*** | (2006.01) |
| ***C07D 333/54*** | (2006.01) |
| ***C07D 333/56*** | (2006.01) |
| ***C07D 213/34*** | (2006.01) |
| ***A01N 43/10*** | (2006.01) |

(52) U.S. Cl.

CPC ............ *C07D 257/04* (2013.01); *C07D 239/20* (2013.01); *C07D 333/56* (2013.01); *C07D 235/12* (2013.01); *C07D 277/26* (2013.01); *C07D 307/40* (2013.01); *C07D 233/66* (2013.01); *C07D 333/54* (2013.01); *C07D 237/08* (2013.01); *A01N 43/08* (2013.01); *A01N 43/10* (2013.01); *A01N 43/22* (2013.01); *A01N 43/40* (2013.01); *A01N 43/46* (2013.01); *A01N 43/50* (2013.01); *A01N 43/54* (2013.01); *A01N 43/56* (2013.01); *A01N 43/58* (2013.01); *A01N 43/60* (2013.01); *A01N 43/62* (2013.01); *A01N 43/647* (2013.01); *A01N 43/66* (2013.01); *A01N 43/713* (2013.01); *A01N 43/72* (2013.01); *A01N 43/78* (2013.01); *A01N 43/80* (2013.01); *A01N 43/82* (2013.01)

FLUORINATED OXA OR THIA HETEROARYLALKYLSULFIDE DERIVATIVES FOR COMBATING INVERTEBRATE PESTS

This application is a U.S. national stage application of International Application No. PCT/EP2010/067248, filed Nov. 11, 2010, which claims the benefit of priority to U.S. Provisional Application No. 61/261,830, filed Nov. 17, 2009.

The present invention relates to alkylsulfide compounds or the enantiomers or veterinarily acceptable salts thereof which are useful for combating or controlling invertebrate pests, in particular arthropod pests and nematodes. The invention also relates to methods for controlling invertebrate pests by using these compounds and to plant propagation material and to agricultural and veterinary compositions comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating invertebrate pests, in particular insects, arachnids and nematodes.

WO 2009/075080, WO 2009/028727, WO 2009/025397 and WO 2009/014268 describe fluorine containing organosulfur compounds and their use as pesticides is mentioned.

It is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by alkylsulfide derivatives of the formula I below, by their stereoisomers and by their salts and N-oxides, in particular their agriculturally or veterinarily acceptable salts.

Therefore, in a first aspect, the invention relates to alkylsulfide compounds of the formula I and the salts and N-oxides thereof (I)

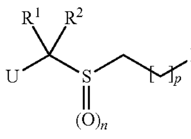

wherein

X is O or $S(=O)_m$;

m is 0, 1, 2 n is 0, 1 or 2;

p is 1 or 2

R3U is $C_1$-$C_{10}$-haloalkyl, $C_2$-$C_6$-haloalkenyl, $C_3$-$C_6$-haloalkynyl, $C_3$-$C_6$-halocycloalkyl, $C_3$-$C_6$-halocycloalkenyl, and wherein at least one halogen is fluorine;

U is a 5- to 12-membered monocyclic or bicyclic heteroaromatic ring-system which may contain 1 to 4 heteroatoms selected from O, S, N, wherein the heteroaromatic ring may be substituted by one to four substituents V, V is independently halogen, $C_1$-$C_6$-alkyl, $C_1$-$C_6$-haloalkyl, $C_3$-$C_6$-cycloalkyl-$C_1$-$C_3$-alkyl which may be substituted with halogen atoms, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, $C_1$-$C_6$-haloalkoxy, $C(=O)R^4$, $C(=S)R^4$, $S(O)_oR^{10}$, CN, $NO_2$, an amino group which may be substituted or disubstituted by $C_1$-$C_4$-alkyl or by $C_1$-$C_4$-acyl;

o is 0, 1 or 2;

$R^1$, $R^2$ are independently of each other selected from the group consisting of hydrogen, halogen, $C_1$-$C_6$-alkyl which may be substituted by halogen, by $C_1$-$C_4$-alkoxy, by $C_1$-$C_4$-alkylthio, by $C_1$-$C_4$-alkylsulfinyl, by $C_1$-$C_6$-alkylsulfonyl, by CN, by $C(=O)R^4$, by $OC(=O)R^4$, by $N-(C_1$-$C_3$-alkyl$)_2$, or by OH, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_3$-alkyl which may be substituted by halogen atom(s), CN, $C(=O)R^7$, $C(=S)R^7$, $C(R^{11})=NR^{12}$, $C(R^{11})=N-OR^{12}$, or $R^1$ and $R^2$ may form together with the carbon atom whereto they are bonded $C_3$-$C_6$-cycloalkyl, $C=C(R^5)R^6$ or $C=N-OR^5$;

$R^4$ is hydrogen, hydroxyl, $C_1$-$C_6$-alkyl, $C_1$-$C_6$-haloalkyl, $C_1$-$C_6$-alkoxy, $NR^8R^9$;

$R^5$ is hydrogen or $C_1$-$C_4$-alkyl;

$R^6$ is $C_1$-$C_6$-alkoxy, $NR^8R^9$;

$R^7$ is hydrogen, $C_1$-$C_6$-alkyl, $C_1$-$C_6$-haloalkyl, OH, $C_1$-$C_6$-alkoxy which may be substituted by halogen, by $C_1$-$C_4$-alkoxy, by $C_1$-$C_4$-alkoxy-$C_1$-$C_4$-alkoxy, by $C_1$-$C_4$-alkylthio, by $C_1$-$C_4$-alkylsulfinyl, by $C_1$-$C_6$-alkylsulfonyl, by $C_3$-$C_6$-cycloalkyl, by tetrahydrofuryl, by phenyl, by pyridyl [wherein the last two mentioned radicals may be substituted by halogen], by CN, by $C(=O)OR^{12}$ or by $C(=O)NR^{11}R^{12}$, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyloxy which may be substituted by halogen, $C_3$-$C_6$-cycloalkylthio which may be substituted by halogen, $NR^8R^9$, $C_1$-$C_6$-alkylthio, $N(R^{13})C(=O)N(R^{14})R^{15}$ or the following groups W to W5:

$W^1$

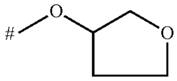

$W^2$

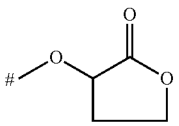

$W^3$

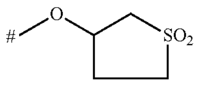

$W^4$

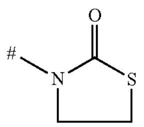

-continued

W5

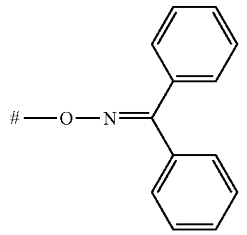

$R^8$ and $R^9$ form together with the nitrogen atom to which they are attached an amino, or mono-($C_1$-$C_6$-alkyl)amino or di-($C_1$-$C_4$-alkyl)amino or $C_2$-$C_5$-cyclic amino groups.

$R^{11}$, $R^{12}$, $R^{13}$, $R^{14}$ and $R^{15}$ are independently and independently from each other hydrogen, $C_1$-$C_6$-alkyl;

$R^{10}$ is $C_1$-$C_6$-alkyl which may be substituted by halogen, by $C_1$-$C_4$-alkoxy, by $C_1$-$C_4$-alkoxy-$C_1$-$C_4$-alkoxy, by $S(O)_o$—$C_1$-$C_6$-alkyl, by phenyl or by tetrahydrofuryl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_3$-alkyl which may be substituted with halogen atoms.

The present invention also provides an agricultural composition comprising at least one compound of the formula I as defined herein and/or an agriculturally acceptable salt thereof and at least one liquid and/or solid carrier.

The present invention also provides a veterinary composition comprising at least one compound of the formula I as defined herein and/or a veterinarily acceptable salt thereof and at least one liquid and/or solid carrier.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof as defined herein.

The present invention also relates to plant propagation material, in particular seed, comprising at least one compound of formula I and/or an agriculturally acceptable salt thereof as defined herein.

The present invention further relates to a method for treating or protecting an animal from infestation or infection by parasites which comprises bringing the animal in contact with a parasiticidally effective amount of a compound of the formula I or a veterinarily acceptable salt thereof as defined herein. Bringing the animal in contact with the compound I, its salt or the veterinary composition of the invention means applying or administering it to the animal.

The term "stereoisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof. Cis/trans isomers may be present with respect to an imine group.

The compounds of the present invention may be amorphous or may exist in one or more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat. Protoc. 2007; 2(5):1225-35, Curr. Opin. Chem. Biol. 2006 October; 10(5): 487-91. Epub 2006 August 28, Biomaterials. 2001 March; 22(5): 405-17, Bioconjug Chem. 2005 January-February; 16(1): 113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from *bacillus thuringiensis*, such as delta-endotoxins, e.g. CrylA(b), CrylA(c), CrylF, CrylF(a2), CryllA(b), CryIIIA, CrylllB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically modified plants capable of synthesizing such toxins are disclosed, for example, in EP-A 374 753, WO 93/007278, WO 95/34656, EP-A 427 529, EP-A 451 878, WO 03/018810 and WO 03/052073. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lyso-zym (e.g. potato cultivars capable of synthesizing these proteins with increased resistance against bacteria such as *Erwinia amylvora*).

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_x$-$C_y$ indicates in each case the possible number of carbon atoms in the group.

The term halogen denotes in each case fluorine, bromine, chlorine or iodine, in particular fluorine, chlorine or bromine.

The term "$C_1$-$C_6$-alkyl" as used herein and in the alkyl moieties of alkoxy, alkylthio, alkylsulfinyl, alkylsulfonyl, and the like refers to saturated straight-chain or branched hydrocarbon radicals having 1 to 2 ("$C_1$-$C_2$-alkyl"), 1 to 4 ("$C_1$-$C_4$-alkyl") or 1 to 6 ("$C_1$-$C_6$-alkyl") carbon atoms. $C_1$-$C_2$-alkyl is methyl or ethyl. $C_1$-$C_4$-alkyl is additionally propyl, isopropyl, butyl, 1-methylpropyl (sec-butyl), 2-methylpropyl (isobutyl) or 1,1-dimethylethyl (tert-butyl). $C_1$-$C_6$-alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_{10}$-haloalkyl" as used herein, which is also expressed as "$C_1$-$C_{10}$-alkyl which may be substituted by halogen", refers to straight-chain or branched alkyl groups having 1 to 2 ("$C_1$-$C_2$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "$C_2$-$C_6$-alkenyl" as used herein and in the alkenyl moiety of alkenyloxy and the like refers to monounsaturated straight-chain or branched hydrocarbon radicals having 2 to 4 ("$C_2$-$C_4$-alkenyl") or 2 to 6 ("$C_2$-$C_6$-alkenyl") carbon atoms and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like and the positional isomers thereof.

The term "$C_2$-$C_6$-haloalkenyl" as used herein, which is also expressed as "$C_2$-$C_6$-alkenyl which may be substituted by halogen", and the haloalkenyl moieties in haloalkenyloxy, haloalkenylcarbonyl and the like refers to unsaturated straight-chain or branched hydrocarbon radicals having 2 to 4 ("$C_2$-$C_4$-haloalkenyl") or 2 to 6 ("$C_2$-$C_6$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "$C_2$-$C_6$-alkynyl" as used herein and the alkynyl moieties in alkynyloxy, alkynylcarbonyl and the like refers to straight-chain or branched hydrocarbon groups having 2 to 4 ("$C_2$-$C_4$-alkynyl") or 2 to 6 ("$C_2$-$C_6$-alkynyl") carbon atoms and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "$C_2$-$C_6$-haloalkynyl" as used herein, which is also expressed as "$C_2$-$C_6$-alkynyl which may be substituted by halogen", and the haloalkynyl moieties in haloalkynyloxy, haloalkynyl-carbonyl and the like refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 3 to 6 ("$C_3$-$C_6$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "$C_3$-$C_6$-cycloalkyl" as used herein refers to mono- or bi- or polycyclic saturated hydrocarbon radicals having 3 to 6 carbon atoms. Examples of monocyclic radicals having 3 to 6 carbon atoms comprise cyclopropyl, cyclobutyl, cyclopentyl and cyclohexyl.

The term "$C_3$-$C_6$-halocycloalkyl" as used herein, which is also expressed as "$C_3$-$C_6$-cycloalkyl which may be substituted by halogen", and the halocycloalkyl moieties in halocycloalkoxy, halocycloalkylcarbonyl and the like refers to mono- or bi- or polycyclic saturated hydrocarbon groups having 3 to 6 ("$C_3$-$C_6$-halocycloalkyl") carbon ring members (as mentioned above) in which some or all of the hydrogen atoms are replaced by halogen atoms as mentioned above, in particular fluorine, chlorine and bromine.

The term "$C_3$-$C_6$-cycloalkyl-$C_1$-$C_3$-alkyl" refers to a $C_3$-$C_6$-cycloalkyl group as defined above which is bound to the remainder of the molecule via a $C_1$-$C_3$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cycloppentylethyl, cyclopentylpropyl, cyclohexylmethyl, cyclohexylethyl, cyclohexylpropyl, and the like.

The term "$C_1$-$C_2$-alkoxy" is a $C_1$-$C_2$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. $C_1$-$C_2$-alkoxy is methoxy or ethoxy. $C_1$-$C_4$-alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

The term "$C_1$-$C_2$-haloalkoxy" is a $C_1$-$C_2$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. $C_1$-$C_2$-haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_2$-alkylthio" is a $C_1$-$C_2$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. $C_1$-$C_2$-alkylthio is methylthio or ethylthio. $C_1$-$C_4$-alkylthio is additionally, for example, n-propylthio, 1-methylethylthio (isopropylthio), butylthio, 1-methylpropylthio (sec-butylthio), 2-methylpropylthio (isobutylthio) or 1,1-dimethylethylthio (tert-butylthio). $C_1$-$C_6$-alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio.

The term "$C_1$-$C_2$-haloalkylthio" is a $C_1$-$C_2$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. $C_1$-$C_2$-haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$alkylsulfinyl" is a $C_1$-$C_6$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropyl-sulfinyl), butylsulfinyl, 1-methylpropylsulfinyl (sec-butylsulfinyl), 2-methylpropylsulfinyl (isobutyl-sulfinyl) or 1,1-dimethylethylsulfinyl (tertbutylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. $C_1$-$C_2$-Haloalkylsulfinyl is, for example, $S(O)CH_2F$, S(O)

$CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-$_2$-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [S(0)2] group. The term "$C_1$-$C_4$-alkylsulfonyl" is a $C_1$-$C_4$-alkyl group, as defined above, attached via a sulfonyl [$S(O)_2$] group. The term "$C_1$-$C_6$-alkylsulfonyl" is a $C_1$-$C_6$-alkyl group, as defined above, attached via a sulfonyl [S(O)2] group. $C_1$-$C_2$-Alkylsulfonyl is methylsulfonyl or ethylsulfonyl. $C_1$-$C_4$-Alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexyl sulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "$C_1$-$C_2$-haloalkylsulfonyl" is a $C_1$-$C_2$-haloalkyl group, as defined above, attached via a sulfonyl [$S(O)_2$] group. The term "$C_1$-$C_4$-haloalkylsulfonyl" is a $C_1$-$C_4$-haloalkyl group, as defined above, attached via a sulfonyl [$S(O)_2$] group. The term "$C_1$-$C_6$-haloalkylsulfonyl" is a $C_1$-$C_6$-haloalkyl group, as defined above, attached via a sulfonyl [$S(O)_2$] group. $C_1$-$C_2$-Haloalkylsulfonyl is, for example, $S(O)_2CH_2F$, $S(O)_2CHF_2$, $S(O)_2CF_3$, $S(O)_2CH_2Cl$, $S(O)_2CHCl_2$, $S(O)_2CCl_3$, chloro-fluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or $S(O)_2C_2F_5$. $C_1$-$C_4$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-($CH_2F$)-2-fluoroethylsulfonyl, 1-($CH_2Cl$)-2-chloroethylsulfonyl, 1-($CH_2Br$)-2-bromoethylsulfonyl, 4-fluorobutylsulfonyl, 4-chlorobutylsulfonyl, 4-bromobutylsulfonyl or nona-fluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dode-cafluorohexylsulfonyl.

The term "3-, 4-, 5-, 6-, 7-, 8-, 9-, 10-, 11- or 12-membered saturated, partially unsaturated or aromatic heterocyclic ring containing 1, 2 or 3 heteroatoms or heteroatom groups (if one or two or at most three heteroatoms of the heterocyclic ring are oxidzed) selected from N, O, S, NO, SO and $SO_2$, as ring members" as used herein refers to monocyclic radicals, the monocyclic radicals being saturated, partially unsaturated or aromatic. The heterocyclic radical may be attached to the remainder of the molecule via a carbon ring member or via a nitrogen ring member.

The hetearomatic ring may be a mono- or bicyclic-heteroaromatic ring system. Exemplary monocyclic heteroaromatic rings systems which may be given include, but are not limited to pyridine, pyrimidine, pyrazine, pyridazine, 1,3,5-triazine, 1,2,4-triazine, pyrrole, pyrazole, imidazole, 1,2,4-triazole, 1,2,3-triazole, tetrazole, furan, oxazole, isoxazole, 1,2,4-oxadiazole, 1,3,4-oxadiazole, 1,2,3-oxadiazole, thiophene, thiazole, isothiazole, 1,3,4-thiadiazole, 1,2,4-thiadiazole, 1,2,3-thiadiazole. Exemplary bicyclic heteroaromatic rings systems which may be given include, but are not limited to quinoline, indole, benzofuran, benzothiophene, benzoimidazole, benzoxazole, benzoisoxazole, benzothiazole, benzoisothiazole.

Examples of 3-, 4-, 5-, 6-, 7-, 8-, 9-, 10-, 11- or 12-membered saturated heterocyclic ring include: Oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3- dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydro-pyridazinyl, 2-di- or tetrahydropyrimidinyl, 4-di- or tetrahydropyrimidinyl, 5-di- or tetrahydro-pyrimidinyl, di- or tetrahydropyrazinyl, 1,3,5-di- or tetrahydrotriazin-2-yl, 1,2,4-di- or tetrahydro-triazin-3-yl, 2,3,4,5-tetrahydro[1H]azepin-1-2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclic ring is 5- or 6-membered aromatic heterocyclic (hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The remarks made below concerning preferred embodiments of the variables of the compounds of formula I, especially with respect to their substituents X, U, V, $R^1$, $R^2$, R3U, $R^4$, $R^5$, $R^6$, $R^7$, $R^8$, $R^9$, $R^{10}$, $R^{11}$, $R^{12}$, $R^{13}$, $R^{14}$, $R^{15}$, m, n, o and p, the features of the use and method according to the invention and of the composition of the invention are valid both on their own and, in particular, in every possible combination with each other.

In a preferred embodiment X is $S(=O)_m$ with m being 0, 1 or 2. Preferably m is 0 or 1 and more preferably m is 0.

In a preferred embodiment n is 0, 1 or 2. Preferably, n is 1, 2 and more preferably, n is 2.

In a preferred embodiment p is 1 or 2. Preferably, p is 1.

Preferably, U is a 5- to 12-membered monocyclic or bicyclic heteroaromatic ring-system which may contain 1 to 4 heteroatoms selected from O, S, N, wherein the heteroaromatic ring may be substituted by one to four substituents V which have each preferencies as recited hereunder for V.

Preferably, U is a 5- to 10-membered monocyclic or bicyclic heteroaromatic ring-system which may contain 1 to 4 heteroatoms selected from O, S, N, wherein the heteroaromatic ring may be substituted by one to four substituents V which have each preferencies as recited hereunder for V.

More preferably, U is a 5- to 10-membered heteroaromatic ring-system selected from the group consisting of pyridine, pyrimidine, pyrazine, pyridazine, 1,3,5-triazine, quinoline, 1H-indole, 1 H-benzoimidazole, benzothiazole, benzooxazole, benzofuran, benzothiophene, 1H-pyrrole, 1H-pyrazole, 1H-1,2,4-triazole, 1H-imidazole, 1H-1,2,3-triazole, 1H-tetrazole, thiophene, thiazole, 1,3,4-thiadiazole, furan, oxazole, isoxazole, 1,2,4-oxadiazole, 1,3,4-oxadiazole, wherein the heteroaromatic ring may be substituted by one to four substituents V which have each preferencies as recited hereunder for V. More preferably, U is a 5-membered heteroaromatic ring selected from the group consisting of 1H-pyrrole, 1H-pyrazole, 1H-1,2,4-triazole, 1H-imidazole, 1H-1,2,3-triazole, 1H-tetrazole, thiophene, thiazole, 1,3,4-thiadiazole, furan, oxazole, isoxazole, 1,2,4-oxadiazole, 1,3,4-oxadiazole, wherein the heteroaromatic ring may be substituted by one to four substituents V which have each preferencies as recited hereunder for V. Even more preferably, U is a 5-membered heteroaromatic ring selected from the group consisting of 1H-pyrrole, 1H-pyrazole, 1H-1,2,4-triazole, 1H-imidazole, 1H-1,2,3-triazole, 1H-tetrazole, thiophene, thiazole, 1,3,4-thiadiazole, furan, oxazole, isoxazole, 1,2,4-oxadiazole, 1,3,4-oxadiazole, wherein the heteroaromatic ring is preferably at least substituted by halogen, CN, $C_1$-$C_6$-alkyl, $C_1$-$C_6$-haloalkyl, $C_3$-$C_6$-cycloalkyl-$C_1$-$C_3$-alkyl which may be substituted with halogen atoms, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, $C_1$-$C_6$-haloalkoxy Even more preferably, U is a 5-membered heteroaromatic ring selected from the group consisting of 1H-pyrazole, 1H-1,2,4-triazole, 1H-imidazole, 1H-tetrazole, isoxazole, thiazole, 1,3,4-thiadiazole, wherein the heteroaromatic ring is preferably at least substituted by CN, tert-butyl, $CF_3$ or halogen being preferably Cl. Most preferably, U is a 5-membered heteroaromatic ring selected from the group consisting of 1H-pyrazole, 1H-1,2,4-triazole, 1,3,4-thiadiazole, wherein the heteroaromatic ring is substituted by one of the groups selected from Cl, CN, tert-butyl and $CF_3$.

Preferably, V is independently selected from the group consisting of halogen, $C_1$-$C_6$-alkyl, $C_1$-$C_6$-haloalkyl, $C_3$-$C_6$-cycloalkyl-$C_1$-$C_3$-alkyl which may be substituted with halogen atoms, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, $C_1$-$C_6$-haloalkoxy, $C(=O)R^4$, $C(=S)R^4$, $S(O)_oR^{10}$, CN, $NO_2$, an amino group which may be substituted by $C_1$-$C_4$-alkyl or by $C_1$-$C_4$-acyl.

Preferably, V is independently selected from the group consisting of halogen, $C_1$-$C_6$-alkyl, $C_1$-$C_6$-haloalkyl, $C_3$-$C_6$-cycloalkyl-$C_1$-$C_3$-alkyl which may be substituted with halogen atoms, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C(=O)R^4$, $C(=S)R^4$, CN, $NO_2$, an amino group which may be substituted by $C_1$-$C_4$-alkyl or by $C_1$-$C_4$-acyl. More preferably V is independently selected from the group consisting of halogen, $C_1$-$C_6$-alkyl, $C_1$-$C_6$-haloalkyl, $C_3$-$C_6$-cycloalkyl-$C_1$-$C_3$-alkyl which may be substituted with halogen atoms, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, $C_1$-$C_6$-haloalkoxy, CN.

More preferably, V is independently selected from the group consisting of halogen, $C_1$-$C_6$-alkyl, $C_1$-$C_6$-haloalkyl and CN.

Even more preferably, V is independently selected from the group consisting of tert-butyl, CN, $CF_3$ and halogen in particular Cl. Most preferably, V is $CF_3$.

Preferably, $R^1$, $R^2$ are independently of each other selected from the group consisting of hydrogen, halogen, $C_1$-$C_6$-alkyl which may be substituted by halogen, by $C_1$-$C_4$-alkoxy, by $C_1$-$C_4$-alkylthio, by $C_1$-$C_4$-alkylsulfinyl, by $C_1$-$C_6$-alkylsulfonyl, by CN, by $C(=O)R^4$, by $OC(=O)R^4$, by $N(C_1$-$C_3$-alkyl$)_2$ or by OH, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_3$-alkyl which may be substituted by halogen atom(s), CN, $C(=O)R^7$, $C(=S)R^7$, C(R11)$=NR^{12}$, $C(R^{11})=N-OR^{12}$, or $R^1$ and $R^2$ may form together with the carbon atom whereto they are bonded $C_3$-$C_6$-cycloalkyl, $C=C(R^5)R^6$ or $C=N-OR^5$.

More preferably, $R^1$, $R^2$ are independently selected from the group consisting of hydrogen, halogen, $C_1$-$C_4$-alkyl, CN, $C(=O)-C_1$-$C_4$-alkyl, $C(=O)-C_1$-$C_4$-alkoxy, $C(=O)-$ $NR^8R^9$, C(═S)—$NR^8R^9$. Even more preferably, $R^1$, $R^2$ are independently selected from the group consisting of hydrogen, $C_1$-$C_4$-alkyl, Cl, CN, C(═O)-Me, C(═O)-Et, C(═O)—OMe, C(═O)—OEt, C(═O)—$NH_2$, C(═O)—NMeH, C(═O)—NetH, C(═O)—$NMe_2$, C(═O)—NMeEt, C(═O)—$NEt_2$, C(═S)—$NH_2$, C(═S)—NMeH, C(═S)—NEtH, C(═S)—$NMe_2$, C(═S)—NMeEt, C(═S)—$NEt_2$.

Even more preferably, $R^1$ and $R^2$ are each combination of $R^1$ selected from the group consisting of H, CN, C(═O)-Me, C(═O)-Et, C(═O)—$NH_2$, C(═O)—NMeH, C(═O)—NEtH, C(═O)—$NMe_2$, C(═O)—NMeEt, C(═O)—$NEt_2$, C(═S)—$NH_2$, C(═S)—NMeH, C(═S)—NEtH, C(═S)—$NMe_2$, C(═S)—NMeEt and C(═S)—$NEt_2$ with $R^2$ selected from the group consisting of hydrogen, $C_1$ and $C_1$-$C_4$-alkyl in particular Me or Et.

Preferably R3U is selected from the group consisting of Ci-Cio-haloalkyl, C2-C6-haloalkenyl, C3-C6-haloalkynyl, C3-C6-halocycloalkyl and C3-C6-halocycloalkenyl and wherein at least one halogen is fluorine.

Preferably, $R^{3U}$ is $C_1$-$C_4$-haloalkyl, $C_2$-$C_4$-haloalkenyl and $C_3$-$C_4$-haloalkynyl wherein halogen is fluorine or additionally chlorine.

More preferably $R^{3U}$ is $C_1$-$C_4$-, e.g. $C_1$-$C_2$ fluoroalkyl. Perfluorinated groups $R^{3U}$ are also preferred. For instance, $R^{3U}$ is $CF_3$, $CF_2H$, $CH_2F$, $CF_2CF_3$ or $CF_2CF_2CF_3$. Even more preferably, $R^{3U}$ is $CF_3$ or $CF_2H$. Most preferably, $R^{3U}$ is $CF_3$.

Following notation for a substituent group are defined as follows when used in the text:

Me=methyl group,
Et=ethyl group,
Pr=propyl group,
i-Pr=isopropyl group,
Bu=n-butyl group,
i-Bu=isobutyl group,
s-Bu=secbutyl group,
t-Bu=tert-butyl group,
c-Pr=cyclopropyl group,
Pen=pentyl group,
c-Pen=cyclopentyl group,
c-Hex=cyclohexyl group,
Ac=acetyl group,
Ph=phenyl group, In addition, the undermentioned notation denotes for example the said meaning of each:

5-$CF_3$ is a trifluoromethyl substituent at position 5;
3-CI-5-$CF_3$ is a chlorine atom at position 3 and a trifluoromethyl substituent at position 5;
2,6-$(CI)_2$ is a chlorine atom substituent at positions 2 and 6.

The substituents represented by E1 to E7 denote the respective undermentioned structures:

$E^1$

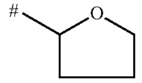

$E^2$

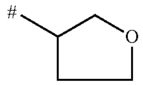

$E^3$

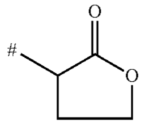

$E^4$

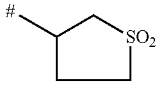

$E^5$

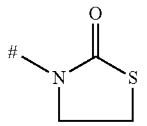

$E^6$

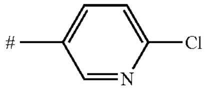

$E^7$

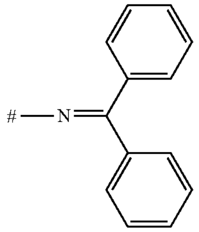

Examples of compounds of general formula I according to the present invention are combinations of the various above mentioned substituents.

In particularly, preferred embodiment of the invention are constituted by each example as depicted in the followings Tables 1 to 9.

TABLE 1 describes examples with compounds number of the type 1-xxxx as represented in the following formula:

1-xxxx

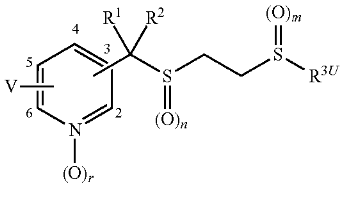

Compounds number 1-01 to 1-0145: m = 0

| No. | Position | V | r | $R^1$ | $R^2$ | $R^{3U}$ | n |
|---|---|---|---|---|---|---|---|
| 1-01. | 2 | 5-$CF_3$ | 0 | H | H | $CF_3$ | 2 |
| 1-02. | 2 | 5-$CF_3$ | 0 | H | H | $CF_2H$ | 2 |

TABLE 1-continued describes examples with compounds number of the type 1-xxxx as represented in the following formula:

1-xxxx

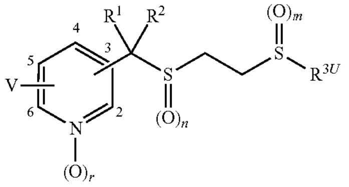

Compounds number 1-01 to 1-0145: m = 0

| No. | Position | V | *r* | $R^1$ | $R^2$ | $R^{3U}$ | *n* |
|---|---|---|---|---|---|---|---|
| 1-03. | 2 | 5-$CF_3$ | 0 | CN | H | $CF_3$ | 2 |
| 1-04. | 2 | 5-$CF_3$ | 0 | CN | H | $CF_2H$ | 2 |
| 1-05. | 2 | 5-$CF_3$ | 0 | COOMe | H | $CF_3$ | 2 |
| 1-06. | 2 | 5-$CF_3$ | 0 | COOMe | H | $CF_2H$ | 2 |
| 1-07. | 2 | 5-$CF_3$ | 0 | COOEt | H | $CF_3$ | 2 |
| 1-08. | 2 | 5-$CF_3$ | 0 | COOEt | H | $CF_2H$ | 2 |
| 1-09. | 2 | 5-$CF_3$ | 0 | COO—i-Pr | H | $CF_3$ | 2 |
| 1-010. | 2 | 5-$CF_3$ | 0 | COO—i-Pr | H | $CF_2H$ | 2 |
| 1-011. | 2 | 5-$CF_3$ | 0 | COO—t-Bu | H | $CF_3$ | 2 |
| 1-012. | 2 | 5-$CF_3$ | 0 | COO—t-Bu | H | $CF_2H$ | 2 |
| 1-013. | 2 | 5-$CF_3$ | 0 | $CON(Me)_2$ | H | $CF_3$ | 2 |
| 1-014. | 2 | 5-$CF_3$ | 0 | $CON(Me)_2$ | H | $CF_2H$ | 2 |
| 1-015. | 2 | 5-$CF_3$ | 0 | 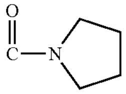 | H | $CF_3$ | 2 |
| 1-016. | 2 | 5-$CF_3$ | 0 | 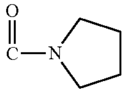 | H | $CF_2H$ | 2 |
| 1-017. | 2 | 5-$CF_3$ | 0 | COOMe | F | $CF_3$ | 2 |
| 1-018. | 2 | 5-$CF_3$ | 0 | COOMe | F | $CF_2H$ | 2 |
| 1-019. | 2 | 5-$CF_3$ | 0 | COOMe | Cl | $CF_3$ | 2 |
| 1-020. | 2 | 5-$CF_3$ | 0 | COOMe | Cl | $CF_2H$ | 2 |
| 1-021. | 2 | 5-$CF_3$ | 0 | COOMe | Me | $CF_3$ | 2 |
| 1-022. | 2 | 5-$CF_3$ | 0 | COOMe | Me | $CF_2H$ | 2 |
| 1-023. | 2 | 5-$CF_3$ | 0 | Me | H | $CF_3$ | 2 |
| 1-024. | 2 | 5-$CF_3$ | 0 | Me | H | $CF_2H$ | 2 |
| 1-025. | 2 | 3-Cl-5-$CF_3$ | 0 | H | H | $CF_3$ | 2 |
| 1-026. | 2 | 3-Cl-5-$CF_3$ | 0 | H | H | $CF_2H$ | 2 |
| 1-027. | 2 | 3-Cl-5-$CF_3$ | 0 | CN | H | $CF_3$ | 2 |
| 1-028. | 2 | 3-Cl-5-$CF_3$ | 0 | CN | H | $CF_2H$ | 2 |
| 1-029. | 2 | 3-Cl-5-$CF_3$ | 0 | COOMe | H | $CF_3$ | 2 |
| 1-030. | 2 | 3-Cl-5-$CF_3$ | 0 | COOMe | H | $CF_2H$ | 2 |
| 1-031. | 2 | 3-Cl-5-$CF_3$ | 0 | COOEt | H | $CF_3$ | 2 |
| 1-032. | 2 | 3-Cl-5-$CF_3$ | 0 | COOEt | H | $CF_2H$ | 2 |
| 1-033. | 2 | 5-CN | 0 | H | H | $CF_3$ | 2 |
| 1-034. | 2 | 5-CN | 0 | H | H | $CF_2H$ | 2 |
| 1-035. | 2 | 5-CN | 0 | CN | H | $CF_3$ | 2 |
| 1-036. | 2 | 5-CN | 0 | CN | H | $CF_2H$ | 2 |
| 1-037. | 3 | 6-Cl | 0 | H | H | $CF_3$ | 0 |
| 1-038. | 3 | 6-Cl | 0 | H | H | $CF_2H$ | 0 |
| 1-039. | 3 | 6-Cl | 0 | H | H | $CF_3$ | 1 |
| 1-040. | 3 | 6-Cl | 0 | H | H | $CF_2H$ | 1 |
| 1-041. | 3 | 6-Cl | 0 | H | H | $CF_3$ | 2 |
| 1-042. | 3 | 6-Cl | 0 | H | H | $CF_2H$ | 2 |
| 1-043. | 3 | 6-Cl | 1 | H | H | $CF_3$ | 2 |
| 1-044. | 3 | 6-Cl | 1 | H | H | $CF_2H$ | 2 |
| 1-045. | 3 | 6-Cl | 0 | Me | H | $CF_3$ | 2 |
| 1-046. | 3 | 6-Cl | 0 | Me | H | $CF_2H$ | 2 |
| 1-047. | 3 | 6-Cl | 0 | Me | Me | $CF_3$ | 2 |
| 1-048. | 3 | 6-Cl | 0 | Me | Me | $CF_2H$ | 2 |
| 1-049. | 3 | 6-Cl | 0 | H | H | $CF_3$ | 0 |
| 1-050. | 3 | 6-Cl | 0 | H | H | $CF_2H$ | 0 |
| 1-051. | 3 | 6-Cl | 0 | H | H | $CF_3$ | 1 |
| 1-052. | 3 | 6-Cl | 0 | H | H | $CF_2H$ | 1 |

TABLE 1-continued describes examples with compounds number of the type 1-xxxx as represented in the following formula:

1-xxxx

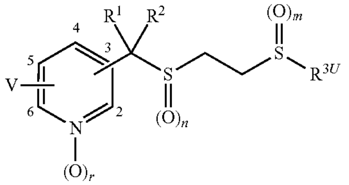

Compounds number 1-01 to 1-0145: m = 0

| No. | Position | V | r | $R^1$ | $R^2$ | $R^{3U}$ | n |
|---|---|---|---|---|---|---|---|
| 1-053. | 3 | 6-Cl | 0 | H | H | $CF_3$ | 2 |
| 1-054. | 3 | 6-Cl | 0 | H | H | $(CF_2)_2CF_3$ | 0 |
| 1-055. | 3 | 6-Cl | 0 | H | H | $(CF_2)_2CF_3$ | 1 |
| 1-056. | 3 | 6-Cl | 0 | H | H | $(CF_2)_2CF_3$ | 2 |
| 1-057. | 3 | 6-Cl | 0 | Me | H | $(CF_2)_2CF_3$ | 2 |
| 1-058. | 3 | 6-Cl | 0 | H | H | $CF_2H$ | 2 |
| 1-059. | 3 | 6-Cl | 0 | F | H | $CF_3$ | 2 |
| 1-060. | 3 | 6-Cl | 0 | F | H | $CF_2H$ | 2 |
| 1-061. | 3 | 6-Cl | 0 | F | F | $CF_3$ | 2 |
| 1-062. | 3 | 6-Cl | 0 | F | F | $CF_2H$ | 2 |
| 1-063. | 3 | 6-Cl | 0 | Cl | H | $CF_3$ | 2 |
| 1-064. | 3 | 6-Cl | 0 | Cl | H | $CF_2H$ | 2 |
| 1-065. | 3 | 6-Cl | 0 | Cl | Cl | $CF_3$ | 2 |
| 1-066. | 3 | 6-Cl | 0 | Cl | Cl | $CF_2H$ | 2 |
| 1-067. | 3 | 6-$CF_3$ | 0 | H | H | $CF_3$ | 0 |
| 1-068. | 3 | 6-$CF_3$ | 0 | H | H | $CF_2H$ | 0 |
| 1-069. | 3 | 6-$CF_3$ | 0 | H | H | $CF_3$ | 1 |
| 1-070. | 3 | 6-$CF_3$ | 0 | H | H | $CF_2H$ | 1 |
| 1-071. | 3 | 6-$CF_3$ | 0 | H | H | $CF_3$ | 2 |
| 1-072. | 3 | 6-$CF_3$ | 0 | H | H | $CF_2H$ | 2 |
| 1-073. | 3 | 6-$CF_3$ | 0 | Me | H | $CF_3$ | 2 |
| 1-074. | 3 | 6-$CF_3$ | 0 | Me | H | $CF_2H$ | 2 |
| 1-075. | 3 | 6-$CF_3$ | 0 | Me | Me | $CF_3$ | 2 |
| 1-076. | 3 | 6-$CF_3$ | 0 | Me | Me | $CF_2H$ | 2 |
| 1-077. | 3 | 6-$CF_3$ | 0 | Et | H | $CF_3$ | 2 |
| 1-078. | 3 | 6-$CF_3$ | 0 | Et | H | $CF_2H$ | 2 |
| 1-079. | 3 | 6-$CF_3$ | 0 | i-Pr | H | $CF_3$ | 2 |
| 1-080. | 3 | 6-$CF_3$ | 0 | i-Pr | H | $CF_2H$ | 2 |
| 1-081. | 3 | 6-$CF_3$ | 0 | Pr | H | $CF_3$ | 2 |
| 1-082. | 3 | 6-$CF_3$ | 0 | Pr | H | $CF_2H$ | 2 |
| 1-083. | 3 | 6-$CF_3$ | 0 | s-Bu | H | $CF_3$ | 2 |
| 1-084. | 3 | 6-$CF_3$ | 0 | s-Bu | H | $CF_2H$ | 2 |
| 1-085. | 3 | 6-$CF_3$ | 0 | i-Bu | H | $CF_3$ | 2 |
| 1-086. | 3 | 6-$CF_3$ | 0 | i-Bu | H | $CF_2H$ | 2 |
| 1-087. | 3 | 6-$CF_3$ | 0 | Bu | H | $CF_3$ | 2 |
| 1-088. | 3 | 6-$CF_3$ | 0 | Bu | H | $CF_2H$ | 2 |
| 1-089. | 3 | 6-$CF_3$ | 0 | $CH_2$—c-Pr | H | $CF_3$ | 2 |
| 1-090. | 3 | 6-$CF_3$ | 0 | $CH_2$—c-Pr | H | $CF_2H$ | 2 |
| 1-091. | 3 | 6-$CF_3$ | 0 | $CH_2CH{=}CH_2$ | H | $CF_3$ | 2 |
| 1-092. | 3 | 6-$CF_3$ | 0 | $CH_2CH{=}CH_2$ | H | $CF_2H$ | 2 |
| 1-093. | 3 | 6-$CF_3$ | 0 | $CH_2C{\equiv}CH$ | H | $CF_3$ | 2 |
| 1-094. | 3 | 6-$CF_3$ | 0 | $CH_2C{\equiv}CH$ | H | $CF_2H$ | 2 |
| 1-095. | 3 | 6-$CF_3$ | 0 | COOMe | H | $CF_3$ | 2 |
| 1-096. | 3 | 6-$CF_3$ | 0 | COOMe | H | $CF_2H$ | 2 |
| 1-097. | 3 | 6-$CF_3$ | 0 | F | H | $CF_3$ | 2 |
| 1-098. | 3 | 6-$CF_3$ | 0 | F | H | $CF_2H$ | 2 |
| 1-099. | 3 | 6-$CF_3$ | 0 | F | F | $CF_3$ | 2 |
| 1-0100. | 3 | 6-$CF_3$ | 0 | F | F | $CF_2H$ | 2 |
| 1-0101. | 3 | 6-$CF_3$ | 0 | Cl | H | $CF_3$ | 2 |
| 1-0102. | 3 | 6-$CF_3$ | 0 | Cl | H | $CF_2H$ | 2 |
| 1-0103. | 3 | 6-$CF_3$ | 0 | Cl | Cl | $CF_3$ | 2 |
| 1-0104. | 3 | 6-$CF_3$ | 0 | Cl | Cl | $CF_2H$ | 2 |
| 1-0105. | 3 | 6-$CF_3$ | 0 | H | H | $CF_2CF_3$ | 0 |
| 1-0106. | 3 | 6-$CF_3$ | 0 | H | H | $CF_2CF_3$ | 1 |
| 1-0107. | 3 | 6-$CF_3$ | 0 | H | H | $CF_2CF_3$ | 2 |
| 1-0108. | 3 | 6-$OCH_2CF_3$ | 0 | H | H | $CF_3$ | 0 |
| 1-0109. | 3 | 6-$OCH_2CF_3$ | 0 | H | H | $CF_2H$ | 0 |
| 1-0110. | 3 | 6-$OCH_2CF_3$ | 0 | H | H | $CF_3$ | 1 |
| 1-0111. | 3 | 6-$OCH_2CF_3$ | 0 | H | H | $CF_2H$ | 1 |
| 1-0112. | 3 | 6-$OCH_2CF_3$ | 0 | H | H | $CF_3$ | 2 |
| 1-0113. | 3 | 6-$OCH_2CF_3$ | 0 | H | H | $CF_2H$ | 2 |

TABLE 1-continued describes examples with compounds number of the type 1-xxxx as represented in the following formula:

1-xxxx

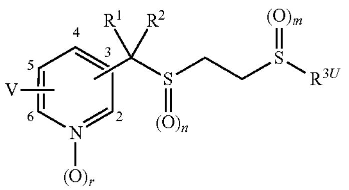

Compounds number 1-01 to 1-0145: m = 0

| No. | Position | V | r | $R^1$ | $R^2$ | $R^{3U}$ | n |
|---|---|---|---|---|---|---|---|
| 1-0114. | 3 | 6-C≡CH | 0 | H | H | $CF_3$ | 0 |
| 1-0115. | 3 | 6-C≡CH | 0 | H | H | $CF_2H$ | 0 |
| 1-0116. | 3 | 6-C≡CH | 0 | H | H | $CF_3$ | 1 |
| 1-0117. | 3 | 6-C≡CH | 0 | H | H | $CF_2H$ | 1 |
| 1-0118. | 3 | 6-C≡CH | 0 | H | H | $CF_3$ | 2 |
| 1-0119. | 3 | 6-C≡CH | 0 | H | H | $CF_2H$ | 2 |
| 1-0120. | 3 | 6-C≡CH | 1 | H | H | $CF_3$ | 2 |
| 1-0121. | 3 | 6-C≡CH | 1 | H | H | $CF_2H$ | 2 |
| 1-0122. | 3 | 6-$SCF_3$ | 0 | H | H | $CF_3$ | 0 |
| 1-0123. | 3 | 6-$SCF_3$ | 0 | H | H | $CF_2H$ | 1 |
| 1-0124. | 3 | 6-$SCF_3$ | 0 | H | H | $CF_3$ | 2 |
| 1-0125. | 3 | 6-$SCF_3$ | 0 | H | H | $CF_2H$ | 2 |
| 1-0126. | 3 | 6-SMe | 0 | H | H | $CF_3$ | 2 |
| 1-0127. | 3 | 6-SMe | 0 | H | H | $CF_2H$ | 2 |
| 1-0128. | 3 | 6-SOMe | 0 | H | H | $CF_3$ | 2 |
| 1-0129. | 3 | 6-SOMe | 0 | H | H | $CF_2H$ | 2 |
| 1-0130. | 3 | 6-$SO_2Me$ | 0 | H | H | $CF_3$ | 2 |
| 1-0131. | 3 | 6-$SO_2Me$ | 0 | H | H | $CF_2H$ | 2 |
| 1-0132. | 4 | 2,6-$(Cl)_2$ | 0 | H | H | $CF_3$ | 0 |
| 1-0133. | 4 | 2,6-$(Cl)_2$ | 0 | H | H | $CF_2H$ | 0 |
| 1-0134. | 4 | 2,6-$(Cl)_2$ | 0 | H | H | $CF_3$ | 1 |
| 1-0135. | 4 | 2,6-$(Cl)_2$ | 0 | H | H | $CF_2H$ | 1 |
| 1-0136. | 4 | 2,6-$(Cl)_2$ | 0 | H | H | $CF_3$ | 2 |
| 1-0137. | 4 | 2,6-$(Cl)_2$ | 0 | H | H | $CF_2H$ | 2 |
| 1-0138. | 4 | 2,6-$(Cl)_2$ | 0 | Me | H | $CF_3$ | 2 |
| 1-0139. | 4 | 2,6-$(Cl)_2$ | 0 | Me | H | $CF_2H$ | 2 |
| 1-0140. | 4 | 2,3,5,6-$(F)_4$ | 0 | H | H | $CF_3$ | 0 |
| 1-0141. | 4 | 2,3,5,6-$(F)_4$ | 0 | H | H | $CF_2H$ | 0 |
| 1-0142. | 4 | 2,3,5,6-$(F)_4$ | 0 | H | H | $CF_3$ | 1 |
| 1-0143. | 4 | 2,3,5,6-$(F)_4$ | 0 | H | H | $CF_2H$ | 1 |
| 1-0144. | 4 | 2,3,5,6-$(F)_4$ | 0 | H | H | $CF_3$ | 2 |
| 1-0145. | 4 | 2,3,5,6-$(F)_4$ | 0 | H | H | $CF_2H$ | 2 |

Analog to the compounds numbered 1-01 to 1-0145 are the compounds numbered 1-1 to 1-145 wherein the variables have the same meaning except m being 1 instead of 0.

TABLE 2 describes examples with compounds number of the type 2-xxxx as represented in the following formula:

2-xxxx

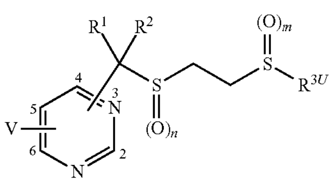

Compounds number 2-01 to 2-01 13: m = 0

| No. | Position | V | $R^1$ | $R^2$ | $R^{3U}$ | n |
|---|---|---|---|---|---|---|
| 2-01. | 2 | 4,6-$(Cl)_2$ | H | H | $CF_3$ | 0 |
| 2-02. | 2 | 4,6-$(Cl)_2$ | H | H | $CF_2H$ | 0 |
| 2-03. | 2 | 4,6-$(Cl)_2$ | H | H | $CF_3$ | 1 |

TABLE 2-continued describes examples with compounds number of the type 2-xxxx as represented in the following formula:

2-xxxx

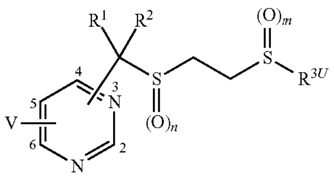

Compounds number 2-01 to 2-01 13: m = 0

| No. | Position | V | $R^1$ | $R^2$ | $R^{3U}$ | n |
|---|---|---|---|---|---|---|
| 2-04. | 2 | 4,6-$(Cl)_2$ | H | H | $CF_2H$ | 1 |
| 2-05. | 2 | 4,6-$(Cl)_2$ | H | H | $CF_3$ | 2 |
| 2-06. | 2 | 4,6-$(Cl)_2$ | H | H | $CF_2H$ | 2 |
| 2-07. | 2 | 4-$CF_3$ | H | H | $CF_3$ | 2 |
| 2-08. | 2 | 4-$CF_3$ | H | H | $CF_2H$ | 2 |
| 2-09. | 2 | 4-$CF_3$ | COOMe | H | $CF_3$ | 2 |
| 2-010. | 2 | 4-$CF_3$ | COOMe | H | $CF_2H$ | 2 |
| 2-011. | 2 | 4-$CF_3$ | COOEt | H | $CF_3$ | 2 |
| 2-012. | 2 | 4-$CF_3$ | COOEt | H | $CF_2H$ | 2 |
| 2-013. | 2 | 4-$CF_3$ | CN | H | $CF_3$ | 2 |
| 2-014. | 2 | 4-$CF_3$ | CN | H | $CF_2H$ | 2 |
| 2-015. | 4 | 2,6-$(Cl)_2$ | H | H | $CF_3$ | 0 |
| 2-016. | 4 | 2,6-$(Cl)_2$ | H | H | $CF_2H$ | 0 |
| 2-017. | 4 | 2,6-$(Cl)_2$ | H | H | $CF_3$ | 1 |
| 2-018. | 4 | 2,6-$(Cl)_2$ | H | H | $CF_2H$ | 1 |
| 2-019. | 4 | 2,6-$(Cl)_2$ | H | H | $CF_3$ | 2 |
| 2-020. | 4 | 2,6-$(Cl)_2$ | H | H | $CF_2H$ | 2 |
| 2-021. | 4 | 2-$CF_3$ | H | H | $CF_3$ | 2 |
| 2-022. | 4 | 2-$CF_3$ | H | H | $CF_2H$ | 2 |
| 2-023. | 4 | 2-$CF_3$ | COOMe | H | $CF_3$ | 2 |
| 2-024. | 4 | 2-$CF_3$ | COOMe | H | $CF_2H$ | 2 |
| 2-025. | 4 | 2-$CF_3$ | COOEt | H | $CF_3$ | 2 |
| 2-026. | 4 | 2-$CF_3$ | COOEt | H | $CF_2H$ | 2 |
| 2-027. | 4 | 2-$CF_3$ | CN | H | $CF_3$ | 2 |
| 2-028. | 4 | 2-$CF_3$ | CN | H | $CF_2H$ | 2 |
| 2-029. | 4 | 6-$CF_3$ | H | H | $CF_3$ | 2 |
| 2-030. | 4 | 6-$CF_3$ | H | H | $CF_2H$ | 2 |
| 2-031. | 4 | 6-$CF_3$ | COOMe | H | $CF_3$ | 2 |
| 2-032. | 4 | 6-$CF_3$ | COOMe | H | $CF_2H$ | 2 |
| 2-033. | 4 | 6-$CF_3$ | COOEt | H | $CF_3$ | 2 |
| 2-034. | 4 | 6-$CF_3$ | COOEt | H | $CF_2H$ | 2 |
| 2-035. | 4 | 6-$CF_3$ | CN | H | $CF_3$ | 2 |
| 2-036. | 4 | 6-$CF_3$ | CN | H | $CF_2H$ | 2 |
| 2-037. | 5 | 2-$CF_3$ | H | H | $CF_3$ | 0 |
| 2-038. | 5 | 2-$CF_3$ | H | H | $CF_2H$ | 0 |
| 2-039. | 5 | 2-$CF_3$ | H | H | $CF_3$ | 1 |
| 2-040. | 5 | 2-$CF_3$ | H | H | $CF_2H$ | 1 |
| 2-041. | 5 | 2-$CF_3$ | H | H | $CF_3$ | 2 |
| 2-042. | 5 | 2-$CF_3$ | H | H | $CF_2H$ | 2 |
| 2-043. | 5 | 2-$CF_3$ | Me | H | $CF_3$ | 2 |
| 2-044. | 5 | 2-$CF_3$ | Me | H | $CF_2H$ | 2 |
| 2-045. | 5 | 2-$CF_3$ | Me | Me | $CF_3$ | 2 |
| 2-046. | 5 | 2-$CF_3$ | Me | Me | $CF_2H$ | 2 |
| 2-047. | 5 | 2-$CF_3$ | Et | H | $CF_3$ | 2 |
| 2-048. | 5 | 2-$CF_3$ | Et | H | $CF_2H$ | 2 |
| 2-049. | 5 | 2-$CF_3$ | i-Pr | H | $CF_3$ | 2 |
| 2-050. | 5 | 2-$CF_3$ | i-Pr | H | $CF_2H$ | 2 |
| 2-051. | 5 | 2-$CF_3$ | Pr | H | $CF_3$ | 2 |
| 2-052. | 5 | 2-$CF_3$ | Pr | H | $CF_2H$ | 2 |
| 2-053. | 5 | 2-$CF_3$ | s-Bu | H | $CF_3$ | 2 |
| 2-054. | 5 | 2-$CF_3$ | s-Bu | H | $CF_2H$ | 2 |
| 2-055. | 5 | 2-$CF_3$ | i-Bu | H | $CF_3$ | 2 |

TABLE 2-continued describes examples with compounds number of the type 2-xxxx as represented in the following formula:

2-xxxx

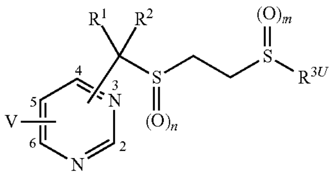

Compounds number 2-01 to 2-01 13: m = 0

| No. | Position | V | $R^1$ | $R^2$ | $R^{3U}$ | n |
|---|---|---|---|---|---|---|
| 2-056. | 5 | $2-CF_3$ | i-Bu | H | $CF_2H$ | 2 |
| 2-057. | 5 | $2-CF_3$ | Bu | H | $CF_3$ | 2 |
| 2-058. | 5 | $2-CF_3$ | Bu | H | $CF_2H$ | 2 |
| 2-059. | 5 | $2-CF_3$ | $CH_2$-c-Pr | H | $CF_3$ | 2 |
| 2-060. | 5 | $2-CF_3$ | $CH_2$-c-Pr | H | $CF_2H$ | 2 |
| 2-061. | 5 | $2-CF_3$ | $CH_2CH{=}CH_2$ | H | $CF_3$ | 2 |
| 2-062. | 5 | $2-CF_3$ | $CH_2CH{=}CH_2$ | H | $CF_2H$ | 2 |
| 2-063. | 5 | $2-CF_3$ | $CH_2C{\equiv}CH$ | H | $CF_3$ | 2 |
| 2-064. | 5 | $2-CF_3$ | $CH_2C{\equiv}CH$ | H | $CF_2H$ | 2 |
| 2-065. | 5 | $2-CF_3$ | COOMe | H | $CF_3$ | 2 |
| 2-066. | 5 | $2-CF_3$ | COOMe | H | $CF_2H$ | 2 |
| 2-067. | 5 | $2-CF_3$ | CONHEt | H | $CF_3$ | 2 |
| 2-068. | 5 | $2-CF_3$ | CONHEt | H | $CF_2H$ | 2 |
| 2-069. | 5 | $2-CF_3$ | CSNHMe | H | $CF_3$ | 2 |
| 2-070. | 5 | $2-CF_3$ | CSNHMe | H | $CF_2H$ | 2 |
| 2-071. | 5 | $2-CF_3$ | F | H | $CF_3$ | 2 |
| 2-072. | 5 | $2-CF_3$ | F | H | $CF_2H$ | 2 |
| 2-073. | 5 | $2-CF_3$ | F | F | $CF_3$ | 2 |
| 2-074. | 5 | $2-CF_3$ | F | F | $CF_2H$ | 2 |
| 2-075. | 5 | $2-CF_3$ | Cl | H | $CF_3$ | 2 |
| 2-076. | 5 | $2-CF_3$ | Cl | H | $CF_2H$ | 2 |
| 2-077. | 5 | $2-CF_3$ | Cl | Cl | $CF_3$ | 2 |
| 2-078. | 5 | $2-CF_3$ | Cl | Cl | $CF_2H$ | 2 |
| 2-079. | 5 | $2-CF_3$ | H | H | $CF_2CF_3$ | 0 |
| 2-080. | 5 | $2-CF_3$ | H | H | $CF_2CF_3$ | 1 |
| 2-081. | 5 | $2-CF_3$ | H | H | $CF_2CF_3$ | 2 |
| 2-082. | 5 | $2-CF_3$-4-Me | H | H | $CF_3$ | 0 |
| 2-083. | 5 | $2-CF_3$-4-Me | H | H | $CF_2H$ | 0 |
| 2-084. | 5 | $2-CF_3$-4-Me | H | H | $CF_3$ | 1 |
| 2-085. | 5 | $2-CF_3$-4-Me | H | H | $CF_2H$ | 1 |
| 2-086. | 5 | $2-CF_3$-4-Me | H | H | $CF_3$ | 2 |
| 2-087. | 5 | $2-CF_3$-4-Me | H | H | $CF_2H$ | 2 |
| 2-088. | 5 | $2-CF_3$-4-Me | Me | H | $CF_3$ | 2 |
| 2-089. | 5 | $2-CF_3$-4-Me | Me | H | $CF_2H$ | 2 |
| 2-090. | 5 | $2-SCF_3$-4-Me | H | H | $CF_3$ | 0 |
| 2-091. | 5 | $2-SCF_3$-4-Me | H | H | $CF_2H$ | 0 |
| 2-092. | 5 | $2-SCF_3$-4-Me | H | H | $CF_3$ | 1 |
| 2-093. | 5 | $2-SCF_3$-4-Me | H | H | $CF_2H$ | 1 |
| 2-094. | 5 | $2-SCF_3$-4-Me | H | H | $CF_3$ | 2 |
| 2-095. | 5 | $2-SCF_3$-4-Me | H | H | $CF_2H$ | 2 |
| 2-096. | 5 | $2-SCF_3$-4-Me | Me | H | $CF_3$ | 2 |
| 2-097. | 5 | $2-SCF_3$-4-Me | Me | H | $CF_2H$ | 2 |
| 2-098. | 5 | 2-c-Pr | H | H | $CF_3$ | 0 |
| 2-099. | 5 | 2-c-Pr | H | H | $CF_2H$ | 0 |
| 2-0100. | 5 | 2-c-Pr | H | H | $CF_3$ | 1 |
| 2-0101. | 5 | 2-c-Pr | H | H | $CF_2H$ | 1 |
| 2-0102. | 5 | 2-c-Pr | H | H | $CF_3$ | 2 |
| 2-0103. | 5 | 2-c-Pr | H | H | $CF_2H$ | 2 |
| 2-0104. | 5 | 2-c-Pr | Me | H | $CF_3$ | 2 |
| 2-0105. | 5 | 2-c-Pr | Me | H | $CF_2H$ | 2 |
| 2-0106. | 5 | 2-t-Bu | H | H | $CF_3$ | 0 |
| 2-0107. | 5 | 2-t-Bu | H | H | $CF_2H$ | 0 |
| 2-0108. | 5 | 2-t-Bu | H | H | $CF_3$ | 1 |
| 2-0109. | 5 | 2-t-Bu | H | H | $CF_2H$ | 1 |
| 2-0110. | 5 | 2-t-Bu | H | H | $CF_3$ | 2 |
| 2-0111. | 5 | 2-t-Bu | H | H | $CF_2H$ | 2 |
| 2-0112. | 5 | 2-t-Bu | Me | H | $CF_3$ | 2 |
| 2-0113. | 5 | 2-t-Bu | Me | H | $CF_2H$ | 2 |

Analog to the compounds numbered 2-01 to 2-01 13 are the compounds numbered 2-1 to 2-1 13 wherein the variables have the same meaning except m being 1 instead of 0.

TABLE 3 describes examples with compounds number of the type 3-xxxx as represented in the following formula:

3-xxxx

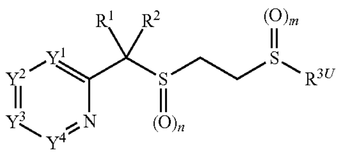

Compounds number 3-01 to 3-062: m = 0

| No. | $Y^1$ | $Y^2$ | $Y^3$ | $Y^4$ | $R^1$ | $R^2$ | $R^{3U}$ | n |
|---|---|---|---|---|---|---|---|---|
| 3-01. | C—H | N | C—H | C—Cl | H | H | $CF_3$ | 2 |
| 3-02. | C—H | N | C—H | C—Cl | H | H | $CF_2H$ | 2 |
| 3-03. | C—H | N | C—H | C—Cl | COOMe | H | $CF_3$ | 2 |
| 3-04. | C—H | N | C—H | C—Cl | COOMe | H | $CF_2H$ | 2 |
| 3-05. | C—H | N | C—H | C—Cl | COOMe | H | $CF_3$ | 2 |
| 3-06. | C—H | N | C—H | C—Cl | COOMe | H | $CF_2H$ | 2 |
| 3-07. | C—H | N | C—H | C—Cl | CN | H | $CF_3$ | 2 |
| 3-08. | C—H | N | C—H | C—Cl | CN | H | $CF_2H$ | 2 |
| 3-09. | C—Cl | N | C—CN | C—CN | H | H | $CF_3$ | 2 |
| 3-010. | C—Cl | N | C—CN | C—CN | H | H | $CF_2H$ | 2 |
| 3-011. | C—Cl | N | C—CN | C—CN | COOMe | H | $CF_3$ | 2 |
| 3-012. | C—Cl | N | C—CN | C—CN | COOMe | H | $CF_2H$ | 2 |
| 3-013. | C—Cl | N | C—CN | C—CN | COOEt | H | $CF_3$ | 2 |
| 3-014. | C—Cl | N | C—CN | C—CN | COOEt | H | $CF_2H$ | 2 |
| 3-015. | C—Cl | N | C—CN | C—CN | CN | H | $CF_3$ | 2 |
| 3-016. | C—Cl | N | C—CN | C—CN | CN | H | $CF_2H$ | 2 |
| 3-017. | C—H | N | C—CN | C—CN | H | H | $CF_3$ | 2 |
| 3-018. | C—H | N | C—CN | C—CN | H | H | $CF_2H$ | 2 |
| 3-019. | C—H | N | C—CN | C—CN | COOMe | H | $CF_3$ | 2 |
| 3-020. | C—H | N | C—CN | C—CN | COOMe | H | $CF_2H$ | 2 |
| 3-021. | C—H | N | C—CN | C—CN | COOEt | H | $CF_3$ | 2 |
| 3-022. | C—H | N | C—CN | C—CN | COOEt | H | $CF_2H$ | 2 |
| 3-023. | C—H | N | C—CN | C—CN | CN | H | $CF_3$ | 2 |
| 3-024. | C—H | N | C—CN | C—CN | CN | H | $CF_2H$ | 2 |
| 3-025. | C—H | C—H | C—Cl | N | H | H | $CF_3$ | 2 |
| 3-026. | C—H | C—H | C—Cl | N | H | H | $CF_2H$ | 2 |
| 3-027. | C—H | C—H | C—Cl | N | COOMe | H | $CF_3$ | 2 |
| 3-028. | C—H | C—H | C—Cl | N | COOMe | H | $CF_2H$ | 2 |
| 3-029. | C—H | C—H | C—Cl | N | COOEt | H | $CF_3$ | 2 |
| 3-030. | C—H | C—H | C—Cl | N | COOEt | H | $CF_2H$ | 2 |
| 3-031. | C—H | C—H | C—Cl | N | CN | H | $CF_3$ | 2 |
| 3-032. | C—H | C—H | C—Cl | N | CN | H | $CF_2H$ | 2 |
| 3-033. | C—H | C—H | C—$CF_3$ | N | H | H | $CF_3$ | 2 |
| 3-034. | C—H | C—H | C—$CF_3$ | N | H | H | $CF_2H$ | 2 |
| 3-035. | C—H | C—H | C—$CF_3$ | N | COOMe | H | $CF_3$ | 2 |
| 3-036. | C—H | C—H | C—$CF_3$ | N | COOMe | H | $CF_2H$ | 2 |
| 3-037. | C—H | C—H | C—$CF_3$ | N | COOEt | H | $CF_3$ | 2 |
| 3-038. | C—H | C—H | C—$CF_3$ | N | COOEt | H | $CF_2H$ | 2 |
| 3-039. | C—H | C—H | C—$CF_3$ | N | CN | H | $CF_3$ | 2 |
| 3-040. | C—H | C—H | C—$CF_3$ | N | CN | H | $CF_2H$ | 2 |
| 3-041. | N | C—Cl | N | C—Cl | H | H | $CF_3$ | 2 |
| 3-042. | N | C—Cl | N | C—Cl | H | H | $CF_2H$ | 2 |
| 3-043. | N | C—Cl | N | C—Cl | COOMe | H | $CF_3$ | 2 |
| 3-044. | N | C—Cl | N | C—Cl | COOMe | H | $CF_2H$ | 2 |
| 3-045. | N | C—Cl | N | C—Cl | COOEt | H | $CF_3$ | 2 |
| 3-046. | N | C—Cl | N | C—Cl | COOEt | H | $CF_2H$ | 2 |
| 3-047. | N | C—Cl | N | C—Cl | CN | H | $CF_3$ | 2 |
| 3-048. | N | C—Cl | N | C—Cl | CN | H | $CF_2H$ | 2 |
| 3-049. | N | C—OMe | N | C—OMe | H | H | $CF_3$ | 2 |
| 3-050. | N | C—OMe | N | C—OMe | H | H | $CF_2H$ | 2 |
| 3-051. | N | C—OMe | N | C—OMe | COOMe | H | $CF_3$ | 2 |
| 3-052. | N | C—OMe | N | C—OMe | COOMe | H | $CF_2H$ | 2 |
| 3-053. | N | C—OMe | N | C—OMe | COOEt | H | $CF_3$ | 2 |
| 3-054. | N | C—OMe | N | C—OMe | COOEt | H | $CF_2H$ | 2 |
| 3-055. | N | C—OMe | N | C—OMe | CN | H | $CF_3$ | 2 |
| 3-056. | N | C—OMe | N | C—OMe | CN | H | $CF_2H$ | 2 |
| 3-057. | C—H | C—H | C—CH═CH—CH═CH—C | | H | H | $CF_3$ | 0 |
| 3-058. | C—H | C—H | C—CH═CH—CH═CH—C | | H | H | $CF_2H$ | 0 |
| 3-059. | C—H | C—H | C—CH═CH—CH═CH—C | | H | H | $CF_3$ | 1 |
| 3-060. | C—H | C—H | C—CH═CH—CH═CH—C | | H | H | $CF_2H$ | 1 |
| 3-061. | C—H | C—H | C—CH═CH—CH═CH—C | | H | H | $CF_3$ | 2 |
| 3-062. | C—H | C—H | C—CH═CH—CH═CH—C | | H | H | $CF_2H$ | 2 |

Analog to the compounds numbered 3-01 to 3-062 are the compounds numbered 3-1 to 3-62 wherein the variables have the same meaning except m being 1 instead of 0.

TABLE 4 describes examples with compounds number of the type 4-xxxx as represented in the following formula:

4-xxxx

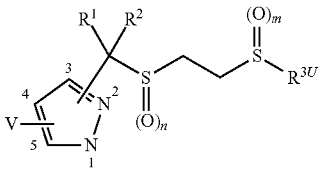

Compounds number 4-01 to 4-0487: m = 0

| No. | Position | V | $R^1$ | $R^2$ | $R^{3U}$ | n |
|---|---|---|---|---|---|---|
| 4-01. | 1 | 3-$CF_3$ | H | H | $CF_3$ | 0 |
| 4-02. | 1 | 3-$CF_3$ | H | H | $CF_2H$ | 0 |
| 4-03. | 1 | 3-$CF_3$ | H | H | $CF_3$ | 1 |
| 4-04. | 1 | 3-$CF_3$ | H | H | $CF_2H$ | 1 |
| 4-05. | 1 | 3-$CF_3$ | H | H | $CF_3$ | 2 |
| 4-06. | 1 | 3-$CF_3$ | H | H | $CF_2H$ | 2 |
| 4-07. | 1 | 3-$CF_3$ | Me | H | $CF_3$ | 0 |
| 4-08. | 1 | 3-$CF_3$ | Me | H | $CF_2H$ | 0 |
| 4-09. | 1 | 3-$CF_3$ | Me | H | $CF_3$ | 1 |
| 4-010. | 1 | 3-$CF_3$ | Me | H | $CF_2H$ | 1 |
| 4-011. | 1 | 3-$CF_3$ | Me | H | $CF_3$ | 2 |
| 4-012. | 1 | 3-$CF_3$ | Me | H | $CF_2H$ | 2 |
| 4-013. | 1 | 3-$CF_3$ | Et | H | $CF_3$ | 0 |
| 4-014. | 1 | 3-$CF_3$ | Et | H | $CF_2H$ | 0 |
| 4-015. | 1 | 3-$CF_3$ | Et | H | $CF_3$ | 1 |
| 4-016. | 1 | 3-$CF_3$ | Et | H | $CF_2H$ | 1 |
| 4-017. | 1 | 3-$CF_3$ | Et | H | $CF_3$ | 2 |
| 4-018. | 1 | 3-$CF_3$ | Et | H | $CF_2H$ | 2 |
| 4-019. | 1 | 3-$CF_3$ | i-Pr | H | $CF_3$ | 0 |
| 4-020. | 1 | 3-$CF_3$ | i-Pr | H | $CF_2H$ | 0 |
| 4-021. | 1 | 3-$CF_3$ | i-Pr | H | $CF_3$ | 1 |
| 4-022. | 1 | 3-$CF_3$ | i-Pr | H | $CF_2H$ | 1 |
| 4-023. | 1 | 3-$CF_3$ | i-Pr | H | $CF_3$ | 2 |
| 4-024. | 1 | 3-$CF_3$ | i-Pr | H | $CF_2H$ | 2 |
| 4-025. | 1 | 3-$CF_3$ | c-Pr | H | $CF_3$ | 0 |
| 4-026. | 1 | 3-$CF_3$ | c-Pr | H | $CF_2H$ | 0 |
| 4-027. | 1 | 3-$CF_3$ | c-Pr | H | $CF_3$ | 1 |
| 4-028. | 1 | 3-$CF_3$ | c-Pr | H | $CF_2H$ | 1 |
| 4-029. | 1 | 3-$CF_3$ | c-Pr | H | $CF_3$ | 2 |
| 4-030. | 1 | 3-$CF_3$ | c-Pr | H | $CF_2H$ | 2 |
| 4-031. | 1 | 3-$CF_3$ | Pr | H | $CF_3$ | 0 |
| 4-032. | 1 | 3-$CF_3$ | Pr | H | $CF_2H$ | 0 |
| 4-033. | 1 | 3-$CF_3$ | Pr | H | $CF_3$ | 1 |
| 4-034. | 1 | 3-$CF_3$ | Pr | H | $CF_2H$ | 1 |
| 4-035. | 1 | 3-$CF_3$ | Pr | H | $CF_3$ | 2 |
| 4-036. | 1 | 3-$CF_3$ | Pr | H | $CF_2H$ | 2 |
| 4-037. | 1 | 3-$CF_3$ | s-Bu | H | $CF_3$ | 0 |
| 4-038. | 1 | 3-$CF_3$ | s-Bu | H | $CF_2H$ | 0 |
| 4-039. | 1 | 3-$CF_3$ | s-Bu | H | $CF_3$ | 1 |
| 4-040. | 1 | 3-$CF_3$ | s-Bu | H | $CF_2H$ | 1 |
| 4-041. | 1 | 3-$CF_3$ | s-Bu | H | $CF_3$ | 2 |
| 4-042. | 1 | 3-$CF_3$ | s-Bu | H | $CF_2H$ | 2 |
| 4-043. | 1 | 3-$CF_3$ | i-Bu | H | $CF_3$ | 0 |
| 4-044. | 1 | 3-$CF_3$ | i-Bu | H | $CF_2H$ | 0 |
| 4-045. | 1 | 3-$CF_3$ | i-Bu | H | $CF_3$ | 1 |
| 4-046. | 1 | 3-$CF_3$ | i-Bu | H | $CF_2H$ | 1 |
| 4-047. | 1 | 3-$CF_3$ | i-Bu | H | $CF_3$ | 2 |
| 4-048. | 1 | 3-$CF_3$ | i-Bu | H | $CF_2H$ | 2 |
| 4-049. | 1 | 3-$CF_3$ | Bu | H | $CF_3$ | 0 |
| 4-050. | 1 | 3-$CF_3$ | Bu | H | $CF_2H$ | 0 |
| 4-051. | 1 | 3-$CF_3$ | Bu | H | $CF_3$ | 1 |
| 4-052. | 1 | 3-$CF_3$ | Bu | H | $CF_2H$ | 1 |
| 4-053. | 1 | 3-$CF_3$ | Bu | H | $CF_3$ | 2 |
| 4-054. | 1 | 3-$CF_3$ | Bu | H | $CF_2H$ | 2 |
| 4-055. | 1 | 3-$CF_3$ | 2-Pen | H | $CF_3$ | 0 |
| 4-056. | 1 | 3-$CF_3$ | 2-Pen | H | $CF_2H$ | 0 |
| 4-057. | 1 | 3-$CF_3$ | 2-Pen | H | $CF_3$ | 1 |
| 4-058. | 1 | 3-$CF_3$ | 2-Pen | H | $CF_2H$ | 1 |

TABLE 4-continued describes examples with compounds number of the type 4-xxxx as represented in the following formula:

4-xxxx

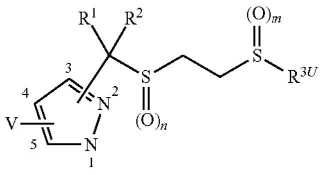

Compounds number 4-01 to 4-0487: m = 0

| No. | Position | V | $R^1$ | $R^2$ | $R^{3U}$ | n |
|---|---|---|---|---|---|---|
| 4-059. | 1 | 3-$CF_3$ | 2-Pen | H | $CF_3$ | 2 |
| 4-060. | 1 | 3-$CF_3$ | 2-Pen | H | $CF_2H$ | 2 |
| 4-061. | 1 | 3-$CF_3$ | 3-Pen | H | $CF_3$ | 0 |
| 4-062. | 1 | 3-$CF_3$ | 3-Pen | H | $CF_2H$ | 0 |
| 4-063. | 1 | 3-$CF_3$ | 3-Pen | H | $CF_3$ | 1 |
| 4-064. | 1 | 3-$CF_3$ | 3-Pen | H | $CF_2H$ | 1 |
| 4-065. | 1 | 3-$CF_3$ | 3-Pen | H | $CF_3$ | 2 |
| 4-066. | 1 | 3-$CF_3$ | 3-Pen | H | $CF_2H$ | 2 |
| 4-067. | 1 | 3-$CF_3$ | c-Pen | H | $CF_3$ | 0 |
| 4-068. | 1 | 3-$CF_3$ | c-Pen | H | $CF_2H$ | 0 |
| 4-069. | 1 | 3-$CF_3$ | c-Pen | H | $CF_3$ | 1 |
| 4-070. | 1 | 3-$CF_3$ | c-Pen | H | $CF_2H$ | 1 |
| 4-071. | 1 | 3-$CF_3$ | c-Pen | H | $CF_3$ | 2 |
| 4-072. | 1 | 3-$CF_3$ | c-Pen | H | $CF_2H$ | 2 |
| 4-073. | 1 | 3-$CF_3$ | c-Hex | H | $CF_3$ | 0 |
| 4-074. | 1 | 3-$CF_3$ | c-Hex | H | $CF_2H$ | 0 |
| 4-075. | 1 | 3-$CF_3$ | c-Hex | H | $CF_3$ | 1 |
| 4-076. | 1 | 3-$CF_3$ | c-Hex | H | $CF_2H$ | 1 |
| 4-077. | 1 | 3-$CF_3$ | c-Hex | H | $CF_3$ | 2 |
| 4-078. | 1 | 3-$CF_3$ | c-Hex | H | $CF_2H$ | 2 |
| 4-079. | 1 | 3-$CF_3$ | CN | H | $CF_3$ | 0 |
| 4-080. | 1 | 3-$CF_3$ | CN | H | $CF_2H$ | 0 |
| 4-081. | 1 | 3-$CF_3$ | CN | H | $CF_3$ | 1 |
| 4-082. | 1 | 3-$CF_3$ | CN | H | $CF_2H$ | 1 |
| 4-083. | 1 | 3-$CF_3$ | CN | H | $CF_3$ | 2 |
| 4-084. | 1 | 3-$CF_3$ | CN | H | $CF_2H$ | 2 |
| 4-085. | 1 | 3-$CF_3$ | COOMe | H | $CF_3$ | 0 |
| 4-086. | 1 | 3-$CF_3$ | COOMe | H | $CF_2H$ | 0 |
| 4-087. | 1 | 3-$CF_3$ | COOMe | H | $CF_3$ | 1 |
| 4-088. | 1 | 3-$CF_3$ | COOMe | H | $CF_2H$ | 1 |
| 4-089. | 1 | 3-$CF_3$ | COOMe | H | $CF_3$ | 2 |
| 4-090. | 1 | 3-$CF_3$ | COOMe | H | $CF_2H$ | 2 |
| 4-091. | 1 | 3-$CF_3$ | COOEt | H | $CF_3$ | 0 |
| 4-092. | 1 | 3-$CF_3$ | COOEt | H | $CF_2H$ | 0 |
| 4-093. | 1 | 3-$CF_3$ | COOEt | H | $CF_3$ | 1 |
| 4-094. | 1 | 3-$CF_3$ | COOEt | H | $CF_2H$ | 1 |
| 4-095. | 1 | 3-$CF_3$ | COOEt | H | $CF_3$ | 2 |
| 4-096. | 1 | 3-$CF_3$ | COOEt | H | $CF_2H$ | 2 |
| 4-097. | 1 | 3-$CF_3$-5-Me | H | H | $CF_3$ | 0 |
| 4-098. | 1 | 3-$CF_3$-5-Me | H | H | $CF_2H$ | 0 |
| 4-099. | 1 | 3-$CF_3$-5-Me | H | H | $CF_3$ | 1 |
| 4-0100. | 1 | 3-$CF_3$-5-Me | H | H | $CF_2H$ | 1 |
| 4-0101. | 1 | 3-$CF_3$-5-Me | H | H | $CF_3$ | 2 |
| 4-0102. | 1 | 3-$CF_3$-5-Me | H | H | $CF_2H$ | 2 |
| 4-0103. | 1 | 3-$CF_3$-5-Me | Me | H | $CF_3$ | 0 |
| 4-0104. | 1 | 3-$CF_3$-5-Me | Me | H | $CF_2H$ | 0 |
| 4-0105. | 1 | 3-$CF_3$-5-Me | Me | H | $CF_3$ | 1 |
| 4-0106. | 1 | 3-$CF_3$-5-Me | Me | H | $CF_2H$ | 1 |
| 4-0107. | 1 | 3-$CF_3$-5-Me | Me | H | $CF_3$ | 2 |
| 4-0108. | 1 | 3-$CF_3$-5-Me | Me | H | $CF_2H$ | 2 |
| 4-0109. | 1 | 3-$CF_3$-5-Me | CN | H | $CF_3$ | 0 |
| 4-0110. | 1 | 3-$CF_3$-5-Me | CN | H | $CF_2H$ | 0 |
| 4-0111. | 1 | 3-$CF_3$-5-Me | CN | H | $CF_3$ | 1 |
| 4-0112. | 1 | 3-$CF_3$-5-Me | CN | H | $CF_2H$ | 1 |
| 4-0113. | 1 | 3-$CF_3$-5-Me | CN | H | $CF_3$ | 2 |
| 4-0114. | 1 | 3-$CF_3$-5-Me | CN | H | $CF_2H$ | 2 |
| 4-0115. | 1 | 3-$CF_3$-5-Me | COOMe | H | $CF_3$ | 0 |
| 4-0116. | 1 | 3-$CF_3$-5-Me | COOMe | H | $CF_2H$ | 0 |
| 4-0117. | 1 | 3-$CF_3$-5-Me | COOMe | H | $CF_3$ | 1 |
| 4-0118. | 1 | 3-$CF_3$-5-Me | COOMe | H | $CF_2H$ | 1 |
| 4-0119. | 1 | 3-$CF_3$-5-Me | COOMe | H | $CF_3$ | 2 |
| 4-0120. | 1 | 3-$CF_3$-5-Me | COOMe | H | $CF_2H$ | 2 |
| 4-0121. | 1 | 3-$CF_3$-5-Me | COOEt | H | $CF_3$ | 0 |

TABLE 4-continued describes examples with compounds number of the type 4-xxxx as represented in the following formula:

4-xxxx

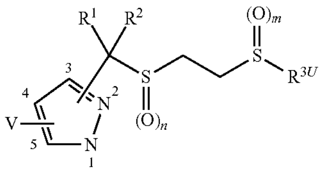

Compounds number 4-01 to 4-0487: m = 0

| No. | Position | V | $R^1$ | $R^2$ | $R^{3U}$ | n |
|---|---|---|---|---|---|---|
| 4-0122. | 1 | 3-$CF_3$-5-Me | COOEt | H | $CF_2H$ | 0 |
| 4-0123. | 1 | 3-$CF_3$-5-Me | COOEt | H | $CF_3$ | 1 |
| 4-0124. | 1 | 3-$CF_3$-5-Me | COOEt | H | $CF_2H$ | 1 |
| 4-0125. | 1 | 3-$CF_3$-5-Me | COOEt | H | $CF_3$ | 2 |
| 4-0126. | 1 | 3-$CF_3$-5-Me | COOEt | H | $CF_2H$ | 2 |
| 4-0127. | 1 | 3-$CF_3$-4-CN | H | H | $CF_3$ | 0 |
| 4-0128. | 1 | 3-$CF_3$-4-CN | H | H | $CF_2H$ | 0 |
| 4-0129. | 1 | 3-$CF_3$-4-CN | H | H | $CF_3$ | 1 |
| 4-0130. | 1 | 3-$CF_3$-4-CN | H | H | $CF_2H$ | 1 |
| 4-0131. | 1 | 3-$CF_3$-4-CN | H | H | $CF_3$ | 2 |
| 4-0132. | 1 | 3-$CF_3$-4-CN | H | H | $CF_2H$ | 2 |
| 4-0133. | 1 | 3-$CF_3$-4-CN | H | H | $CF_3$ | 2 |
| 4-0134. | 1 | 3-$CF_3$-4-CN | H | H | $CF_2H$ | 2 |
| 4-0135. | 1 | 3-$CF_3$-4-CN | Me | H | $CF_3$ | 0 |
| 4-0136. | 1 | 3-$CF_3$-4-CN | Me | H | $CF_2H$ | 0 |
| 4-0137. | 1 | 3-$CF_3$-4-CN | Me | H | $CF_3$ | 1 |
| 4-0138. | 1 | 3-$CF_3$-4-CN | Me | H | $CF_2H$ | 1 |
| 4-0139. | 1 | 3-$CF_3$-4-CN | Me | H | $CF_2H$ | 2 |
| 4-0140. | 1 | 3-$CF_3$-4-CN | Me | H | $CF_2H$ | 2 |
| 4-0141. | 1 | 4-$CF_3$ | H | H | $CF_3$ | 0 |
| 4-0142. | 1 | 4-$CF_3$ | H | H | $CF_2H$ | 0 |
| 4-0143. | 1 | 4-$CF_3$ | H | H | $CF_3$ | 1 |
| 4-0144. | 1 | 4-$CF_3$ | H | H | $CF_2H$ | 1 |
| 4-0145. | 1 | 4-$CF_3$ | H | H | $CF_3$ | 2 |
| 4-0146. | 1 | 4-$CF_3$ | H | H | $CF_2H$ | 2 |
| 4-0147. | 1 | 4-$CF_3$ | Me | H | $CF_3$ | 0 |
| 4-0148. | 1 | 4-$CF_3$ | Me | H | $CF_2H$ | 0 |
| 4-0149. | 1 | 4-$CF_3$ | Me | H | $CF_3$ | 1 |
| 4-0150. | 1 | 4-$CF_3$ | Me | H | $CF_2H$ | 1 |
| 4-0151. | 1 | 4-$CF_3$ | Me | H | $CF_3$ | 2 |
| 4-0152. | 1 | 4-$CF_3$ | Me | H | $CF_2H$ | 2 |
| 4-0153. | 1 | 4-$CF_3$ | Et | H | $CF_3$ | 0 |
| 4-0154. | 1 | 4-$CF_3$ | Et | H | $CF_2H$ | 0 |
| 4-0155. | 1 | 4-$CF_3$ | Et | H | $CF_3$ | 1 |
| 4-0156. | 1 | 4-$CF_3$ | Et | H | $CF_2H$ | 1 |
| 4-0157. | 1 | 4-$CF_3$ | Et | H | $CF_3$ | 2 |
| 4-0158. | 1 | 4-$CF_3$ | Et | H | $CF_2H$ | 2 |
| 4-0159. | 1 | 4-$CF_3$ | i-Pr | H | $CF_3$ | 0 |
| 4-0160. | 1 | 4-$CF_3$ | i-Pr | H | $CF_2H$ | 0 |
| 4-0161. | 1 | 4-$CF_3$ | i-Pr | H | $CF_3$ | 1 |
| 4-0162. | 1 | 4-$CF_3$ | i-Pr | H | $CF_2H$ | 1 |
| 4-0163. | 1 | 4-$CF_3$ | i-Pr | H | $CF_3$ | 2 |
| 4-0164. | 1 | 4-$CF_3$ | i-Pr | H | $CF_2H$ | 2 |
| 4-0165. | 1 | 4-$CF_3$ | c-Pr | H | $CF_3$ | 0 |
| 4-0166. | 1 | 4-$CF_3$ | c-Pr | H | $CF_2H$ | 0 |
| 4-0167. | 1 | 4-$CF_3$ | c-Pr | H | $CF_3$ | 1 |
| 4-0168. | 1 | 4-$CF_3$ | c-Pr | H | $CF_2H$ | 1 |
| 4-0169. | 1 | 4-$CF_3$ | c-Pr | H | $CF_3$ | 2 |
| 4-0170. | 1 | 4-$CF_3$ | c-Pr | H | $CF_2H$ | 2 |
| 4-0171. | 1 | 4-$CF_3$ | Pr | H | $CF_3$ | 0 |
| 4-0172. | 1 | 4-$CF_3$ | Pr | H | $CF_2H$ | 0 |
| 4-0173. | 1 | 4-$CF_3$ | Pr | H | $CF_3$ | 1 |
| 4-0174. | 1 | 4-$CF_3$ | Pr | H | $CF_2H$ | 1 |
| 4-0175. | 1 | 4-$CF_3$ | Pr | H | $CF_3$ | 2 |
| 4-0176. | 1 | 4-$CF_3$ | Pr | H | $CF_2H$ | 2 |
| 4-0177. | 1 | 4-$CF_3$ | s-Bu | H | $CF_3$ | 0 |
| 4-0178. | 1 | 4-$CF_3$ | s-Bu | H | $CF_2H$ | 0 |
| 4-0179. | 1 | 4-$CF_3$ | s-Bu | H | $CF_3$ | 1 |
| 4-0180. | 1 | 4-$CF_3$ | s-Bu | H | $CF_2H$ | 1 |
| 4-0181. | 1 | 4-$CF_3$ | s-Bu | H | $CF_3$ | 2 |
| 4-0182. | 1 | 4-$CF_3$ | s-Bu | H | $CF_2H$ | 2 |
| 4-0183. | 1 | 4-$CF_3$ | i-Bu | H | $CF_3$ | 0 |
| 4-0184. | 1 | 4-$CF_3$ | i-Bu | H | $CF_2H$ | 0 |

TABLE 4-continued describes examples with compounds number of the type 4-xxxx as represented in the following formula:

4-xxxx

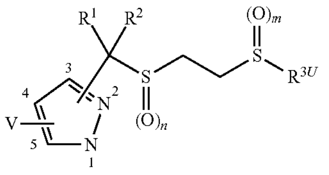

Compounds number 4-01 to 4-0487: m = 0

| No. | Position | V | $R^1$ | $R^2$ | $R^{3U}$ | n |
|---|---|---|---|---|---|---|
| 4-0185. | 1 | 4-$CF_3$ | i-Bu | H | $CF_3$ | 1 |
| 4-0186. | 1 | 4-$CF_3$ | i-Bu | H | $CF_2H$ | 1 |
| 4-0187. | 1 | 4-$CF_3$ | i-Bu | H | $CF_3$ | 2 |
| 4-0188. | 1 | 4-$CF_3$ | i-Bu | H | $CF_2H$ | 2 |
| 4-0189. | 1 | 4-$CF_3$ | Bu | H | $CF_3$ | 0 |
| 4-0190. | 1 | 4-$CF_3$ | Bu | H | $CF_2H$ | 0 |
| 4-0191. | 1 | 4-$CF_3$ | Bu | H | $CF_3$ | 1 |
| 4-0192. | 1 | 4-$CF_3$ | Bu | H | $CF_2H$ | 1 |
| 4-0193. | 1 | 4-$CF_3$ | Bu | H | $CF_3$ | 2 |
| 4-0194. | 1 | 4-$CF_3$ | Bu | H | $CF_2H$ | 2 |
| 4-0195. | 1 | 4-$CF_3$ | 2-Pen | H | $CF_3$ | 0 |
| 4-0196. | 1 | 4-$CF_3$ | 2-Pen | H | $CF_2H$ | 0 |
| 4-0197. | 1 | 4-$CF_3$ | 2-Pen | H | $CF_3$ | 1 |
| 4-0198. | 1 | 4-$CF_3$ | 2-Pen | H | $CF_2H$ | 1 |
| 4-0199. | 1 | 4-$CF_3$ | 2-Pen | H | $CF_3$ | 2 |
| 4-0200. | 1 | 4-$CF_3$ | 2-Pen | H | $CF_2H$ | 2 |
| 4-0201. | 1 | 4-$CF_3$ | 3-Pen | H | $CF_3$ | 0 |
| 4-0202. | 1 | 4-$CF_3$ | 3-Pen | H | $CF_2H$ | 0 |
| 4-0203. | 1 | 4-$CF_3$ | 3-Pen | H | $CF_3$ | 1 |
| 4-0204. | 1 | 4-$CF_3$ | 3-Pen | H | $CF_2H$ | 1 |
| 4-0205. | 1 | 4-$CF_3$ | 3-Pen | H | $CF_3$ | 2 |
| 4-0206. | 1 | 4-$CF_3$ | 3-Pen | H | $CF_2H$ | 2 |
| 4-0207. | 1 | 4-$CF_3$ | c-Pen | H | $CF_3$ | 0 |
| 4-0208. | 1 | 4-$CF_3$ | c-Pen | H | $CF_2H$ | 0 |
| 4-0209. | 1 | 4-$CF_3$ | c-Pen | H | $CF_3$ | 1 |
| 4-0210. | 1 | 4-$CF_3$ | c-Pen | H | $CF_2H$ | 1 |
| 4-0211. | 1 | 4-$CF_3$ | c-Pen | H | $CF_3$ | 2 |
| 4-0212. | 1 | 4-$CF_3$ | c-Pen | H | $CF_2H$ | 2 |
| 4-0213. | 1 | 4-$CF_3$ | c-Hex | H | $CF_3$ | 0 |
| 4-0214. | 1 | 4-$CF_3$ | c-Hex | H | $CF_2H$ | 0 |
| 4-0215. | 1 | 4-$CF_3$ | c-Hex | H | $CF_3$ | 1 |
| 4-0216. | 1 | 4-$CF_3$ | c-Hex | H | $CF_2H$ | 1 |
| 4-0217. | 1 | 4-$CF_3$ | c-Hex | H | $CF_3$ | 2 |
| 4-0218. | 1 | 4-$CF_3$ | c-Hex | H | $CF_2H$ | 2 |
| 4-0219. | 1 | 4-$CF_3$ | CN | H | $CF_3$ | 0 |
| 4-0220. | 1 | 4-$CF_3$ | CN | H | $CF_2H$ | 0 |
| 4-0221. | 1 | 4-$CF_3$ | CN | H | $CF_3$ | 1 |
| 4-0222. | 1 | 4-$CF_3$ | CN | H | $CF_2H$ | 1 |
| 4-0223. | 1 | 4-$CF_3$ | CN | H | $CF_3$ | 2 |
| 4-0224. | 1 | 4-$CF_3$ | CN | H | $CF_2H$ | 2 |
| 4-0225. | 1 | 4-$CF_3$ | COOMe | H | $CF_3$ | 0 |
| 4-0226. | 1 | 4-$CF_3$ | COOMe | H | $CF_2H$ | 0 |
| 4-0227. | 1 | 4-$CF_3$ | COOMe | H | $CF_3$ | 1 |
| 4-0228. | 1 | 4-$CF_3$ | COOMe | H | $CF_2H$ | 1 |
| 4-0229. | 1 | 4-$CF_3$ | COOMe | H | $CF_3$ | 2 |
| 4-0230. | 1 | 4-$CF_3$ | COOMe | H | $CF_2H$ | 2 |
| 4-0231. | 1 | 4-$CF_3$ | COOEt | H | $CF_3$ | 0 |
| 4-0232. | 1 | 4-$CF_3$ | COOEt | H | $CF_2H$ | 0 |
| 4-0233. | 1 | 4-$CF_3$ | COOEt | H | $CF_3$ | 1 |
| 4-0234. | 1 | 4-$CF_3$ | COOEt | H | $CF_2H$ | 1 |
| 4-0235. | 1 | 4-$CF_3$ | COOEt | H | $CF_3$ | 2 |
| 4-0236. | 1 | 4-$CF_3$ | COOEt | H | $CF_2H$ | 2 |
| 4-0237. | 3 | 1-Me-5-$OCHF_2$ | H | H | $CF_3$ | 0 |
| 4-0238. | 3 | 1-Me-5-$OCHF_2$ | H | H | $CF_2H$ | 0 |
| 4-0239. | 3 | 1-Me-5-$OCHF_2$ | H | H | $CF_3$ | 1 |
| 4-0240. | 3 | 1-Me-5-$OCHF_2$ | H | H | $CF_2H$ | 1 |
| 4-0241. | 3 | 1-Me-5-$OCHF_2$ | H | H | $CF_3$ | 2 |
| 4-0242. | 3 | 1-Me-5-$OCHF_2$ | H | H | $CF_2H$ | 2 |
| 4-0243. | 4 | 1-t-Bu | H | H | $CF_3$ | 0 |
| 4-0244. | 4 | 1-t-Bu | H | H | $CF_2H$ | 0 |
| 4-0245. | 4 | 1-t-Bu | H | H | $CF_3$ | 1 |
| 4-0246. | 4 | 1-t-Bu | H | H | $CF_2H$ | 1 |
| 4-0247. | 4 | 1-t-Bu | H | H | $CF_3$ | 2 |

TABLE 4-continued describes examples with compounds number of the type 4-xxxx as represented in the following formula:

4-xxxx

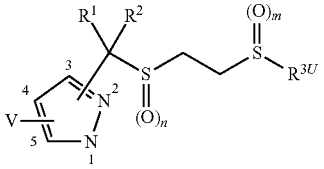

Compounds number 4-01 to 4-0487: m = 0

| No. | Position | V | $R^1$ | $R^2$ | $R^{3U}$ | n |
|---|---|---|---|---|---|---|
| 4-0248. | 4 | 1-t-Bu | H | H | $CF_2H$ | 2 |
| 4-0249. | 4 | 1-$CHF_2$ | H | H | $CF_3$ | 0 |
| 4-0250. | 4 | 1-$CHF_2$ | H | H | $CF_2H$ | 0 |
| 4-0251. | 4 | 1-$CHF_2$ | H | H | $CF_3$ | 1 |
| 4-0252. | 4 | 1-$CHF_2$ | H | H | $CF_2H$ | 1 |
| 4-0253. | 4 | 1-$CHF_2$ | H | H | $CF_3$ | 2 |
| 4-0254. | 4 | 1-$CHF_2$ | H | H | $CF_2H$ | 2 |
| 4-0255. | 4 | 1-Me-3-$CF_3$-5-$OCHF_2$ | H | H | $CF_3$ | 0 |
| 4-0256. | 4 | 1-Me-3-$CF_3$-5-$OCHF_2$ | H | H | $CF_2H$ | 0 |
| 4-0257. | 4 | 1-Me -3-$CF_3$-5-$OCHF_2$ | H | H | $CF_3$ | 1 |
| 4-0258. | 4 | 1-Me-3-$CF_3$-5-$OCHF_2$ | H | H | $CF_2H$ | 1 |
| 4-0259. | 4 | 1-Me-3-$CF_3$-5-$OCHF_2$ | H | H | $CF_3$ | 2 |
| 4-0260. | 4 | 1-Me-3-$CF_3$-5-$OCHF_2$ | H | H | $CF_2H$ | 2 |
| 4-0261. | 5 | 1-Me-3-$OCHF_2$ | H | H | $CF_3$ | 0 |
| 4-0262. | 5 | 1-Me-3-$OCHF_2$ | H | H | $CF_2H$ | 0 |
| 4-0263. | 5 | 1-Me-3-$OCHF_2$ | H | H | $CF_3$ | 1 |
| 4-0264. | 5 | 1-Me-3-$OCHF_2$ | H | H | $CF_2H$ | 1 |
| 4-0265. | 5 | 1-Me-3-$OCHF_2$ | H | H | $CF_3$ | 2 |
| 4-0266. | 5 | 1-Me-3-$OCHF_2$ | H | H | $CF_2H$ | 2 |
| 4-0267. | 1 | 3-$CF_3$ | $CO_2Me$ | Me | $CF_3$ | 0 |
| 4-0268. | 1 | 3-$CF_3$ | $CO_2Me$ | Me | $CF_2H$ | 0 |
| 4-0269. | 1 | 3-$CF_3$ | $CO_2Me$ | Me | $CF_3$ | 1 |
| 4-0270. | 1 | 3-$CF_3$ | $CO_2Me$ | Me | $CF_2H$ | 1 |
| 4-0271. | 1 | 3-$CF_3$ | $CO_2Me$ | Me | $CF_3$ | 2 |
| 4-0272. | 1 | 3-$CF_3$ | $CO_2Me$ | Me | $CF_2H$ | 2 |
| 4-0273. | 1 | 3-$CF_3$ | $CO_2Et$ | Me | $CF_3$ | 0 |
| 4-0274. | 1 | 3-$CF_3$ | $CO_2Et$ | Me | $CF_2H$ | 0 |
| 4-0275. | 1 | 3-$CF_3$ | $CO_2Et$ | Me | $CF_3$ | 1 |
| 4-0276. | 1 | 3-$CF_3$ | $CO_2Et$ | Me | $CF_2H$ | 1 |
| 4-0277. | 1 | 3-$CF_3$ | $CO_2Et$ | Me | $CF_3$ | 2 |
| 4-0278. | 1 | 3-$CF_3$ | $CO_2Et$ | Me | $CF_2H$ | 2 |
| 4-0279. | 1 | 3-$CF_3$ | $CO_2$-i-Pr | Me | $CF_3$ | 0 |
| 4-0280. | 1 | 3-$CF_3$ | $CO_2$-i-Pr | Me | $CF_2H$ | 0 |
| 4-0281. | 1 | 3-$CF_3$ | $CO_2$-i-Pr | Me | $CF_3$ | 1 |
| 4-0282. | 1 | 3-$CF_3$ | $CO_2$-i-Pr | Me | $CF_2H$ | 1 |
| 4-0283. | 1 | 3-$CF_3$ | $CO_2$-i-Pr | Me | $CF_3$ | 2 |
| 4-0284. | 1 | 3-$CF_3$ | $CO_2$-i-Pr | Me | $CF_2H$ | 2 |
| 4-0285. | 1 | 3-$CF_3$ | $CO_2$-i-Pr | Me | $CF_3$ | 2 |
| 4-0286. | 1 | 3-$CF_3$ | $CO_2$-t-Bu | H | $CF_2H$ | 0 |
| 4-0287. | 1 | 3-$CF_3$ | $CO_2$-t-Bu | H | $CF_3$ | 0 |
| 4-0288. | 1 | 3-$CF_3$ | $CO_2$-t-Bu | H | $CF_2H$ | 1 |
| 4-0289. | 1 | 3-$CF_3$ | $CO_2$-t-Bu | H | $CF_3$ | 1 |
| 4-0290. | 1 | 3-$CF_3$ | $CO_2$-t-Bu | H | $CF_2H$ | 2 |
| 4-0291. | 1 | 3-$CF_3$ | $CO_2$-t-Bu | H | $CF_3$ | 2 |
| 4-0292. | 1 | 3-$CF_3$ | $CO_2$-t-Bu | Me | $CF_2H$ | 0 |
| 4-0293. | 1 | 3-$CF_3$ | $CO_2$-t-Bu | Me | $CF_3$ | 0 |
| 4-0294. | 1 | 3-$CF_3$ | $CO_2$-t-Bu | Me | $CF_2H$ | 1 |
| 4-0295. | 1 | 3-$CF_3$ | $CO_2$-t-Bu | Me | $CF_3$ | 1 |
| 4-0296. | 1 | 3-$CF_3$ | $CO_2$-t-Bu | Me | $CF_2H$ | 2 |
| 4-0297. | 1 | 3-$CF_3$ | $CO_2$-t-Bu | Me | $CF_3$ | 2 |
| 4-0298. | 1 | 3-$CF_3$ | $CO_2$-c-Pen | Me | $CF_2H$ | 0 |
| 4-0299. | 1 | 3-$CF_3$ | $CO_2$-c-Pen | Me | $CF_3$ | 0 |
| 4-0300. | 1 | 3-$CF_3$ | $CO_2$-c-Pen | Me | $CF_2H$ | 1 |
| 4-0301. | 1 | 3-$CF_3$ | $CO_2$-c-Pen | Me | $CF_3$ | 1 |
| 4-0302. | 1 | 3-$CF_3$ | $CO_2$-c-Pen | Me | $CF_2H$ | 2 |
| 4-0303. | 1 | 3-$CF_3$ | $CO_2$-c-Pen | Me | $CF_3$ | 2 |
| 4-0304. | 1 | 3-$CF_3$ | $CO_2CH_2CF_3$ | Me | $CF_2H$ | 0 |
| 4-0305. | 1 | 3-$CF_3$ | $CO_2CH_2CF_3$ | Me | $CF_3$ | 0 |
| 4-0306. | 1 | 3-$CF_3$ | $CO_2CH_2CF_3$ | Me | $CF_2H$ | 1 |
| 4-0307. | 1 | 3-$CF_3$ | $CO_2CH_2CF_3$ | Me | $CF_3$ | 1 |
| 4-0308. | 1 | 3-$CF_3$ | $CO_2CH_2CF_3$ | Me | $CF_2H$ | 2 |
| 4-0309. | 1 | 3-$CF_3$ | $CO_2CH_2CF_3$ | Me | $CF_3$ | 2 |
| 4-0310. | 1 | 3-$CF_3$ | $CO_2(CH_2)_2OMe$ | Me | $CF_2H$ | 0 |

TABLE 4-continued describes examples with compounds number of the type 4-xxxx as represented in the following formula:

4-xxxx

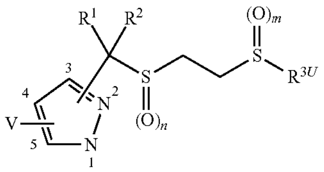

Compounds number 4-01 to 4-0487: m = 0

| No. | Position | V | $R^1$ | $R^2$ | $R^{3U}$ | n |
|---|---|---|---|---|---|---|
| 4-0311. | 1 | 3-$CF_3$ | $CO_2(CH_2)_2OMe$ | Me | $CF_3$ | 0 |
| 4-0312. | 1 | 3-$CF_3$ | $CO_2(CH_2)_2OMe$ | Me | $CF_2H$ | 1 |
| 4-0313. | 1 | 3-$CF_3$ | $CO_2(CH_2)_2OMe$ | Me | $CF_3$ | 1 |
| 4-0314. | 1 | 3-$CF_3$ | $CO_2(CH_2)_2OMe$ | Me | $CF_2H$ | 2 |
| 4-0315. | 1 | 3-$CF_3$ | $CO_2(CH_2)_2OMe$ | Me | $CF_3$ | 2 |
| 4-0316. | 1 | 3-$CF_3$ | $CO_2CH(Me)CH_2OMe$ | Me | $CF_2H$ | 0 |
| 4-0317. | 1 | 3-$CF_3$ | $CO_2CH(Me)CH_2OMe$ | Me | $CF_3$ | 0 |
| 4-0318. | 1 | 3-$CF_3$ | $CO_2CH(Me)CH_2OMe$ | Me | $CF_2H$ | 1 |
| 4-0319. | 1 | 3-$CF_3$ | $CO_2CH(Me)CH_2OMe$ | Me | $CF_3$ | 1 |
| 4-0320. | 1 | 3-$CF_3$ | $CO_2CH(Me)CH_2OMe$ | Me | $CF_2H$ | 2 |
| 4-0321. | 1 | 3-$CF_3$ | $CO_2CH(Me)CH_2OMe$ | Me | $CF_3$ | 2 |
| 4-0322. | 1 | 3-$CF_3$ | $CO_2(CH_2)_2O(CH_2)_2OMe$ | Me | $CF_2H$ | 0 |
| 4-0323. | 1 | 3-$CF_3$ | $CO_2(CH_2)_2O(CH_2)_2OMe$ | Me | $CF_3$ | 0 |
| 4-0324. | 1 | 3-$CF_3$ | $CO_2(CH_2)_2O(CH_2)_2OMe$ | Me | $CF_2H$ | 1 |
| 4-0325. | 1 | 3-$CF_3$ | $CO_2(CH_2)_2O(CH_2)_2OMe$ | Me | $CF_3$ | 1 |
| 4-0326. | 1 | 3-$CF_3$ | $CO_2CH(Me)CH_2OMe$ | Me | $CF_2H$ | 2 |
| 4-0327. | 1 | 3-$CF_3$ | $CO_2CH(Me)CH_2OMe$ | Me | $CF_3$ | 2 |
| 4-0328. | 1 | 3-$CF_3$ | $CO_2(CH_2)_2O(CH_2)_2OMe$ | Me | $CF_2H$ | 0 |
| 4-0329. | 1 | 3-$CF_3$ | $CO_2(CH_2)_2O(CH_2)_2OMe$ | Me | $CF_3$ | 0 |
| 4-0330. | 1 | 3-$CF_3$ | $CO_2(CH_2)_2O(CH_2)_2OMe$ | Me | $CF_2H$ | 1 |
| 4-0331. | 1 | 3-$CF_3$ | $CO_2(CH_2)_2O(CH_2)_2OMe$ | Me | $CF_3$ | 1 |
| 4-0332. | 1 | 3-$CF_3$ | $CO_2(CH_2)_2O(CH_2)_2OMe$ | Me | $CF_2H$ | 2 |
| 4-0333. | 1 | 3-$CF_3$ | $CO_2(CH_2)_2O(CH_2)_2OMe$ | Me | $CF_3$ | 2 |
| 4-0334. | 1 | 3-$CF_3$ | $CO_2(CH_2)_2SMe$ | Me | $CF_2H$ | 0 |
| 4-0335. | 1 | 3-$CF_3$ | $CO_2(CH_2)_2SMe$ | Me | $CF_3$ | 0 |
| 4-0336. | 1 | 3-$CF_3$ | $CO_2(CH_2)_2SO_2Me$ | Me | $CF_2H$ | 2 |
| 4-0337. | 1 | 3-$CF_3$ | $CO_2(CH_2)_2SO_2Me$ | Me | $CF_3$ | 2 |
| 4-0338. | 1 | 3-$CF_3$ | $CO_2CH_2CONH_2$ | Me | $CF_2H$ | 0 |
| 4-0339. | 1 | 3-$CF_3$ | $CO_2CH_2CONH_2$ | Me | $CF_3$ | 0 |
| 4-0340. | 1 | 3-$CF_3$ | $CO_2CH_2CONH_2$ | Me | $CF_2H$ | 1 |
| 4-0341. | 1 | 3-$CF_3$ | $CO_2CH_2CONH_2$ | Me | $CF_3$ | 1 |
| 4-0342. | 1 | 3-$CF_3$ | $CO_2CH_2CONH_2$ | Me | $CF_2H$ | 2 |
| 4-0343. | 1 | 3-$CF_3$ | $CO_2CH_2CONH_2$ | Me | $CF_3$ | 2 |
| 4-0344. | 1 | 3-$CF_3$ | $CO_2CH(Me)CONH_2$ | Me | $CF_2H$ | 0 |
| 4-0345. | 1 | 3-$CF_3$ | $CO_2CH(Me)CONH_2$ | Me | $CF_3$ | 0 |
| 4-0346. | 1 | 3-$CF_3$ | $CO_2CH(Me)CONH_2$ | Me | $CF_2H$ | 1 |
| 4-0347. | 1 | 3-$CF_3$ | $CO_2CH(Me)CONH_2$ | Me | $CF_3$ | 1 |
| 4-0348. | 1 | 3-$CF_3$ | $CO_2CH(Me)CONH_2$ | Me | $CF_2H$ | 2 |
| 4-0349. | 1 | 3-$CF_3$ | $CO_2CH(CH_3)CONH_2$ | Me | $CF_3$ | 2 |
| 4-0350. | 1 | 3-$CF_3$ | $CO_2CH(Me)CN$ | Me | $CF_2H$ | 0 |
| 4-0351. | 1 | 3-$CF_3$ | $CO_2CH(Me)CN$ | Me | $CF_3$ | 0 |
| 4-0352. | 1 | 3-$CF_3$ | $CO_2CH(Me)CN$ | Me | $CF_2H$ | 1 |
| 4-0353. | 1 | 3-$CF_3$ | $CO_2CH(Me)CN$ | Me | $CF_3$ | 1 |
| 4-0354. | 1 | 3-$CF_3$ | $CO_2CH(Me)CN$ | Me | $CF_3$ | 2 |
| 4-0355. | 1 | 3-$CF_3$ | $CO_2CH(Me)CN$ | Me | $CF_2H$ | 2 |
| 4-0356. | 1 | 3-$CF_3$ | $CO_2CH_2CH_2Cl$ | Me | $CF_3$ | 0 |
| 4-0357. | 1 | 3-$CF_3$ | $CO_2CH_2CH_2Cl$ | Me | $CF_2H$ | 0 |
| 4-0358. | 1 | 3-$CF_3$ | $CO_2CH_2CH_2Cl$ | Me | $CF_3$ | 1 |
| 4-0359. | 1 | 3-$CF_3$ | $CO_2CH_2CH_2Cl$ | Me | $CF_2H$ | 1 |
| 4-0360. | 1 | 3-$CF_3$ | $CO_2CH_2CH_2Cl$ | Me | $CF_3$ | 2 |
| 4-0361. | 1 | 3-$CF_3$ | $CO_2CH_2CH_2Cl$ | Me | $CF_2H$ | 2 |
| 4-0362. | 1 | 3-$CF_3$ | $CO_2C(Me)_2CO_2Et$ | H | $CF_3$ | 0 |
| 4-0363. | 1 | 3-$CF_3$ | $CO_2C(Me)_2CO_2Et$ | H | $CF_2H$ | 0 |
| 4-0364. | 1 | 3-$CF_3$ | $CO_2C(Me)_2CO_2Et$ | H | $CF_3$ | 1 |
| 4-0365. | 1 | 3-$CF_3$ | $CO_2C(Me)_2CO_2Et$ | H | $CF_2H$ | 1 |
| 4-0366. | 1 | 3-$CF_3$ | $CO_2C(Me)_2CO_2Et$ | H | $CF_3$ | 2 |
| 4-0367. | 1 | 3-$CF_3$ | $CO_2C(Me)_2CO_2Et$ | H | $CF_2H$ | 2 |
| 4-0368. | 1 | 3-$CF_3$ | $CO_2C(Me)_2CO_2Et$ | Me | $CF_3$ | 0 |
| 4-0369. | 1 | 3-$CF_3$ | $CO_2C(Me)_2CO_2Et$ | Me | $CF_2H$ | 0 |
| 4-0370. | 1 | 3-$CF_3$ | $CO_2C(Me)_2CO_2Et$ | Me | $CF_3$ | 1 |
| 4-0371. | 1 | 3-$CF_3$ | $CO_2C(Me)_2CO_2Et$ | Me | $CF_2H$ | 1 |

TABLE 4-continued describes examples with compounds number of the type 4-xxxx as represented in the following formula:

4-xxxx

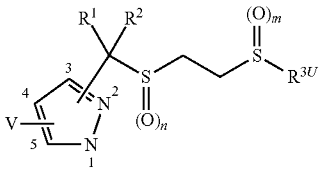

Compounds number 4-01 to 4-0487: m = 0

| No. | Position | V | $R^1$ | $R^2$ | $R^{3U}$ | n |
|---|---|---|---|---|---|---|
| 4-0372. | 1 | 3-$CF_3$ | $CO_2C(Me)_2CO_2Et$ | Me | $CF_3$ | 2 |
| 4-0373. | 1 | 3-$CF_3$ | $CO_2C(Me)_2CO_2Et$ | Me | $CF_2H$ | 2 |
| 4-0374. | 1 | 3-$CF_3$ | COO-$E^2$ | Me | $CF_3$ | 0 |
| 4-0375. | 1 | 3-$CF_3$ | COO-$E^2$ | Me | $CF_2H$ | 0 |
| 4-0376. | 1 | 3-$CF_3$ | COO-$E^2$ | Me | $CF_3$ | 1 |
| 4-0377. | 1 | 3-$CF_3$ | COO-$E^2$ | Me | $CF_2H$ | 1 |
| 4-0378. | 1 | 3-$CF_3$ | COO-$E^2$ | Me | $CF_3$ | 2 |
| 4-0379. | 1 | 3-$CF_3$ | COO-$E^2$ | Me | $CF_2H$ | 2 |
| 4-0380. | 1 | 3-$CF_3$ | COO-$E^3$ | Me | $CF_3$ | 0 |
| 4-0381. | 1 | 3-$CF_3$ | COO-$E^3$ | Me | $CF_2H$ | 0 |
| 4-0382. | 1 | 3-$CF_3$ | COO-$E^3$ | Me | $CF_3$ | 1 |
| 4-0383. | 1 | 3-$CF_3$ | COO-$E^3$ | Me | $CF_2H$ | 1 |
| 4-0384. | 1 | 3-$CF_3$ | COO-$E^3$ | Me | $CF_3$ | 2 |
| 4-0385. | 1 | 3-$CF_3$ | COO-$E^3$ | Me | $CF_2H$ | 2 |
| 4-0386. | 1 | 3-$CF_3$ | COO-$E^4$ | Me | $CF_3$ | 0 |
| 4-0387. | 1 | 3-$CF_3$ | COO-$E^4$ | Me | $CF_2H$ | 0 |
| 4-0388. | 1 | 3-$CF_3$ | COO-$E^4$ | Me | $CF_3$ | 1 |
| 4-0389. | 1 | 3-$CF_3$ | COO-$E^4$ | Me | $CF_2H$ | 1 |
| 4-0390. | 1 | 3-$CF_3$ | COO-$E^4$ | Me | $CF_3$ | 2 |
| 4-0391. | 1 | 3-$CF_3$ | COO-$E^4$ | Me | $CF_2H$ | 2 |
| 4-0392. | 1 | 3-$CF_3$ | $COOCH_2$-$E^1$ | Me | $CF_3$ | 0 |
| 4-0393. | 1 | 3-$CF_3$ | $COOCH_2$-$E^1$ | Me | $CF_2H$ | 0 |
| 4-0394. | 1 | 3-$CF_3$ | $COOCH_2$-$E^1$ | Me | $CF_3$ | 1 |
| 4-0395. | 1 | 3-$CF_3$ | $COOCH_2$-$E^1$ | Me | $CF_2H$ | 1 |
| 4-0396. | 1 | 3-$CF_3$ | $COOCH_2$-$E^1$ | Me | $CF_3$ | 2 |
| 4-0397. | 1 | 3-$CF_3$ | $COOCH_2$-$E^1$ | Me | $CF_2H$ | 2 |
| 4-0398. | 1 | 3-$CF_3$ | $COOCH_2$-$E^2$ | Me | $CF_3$ | 0 |
| 4-0399. | 1 | 3-$CF_3$ | $COOCH_2$-$E^2$ | Me | $CF_2H$ | 0 |
| 4-0400. | 1 | 3-$CF_3$ | $COOCH_2$-$E^2$ | Me | $CF_3$ | 1 |
| 4-0401. | 1 | 3-$CF_3$ | $COOCH_2$-$E^2$ | Me | $CF_2H$ | 1 |
| 4-0402. | 1 | 3-$CF_3$ | $COOCH_2$-$E^2$ | Me | $CF_3$ | 2 |
| 4-0403. | 1 | 3-$CF_3$ | $COOCH_2$-$E^2$ | Me | $CF_2H$ | 2 |
| 4-0404. | 1 | 3-$CF_3$ | CONH-i-Pr | Me | $CF_3$ | 0 |
| 4-0405. | 1 | 3-$CF_3$ | CONH-i-Pr | Me | $CF_2H$ | 0 |
| 4-0406. | 1 | 3-$CF_3$ | CONH-i-Pr | Me | $CF_3$ | 1 |
| 4-0407. | 1 | 3-$CF_3$ | CONH-i-Pr | Me | $CF_2H$ | 1 |
| 4-0408. | 1 | 3-$CF_3$ | CONH-i-Pr | Me | $CF_3$ | 2 |
| 4-0409. | 1 | 3-$CF_3$ | CONH-i-Pr | Me | $CF_2H$ | 2 |
| 4-0410. | 1 | 3-$CF_3$ | Ac | H | $CF_3$ | 0 |
| 4-0411. | 1 | 3-$CF_3$ | Ac | H | $CF_2H$ | 0 |
| 4-0412. | 1 | 3-$CF_3$ | Ac | H | $CF_3$ | 1 |
| 4-0413. | 1 | 3-$CF_3$ | Ac | H | $CF_2H$ | 1 |
| 4-0414. | 1 | 3-$CF_3$ | Ac | H | $CF_3$ | 2 |
| 4-0415. | 1 | 3-$CF_3$ | Ac | H | $CF_2H$ | 2 |
| 4-0416. | 1 | 3-$CF_3$ | Ac | Me | $CF_3$ | 0 |
| 4-0417. | 1 | 3-$CF_3$ | Ac | Me | $CF_2H$ | 0 |
| 4-0418. | 1 | 3-$CF_3$ | Ac | Me | $CF_3$ | 1 |
| 4-0419. | 1 | 3-$CF_3$ | Ac | Me | $CF_2H$ | 1 |
| 4-0420. | 1 | 3-$CF_3$ | Ac | Me | $CF_3$ | 2 |
| 4-0421. | 1 | 3-$CF_3$ | Ac | Me | $CF_2H$ | 2 |
| 4-0422. | 1 | 3-$CF_3$-4-Cl | COO-t-Bu | H | $CF_3$ | 0 |
| 4-0423. | 1 | 3-$CF_3$-4-Cl | COO-t-Bu | H | $CF_2H$ | 0 |
| 4-0424. | 1 | 3-$CF_3$-4-Cl | COO-t-Bu | H | $CF_3$ | 1 |
| 4-0425. | 1 | 3-$CF_3$-4-Cl | COO-t-Bu | H | $CF_2H$ | 1 |
| 4-0426. | 1 | 3-$CF_3$-4-Cl | COO-t-Bu | H | $CF_3$ | 2 |
| 4-0427. | 1 | 3-$CF_3$-4-Cl | COO-t-Bu | H | $CF_2H$ | 2 |
| 4-0428. | 1 | 3-$CF_3$-4-Cl | COO-t-Bu | Me | $CF_3$ | 0 |
| 4-0429. | 1 | 3-$CF_3$-4-Cl | COO-t-Bu | Me | $CF_2H$ | 0 |
| 4-0430. | 1 | 3-$CF_3$-4-Cl | COO-t-Bu | Me | $CF_3$ | 1 |

TABLE 4-continued describes examples with compounds number of the type 4-xxxx as represented in the following formula:

4-xxxx

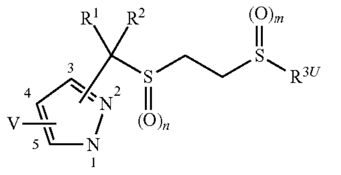

Compounds number 4-01 to 4-0487: m = 0

| No. | Position | V | $R^1$ | $R^2$ | $R^{3U}$ | n |
|---|---|---|---|---|---|---|
| 4-0431. | 1 | 3-$CF_3$-4-Cl | COO-t-Bu | Me | $CF_2H$ | 1 |
| 4-0432. | 1 | 3-$CF_3$-4-Cl | COO-t-Bu | Me | $CF_3$ | 2 |
| 4-0433. | 1 | 3-$CF_3$-4-Cl | COO-t-Bu | Me | $CF_2H$ | 2 |
| 4-0434. | 1 | 3-$CF_3$-4-$NO_2$ | COO-t-Bu | H | $CF_3$ | 0 |
| 4-0435. | 1 | 3-$CF_3$-4-$NO_2$ | COO-t-Bu | H | $CF_2H$ | 0 |
| 4-0436. | 1 | 3-$CF_3$-4-$NO_2$ | COO-t-Bu | H | $CF_3$ | 1 |
| 4-0437. | 1 | 3-$CF_3$-4-$NO_2$ | COO-t-Bu | H | $CF_2H$ | 1 |
| 4-0438. | 1 | 3-$CF_3$-4-$NO_2$ | COO-t-Bu | H | $CF_3$ | 2 |
| 4-0439. | 1 | 3-$CF_3$-4-$NO_2$ | COO-t-Bu | H | $CF_2H$ | 2 |
| 4-0440. | 1 | 3-$CF_3$-4-$NO_2$ | COO-t-Bu | Me | $CF_3$ | 0 |
| 4-0441. | 1 | 3-$CF_3$-4-$NO_2$ | COO-t-Bu | Me | $CF_2H$ | 0 |
| 4-0442. | 1 | 3-$CF_3$-4-$NO_2$ | COO-t-Bu | Me | $CF_3$ | 1 |
| 4-0443. | 1 | 3-$CF_3$-4-$NO_2$ | COO-t-Bu | Me | $CF_2H$ | 1 |
| 4-0444. | 1 | 3-$CF_3$-4-$NO_2$ | COO-t-Bu | Me | $CF_3$ | 2 |
| 4-0445. | 1 | 3-$CF_3$-4-$NO_2$ | COO-t-Bu | Me | $CF_2H$ | 2 |
| 4-0446. | 1 | 3-$CF_3$-5-Me | COO-t-Bu | H | $CF_3$ | 0 |
| 4-0447. | 1 | 3-$CF_3$-5-Me | COO-t-Bu | H | $CF_2H$ | 0 |
| 4-0448. | 1 | 3-$CF_3$-5-Me | COO-t-Bu | H | $CF_3$ | 1 |
| 4-0449. | 1 | 3-$CF_3$-5-Me | COO-t-Bu | H | $CF_2H$ | 1 |
| 4-0450. | 1 | 3-$CF_3$-5-Me | COO-t-Bu | H | $CF_3$ | 2 |
| 4-0451. | 1 | 3-$CF_3$-5-Me | COO-t-Bu | H | $CF_2H$ | 2 |
| 4-0452. | 1 | 3-$CF_3$-5-Me | COO-t-Bu | Me | $CF_3$ | 0 |
| 4-0453. | 1 | 3-$CF_3$-5-Me | COO-t-Bu | Me | $CF_2H$ | 0 |
| 4-0454. | 1 | 3-$CF_3$-5-Me | COO-t-Bu | Me | $CF_3$ | 1 |
| 4-0455. | 1 | 3-$CF_3$-5-Me | COO-t-Bu | Me | $CF_2H$ | 1 |
| 4-0456. | 1 | 3-$CF_3$-5-Me | COO-t-Bu | Me | $CF_3$ | 2 |
| 4-0457. | 1 | 3-$CF_3$-5-Me | COO-t-Bu | Me | $CF_2H$ | 2 |
| 4-0458. | 1 | 5-$CF_3$ | COOMe | H | $CF_3$ | 0 |
| 4-0459. | 1 | 5-$CF_3$ | COOMe | H | $CF_2H$ | 0 |
| 4-0460. | 1 | 5-$CF_3$ | COOMe | H | $CF_3$ | 1 |
| 4-0461. | 1 | 5-$CF_3$ | COOMe | H | $CF_2H$ | 1 |
| 4-0462. | 1 | 5-$CF_3$ | COOMe | H | $CF_3$ | 2 |
| 4-0463. | 1 | 5-$CF_3$ | COOMe | H | $CF_2H$ | 2 |
| 4-0464. | 1 | 3-t-Bu | COO-t-Bu | Me | $CF_3$ | 0 |
| 4-0465. | 1 | 3-t-Bu | COO-t-Bu | Me | $CF_2H$ | 0 |
| 4-0466. | 1 | 3-t-Bu | COO-t-Bu | Me | $CF_3$ | 1 |
| 4-0467. | 1 | 3-t-Bu | COO-t-Bu | Me | $CF_2H$ | 1 |
| 4-0466. | 1 | 3-t-Bu | COO-t-Bu | Me | $CF_3$ | 2 |
| 4-0469. | 1 | 3-t-Bu | COO-t-Bu | Me | $CF_2H$ | 2 |
| 4-0470. | 4 | 1-t-Bu-3-$CF_3$-5-Cl | H | H | $CF_3$ | 0 |
| 4-0471. | 4 | 1-t-Bu-3-$CF_3$-5-Cl | H | H | $CF_2H$ | 0 |
| 4-0472. | 4 | 1-t-Bu-3-$CF_3$-5-Cl | H | H | $CF_3$ | 1 |
| 4-0473. | 4 | 1-t-Bu-3-$CF_3$-5-Cl | H | H | $CF_2H$ | 1 |
| 4-0474. | 4 | 1-t-Bu-3-$CF_3$-5-Cl | H | H | $CF_3$ | 2 |
| 4-0475. | 4 | 1-t-Bu-3-$CF_3$-5-Cl | H | H | $CF_2H$ | 2 |
| 4-0476. | 4 | 1-t-Bu-3-$CF_3$-5-Cl | Me | H | $CF_3$ | 2 |
| 4-0477. | 4 | 1-t-Bu-3-$CF_3$-5-Cl | Me | H | $CF_2H$ | 2 |
| 4-0478. | 4 | 1-t-Bu-3-$CF_3$ | Me | H | $CF_3$ | 2 |
| 4-0479. | 4 | 1-t-Bu-3-$CF_3$ | Me | H | $CF_2H$ | 2 |
| 4-0480. | 1 | 3-$CF_3$ | COO-i-Pr | H | $CF_3$ | 0 |
| 4-0481. | 1 | 3-$CF_3$ | COO-i-Pr | H | $CF_2H$ | 0 |
| 4-0482. | 1 | 3-$CF_3$ | COO-i-Pr | H | $CF_3$ | 1 |
| 4-0483. | 1 | 3-$CF_3$ | COO-i-Pr | H | $CF_2H$ | 1 |
| 4-0484. | 1 | 3-$CF_3$ | COO-i-Pr | H | $CF_3$ | 2 |
| 4-0485. | 1 | 3-$CF_3$ | COO-i-Pr | H | $CF_2H$ | 2 |
| 4-0486. | 1 | 3-$CF_3$ | COOH | Me | $CF_3$ | 0 |
| 4-0487. | 1 | 3-$CF_3$ | COOH | Me | $CF_2H$ | 0 |

Analog to the compounds numbered 4-01 to 4-487 are the compounds numbered 4-1 to 4-487 wherein the variables have the same meaning except m being 1 instead of 0.

TABLE 5 describes examples with compounds number of the type 5-xxxx as represented in the following formula:

5-xxxx

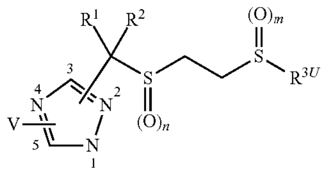

Compounds number 5-01 to 5-0973: m = 0

| No. | position | V | $R^1$ | $R^2$ | $R^{3U}$ | n |
|---|---|---|---|---|---|---|
| 5-01. | 1 | 3-$CF_3$ | H | H | $CF_3$ | 0 |
| 5-02. | 1 | 3-$CF_3$ | H | H | $CF_3$ | 1 |
| 5-03. | 1 | 3-$CF_3$ | H | H | $CF_3$ | 2 |
| 5-04. | 1 | 3-$CF_3$ | Me | H | $CF_3$ | 0 |
| 5-05. | 1 | 3-$CF_3$ | Me | H | $CF_3$ | 1 |
| 5-06. | 1 | 3-$CF_3$ | Me | H | $CF_3$ | 2 |
| 5-07. | 1 | 3-$CF_3$ | Me | Me | $CF_3$ | 2 |
| 5-08. | 1 | 3-$CF_3$ | Et | H | $CF_3$ | 0 |
| 5-09. | 1 | 3-$CF_3$ | Et | H | $CF_3$ | 1 |
| 5-010. | 1 | 3-$CF_3$ | Et | H | $CF_3$ | 2 |
| 5-011. | 1 | 3-$CF_3$ | i-Pr | H | $CF_3$ | 0 |
| 5-012. | 1 | 3-$CF_3$ | i-Pr | H | $CF_3$ | 1 |
| 5-013. | 1 | 3-$CF_3$ | i-Pr | H | $CF_3$ | 2 |
| 5-014. | 1 | 3-$CF_3$ | c-Pr | H | $CF_3$ | 0 |
| 5-015. | 1 | 3-$CF_3$ | c-Pr | H | $CF_3$ | 1 |
| 5-016. | 1 | 3-$CF_3$ | c-Pr | H | $CF_3$ | 0 |
| 5-017. | 1 | 3-$CF_3$ | Pr | H | $CF_3$ | 0 |
| 5-018. | 1 | 3-$CF_3$ | Pr | H | $CF_3$ | 1 |
| 5-019. | 1 | 3-$CF_3$ | Pr | H | $CF_3$ | 2 |
| 5-020. | 1 | 3-$CF_3$ | s-Bu | H | $CF_3$ | 0 |
| 5-021. | 1 | 3-$CF_3$ | s-Bu | H | $CF_3$ | 1 |
| 5-022. | 1 | 3-$CF_3$ | s-Bu | H | $CF_3$ | 2 |
| 5-023. | 1 | 3-$CF_3$ | i-Bu | H | $CF_3$ | 0 |
| 5-024. | 1 | 3-$CF_3$ | i-Bu | H | $CF_3$ | 1 |
| 5-025. | 1 | 3-$CF_3$ | i-Bu | H | $CF_3$ | 2 |
| 5-026. | 1 | 3-$CF_3$ | Bu | H | $CF_3$ | 0 |
| 5-027. | 1 | 3-$CF_3$ | Bu | H | $CF_3$ | 1 |
| 5-028. | 1 | 3-$CF_3$ | Bu | H | $CF_3$ | 2 |
| 5-029. | 1 | 3-$CF_3$ | 2-Pen | H | $CF_3$ | 0 |
| 5-030. | 1 | 3-$CF_3$ | 2-Pen | H | $CF_3$ | 1 |
| 5-031. | 1 | 3-$CF_3$ | 2-Pen | H | $CF_3$ | 2 |
| 5-032. | 1 | 3-$CF_3$ | 3-Pen | H | $CF_3$ | 0 |
| 5-033. | 1 | 3-$CF_3$ | 3-Pen | H | $CF_3$ | 1 |
| 5-034. | 1 | 3-$CF_3$ | 3-Pen | H | $CF_3$ | 2 |
| 5-035. | 1 | 3-$CF_3$ | c-Pen | H | $CF_3$ | 0 |
| 5-036. | 1 | 3-$CF_3$ | c-Pen | H | $CF_3$ | 1 |
| 5-037. | 1 | 3-$CF_3$ | c-Pen | H | $CF_3$ | 2 |
| 5-038. | 1 | 3-$CF_3$ | c-Hex | H | $CF_3$ | 0 |
| 5-039. | 1 | 3-$CF_3$ | c-Hex | H | $CF_3$ | 1 |
| 5-040. | 1 | 3-$CF_3$ | c-Hex | H | $CF_3$ | 2 |
| 5-041. | 1 | 3-$CF_3$ | CN | H | $CF_3$ | 0 |
| 5-042. | 1 | 3-$CF_3$ | CN | H | $CF_3$ | 1 |
| 5-043. | 1 | 3-$CF_3$ | CN | H | $CF_3$ | 2 |
| 5-044. | 1 | 3-$CF_3$ | COOMe | H | $CF_3$ | 0 |
| 5-045. | 1 | 3-$CF_3$ | COOMe | H | $CF_3$ | 1 |
| 5-046. | 1 | 3-$CF_3$ | COOMe | H | $CF_3$ | 2 |
| 5-047. | 1 | 3-$CF_3$ | COOEt | H | $CF_3$ | 0 |
| 5-048. | 1 | 3-$CF_3$ | COOEt | H | $CF_3$ | 1 |
| 5-049. | 1 | 3-$CF_3$ | COOEt | H | $CF_3$ | 2 |
| 5-050. | 1 | 3-$SCF_3$ | H | H | $CF_3$ | 0 |
| 5-051. | 1 | 3-$SCF_3$ | H | H | $CF_3$ | 1 |
| 5-052. | 1 | 3-$SCF_3$ | H | H | $CF_3$ | 2 |
| 5-053. | 1 | 3-$SCF_3$ | Me | H | $CF_3$ | 0 |
| 5-054. | 1 | 3-$SCF_3$ | Me | H | $CF_3$ | 1 |
| 5-055. | 1 | 3-$SCF_3$ | Me | H | $CF_3$ | 2 |
| 5-056. | 1 | 3-$CF_3$-5-Me | H | H | $CF_3$ | 0 |
| 5-057. | 1 | 3-$CF_3$-5-Me | H | H | $CF_3$ | 1 |
| 5-058. | 1 | 3-$CF_3$-5-Me | H | H | $CF_3$ | 2 |
| 5-059. | 1 | 3-$CF_3$-5-Me | Me | H | $CF_3$ | 0 |
| 5-060. | 1 | 3-$CF_3$-5-Me | Me | H | $CF_3$ | 1 |
| 5-061. | 1 | 3-$CF_3$-5-Me | Me | H | $CF_3$ | 2 |
| 5-062. | 1 | 3-$CF_3$-5-Me | CN | H | $CF_3$ | 0 |
| 5-063. | 1 | 3-$CF_3$-5-Me | CN | H | $CF_3$ | 1 |

TABLE 5-continued describes examples with compounds number of the type 5-xxxx as represented in the following formula:

5-xxxx

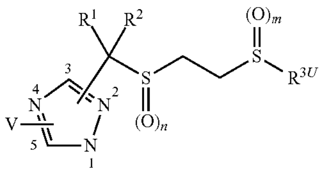

Compounds number 5-01 to 5-0973: m = 0

| No. | position | V | $R^1$ | $R^2$ | $R^{3U}$ | n |
|---|---|---|---|---|---|---|
| 5-064. | 1 | $3-CF_3-5-Me$ | CN | H | $CF_3$ | 2 |
| 5-065. | 1 | $3-CF_3-5-Me$ | COOMe | H | $CF_3$ | 0 |
| 5-066. | 1 | $3-CF_3-5-Me$ | COOMe | H | $CF_3$ | 1 |
| 5-067. | 1 | $3-CF_3-5-Me$ | COOMe | H | $CF_3$ | 2 |
| 5-068. | 1 | $3-CF_3-5-Me$ | COOEt | H | $CF_3$ | 0 |
| 5-069. | 1 | $3-CF_3-5-Me$ | COOEt | H | $CF_3$ | 1 |
| 5-070. | 1 | $3-CF_3-5-Me$ | COOEt | H | $CF_3$ | 2 |
| 5-071. | 3 | — | H | H | $CF_3$ | 0 |
| 5-072. | 3 | $1-CH_2CF_3$ | H | H | $CF_3$ | 0 |
| 5-073. | 3 | $1-CH_2CF_3$ | H | H | $CF_3$ | 1 |
| 5-074. | 3 | $1-CH_2CF_3$ | H | H | $CF_3$ | 2 |
| 5-075. | 3 | $1-CBrF_2$ | H | H | $CF_3$ | 0 |
| 5-076. | 3 | $1-CBrF_2$ | H | H | $CF_3$ | 1 |
| 5-077. | 3 | $1-CBrF_2$ | H | H | $CF_3$ | 2 |
| 5-078. | 3 | $1-CHF_2$ | H | H | $CF_3$ | 0 |
| 5-079. | 3 | $1-CHF_2$ | H | H | $CF_3$ | 1 |
| 5-080. | 3 | $1-CHF_2$ | H | H | $CF_3$ | 2 |
| 5-081. | 3 | $1-CH_2-c-Pr$ | H | H | $CF_3$ | 0 |
| 5-082. | 3 | $1-CH_2-c-Pr$ | H | H | $CF_3$ | 1 |
| 5-083. | 3 | $1-CH_2-c-Pr$ | H | H | $CF_3$ | 2 |
| 5-084. | 3 | $1-CF_2CHF_2$ | H | H | $CF_3$ | 0 |
| 5-085. | 3 | $1-CF_2CHF_2$ | H | H | $CF_3$ | 1 |
| 5-086. | 3 | $1-CF_2CHF_2$ | H | H | $CF_3$ | 2 |
| 5-087. | 3 | $1-CF{=}F_2$ | H | H | $CF_3$ | 0 |
| 5-088. | 3 | $1-CF{=}F_2$ | H | H | $CF_3$ | 1 |
| 5-089. | 3 | $1-CF{=}F_2$ | H | H | $CF_3$ | 2 |
| 5-090. | 5 | $1-CBrF_2$ | H | H | $CF_3$ | 0 |
| 5-091. | 5 | $1-CBrF_2$ | H | H | $CF_3$ | 1 |
| 5-092. | 5 | $1-CBrF_2$ | H | H | $CF_3$ | 2 |
| 5-093. | 1 | $3-CF_3$ | $CH_2OH$ | H | $CF_3$ | 0 |
| 5-094. | 1 | $3-CF_3$ | $CH_2OH$ | H | $CF_3$ | 1 |
| 5-095. | 1 | $3-CF_3$ | $CH_2OH$ | H | $CF_3$ | 2 |
| 5-096. | 1 | $3-CF_3$ | $CH_2OH$ | Me | $CF_3$ | 0 |
| 5-097. | 1 | $3-CF_3$ | $CH_2OH$ | Me | $CF_3$ | 1 |
| 5-098. | 1 | $3-CF_3$ | $CH_2OH$ | Me | $CF_3$ | 2 |
| 5-099. | 1 | $3-CF_3$ | $CH_2OMe$ | Me | $CF_3$ | 0 |
| 5-010. | 1 | $3-CF_3$ | $CH_2OMe$ | Me | $CF_3$ | 1 |
| 5-0101. | 1 | $3-CF_3$ | $CH_2OMe$ | Me | $CF_3$ | 2 |
| 5-0102. | 1 | $3-CF_3$ | $CH_2OAc$ | Me | $CF_3$ | 0 |
| 5-0103. | 1 | $3-CF_3$ | $CH_2OAc$ | Me | $CF_3$ | 1 |
| 5-0104. | 1 | $3-CF_3$ | $CH_2OAc$ | Me | $CF_3$ | 2 |
| 5-0105. | 1 | $3-CF_3$ | $CH_2OCO-t-Bu$ | Me | $CF_3$ | 0 |
| 5-0106. | 1 | $3-CF_3$ | $CH_2OCO-t-Bu$ | Me | $CF_3$ | 1 |
| 5-0107. | 1 | $3-CF_3$ | $CH_2OCO-t-Bu$ | Me | $CF_3$ | 2 |
| 5-0108. | 1 | $3-CF_3$ | $CH_2OCONMe_2$ | Me | $CF_3$ | 0 |
| 5-0109. | 1 | $3-CF_3$ | $CH_2OCONMe_2$ | Me | $CF_3$ | 1 |
| 5-0110. | 1 | $3-CF_3$ | $CH_2OCONMe_2$ | Me | $CF_3$ | 2 |
| 5-0111. | 1 | $3-CF_3$ | CH(Me)OH | Me | $CF_3$ | 0 |
| 5-0112. | 1 | $3-CF_3$ | CH(Me)OH | Me | $CF_3$ | 2 |
| 5-0113. | 1 | $3-CF_3$ | CH(Me)OMe | Me | $CF_3$ | 0 |
| 5-0114. | 1 | $3-CF_3$ | CH(Me)OMe | Me | $CF_3$ | 2 |
| 5-0115. | 1 | $3-CF_3$ | CH(OH)-t-Bu | Me | $CF_3$ | 0 |
| 5-0116. | 1 | $3-CF_3$ | COOH | Me | $CF_3$ | 0 |
| 5-0117. | 1 | $3-CF_3$ | COOMe | Me | $CF_3$ | 0 |
| 5-0118. | 1 | $3-CF_3$ | COOMe | Me | $CF_3$ | 1 |
| 5-0119. | 1 | $3-CF_3$ | COOMe | Me | $CF_3$ | 2 |
| 5-0120. | 1 | $3-CF_3$ | COOEt | Me | $CF_3$ | 0 |
| 5-0121. | 1 | $3-CF_3$ | COOEt | Me | $CF_3$ | 1 |
| 5-0122. | 1 | $3-CF_3$ | COOEt | Me | $CF_3$ | 2 |
| 5-0123. | 1 | $3-CF_3$ | COO-i-Pr | H | $CF_3$ | 0 |
| 5-0124. | 1 | $3-CF_3$ | COO-i-Pr | H | $CF_3$ | 1 |
| 5-0125. | 1 | $3-CF_3$ | COO-i-Pr | H | $CF_3$ | 2 |
| 5-0126. | 1 | $3-CF_3$ | COO-i-Pr | Me | $CF_3$ | 0 |

TABLE 5-continued describes examples with compounds number of the type 5-xxxx as represented in the following formula:

5-xxxx

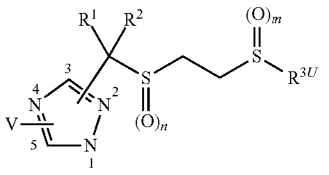

Compounds number 5-01 to 5-0973: m = 0

| No. | position | V | $R^1$ | $R^2$ | $R^{3U}$ | n |
|---|---|---|---|---|---|---|
| 5-0127. | 1 | 3-$CF_3$ | COO-i-Pr | Me | $CF_3$ | 1 |
| 5-0128. | 1 | 3-$CF_3$ | COO-i-Pr | Me | $CF_3$ | 2 |
| 5-0129. | 1 | 3-$CF_3$ | COO-t-Bu | H | $CF_3$ | 0 |
| 5-0130. | 1 | 3-$CF_3$ | COO-t-Bu | H | $CF_3$ | 1 |
| 5-0131. | 1 | 3-$CF_3$ | COO-t-Bu | H | $CF_3$ | 2 |
| 5-0132. | 1 | 3-$CF_3$ | COO-t-Bu | Me | $CF_3$ | 0 |
| 5-0133. | 1 | 3-$CF_3$ | COO-t-Bu | Me | $CF_3$ | 1 |
| 5-0134. | 1 | 3-$CF_3$ | COO-t-Bu | Me | $CF_3$ | 2 |
| 5-0135. | 1 | 3-$CF_3$ | COO-i-Bu | Me | $CF_3$ | 0 |
| 5-0136. | 1 | 3-$CF_3$ | COO-i-Bu | Me | $CF_3$ | 1 |
| 5-0137. | 1 | 3-$CF_3$ | COO-i-Bu | Me | $CF_3$ | 2 |
| 5-0138. | 1 | 3-$CF_3$ | COO-s-Bu | Me | $CF_3$ | 0 |
| 5-0139. | 1 | 3-$CF_3$ | COO-s-Bu | Me | $CF_3$ | 1 |
| 5-0140. | 1 | 3-$CF_3$ | COO-s-Bu | Me | $CF_3$ | 2 |
| 5-0141. | 1 | 3-$CF_3$ | COO-c-Pen | Me | $CF_3$ | 0 |
| 5-0142. | 1 | 3-$CF_3$ | COO-c-Pen | Me | $CF_3$ | 1 |
| 5-0143. | 1 | 3-$CF_3$ | COO-c-Pen | Me | $CF_3$ | 2 |
| 5-0144. | 1 | 3-$CF_3$ | $COOCH_2$-t-Bu | Me | $CF_3$ | 0 |
| 5-0145. | 1 | 3-$CF_3$ | $COOCH_2$-t-Bu | Me | $CF_3$ | 1 |
| 5-0146. | 1 | 3-$CF_3$ | $COOCH_2$-t-Bu | Me | $CF_3$ | 2 |
| 5-0147. | 1 | 3-$CF_3$ | $COOCH_2$-c-Pr | Me | $CF_3$ | 0 |
| 5-0148. | 1 | 3-$CF_3$ | $COOCH_2$-c-Pr | Me | $CF_3$ | 1 |
| 5-0149. | 1 | 3-$CF_3$ | $COOCH_2$-c-Pr | Me | $CF_3$ | 2 |
| 5-0150. | 1 | 3-$CF_3$ | $COOCH_2CF_3$ | Me | $CF_3$ | 0 |
| 5-0151. | 1 | 3-$CF_3$ | $COOCH_2CF_3$ | Me | $CF_3$ | 1 |
| 5-0152. | 1 | 3-$CF_3$ | $COOCH_2CF_3$ | Me | $CF_3$ | 2 |
| 5-0153. | 1 | 3-$CF_3$ | $CO_2CH_2C{\equiv}CH$ | Me | $CF_3$ | 0 |
| 5-0154. | 1 | 3-$CF_3$ | $CO_2CH_2C{\equiv}CH$ | Me | $CF_3$ | 1 |
| 5-0155. | 1 | 3-$CF_3$ | $CO_2CH_2C{\equiv}CH$ | Me | $CF_3$ | 2 |
| 5-0156. | 1 | 3-$CF_3$ | $CO_2CH_2CH{=}CH_2$ | Me | $CF_3$ | 0 |
| 5-0157. | 1 | 3-$CF_3$ | $CO_2CH_2CH{=}CH_2$ | Me | $CF_3$ | 1 |
| 5-0158. | 1 | 3-$CF_3$ | $CO_2CH_2CH{=}CH_2$ | Me | $CF_3$ | 2 |
| 5-0159. | 1 | 3-$CF_3$ | $CO_2CH_2CH_2OMe$ | Me | $CF_3$ | 0 |
| 5-0160. | 1 | 3-$CF_3$ | $CO_2CH_2CH_2OMe$ | Me | $CF_3$ | 1 |
| 5-0161. | 1 | 3-$CF_3$ | $CO_2CH_2CH_2OMe$ | Me | $CF_3$ | 2 |
| 5-0162. | 1 | 3-$CF_3$ | $CO_2CH_2CH_2SMe$ | Me | $CF_3$ | 0 |
| 5-0163. | 1 | 3-$CF_3$ | $CO_2CH_2CH_2SO_2Me$ | Me | $CF_3$ | 0 |
| 5-0164. | 1 | 3-$CF_3$ | $CO_2CH_2CH_2SO_2Me$ | Me | $CF_3$ | 1 |
| 5-0165. | 1 | 3-$CF_3$ | $CO_2CH_2CH_2SO_2Me$ | Me | $CF_3$ | 2 |
| 5-0166. | 1 | 3-$CF_3$ | $CO_2CH_2CONH_2$ | Me | $CF_3$ | 0 |
| 5-0167. | 1 | 3-$CF_3$ | $CO_2CH_2CONH_2$ | Me | $CF_3$ | 1 |
| 5-0168. | 1 | 3-$CF_3$ | $CO_2CH_2CONH_2$ | Me | $CF_3$ | 2 |
| 5-0169. | 1 | 3-$CF_3$ | $CO_2CH(Me)C{\equiv}CH$ | Me | $CF_3$ | 0 |
| 5-0170. | 1 | 3-$CF_3$ | $CO_2CH(Me)C{\equiv}CH$ | Me | $CF_3$ | 1 |
| 5-0171. | 1 | 3-$CF_3$ | $CO_2CH(Me)C{\equiv}CH$ | Me | $CF_3$ | 2 |
| 5-0172. | 1 | 3-$CF_3$ | $CO_2CH(Me)CN$ | Me | $CF_3$ | 0 |
| 5-0173. | 1 | 3-$CF_3$ | $CO_2CH(Me)CN$ | Me | $CF_3$ | 1 |
| 5-0174. | 1 | 3-$CF_3$ | $CO_2CH(Me)CN$ | Me | $CF_3$ | 2 |
| 5-0175. | 1 | 3-$CF_3$ | $CO_2CH(Me)CONH_2$ | Me | $CF_3$ | 0 |
| 5-0176. | 1 | 3-$CF_3$ | $CO_2CH(Me)CONH_2$ | Me | $CF_3$ | 1 |
| 5-0177. | 1 | 3-$CF_3$ | $CO_2CH(Me)CONH_2$ | Me | $CF_3$ | 2 |
| 5-0178. | 1 | 3-$CF_3$ | $CO_2C(Me)_2COOEt$ | H | $CF_3$ | 0 |
| 5-0179. | 1 | 3-$CF_3$ | $CO_2C(Me)_2COOEt$ | H | $CF_3$ | 1 |
| 5-0180. | 1 | 3-$CF_3$ | $CO_2C(Me)_2COOEt$ | H | $CF_3$ | 2 |
| 5-0181. | 1 | 3-$CF_3$ | $CO_2C(Me)_2COOEt$ | Me | $CF_3$ | 0 |
| 5-0182. | 1 | 3-$CF_3$ | $CO_2C(Me)_2COOEt$ | Me | $CF_3$ | 1 |
| 5-0183. | 1 | 3-$CF_3$ | $CO_2C(Me)_2COOEt$ | Me | $CF_3$ | 2 |
| 5-0184. | 1 | 3-$CF_3$ | $COOCH_2$-$E^1$ | Me | $CF_3$ | 0 |
| 5-0185. | 1 | 3-$CF_3$ | $COOCH_2$-$E^1$ | Me | $CF_3$ | 1 |
| 5-0186. | 1 | 3-$CF_3$ | $COOCH_2$-$E^1$ | Me | $CF_3$ | 2 |
| 5-0187. | 1 | 3-$CF_3$ | COO-$E^2$ | Me | $CF_3$ | 0 |
| 5-0188. | 1 | 3-$CF_3$ | COO-$E^2$ | Me | $CF_3$ | 1 |
| 5-0189. | 1 | 3-$CF_3$ | COO-$E^2$ | Me | $CF_3$ | 2 |

TABLE 5-continued describes examples with compounds number of the type 5-xxxx as represented in the following formula:

5-xxxx

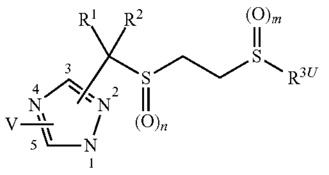

Compounds number 5-01 to 5-0973: m = 0

| No. | position | V | $R^1$ | $R^2$ | $R^{3U}$ | n |
|---|---|---|---|---|---|---|
| 5-0190. | 1 | 3-$CF_3$ | COO-$E^3$ | Me | $CF_3$ | 0 |
| 5-0191. | 1 | 3-$CF_3$ | COO-$E^3$ | Me | $CF_3$ | 1 |
| 5-0192. | 1 | 3-$CF_3$ | COO-$E^3$ | Me | $CF_3$ | 2 |
| 5-0193. | 1 | 3-$CF_3$ | COO-$E^4$ | Me | $CF_3$ | 0 |
| 5-0194. | 1 | 3-$CF_3$ | COO-$E^4$ | Me | $CF_3$ | 1 |
| 5-0195. | 1 | 3-$CF_3$ | COO-$E^4$ | Me | $CF_3$ | 2 |
| 5-0196. | 1 | 3-$CF_3$ | $COOCH_2Ph$ | Me | $CF_3$ | 0 |
| 5-0197. | 1 | 3-$CF_3$ | $COOCH_2Ph$ | Me | $CF_3$ | 1 |
| 5-0198. | 1 | 3-$CF_3$ | $COOCH_2Ph$ | Me | $CF_3$ | 2 |
| 5-0199. | 1 | 3-$CF_3$ | $CO_2CH(Me)$-$E^6$ | Me | $CF_3$ | 0 |
| 5-0200. | 1 | 3-$CF_3$ | $CO_2CH(Me)$-$E^6$ | Me | $CF_3$ | 1 |
| 5-0201. | 1 | 3-$CF_3$ | $CO_2CH(Me)$-$E^6$ | Me | $CF_3$ | 2 |
| 5-0202. | 1 | 3-$CF_3$ | COO-$E^7$ | Me | $CF_3$ | 0 |
| 5-0203. | 1 | 3-$CF_2$ | COO-$E^7$ | Me | $CF_3$ | 1 |
| 5-0204. | 1 | 3-$CF_3$ | COO-$E^7$ | Me | $CF_3$ | 2 |
| 5-0205. | 1 | 3-$CF_3$ | COS-i-Pr | Me | $CF_3$ | 0 |
| 5-0206. | 1 | 3-$CF_3$ | COS-i-Pr | Me | $CF_3$ | 1 |
| 5-0207. | 1 | 3-$CF_3$ | COS-i-Pr | Me | $CF_3$ | 2 |
| 5-0208. | 1 | 3-$CF_3$ | COS-t-Bu | Me | $CF_3$ | 0 |
| 5-0209. | 1 | 3-$CF_3$ | COS-t-Bu | Me | $CF_3$ | 1 |
| 5-0210. | 1 | 3-$CF_3$ | COS-t-Bu | Me | $CF_3$ | 2 |
| 5-0211. | 1 | 3-$CF_3$ | COS-c-Hex | Me | $CF_3$ | 0 |
| 5-0212. | 1 | 3-$CF_3$ | COS-c-Hex | Me | $CF_3$ | 1 |
| 5-0213. | 1 | 3-$CF_3$ | COS-c-Hex | Me | $CF_3$ | 2 |
| 5-0214. | 1 | 3-$CF_3$ | CONHMe | Me | $CF_3$ | 2 |
| 5-0215. | 1 | 3-$CF_3$ | CONH-i-Pr | Me | $CF_3$ | 2 |
| 5-0216. | 1 | 3-$CF_3$ | $CONHCONH_2$ | Me | $CF_3$ | 0 |
| 5-0217. | 1 | 3-$CF_3$ | $CONHCONH_2$ | Me | $CF_3$ | 1 |
| 5-0218. | 1 | 3-$CF_3$ | $CONHCONH_2$ | Me | $CF_3$ | 2 |
| 5-0219. | 1 | 3-$CF_3$ | CONHCONHMe | Me | $CF_3$ | 0 |
| 5-0220. | 1 | 3-$CF_3$ | $CON(Me)CONH_2$ | Me | $CF_3$ | 0 |
| 5-0221. | 1 | 3-$CF_3$ | $CON(Me)CONH_2$ | Me | $CF_3$ | 2 |
| 5-0222. | 1 | 3-$CF_3$ | CON(Me)CONHMe | Me | $CF_3$ | 0 |
| 5-0223. | 1 | 3-$CF_3$ | CON(Me)CONHMe | Me | $CF_3$ | 2 |
| 5-0224. | 1 | 3-$CF_3$ | CN | H | $CF_3$ | 0 |
| 5-0225. | 1 | 3-$CF_3$ | CN | Me | $CF_3$ | 0 |
| 5-0226. | 1 | 3-$CF_3$ | CN | Me | $CF_3$ | 1 |
| 5-0227. | 1 | 3-$CF_3$ | CN | Me | $CF_3$ | 2 |
| 5-0228. | 1 | 3-$CF_3$ | CHO | Me | $CF_3$ | 0 |
| 5-0229. | 1 | 3-$CF_3$ | Ac | H | $CF_3$ | 0 |
| 5-0230. | 1 | 3-$CF_3$ | Ac | Me | $CF_3$ | 0 |
| 5-0231. | 1 | 3-$CF_3$ | Ac | Me | $CF_3$ | 1 |
| 5-0232. | 1 | 3-$CF_3$ | Ac | Me | $CF_3$ | 2 |
| 5-0233. | 1 | 3-$CF_3$ | CO-i-Pr | Me | $CF_3$ | 0 |
| 5-0234. | 1 | 3-$CF_3$ | CO-t-Bu | Me | $CF_3$ | 0 |
| 5-0235. | 1 | 3-$CF_3$ | CO-t-Bu | Me | $CF_3$ | 1 |
| 5-0236. | 1 | 3-$CF_3$ | CO-t-Bu | Me | $CF_3$ | 2 |
| 5-0237. | 1 | 3-$CF_3$ | CH═N—OH | Me | $CF_3$ | 0 |
| 5-0238. | 1 | 3-$CF_3$ | CH═N—OH | Me | $CF_3$ | 1 |
| 5-0239. | 1 | 3-$CF_3$ | CH═N—OH | Me | $CF_3$ | 2 |
| 5-0240. | 1 | 3-$CF_3$ | CH═N—OMe | Me | $CF_3$ | 0 |
| 5-0241. | 1 | 3-$CF_3$ | CH═N—OMe | Me | $CF_3$ | 1 |
| 5-0242. | 1 | 3-$CF_3$ | CH═N—OMe | Me | $CF_3$ | 2 |
| 5-0243. | 1 | 3-$CF_3$ | C(Me)═N—OH | Me | $CF_3$ | 0 |
| 5-0244. | 1 | 3-$CF_3$ | C(Me)═N—OH | Me | $CF_3$ | 1 |
| 5-0245. | 1 | 3-$CF_3$ | C(Me)═N—OH | Me | $CF_3$ | 2 |
| 5-0246. | 1 | 3-$CF_3$ | C(Me)═N—OMe | H | $CF_3$ | 0 |
| 5-0247. | 1 | 3-$CF_3$ | C(Me)═N—OMe | H | $CF_3$ | 1 |
| 5-0248. | 1 | 3-$CF_3$ | C(Me)═N—OMe | H | $CF_3$ | 2 |
| 5-0249. | 1 | 3-$CF_3$ | C(Me)═N-i-Pr | Me | $CF_3$ | 0 |
| 5-0250. | 1 | 3-$CF_3$-5-Me | COO-t-Bu | H | $CF_3$ | 0 |
| 5-0251. | 1 | 3-$CF_3$-5-Me | COO-t-Bu | H | $CF_3$ | 1 |
| 5-0252. | 1 | 3-$CF_3$-5-Me | COO-t-Bu | H | $CF_3$ | 2 |

TABLE 5-continued describes examples with compounds number of the type 5-xxxx as represented in the following formula:

5-xxxx

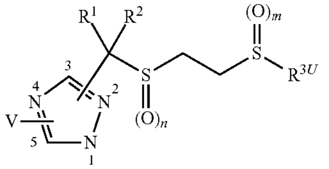

Compounds number 5-01 to 5-0973: m = 0

| No. | position | V | $R^1$ | $R^2$ | $R^{3U}$ | n |
|---|---|---|---|---|---|---|
| 5-0253. | 1 | 3-$CF_3$-5-Me | COO-t-Bu | Me | $CF_3$ | 0 |
| 5-0254. | 1 | 3-$CF_3$-5-Me | COO-t-Bu | Me | $CF_3$ | 1 |
| 5-0255. | 1 | 3-$CF_3$-5-Me | COO-t-Bu | Me | $CF_3$ | 2 |
| 5-0256. | 1 | 3-$CF_3$-5-$CF_3$ | COO-t-Bu | H | $CF_3$ | 0 |
| 5-0257. | 1 | 3-$CF_3$-5-$CF_3$ | COO-t-Bu | H | $CF_3$ | 1 |
| 5-0258. | 1 | 3-$CF_3$-5-$CF_3$ | COO-t-Bu | H | $CF_3$ | 2 |
| 5-0259. | 1 | 3-$CF_3$-5-$CF_3$ | COO-t-Bu | Me | $CF_3$ | 0 |
| 5-0260. | 1 | 3-$CF_3$-5-$CF_3$ | COO-t-Bu | Me | $CF_3$ | 1 |
| 5-0261. | 1 | 3-$CF_3$-5-$CF_3$ | COO-t-Bu | Me | $CF_3$ | 2 |
| 5-0262. | 1 | 3-$CF_3$-5-$NH_2$ | COO-t-Bu | H | $CF_3$ | 0 |
| 5-0253. | 1 | 3-$CF_3$-5-$NH_2$ | COO-t-Bu | H | $CF_3$ | 2 |
| 5-0264. | 1 | 3-$CF_3$-5-$NH_2$ | COO-t-Bu | Me | $CF_3$ | 0 |
| 5-0265. | 1 | 3-$CF_3$-5-$NH_2$ | COO-t-Bu | Me | $CF_3$ | 2 |
| 5-0266. | 1 | 3-$CF_3$-5-$NMe_2$ | COO-t-Bu | Me | $CF_3$ | 0 |
| 5-0267. | 1 | 3-$CF_3$-5-$NMe_2$ | COO-t-Bu | Me | $CF_3$ | 2 |
| 5-0268. | 1 | 3-$CF_3$-5-NHAc | COO-t-Bu | Me | $CF_3$ | 0 |
| 5-0269. | 1 | 3-$CF_3$-5-NHAc | COO-t-Bu | Me | $CF_3$ | 2 |
| 5-0270. | 1 | 3-$CF_3$-5-SMe | COOEt | H | $CF_3$ | 0 |
| 5-0271. | 1 | 3-$CF_3$-5-SMe | COOEt | H | $CF_3$ | 1 |
| 5-0272. | 1 | 3-$CF_3$-5-SMe | COOEt | Me | $CF_3$ | 0 |
| 5-0273. | 1 | 3-$CF_3$-5-SMe | COOEt | Me | $CF_3$ | 1 |
| 5-0274. | 1 | 3-$CF_3$-5-$SO_2$Me | COOEt | Me | $CF_3$ | 2 |
| 5-0275. | 1 | 3-$CF_3$-5-SMe | COO-i-Pr | Me | $CF_3$ | 0 |
| 5-0276. | 1 | 3-$CF_3$-5-$SO_2$Me | COO-i-Pr | Me | $CF_3$ | 2 |
| 5-0277. | 1 | 3-$CF_3$-5-SMe | COO-t-Bu | H | $CF_3$ | 0 |
| 5-0278. | 1 | 3-$CF_3$-5-$SO_2$Me | COO-t-Bu | H | $CF_3$ | 2 |
| 5-0279. | 1 | 3-$CF_3$-5-SMe | COO-i-Bu | Me | $CF_3$ | 0 |
| 5-0280. | 1 | 3-$CF_3$-5-$SO_2$Me | COO-i-Bu | Me | $CF_3$ | 2 |
| 5-0281. | 1 | 3-$CF_3$-5-SMe | COO-s-Bu | Me | $CF_3$ | 0 |
| 5-0282. | 1 | 3-$CF_3$-5-$SO_2$Me | COO-s-Bu | Me | $CF_3$ | 2 |
| 5-0283. | 1 | 3-$CF_3$-5-SMe | $CO_2CH_2CH_2OMe$ | H | $CF_3$ | 0 |
| 5-0284. | 1 | 3-$CF_3$-5-SMe | $CO_2CH_2CH_2OMe$ | Me | $CF_3$ | 0 |
| 5-0285. | 1 | 3-$CF_3$-5-$SO_2$Me | $CO_2CH_2CH_2OMe$ | Me | $CF_3$ | 2 |
| 5-0286. | 1 | 3-$CF_3$-5-SMe | $CO_2CH_2CONH_2$ | H | $CF_3$ | 0 |
| 5-0287. | 1 | 3-$CF_3$-5-SMe | $CO_2CH_2CONH_2$ | Me | $CF_3$ | 0 |
| 5-0288. | 1 | 3-$CF_3$-5-$SO_2$Me | $CO_2CH_2CONH_2$ | Me | $CF_3$ | 2 |
| 5-0289. | 1 | 3-$CF_3$-5-$SO_2$Me | Me | H | $CF_3$ | 2 |
| 5-0290. | 1 | 3-$CF_3$-5-SMe | Ac | H | $CF_3$ | 0 |
| 5-0291. | 1 | 3-$CF_3$-5-SMe | Ac | Me | $CF_3$ | 0 |
| 5-0292. | 1 | 3-$CF_3$-5-$SO_2$Me | Ac | Me | $CF_3$ | 2 |
| 5-0293. | 1 | 3-$CF_3$-5-SEt | COO-t-Bu | H | $CF_3$ | 0 |
| 5-0294. | 1 | 3-$CF_3$-5-SEt | COO-t-Bu | Me | $CF_3$ | 0 |
| 5-0295. | 1 | 3-$CF_3$-5-$SO_2$Et | COO-t-Bu | Me | $CF_3$ | 2 |
| 5-0296. | 1 | 3-$CF_3$-5-S—Pr | COOEt | H | $CF_3$ | 0 |
| 5-0297. | 1 | 3-$CF_3$-5-S—Pr | COOEt | Me | $CF_3$ | 0 |
| 5-0298. | 1 | 3-$CF_3$-5-SO—Pr | COOEt | Me | $CF_3$ | 2 |
| 5-0299. | 1 | 3-$CF_3$-5-$SO_2$—Pr | Me | H | $CF_3$ | 2 |
| 5-0300. | 1 | 3-$CF_3$-5-S-i-Pr | COOEt | H | $CF_3$ | 0 |
| 5-0301. | 1 | 3-$CF_3$-5-S-i-Pr | COOEt | Me | $CF_3$ | 0 |
| 5-0302. | 1 | 3-$CF_3$-5-$SO_2$-i-Pr | COOEt | Me | $CF_3$ | 2 |
| 5-0303. | 1 | 3-$CF_3$-5-$SO_2$-i-Pr | Me | H | $CF_3$ | 2 |
| 5-0304. | 1 | 3-$CF_3$-5-S—Bu | COOMe | H | $CF_3$ | 0 |
| 5-0305. | 1 | 3-$CF_3$-5-S—Bu | COOMe | Me | $CF_3$ | 0 |
| 5-0306. | 1 | 3-$CF_3$-5-$SO_2$—Bu | COOMe | Me | $CF_3$ | 2 |
| 5-0307. | 1 | 3-$CF_3$-5-S-i-Bu | COOMe | H | $CF_3$ | 0 |
| 5-0308. | 1 | 3-$CF_3$-5-S-i-Bu | COOMe | Me | $CF_3$ | 0 |
| 5-0309. | 1 | 3-$CF_3$-5-$SO_2$-i-Bu | COOMe | Me | $CF_3$ | 2 |
| 5-0310. | 1 | 3-$CF_3$-5-S-s-Bu | COOMe | H | $CF_3$ | 0 |
| 5-0311. | 1 | 3-$CF_3$-5-S-s-Bu | COOMe | Me | $CF_3$ | 0 |
| 5-0312. | 1 | 3-$CF_3$-5-$SO_2$-s-Bu | COOMe | Me | $CF_3$ | 2 |
| 5-0313. | 1 | 3-$CF_3$-5-S-c-Pen | COOMe | H | $CF_3$ | 0 |

TABLE 5-continued describes examples with compounds number of the type 5-xxxx as represented in the following formula:

5-xxxx

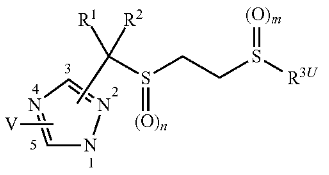

Compounds number 5-01 to 5-0973: m = 0

| No. | position | V | $R^1$ | $R^2$ | $R^{3U}$ | n |
|---|---|---|---|---|---|---|
| 5-0314. | 1 | 3-$CF_3$-5-S-c-Pen | COOMe | Me | $CF_3$ | 0 |
| 5-0315. | 1 | 3-$CF_3$-5-$SO_2$-c-Pen | COOMe | Me | $CF_3$ | 2 |
| 5-0316. | 1 | 3-$CF_3$-5-$SCH_2$-c-Pr | COOMe | H | $CF_3$ | 0 |
| 5-0317. | 1 | 3-$CF_3$-5-$SCH_2$-c-Pr | COOMe | Me | $CF_3$ | 0 |
| 5-0318. | 1 | 3-$CF_3$-5-$SO_2CH_2$-c-Pr | COOMe | Me | $CF_3$ | 2 |
| 5-0319. | 1 | 3-$CF_3$-5-$SCH_2CF_3$ | COOEt | H | $CF_3$ | 0 |
| 5-0320. | 1 | 3-$CF_3$-5-$SCH_2CF_3$ | COOEt | Me | $CF_3$ | 0 |
| 5-0321. | 1 | 3-$CF_3$-5-$SCH_2CF_3$ | COOEt | Me | $CF_3$ | 1 |
| 5-0322. | 1 | 3-$CF_3$-5-$SOCH_2CF_3$ | COOEt | Me | $CF_3$ | 2 |
| 5-0323. | 1 | 3-$CF_3$-5-$S(CH_2)_2CF_3$ | COOMe | Me | $CF_3$ | 0 |
| 5-0324. | 1 | 3-$CF_3$-5-$SO_2(CH_2)_2CF_3$ | COOMe | Me | $CF_3$ | 2 |
| 5-0325. | 1 | 3-$CF_3$-5-$S(CH_2)_2OMe$ | COOEt | H | $CF_3$ | 0 |
| 5-0326. | 1 | 3-$CF_3$-5-$SO_2(CH_2)_2OMe$ | COOEt | H | $CF_3$ | 2 |
| 5-0327. | 1 | 3-$CF_3$-5-$S(CH_2)_2OMe$ | COOEt | Me | $CF_3$ | 0 |
| 5-0328. | 1 | 3-$CF_3$-5-$SO_2(CH_2)_2OMe$ | COOEt | Me | $CF_3$ | 2 |
| 5-0329. | 1 | 3-$CF_3$-5-$S(CH_2)_2OEt$ | COOMe | H | $CF_3$ | 0 |
| 5-0330. | 1 | 3-$CF_3$-5-$S(CH_2)_2OEt$ | COOMe | Me | $CF_3$ | 0 |
| 5-0331. | 1 | 3-$CF_3$-5-$SO_2(CH_2)_2OEt$ | COOMe | Me | $CF_3$ | 2 |
| 5-0332. | 1 | 3-$CF_3$-5-$S(CH_2)_2O(CH_2)_2OMe$ | COOEt | H | $CF_3$ | 0 |
| 5-0333. | 1 | 3-$CF_3$-5-$S(CH_2)_2O(CH_2)_2OMe$ | COOEt | Me | $CF_3$ | 0 |
| 5-0334. | 1 | 3-$CF_3$-5-$SO_2(CH_2)_2O(CH_2)_2OMe$ | COOEt | Me | $CF_3$ | 2 |
| 5-0335. | 1 | 3-$CF_3$-5-$SCH_2$-$E^1$ | COOEt | H | $CF_3$ | 0 |
| 5-0336. | 1 | 3-$CF_3$-5-$SCH_2$-$E^1$ | COOEt | Me | $CF_3$ | 0 |
| 5-0337. | 1 | 3-$CF_2$-5-$SO_2CH_2$-$E^1$ | COOEt | Me | $CF_3$ | 2 |
| 5-0338. | 1 | 3-$CF_3$-5-$SCH_2Ph$ | COOEt | H | $CF_3$ | 0 |
| 5-0339. | 1 | 3-$CF_3$-5-$SO_2CH_2Ph$ | COOEt | H | $CF_3$ | 2 |
| 5-0340. | 1 | 3-$CF_2$-5-$SCH_2Ph$ | COOEt | Me | $CF_3$ | 0 |
| 5-0341. | 1 | 3-$CF_2$-5-$SO_2CH_2Ph$ | COOEt | Me | $CF_3$ | 2 |
| 5-0342. | 1 | 3-$CF_3$-5-F | COOMe | H | $CF_3$ | 0 |
| 5-0343. | 1 | 3-$CF_3$-5-F | COOMe | H | $CF_3$ | 2 |
| 5-0344. | 1 | 3-$CF_3$-5-F | COOMe | Me | $CF_3$ | 0 |
| 5-0345. | 1 | 3-$CF_3$-5-F | COOMe | Me | $CF_3$ | 2 |
| 5-0346. | 1 | 3-$CF_3$-5-Cl | COOMe | H | $CF_3$ | 0 |
| 5-0347. | 1 | 3-$CF_3$-5-Cl | COOMe | H | $CF_3$ | 2 |
| 5-0348. | 1 | 3-$CF_3$-5-Cl | COOMe | Me | $CF_3$ | 0 |
| 5-0349. | 1 | 3-$CF_3$-5-Cl | COOMe | Me | $CF_3$ | 2 |
| 5-0350. | 1 | 3-$CF_3$-5-Br | COOMe | H | $CF_3$ | 0 |
| 5-0351. | 1 | 3-$CF_3$-5-Br | COOMe | H | $CF_3$ | 2 |
| 5-0352. | 1 | 3-$CF_3$-5-Br | COOMe | Me | $CF_3$ | 0 |
| 5-0353. | 1 | 3-$CF_3$-5-Br | COOMe | Me | $CF_3$ | 2 |
| 5-0354. | 1 | 3-$CF_3$-5-COOEt | COO-t-Bu | H | $CF_3$ | 0 |
| 5-0355. | 1 | 3-$CF_3$-5-COOEt | COO-t-Bu | Me | $CF_3$ | 0 |
| 5-0356. | 1 | 3-$CF_3$-5-COOEt | COO-t-Bu | Me | $CF_3$ | 2 |
| 5-0357. | 1 | 3-$CF_3$-5-CN | COO-t-Bu | H | $CF_3$ | 0 |
| 5-0358. | 1 | 3-$CF_3$-5-CN | COO-t-Bu | Me | $CF_3$ | 0 |
| 5-0359. | 1 | 3-$CF_3$-5-CN | COO-t-Bu | Me | $CF_3$ | 2 |
| 5-0360. | 1 | 3-t-Bu | Me | H | $CF_3$ | 0 |
| 5-0361. | 1 | 3-t-Bu | Me | H | $CF_3$ | 1 |
| 5-0362. | 1 | 3-t-Bu | Me | H | $CF_3$ | 2 |
| 5-0363. | 1 | 3-t-Bu | COOH | Me | $CF_3$ | 0 |
| 5-0364. | 1 | 3-t-Bu | COOMe | H | $CF_3$ | 0 |
| 5-0365. | 1 | 3-t-Bu | COOMe | Me | $CF_3$ | 0 |
| 5-0366. | 1 | 3-t-Bu | COOMe | Me | $CF_3$ | 2 |
| 5-0367. | 1 | 3-t-Bu | COOEt | Me | $CF_3$ | 0 |
| 5-0368. | 1 | 3-t-Bu | COOEt | Me | $CF_3$ | 2 |
| 5-0369. | 1 | 3-t-Bu | COO-i-Pr | Me | $CF_3$ | 0 |
| 5-0370. | 1 | 3-t-Bu | COO-i-Pr | Me | $CF_3$ | 2 |
| 5-0371. | 1 | 3-t-Bu | $COOCH_2CH_2OMe$ | Me | $CF_3$ | 0 |
| 5-0372. | 1 | 3-t-Bu | $COOCH_2CH_2OMe$ | Me | $CF_3$ | 2 |
| 5-0373. | 1 | 3-t-Bu | $COOCH_2CONH_2$ | Me | $CF_3$ | 0 |
| 5-0374. | 1 | 3-t-Bu | $COOCH_2CONH_2$ | Me | $CF_3$ | 2 |

TABLE 5-continued describes examples with compounds number of the type 5-xxxx as represented in the following formula:

5-xxxx

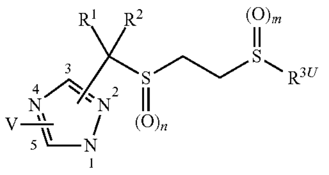

Compounds number 5-01 to 5-0973: m = 0

| No. | position | V | $R^1$ | $R^2$ | $R^{3U}$ | n |
|---|---|---|---|---|---|---|
| 5-0375. | 1 | 3-t-Bu | COO-t-Bu | H | $CF_3$ | 0 |
| 5-0376. | 1 | 3-t-Bu | COO-t-Bu | H | $CF_3$ | 1 |
| 5-0377. | 1 | 3-t-Bu | COO-t-Bu | H | $CF_3$ | 2 |
| 5-0378. | 1 | 3-t-Bu | COO-t-Bu | Me | $CF_3$ | 0 |
| 5-0379. | 1 | 3-t-Bu | COO-t-Bu | Me | $CF_3$ | 1 |
| 5-0380. | 1 | 3-t-Bu | COO-i-Bu | Me | $CF_3$ | 2 |
| 5-0381. | 1 | 3-t-Bu-5-SMe | COO-t-Bu | Me | $CF_3$ | 0 |
| 5-0382. | 1 | 3-t-Bu-5-$SO_2$Me | COO-t-Bu | Me | $CF_3$ | 2 |
| 5-0383. | 1 | 3-t-Bu-5-F | COOEt | H | $CF_3$ | 0 |
| 5-0384. | 1 | 3-t-Bu-5-F | COOEt | H | $CF_3$ | 2 |
| 5-0385. | 1 | 3-t-Bu-5-F | COOEt | Me | $CF_3$ | 0 |
| 5-0386. | 1 | 3-t-Bu-5-F | COOEt | Me | $CF_3$ | 2 |
| 5-0387. | 1 | 3-t-Bu-5-Cl | COOEt | H | $CF_3$ | 0 |
| 5-0388. | 1 | 3-t-Bu-5-Cl | COOEt | H | $CF_3$ | 2 |
| 5-0389. | 1 | 3-t-Bu-5-Cl | COOEt | Me | $CF_3$ | 0 |
| 5-0390. | 1 | 3-t-Bu-5-Cl | COOEt | Me | $CF_3$ | 2 |
| 5-0391. | 1 | 3-t-Bu-5-Br | COOEt | H | $CF_3$ | 0 |
| 5-0392. | 1 | 3-t-Bu-5-Br | COOEt | H | $CF_3$ | 2 |
| 5-0393. | 1 | 3-t-Bu-5-Br | COOEt | Me | $CF_3$ | 0 |
| 5-0394. | 1 | 3-t-Bu-5-Br | COOEt | Me | $CF_3$ | 2 |
| 5-0395. | 1 | 3-c-Pr | COO-t-Bu | H | $CF_3$ | 0 |
| 5-0396. | 1 | 3-c-Pr | COO-t-Bu | H | $CF_3$ | 1 |
| 5-0397. | 1 | 3-c-Pr | COO-t-Bu | H | $CF_3$ | 2 |
| 5-0398. | 1 | 3-c-Pr | COO-t-Bu | Me | $CF_3$ | 0 |
| 5-0399. | 1 | 3-c-Pr | COO-t-Bu | Me | $CF_3$ | 1 |
| 5-0400. | 1 | 3-c-Pr | COO-t-Bu | Me | $CF_3$ | 2 |
| 5-0401. | 1 | 5-c-Pr | COO-t-Bu | Me | $CF_3$ | 2 |
| 5-0402. | 1 | 3-$CHF_2$ | COOEt | H | $CF_3$ | 0 |
| 5-0403. | 1 | 3-$CHF_2$ | COOEt | H | $CF_3$ | 1 |
| 5-0404. | 1 | 3-$CHF_2$ | COOEt | H | $CF_3$ | 2 |
| 5-0405. | 1 | 3-$CHF_2$ | COOEt | Me | $CF_3$ | 0 |
| 5-0406. | 1 | 3-$CHF_2$ | COOEt | Me | $CF_3$ | 1 |
| 5-0407. | 1 | 3-$CHF_2$ | COOEt | Me | $CF_3$ | 2 |
| 5-0408. | 1 | 3-$CF_2CF_3$ | COO-t-Bu | H | $CF_3$ | 0 |
| 5-0409. | 1 | 3-$CF_2CF_3$ | COO-t-Bu | H | $CF_3$ | 1 |
| 5-0410. | 1 | 3-$CF_2CF_3$ | COO-t-Bu | H | $CF_3$ | 2 |
| 5-0411. | 1 | 3-$CF_2CF_3$ | COO-t-Bu | Me | $CF_3$ | 0 |
| 5-0412. | 1 | S-$CF_2CF_3$ | COO-t-Bu | Me | $CF_3$ | 1 |
| 5-0413. | 1 | 3-$CF_2CF_3$ | COO-t-Bu | Me | $CF_3$ | 2 |
| 5-0414. | 1 | 3-$CF_2CF_3$ | Me | H | $CF_3$ | 0 |
| 5-0415. | 1 | S-$CF_2CF_3$ | Me | H | $CF_3$ | 1 |
| 5-0416. | 1 | 3-$CF_2CF_3$ | Me | H | $CF_3$ | 2 |
| 5-0417. | 1 | 3-$CH(CF_3)_2$ | COO-t-Bu | H | $CF_3$ | 0 |
| 5-0418. | 1 | 3-$CH(CF_3)_2$ | COO-t-Bu | H | $CF_3$ | 1 |
| 5-0419. | 1 | 3-$CH(CF_3)_2$ | COO-t-Bu | H | $CF_3$ | 2 |
| 5-0420. | 1 | 3-$CH(CF_3)_2$ | COO-t-Bu | Me | $CF_3$ | 0 |
| 5-0421. | 1 | 3-$CH(CF_3)_2$ | COO-t-Bu | Me | $CF_3$ | 1 |
| 5-0422. | 1 | 3-$CH(CF_3)_2$ | COO-t-Bu | Me | $CF_3$ | 2 |
| 5-0423. | 1 | 3-$CH(CF_3)_2$ | Me | H | $CF_3$ | 0 |
| 5-0424. | 1 | 3-$CH(CF_3)_2$ | Me | H | $CF_3$ | 1 |
| 5-0425. | 1 | 3-$CH(CF_3)_2$ | Me | H | $CF_3$ | 2 |
| 5-0426. | 1 | — | COO-t-Bu | H | $CF_3$ | 0 |
| 5-0427. | 1 | — | COO-t-Bu | H | $CF_3$ | 1 |
| 5-0428. | 1 | — | COO-t-Bu | H | $CF_3$ | 2 |
| 5-0429. | 1 | — | COO-t-Bu | Me | $CF_3$ | 0 |
| 5-0430. | 1 | — | COO-t-Bu | Me | $CF_3$ | 1 |
| 5-0431. | 1 | — | COO-t-Bu | Me | $CF_3$ | 2 |
| 5-0432. | 1 | 3-$NO_2$ | COO-t-Bu | Me | $CF_3$ | 0 |
| 5-0433. | 1 | 3-$NO_2$ | COO-t-Bu | Me | $CF_3$ | 1 |
| 5-0434. | 1 | 3-$NO_2$ | COO-t-Bu | Me | $CF_3$ | 2 |

TABLE 5-continued describes examples with compounds number of the type 5-xxxx as represented in the following formula:

5-xxxx

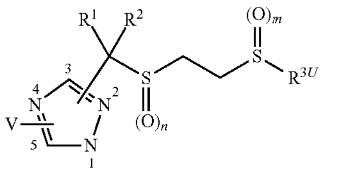

Compounds number 5-01 to 5-0973: m = 0

| No. | position | V | $R^1$ | $R^2$ | $R^{3U}$ | n |
|---|---|---|---|---|---|---|
| 5-0435. | 1 | 3-NHAc | COO-t-Bu | Me | $CF_3$ | 0 |
| 5-0436. | 1 | 3-NHAc | COO-t-Bu | Me | $CF_3$ | 1 |
| 5-0437. | 1 | 3-NHAc | COO-t-Bu | Me | $CF_3$ | 2 |
| 5-0438. | 1 | $3-SCF_3$ | COO-t-Bu | H | $CF_3$ | 0 |
| 5-0439. | 1 | $3-SCF_3$ | COO-t-Bu | Me | $CF_3$ | 0 |
| 5-0440. | 1 | $3-SOCF_3$ | COO-t-Bu | Me | $CF_3$ | 2 |
| 5-0441. | 1 | 3-SMe | COO-t-Bu | H | $CF_3$ | 0 |
| 5-0442. | 1 | 3-SMe | COO-t-Bu | Me | $CF_3$ | 0 |
| 5-0443. | 1 | $3-SO_2Me$ | Me | H | $CF_3$ | 2 |
| 5-0444. | 1 | $3,5-(SMe)_2$ | COO-t-Bu | H | $CF_3$ | 0 |
| 5-0445. | 1 | $3,5-(SO_2Me)_2$ | COO-t-Bu | H | $CF_3$ | 2 |
| 5-0446. | 1 | $3,5-(SMe)_2$ | COO-t-Bu | Me | $CF_3$ | 0 |
| 5-0447. | 1 | $3,5-(SO_2Me)_2$ | COO-t-Bu | Me | $CF_3$ | 2 |
| 5-0448. | 1 | $3-SMe-5-CF_2$ | COOEt | H | $CF_3$ | 0 |
| 5-0449. | 1 | $3-SMe-5-CF_3$ | COOEt | Me | $CF_3$ | 0 |
| 5-0450. | 1 | $3-SO_2Me-5-CF_3$ | COOEt | Me | $CF_3$ | 2 |
| 5-0451. | 1 | $3-SO_2Me-5-CF_3$ | Me | H | $CF_3$ | 2 |
| 5-0452. | 1 | $3-SEt-5-CF_3$ | COO-t-Bu | Me | $CF_3$ | 0 |
| 5-0453. | 1 | $3-SO_2Et-5-CF_3$ | COO-t-Bu | Me | $CF_3$ | 2 |
| 5-0454. | 1 | $3-SO_2Et-5-CF_3$ | Me | H | $CF_3$ | 2 |
| 5-0455. | 1 | $3-S—Pr-5-CF_3$ | COO-t-Bu | Me | $CF_3$ | 0 |
| 5-0456. | 1 | $3-SO_2—Pr-5-CF_3$ | COO-t-Bu | Me | $CF_3$ | 2 |
| 5-0457. | 1 | $3-SO_2—Pr-5-CF_3$ | Me | H | $CF_3$ | 2 |
| 5-0458. | 1 | $3-SO_2(CH_2)_2CF_3-5-CF_3$ | COOMe | Me | $CF_3$ | 2 |
| 5-0459. | 1 | $3-SO_2(CH_2)_2CF_3-5-CF_3$ | Me | H | $CF_3$ | 2 |
| 5-0460. | 1 | $3-COOEt-5-CF_3$ | COO-t-Bu | H | $CF_3$ | 0 |
| 5-0461. | 1 | $3-COOEt-5-CF_3$ | COO-t-Bu | H | $CF_3$ | 2 |
| 5-0462. | 1 | $3-COOEt-5-CF_3$ | COO-t-Bu | Me | $CF_3$ | 0 |
| 5-0463. | 1 | $3-COOEt-5-CF_3$ | COO-t-Bu | Me | $CF_3$ | 2 |
| 5-0464. | 3 | $1-Me-5-CF_3$ | H | H | $CF_3$ | 0 |
| 5-0465. | 3 | $1-Me-5-CF_3$ | H | H | $CF_3$ | 1 |
| 5-0466. | 3 | $1-Me-5-CF_3$ | H | H | $CF_3$ | 2 |
| 5-0467. | 3 | $1-Me-5-CF_3$ | Me | H | $CF_3$ | 0 |
| 5-0468. | 3 | $1-Me-5-CF_3$ | Me | H | $CF_3$ | 1 |
| 5-0469. | 3 | $1-Me-5-CF_3$ | Me | H | $CF_3$ | 2 |
| 5-0470. | 5 | $1-Me-3-CF_3$ | H | H | $CF_3$ | 0 |
| 5-0471. | 5 | $1-Me-3-CF_3$ | H | H | $CF_3$ | 1 |
| 5-0472. | 5 | $1-Me-5-CF_3$ | H | H | $CF_3$ | 2 |
| 5-0473. | 5 | $1-Me-5-CF_3$ | Me | H | $CF_3$ | 0 |
| 5-0474. | 5 | $1-Me-3-CF_3$ | Me | H | $CF_3$ | 1 |
| 5-0475. | 5 | $1-Me-3-CF_3$ | Me | H | $CF_3$ | 2 |
| 5-0476. | 5 | $1-Me-3-CF_3$ | Me | Me | $CF_3$ | 2 |
| 5-0477. | 1 | $3-CF_3-5-COOEt$ | COO-t-Bu | H | $CF_3$ | 2 |
| 5-0478. | 1 | $3-CF_3-5-SCH_2CH{=}CH_2$ | COOMe | H | $CF_3$ | 0 |
| 5-0479. | 1 | $3-CF_3-5-SCH_2CH{=}CH_2$ | COOMe | Me | $CF_3$ | 0 |
| 5-0480. | 1 | $3-CF_3-5-SO_2CH_2CH{=}CH_2$ | COOMe | Me | $CF_3$ | 2 |
| 5-0481. | 1 | $3-CF_3-5-SCH_2CH{=}CHCl$ | COOMe | H | $CF_3$ | 0 |
| 5-0482. | 1 | $3-CF_3-5-SCH_2CH{=}CHCl$ | COOMe | Me | $CF_3$ | 0 |
| 5-0483. | 1 | $3-CF_3-5-SO_2CH_2CH{=}CHCl$ | COOMe | Me | $CF_3$ | 2 |
| 5-0484. | 1 | $3-CF_3-5-SCH_2CH{=}CH$ | COOMe | H | $CF_3$ | 0 |
| 5-0485. | 1 | $3-CF_3-5-SCH_2CH{=}CH$ | COOMe | Me | $CF_3$ | 0 |
| 5-0486. | 1 | $3-CF_3-5-SO_2CH_2CH{=}CH$ | COOMe | Me | $CF_3$ | 2 |

In analogy to the above table, further examples are the compounds numbered 5-0487 to 5-0973 wherein $R^{3U}$ is $CF_2H$ and all remain variables have the same meaning as represented in each line of table 5. Analog to the compounds numbered 5-01 to 5-0973 are the compounds numbered 5-1 to 5-973 wherein the variables have the same meaning except m being 1 instead of 0.

TABLE 6 describes examples with compounds number of the type 6-xxxx as represented in the following formula:

6-xxxx

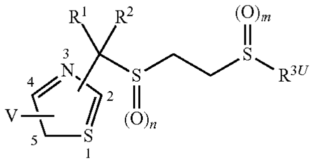

Compounds number 6-01 to 6-0267: m = 0

| No. | Position | V | $R^1$ | $R^2$ | $R^{3U}$ | n |
|---|---|---|---|---|---|---|
| 6-01. | 2 | 4-$CF_3$ | H | H | $CF_3$ | 0 |
| 6-02. | 2 | 4-$CF_3$ | H | H | $CF_3$ | 1 |
| 6-03. | 2 | 4-$CF_3$ | H | H | $CF_3$ | 2 |
| 6-04. | 2 | 4-$CF_3$ | Me | H | $CF_3$ | 0 |
| 6-05. | 2 | 4-$CF_3$ | Me | H | $CF_3$ | 1 |
| 6-06. | 2 | 4-$CF_3$ | Me | H | $CF_3$ | 2 |
| 6-07. | 2 | 4-$CF_3$ | Me | F | $CF_3$ | 2 |
| 6-08. | 2 | 4-$CF_3$ | Me | Cl | $CF_3$ | 2 |
| 6-09. | 2 | 4-$CF_3$ | Me | $CH_2CH_2Cl$ | $CF_3$ | 2 |
| 6-010. | 2 | 4-$CF_3$ | Me | $CH_2OMe$ | $CF_3$ | 2 |
| 6-011. | 2 | 4-$CF_3$ | Me | $CH_2CH_2OMe$ | $CF_3$ | 2 |
| 6-012. | 2 | 4-$CF_3$ | Me | $CH_2OH$ | $CF_3$ | 2 |
| 6-013. | 2 | 4-$CF_3$ | Me | $CH_2F$ | $CF_3$ | 2 |
| 6-048. | 5 | 2-$CF_3$ | Me | H | $CF_3$ | 2 |
| 6-049. | 5 | 2-$CF_3$ | Me | Me | $CF_3$ | 2 |
| 6-050. | 5 | 2-$CF_3$ | Et | H | $CF_3$ | 2 |
| 6-051. | 5 | 2-$CF_3$ | Et | Et | $CF_3$ | 2 |
| 6-052. | 5 | 2-$CF_3$ | i-Pr | H | $CF_3$ | 2 |
| 6-053. | 5 | 2-$CF_3$ | Pr | H | $CF_3$ | 2 |
| 6-054. | 5 | 2-$CF_3$ | Pr | Pr | $CF_3$ | 2 |
| 6-065. | 5 | 2-$CF_3$ | s-Bu | H | $CF_3$ | 2 |
| 6-056. | 5 | 2-$CF_3$ | i-Bu | H | $CF_3$ | 2 |
| 6-057. | 5 | 2-$CF_3$ | Bu | H | $CF_3$ | 2 |
| 6-058. | 5 | 2-$CF_3$ | $CH_2$—c-Pr | H | $CF_3$ | 2 |
| 6-059. | 5 | 2-$CF_3$ | $CH_2CH{=}CH_2$ | H | $CF_3$ | 2 |
| 6-060. | 5 | 2-$CF_3$ | $CH_2CH{=}CH_2$ | $CH_2CH{=}CH_2$ | $CF_3$ | 2 |
| 6-061. | 5 | 2-$CF_3$ | $CH_2C{\equiv}CH$ | H | $CF_3$ | 2 |
| 6-062. | 5 | 2-$CF_3$ | $CH_2C{\equiv}CH$ | $CH_2C{\equiv}CH$ | $CF_3$ | 2 |
| 6-063. | 5 | 2-$CF_3$ | $CH_2C(Cl){=}CH_2$ | H | $CF_3$ | 2 |
| 6-064. | 5 | 2-$CF_3$ | F | H | $CF_3$ | 2 |
| 6-065. | 5 | 2-$CF_3$ | F | F | $CF_3$ | 2 |
| 6-066. | 5 | 2-$CF_3$ | Cl | H | $CF_3$ | 2 |

TABLE 6-continued describes examples with compounds number of the type 6-xxxx as represented in the following formula:

6-xxxx

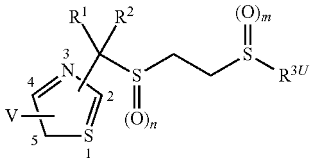

Compounds number 6-01 to 6-0267: m = 0

| No. | Position | V | $R^1$ | $R^2$ | $R^{3U}$ | n |
|---|---|---|---|---|---|---|
| 6-067. | 5 | 2-$CF_3$ | Cl | Cl | $CF_3$ | 2 |
| 6-068. | 5 | 2-$CF_3$ | COOMe | H | $CF_3$ | 2 |
| 6-069. | 5 | 2-$CF_3$ | COOEt | H | $CF_3$ | 2 |
| 6-070. | 5 | 2-$CF_3$ | $CH_2CN$ | H | $CF_3$ | 2 |
| 6-071. | 5 | 2-$CF_3$ | $CH_2COOMe$ | H | $CF_3$ | 2 |
| 6-072. | 5 | 2-$CF_3$ | $CONH_2$ | H | $CF_3$ | 2 |
| 6-073. | 5 | 2-$CF_3$ | CONHEt | H | $CF_3$ | 2 |
| 6-074. | 5 | 2-$CF_3$ | CSNHMe | H | $CF_3$ | 2 |
| 6-075. | 5 | 2-$CF_3$ | $CON(Me)_2$ | H | $CF_3$ | 2 |
| 6-076. | 5 | 2-$CF_3$ | CHO | H | $CF_3$ | 2 |
| 6-077. | 5 | 2-$CF_3$ | Ac | H | $CF_3$ | 2 |
| 6-078. | 5 | 2-$CF_3$ | COEt | H | $CF_3$ | 2 |
| 6-079. | 5 | 2-$CF_3$ | CO—i-Pr | H | $CF_3$ | 2 |
| 6-080. | 5 | 2-$CF_3$ | $COCH_2Cl$ | H | $CF_3$ | 2 |
| 6-081. | 5 | 2-$CF_3$ | $—CH_2—CH_2—$ | | $CF_3$ | 2 |
| 6-082. | 5 | 2-$CF_3$ | $—CH_2—CH_2—CH_2—$ | | $CF_3$ | 2 |
| 6-083. | 5 | 2-$CF_3$ | $—CH_2—CH_2—CH_2—CH_2—$ | | $CF_3$ | 2 |
| 6-084. | 5 | 2-$CF_3$ | $=CH—N(Me)_2$ | | $CF_3$ | 2 |
| 6-085. | 5 | 2-$CF_3$ | =CH—NHMe | | $CF_3$ | 2 |
| 6-086. | 5 | 2-$CF_3$ | $=CH—NH_2$ | | $CF_3$ | 2 |
| 6-087. | 5 | 2-$CF_3$ | 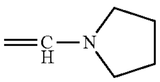 | | $CF_3$ | 2 |
| 6-088. | 5 | 2-$CF_3$ | =CH—OMe | | $CF_3$ | 2 |
| 6-089. | 5 | 2-$CF_3$ | =CH—OEt | | $CF_3$ | 2 |
| 6-090. | 5 | 2-$CF_3$ | =C(Me)—OEt | | $CF_3$ | 2 |
| 6-091. | 5 | 2-$CF_3$ | =N—OH | | 2-$CF_3$ | 0 |
| 6-092. | 5 | 2-$CF_3$ | =N—OMe | | 2-$CF_3$ | 0 |
| 6-093. | 5 | 2-$CF_3$ | =N—OMe | | 2-$CF_3$ | 1 |
| 6-094. | 5 | 2-$CF_3$ | =N—OMe | | 2-$CF_3$ | 2 |
| 6-095. | 5 | 2-$CF_3$ | =N—OEt | | 2-$CF_3$ | 0 |
| 6-096. | 5 | 2-$CF_3$ | =N—OEt | | 2-$CF_3$ | 1 |

TABLE 6-continued describes examples with compounds number of the type 6-xxxx as represented in the following formula:

6-xxxx

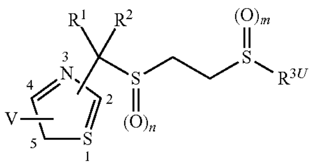

Compounds number 6-01 to 6-0267: m = 0

| No. | Position | V | $R^1$ | $R^2$ | $R^{3U}$ | n |
|---|---|---|---|---|---|---|
| 6-097. | 5 | 2-$CF_3$ | =N—OEt | | 2-$CF_3$ | 2 |
| 6-098. | 5 | 2-$CF_3$ | H | H | $CF_2CF_3$ | 0 |
| 6-099. | 5 | 2-$CF_3$ | H | H | $CF_2CF_3$ | 1 |
| 6-0100. | 5 | 2-$CF_3$ | H | H | $CF_2CF_3$ | 2 |
| 6-0101. | 5 | 2-$CF_3$ | H | H | $CF_2CF_2CF_3$ | 0 |
| 6-0102. | 5 | 2-$CF_3$ | H | H | $CF_2CF_2CF_3$ | 1 |
| 6-0103. | 5 | 2-$CF_3$ | H | H | $CF_2CF_2CF_3$ | 2 |
| 6-0104. | 5 | 2-$CF_3$-4-Me | H | H | $CF_3$ | 0 |
| 6-0105. | 5 | 2-$CF_3$-4-Me | H | H | $CF_3$ | 1 |
| 6-0106. | 5 | 2-$CF_3$-4-Me | H | H | $CF_3$ | 2 |
| 6-0107. | 5 | 2-$CF_3$-4-Me | Me | H | $CF_3$ | 2 |
| 6-0108. | 5 | 2-Cl | H | H | $CF_3$ | 0 |
| 6-0109. | 5 | 2-Cl | H | H | $CF_3$ | 1 |
| 6-0110. | 5 | 2-Cl | H | H | $CF_3$ | 2 |
| 6-0111. | 5 | 2-Cl | Me | H | $CF_3$ | 2 |
| 6-0112. | 5 | 2-Cl | H | H | $CF_3$ | 0 |
| 6-0113. | 5 | 2-Cl | H | H | $CF_3$ | 1 |
| 6-0114. | 5 | 2-Cl | H | H | $CF_3$ | 2 |
| 6-0115. | 5 | 2-Cl | H | H | $CF_2CF_2CF_3$ | 0 |
| 6-0116. | 5 | 2-Cl | H | H | $CF_2CF_2CF_3$ | 1 |
| 6-0117. | 5 | 2-Cl | H | H | $CF_2CF_2CF_3$ | 2 |
| 6-0118. | 5 | 2-Me | H | H | $CF_3$ | 0 |
| 6-0119. | 5 | 2-Me | H | H | $CF_3$ | 1 |
| 6-0120. | 5 | 2-Me | H | H | $CF_3$ | 2 |
| 6-0121. | 5 | 2-Et | H | H | $CF_3$ | 0 |
| 6-0122. | 5 | 2-Et | H | H | $CF_3$ | 1 |
| 6-0123. | 5 | 2-Et | H | H | $CF_3$ | 2 |
| 6-0124. | 5 | 2-i-Pr | H | H | $CF_3$ | 0 |
| 6-0125. | 5 | 2-i-Pr | H | H | $CF_3$ | 1 |
| 6-0126. | 5 | 2-i-Pr | H | H | $CF_3$ | 2 |

TABLE 6-continued describes examples with compounds number of the type 6-xxxx as represented in the following formula:

6-xxxx

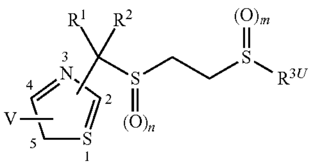

Compounds number 6-01 to 6-0267: m = 0

| No. | Position | V | $R^1$ | $R^2$ | $R^{3U}$ | n |
|---|---|---|---|---|---|---|
| 6-0127. | 5 | 2-c-Pr | H | H | $CF_3$ | 0 |
| 6-0128. | 5 | 2-c-Pr | H | H | $CF_3$ | 1 |
| 6-0129. | 5 | 2-c-Pr | H | H | $CF_3$ | 2 |
| 6-0130. | 5 | 2-t-Bu | H | H | $CF_3$ | 0 |
| 6-0131. | 5 | 2-t-Bu | H | H | $CF_3$ | 1 |
| 6-0132. | 5 | 2-t-Bu | H | H | $CF_3$ | 2 |
| 6-0133. | 4 | 2-$CF_3$ | Me | H | $CF_3$ | 2 |

In analogy to the above table, further examples are the compounds numbered 6-0134 to 6-0267 wherein $R^{3U}$ is $CF_2H$ and all remain variables have the same meaning as represented in each line of table 6. Analog to the compounds numbered 6-01 to 6-0267 are the compounds numbered 6-1 to 6-267 wherein the variables have the same meaning except m being 1 instead of 0.

TABLE 7 describes examples with compounds number of the type 7-xxxx as represented in the following formula:

7-xxxx

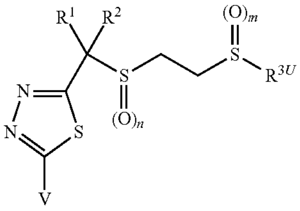

Compounds number 7-01 to 7-0207

| No. | V | $R^1$ | $R^2$ | $R^{3U}$ | n |
|---|---|---|---|---|---|
| 7-01. | $CF_3$ | H | H | $CF_3$ | 0 |
| 7-02. | $CF_3$ | H | H | $CF_3$ | 1 |
| 7-03. | $CF_3$ | H | H | $CF_3$ | 2 |
| 7-04. | $CF_3$ | Me | H | $CF_3$ | 0 |
| 7-05. | $CF_3$ | Me | H | $CF_3$ | 1 |
| 7-06. | $CF_3$ | Me | H | $CF_3$ | 2 |
| 7-07. | $CF_3$ | Me | Me | $CF_3$ | 2 |
| 7-08. | $CF_3$ | Me | F | $CF_3$ | 2 |
| 7-09. | $CF_3$ | Me | Cl | $CF_3$ | 2 |
| 7-010. | $CF_3$ | Me | $CH_2OMe$ | $CF_3$ | 2 |
| 7-011. | $CF_3$ | Me | $CH_2OH$ | $CF_3$ | 2 |
| 7-012. | $CF_3$ | Me | $CH_2F$ | $CF_3$ | 2 |
| 7-013. | $CF_3$ | Me | $CH_2N(Me)_2$ | $CF_3$ | 2 |

TABLE 7-continued describes examples with compounds number of the type 7-xxxx as represented in the following formula:

7-xxxx

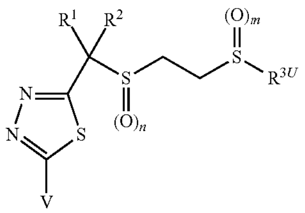

Compounds number 7-01 to 7-0207

| No. | V | $R^1$ | $R^2$ | $R^{3U}$ | n |
|---|---|---|---|---|---|
| 7-014. | $CF_3$ | Me | $CH_2CN$ | $CF_3$ | 2 |
| 7-015. | $CF_3$ | Et | H | $CF_3$ | 0 |
| 7-016. | $CF_3$ | Et | H | $CF_3$ | 1 |
| 7-017. | $CF_3$ | Et | H | $CF_3$ | 2 |
| 7-018. | $CF_3$ | i-Pr | H | $CF_3$ | 0 |
| 7-019. | $CF_3$ | i-Pr | H | $CF_3$ | 1 |
| 7-020. | $CF_3$ | i-Pr | H | $CF_3$ | 2 |
| 7-021. | $CF_3$ | Pr | H | $CF_3$ | 2 |
| 7-022. | $CF_3$ | s-Bu | H | $CF_3$ | 2 |
| 7-023. | $CF_3$ | i-Bu | H | $CF_3$ | 2 |
| 7-024. | $CF_3$ | Bu | H | $CF_3$ | 2 |
| 7-025. | $CF_3$ | $CH_2$—c-Pr | H | $CF_3$ | 2 |
| 7-026. | $CF_3$ | $CH_2CH{=}CH_2$ | H | $CF_3$ | 2 |
| 7-027. | $CF_3$ | $CH_2CH{=}CH_2$ | $CH_2CH{=}CH_2$ | $CF_3$ | 2 |
| 7-028. | $CF_3$ | $CH_2C{\equiv}CH$ | H | $CF_3$ | 2 |
| 7-029. | $CF_3$ | $CH_2C{\equiv}CH$ | $CH_2C{\equiv}CH$ | $CF_3$ | 2 |
| 7-030. | $CF_3$ | COOMe | H | $CF_3$ | 2 |
| 7-031. | $CF_3$ | COOMe | Me | $CF_3$ | 2 |
| 7-032. | $CF_3$ | COOMe | F | $CF_3$ | 2 |
| 7-033. | $CF_3$ | COOMe | Cl | $CF_3$ | 2 |
| 7-034. | $CF_3$ | COOEt | H | $CF_3$ | 2 |
| 7-035. | $CF_3$ | CN | H | $CF_3$ | 2 |
| 7-036. | $CF_3$ | CHO | H | $CF_3$ | 2 |
| 7-037. | $CF_3$ | Ac | H | $CF_3$ | 2 |
| 7-038. | $CF_3$ | COEt | H | $CF_3$ | 2 |
| 7-039. | $CF_3$ | CO—i-Pr | H | $CF_3$ | 2 |
| 7-040. | $CF_3$ | $COCH_2Cl$ | H | $CF_3$ | 2 |
| 7-041. | $CF_3$ | $CON(Me)_2$ | H | $CF_3$ | 2 |
| 7-042. | $CF_3$ | F | H | $CF_3$ | 2 |
| 7-043. | $CF_3$ | F | F | $CF_3$ | 2 |
| 7-044. | $CF_3$ | Cl | H | $CF_3$ | 2 |
| 7-045. | $CF_3$ | Cl | Cl | $CF_3$ | 2 |
| 7-046. | $CF_3$ | =CH—OMe | | $CF_3$ | 2 |
| 7-047. | $CF_3$ | =CH—OEt | | $CF_3$ | 2 |
| 7-048. | $CF_3$ | =C(Me)—OEt | | $CF_3$ | 2 |
| 7-049. | $CF_3$ | =CH—$N(Me)_2$ | | $CF_3$ | 2 |
| 7-050. | $CF_3$ | =N—OH | | $CF_3$ | 0 |
| 7-051. | $CF_3$ | =N—OMe | | $CF_3$ | 0 |
| 7-052. | $CF_3$ | =N—OMe | | $CF_3$ | 1 |
| 7-053. | $CF_3$ | =N—OMe | | $CF_3$ | 2 |
| 7-054. | $CF_3$ | =N—OEt | | $CF_3$ | 0 |
| 7-055. | $CF_3$ | =N—OEt | | $CF_3$ | 1 |
| 7-056. | $CF_3$ | =N—OEt | | $CF_3$ | 2 |
| 7-057. | $CF_2CF_3$ | Me | H | $CF_3$ | 0 |
| 7-058. | $CF_2CF_3$ | Me | H | $CF_3$ | 1 |
| 7-059. | $CF_2CF_3$ | Me | H | $CF_3$ | 2 |
| 7-060. | $CF(CF_3)_2$ | Me | H | $CF_3$ | 0 |
| 7-061. | $CF(CF_3)_2$ | Me | H | $CF_3$ | 1 |
| 7-062. | $CF(CF_3)_2$ | Me | H | $CF_3$ | 2 |
| 7-063. | $C(Me)(CF_3)_2$ | Me | H | $CF_3$ | 0 |
| 7-064. | $C(Me)(CF_3)_2$ | Me | H | $CF_3$ | 1 |
| 7-065. | $C(Me)(CF_3)_2$ | Me | H | $CF_3$ | 2 |
| 7-066. | $NH_2$ | Me | H | $CF_3$ | 0 |
| 7-067. | Cl | Me | H | $CF_3$ | 0 |
| 7-068. | Cl | Me | H | $CF_3$ | 1 |
| 7-069. | Cl | Me | H | $CF_3$ | 2 |
| 7-070. | Br | Me | H | $CF_3$ | 0 |
| 7-071. | Br | Me | H | $CF_3$ | 1 |
| 7-072. | Br | Me | H | $CF_3$ | 2 |
| 7-073. | I | Me | H | $CF_3$ | 0 |

TABLE 7-continued describes examples with compounds number of the type 7-xxxx as represented in the following formula:

7-xxxx

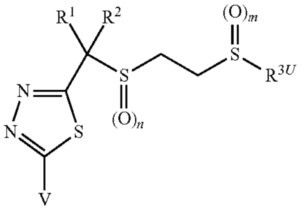

Compounds number 7-01 to 7-0207

| No. | V | $R^1$ | $R^2$ | $R^{3U}$ | n |
|---|---|---|---|---|---|
| 7-074. | I | Me | H | $CF_3$ | 1 |
| 7-075. | I | Me | H | $CF_3$ | 2 |
| 7-076. | Me | Me | H | $CF_3$ | 0 |
| 7-077. | Me | Me | H | $CF_3$ | 1 |
| 7-078. | Me | Me | H | $CF_3$ | 2 |
| 7-079. | Et | Me | H | $CF_3$ | 0 |
| 7-080. | Et | Me | H | $CF_3$ | 1 |
| 7-081. | Et | Me | H | $CF_3$ | 2 |
| 7-082. | i-Pr | Me | H | $CF_3$ | 0 |
| 7-083. | i-Pr | Me | H | $CF_3$ | 1 |
| 7-084. | i-Pr | Me | H | $CF_3$ | 2 |
| 7-085. | c-Pr | Me | H | $CF_3$ | 0 |
| 7-086. | c-Pr | Me | H | $CF_3$ | 1 |
| 7-087. | c-Pr | Me | H | $CF_3$ | 2 |
| 7-088. | t-Bu | Me | H | $CF_3$ | 0 |
| 7-089. | t-Bu | Me | H | $CF_3$ | 1 |
| 7-090. | t-Bu | Me | H | $CF_3$ | 2 |
| 7-091. | $CF_3$ | Cl | H | $CF_3$ | 0 |
| 7-092. | $CF_3$ | Cl | H | $CF_3$ | 1 |
| 7-093. | $CF_3$ | COO—t-Bu | H | $CF_3$ | 2 |
| 7-094. | $CF_3$ | $CH_2Cl$ | Cl | $CF_3$ | 0 |
| 7-095. | $CF_3$ | Me | $CH_2OH$ | $CF_3$ | 0 |
| 7-096. | $CF_3$ | Me | $CH_2OH$ | $CF_3$ | 1 |
| 7-097. | $CF_3$ | Et | $CH_2OH$ | $CF_3$ | 0 |
| 7-098. | $CF_3$ | Et | $CH_2OH$ | $CF_3$ | 1 |
| 7-099. | $CF_3$ | Et | $CH_2OH$ | $CF_3$ | 2 |
| 7-0100. | $CF_3$ | Et | $CH_2OMe$ | $CF_3$ | 2 |
| 7-0101. | $CF_3$ | Et | F | $CF_3$ | 2 |
| 7-0102. | $CF_3$ | Et | Cl | $CF_3$ | 2 |
| 7-0103. | $CF_3$ | Et | $CH_2F$ | $CF_3$ | 2 |

In analogy to the above table, further examples are the compounds numbered 7-0104 to 7-0207 wherein $R^{3U}$ is $CF_2H$ and all remain variables have the same meaning as represented in each line of table 7.

Analog to the compounds numbered 7-01 to 7-0207 are the compounds numbered 7-1 to 7-207 wherein the variables have the same meaning except m being 1 instead of 0.

TABLE 8 describes examples with compounds number of the type 8-xxxx as represented in following formula:

8-xxxx

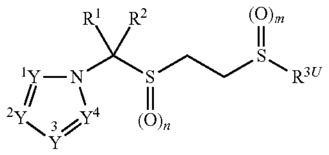

Compounds number 8-01 to 8-0245: m = 0

| No. | $Y^1$ | $Y^2$ | $Y^3$ | $Y^4$ | $R^1$ | $R^2$ | $R^{3U}$ | n |
|---|---|---|---|---|---|---|---|---|
| 8-01. | C—H | C—$NO_2$ | C—H | C—H | H | H | $CF_3$ | 0 |
| 8-02. | C—H | C—$NO_2$ | C—H | C—H | H | H | $CF_3$ | 1 |
| 8-03. | C—H | C—$NO_3$ | C—H | C—H | H | H | $CF_3$ | 2 |
| 8-04. | C—Me | C—Ac | C—Me | C—H | H | H | $CF_3$ | 0 |
| 8-05. | C—Me | C—Ac | C—Me | C—H | H | H | $CF_3$ | 1 |
| 8-06. | C—Me | C—Ac | C—Me | C—H | H | H | $CF_3$ | 2 |
| 8-07. | C—H | N | C—$CF_3$ | C—H | H | H | $CF_3$ | 0 |
| 8-08. | C—H | N | C—$CF_3$ | C—H | H | H | $CF_3$ | 1 |
| 8-09. | C—H | N | C—$CF_3$ | C—H | H | H | $CF_3$ | 2 |
| 8-010. | C—H | N | C—$CF_3$ | C—H | Me | H | $CF_3$ | 0 |
| 8-011. | C—H | N | C—$CF_3$ | C—H | Me | H | $CF_3$ | 1 |
| 8-012. | C—H | N | C—$CF_3$ | C—H | Me | H | $CF_3$ | 2 |
| 8-013. | C—H | N | C—$CF_3$ | C—H | Et | H | $CF_3$ | 0 |
| 8-014. | C—H | N | C—$CF_3$ | C—H | Et | H | $CF_3$ | 1 |
| 8-015. | C—H | N | C—$CF_3$ | C—H | Et | H | $CF_3$ | 2 |
| 8-016. | C—H | N | C—$CF_3$ | C—H | i-Pr | H | $CF_3$ | 0 |
| 8-017. | C—H | N | C—$CF_3$ | C—H | i-Pr | H | $CF_3$ | 1 |
| 8-018. | C—H | N | C—$CF_3$ | C—H | i-Pr | H | $CF_3$ | 2 |
| 8-019. | C—H | N | C—$CF_3$ | C—H | c-Pr | H | $CF_3$ | 0 |
| 8-020. | C—H | N | C—$CF_3$ | C—H | c-Pr | H | $CF_3$ | 1 |
| 8-021. | C—H | N | C—$CF_3$ | C—H | c-Pr | H | $CF_3$ | 2 |
| 8-022. | C—H | N | C—$CF_3$ | C—H | Pr | H | $CF_3$ | 0 |
| 8-023. | C—H | N | C—$CF_3$ | C—H | Pr | H | $CF_3$ | 1 |
| 8-024. | C—H | N | C—$CF_3$ | C—H | Pr | H | $CF_3$ | 2 |
| 8-025. | C—H | N | C—$CF_3$ | C—H | s-Bu | H | $CF_3$ | 0 |
| 8-026. | C—H | N | C—$CF_3$ | C—H | s-Bu | H | $CF_3$ | 1 |
| 8-027. | C—H | N | C—$CF_3$ | C—H | s-Bu | H | $CF_3$ | 2 |
| 8-028. | C—H | N | C—$CF_3$ | C—H | i-Bu | H | $CF_3$ | 0 |
| 8-029. | C—H | N | C—$CF_3$ | C—H | i-Bu | H | $CF_3$ | 1 |
| 8-030. | C—H | N | C—$CF_3$ | C—H | i-Bu | H | $CF_3$ | 2 |
| 8-031. | C—H | N | C—$CF_3$ | C—H | Bu | H | $CF_3$ | 0 |
| 8-032. | C—H | N | C—$CF_3$ | C—H | Bu | H | $CF_3$ | 1 |
| 8-033. | C—H | N | C—$CF_3$ | C—H | Bu | H | $CF_3$ | 2 |
| 8-034. | C—H | N | C—$CF_3$ | C—H | 2-Pen | H | $CF_3$ | 0 |

TABLE 8-continued describes examples with compounds number of the type 8-xxxx as represented in following formula:

8-xxxx

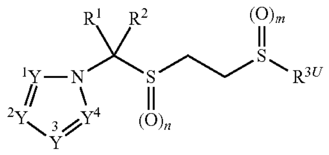

Compounds number 8-01 to 8-0245: m = 0

| No. | $Y^1$ | $Y^2$ | $Y^3$ | $Y^4$ | $R^1$ | $R^2$ | $R^{3U}$ | n |
|---|---|---|---|---|---|---|---|---|
| 8-035. | C—H | N | C—$CF_3$ | C—H | 2-Pen | H | $CF_3$ | 1 |
| 8-036. | C—H | N | C—$CF_3$ | C—H | 2-Pen | H | $CF_3$ | 2 |
| 8-037. | C—H | N | C—$CF_3$ | C—H | 3-Pen | H | $CF_3$ | 0 |
| 8-038. | C—H | N | C—$CF_3$ | C—H | 3-Pen | H | $CF_3$ | 1 |
| 8-039. | C—H | N | C—$CF_3$ | C—H | 3-Pen | H | $CF_3$ | 2 |
| 8-040. | C—H | N | C—$CF_3$ | C—H | c-Pen | H | $CF_3$ | 0 |
| 8-041. | C—H | N | C—$CF_3$ | C—H | c-Pen | H | $CF_3$ | 1 |
| 8-042. | C—H | N | C—$CF_3$ | C—H | c-Pen | H | $CF_3$ | 2 |
| 8-043. | C—H | N | C—$CF_3$ | C—H | c-Hex | H | $CF_3$ | 0 |
| 8-044. | C—H | N | C—$CF_3$ | C—H | c-Hex | H | $CF_3$ | 1 |
| 8-045. | C—H | N | C—$CF_3$ | C—H | c-Hex | H | $CF_3$ | 2 |
| 8-046. | C—H | N | C—$CF_3$ | C—H | CN | H | $CF_3$ | 0 |
| 8-047. | C—H | N | C—$CF_3$ | C—H | CN | H | $CF_3$ | 1 |
| 8-048. | C—H | N | C—$CF_3$ | C—H | CN | H | $CF_3$ | 2 |
| 8-049. | C—H | N | C—$CF_3$ | C—H | COOMe | H | $CF_3$ | 0 |
| 8-050. | C—H | N | C—$CF_3$ | C—H | COOMe | H | $CF_3$ | 1 |
| 8-051. | C—H | N | C—$CF_3$ | C—H | COOMe | H | $CF_3$ | 2 |
| 8-052. | C—H | N | C—$CF_3$ | C—H | COOEt | H | $CF_3$ | 0 |
| 8-053. | C—H | N | C—$CF_3$ | C—H | COOEt | H | $CF_3$ | 1 |
| 8-054. | C—H | N | C—$CF_3$ | C—H | COOEt | H | $CF_3$ | 2 |
| 8-055. | N | N | C—$CF_3$ | C—H | H | H | $CF_3$ | 0 |
| 8-056. | N | N | C—$CF_3$ | C—H | H | H | $CF_3$ | 1 |
| 8-057. | N | N | C—$CF_3$ | C—H | H | H | $CF_3$ | 2 |
| 8-058. | N | N | C—$CF_3$ | N | H | H | $CF_3$ | 0 |
| 8-059. | N | N | C—$CF_3$ | N | H | H | $CF_3$ | 1 |
| 8-060. | N | N | C—$CF_3$ | N | H | H | $CF_3$ | 2 |
| 8-061. | N | N | C—$CF_3$ | N | Me | H | $CF_3$ | 0 |
| 8-062. | N | N | C—$CF_3$ | N | Me | H | $CF_3$ | 1 |
| 8-063. | N | N | C—$CF_3$ | N | Me | H | $CF_3$ | 2 |
| 8-064. | N | N | C—$CF_3$ | N | Et | H | $CF_3$ | 0 |
| 8-065. | N | N | C—$CF_3$ | N | Et | H | $CF_3$ | 1 |
| 8-066. | N | N | C—$CF_3$ | N | Et | H | $CF_3$ | 2 |
| 8-067. | N | N | C—$CF_3$ | N | i-Pr | H | $CF_3$ | 0 |
| 8-068. | N | N | C—$CF_3$ | N | i-Pr | H | $CF_3$ | 1 |

TABLE 8-continued describes examples with compounds number of the type 8-xxxx as represented in following formula:

8-xxxx

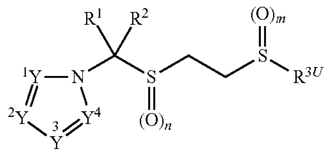

Compounds number 8-01 to 8-0245: m = 0

| No. | $Y^1$ | $Y^2$ | $Y^3$ | $Y^4$ | $R^1$ | $R^2$ | $R^{3U}$ | n |
|---|---|---|---|---|---|---|---|---|
| 6-069. | N | N | C—$CF_3$ | N | i-Pr | H | $CF_3$ | 2 |
| 8-070. | N | N | C—$CF_3$ | N | c-Pr | H | $CF_3$ | 0 |
| 8-071. | N | N | C—$CF_3$ | N | c-Pr | H | $CF_3$ | 1 |
| 8-072. | N | N | C—$CF_3$ | N | c-Pr | H | $CF_3$ | 2 |
| 8-073. | N | N | C—$CF_3$ | N | Pr | H | $CF_3$ | 0 |
| 8-074. | N | N | C—$CF_3$ | N | Pr | H | $CF_3$ | 1 |
| 8-075. | N | N | C—$CF_3$ | N | Pr | H | $CF_3$ | 2 |
| 8-076. | N | N | C—$CF_3$ | N | s-Bu | H | $CF_3$ | 0 |
| 8-077. | N | N | C—$CF_3$ | N | s-Bu | H | $CF_3$ | 1 |
| 8-078. | N | N | C—$CF_3$ | N | s-Bu | H | $CF_3$ | 2 |
| 8-079. | N | N | C—$CF_3$ | N | i-Bu | H | $CF_3$ | 0 |
| 8-080. | N | N | C—$CF_3$ | N | i-Bu | H | $CF_3$ | 1 |
| 8-081. | N | N | C—$CF_3$ | N | i-Bu | H | $CF_3$ | 2 |
| 8-082. | N | N | C—$CF_3$ | N | Bu | H | $CF_3$ | 0 |
| 8-083. | N | N | C—$CF_3$ | N | Bu | H | $CF_3$ | 1 |
| 8-084. | N | N | C—$CF_3$ | N | Bu | H | $CF_3$ | 2 |
| 6-085. | N | N | C—$CF_3$ | N | 2-Pen | H | $CF_3$ | 0 |
| 8-086. | N | N | C—$CF_3$ | N | 2-Pen | H | $CF_3$ | 1 |
| 8-087. | N | N | C—$CF_3$ | N | 2-Pen | H | $CF_3$ | 2 |
| 8-088. | N | N | C—$CF_3$ | N | 3-Pen | H | $CF_3$ | 0 |
| 8-089. | N | N | C—$CF_3$ | N | 3-Pen | H | $CF_3$ | 1 |
| 8-090. | N | N | C—$CF_3$ | N | 3-Pen | H | $CF_3$ | 2 |
| 8-091. | N | N | C—$CF_3$ | N | c-Pen | H | $CF_3$ | 0 |
| 8-092. | N | N | C—$CF_3$ | N | c-Pen | H | $CF_3$ | 1 |
| 8-093. | N | N | C—$CF_3$ | N | c-Pen | H | $CF_3$ | 2 |
| 8-094. | N | N | C—$CF_3$ | N | c-Hex | H | $CF_3$ | 0 |
| 8-095. | N | N | C—$CF_3$ | N | c-Hex | H | $CF_3$ | 1 |
| 8-096. | N | N | C—$CF_3$ | N | c-Hex | H | $CF_3$ | 2 |
| 8-097. | N | N | C—$CF_3$ | N | CN | H | $CF_3$ | 0 |
| 8-098. | N | N | C—$CF_3$ | N | CN | H | $CF_3$ | 1 |
| 8-099. | N | N | C—$CF_3$ | N | CN | H | $CF_3$ | 2 |
| 8-0100. | N | N | C—$CF_3$ | N | $CO_2Me$ | H | $CF_3$ | 0 |
| 8-0101. | N | N | C—$CF_3$ | N | $CO_2Me$ | H | $CF_3$ | 1 |
| 8-0102. | N | N | C—$CF_3$ | N | $CO_2Me$ | H | $CF_3$ | 2 |

TABLE 8-continued describes examples with compounds number of the type 8-xxxx as represented in following formula:

8-xxxx

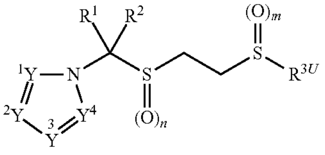

Compounds number 8-01 to 8-0245: m = 0

| No. | $Y^1$ | $Y^2$ | $Y^3$ | $Y^4$ | $R^1$ | $R^2$ | $R^{3U}$ | n |
|---|---|---|---|---|---|---|---|---|
| 8-0103. | N | N | C—$CF_3$ | N | $CO_2Et$ | H | $CF_3$ | 0 |
| 8-0104. | N | N | C—$CF_3$ | N | $CO_2Et$ | H | $CF_3$ | 1 |
| 8-0105. | N | N | C—$CF_3$ | N | $CO_2Et$ | H | $CF_3$ | 2 |
| 8-0106. | N | N | C—$CF_3$ | C—H | $CO_2$—t-Bu | H | $CF_3$ | 0 |
| 8-0107. | N | N | C—$CF_3$ | C—H | $CO_2$—t-Bu | H | $CF_3$ | 1 |
| 8-0108. | N | N | C—$CF_3$ | C—H | $CO_2$—t-Bu | H | $CF_3$ | 2 |
| 8-0109. | C—$CF_3$ | N | C—Et | C—H | $CO_2Me$ | H | $CF_3$ | 2 |
| 8-0110. | C—H | N | C—H | C—$CF_3$ | Me | H | $CF_3$ | 2 |
| 8-0111. | C—Me | N | C—$CF_3$ | C—H | H | H | $CF_3$ | 0 |
| 8-0112. | C—Me | N | C—$CF_3$ | C—H | H | H | $CF_3$ | 1 |
| 8-0113. | C—Me | N | C—$CF_3$ | C—H | H | H | $CF_3$ | 2 |
| 8-0114. | C—$CF_3$ | N | C—t-Bu | C—H | $CO_2$—t-Bu | H | $CF_3$ | 0 |
| 8-0115. | C—$CF_3$ | N | C—t-Bu | C—H | $CO_2$—t-Bu | H | $CF_3$ | 1 |
| 8-0116. | C—$CF_3$ | N | C—t-Bu | C—H | $CO_2$—t-Bu | H | $CF_3$ | 2 |
| 8-0117. | C—H | N | C—t-Bu | C—H | $CO_2$—t-Bu | Me | $CF_3$ | 0 |
| 8-0118. | C—H | N | C—t-Bu | C—H | $CO_2$—t-Bu | Me | $CF_3$ | 1 |
| 8-0119. | C—H | N | C—t-Bu | C—H | $CO_2$—t-Bu | Me | $CF_3$ | 2 |
| 8-0120. | C—H | C—$NO_2$ | C—H | C—H | $CO_2$—t-Bu | H | $CF_3$ | 0 |
| 8-0121. | C—H | C—$NO_2$ | C—H | C—H | $CO_2$—t-Bu | Me | $CF_3$ | 0 |
| 8-0122. | C—H | C—$NO_2$ | C—H | C—H | $CO_2$—t-Bu | Me | $CF_3$ | 2 |

In analogy to the above table, further examples are the compounds numbered 8-0123 to 8-0245 wherein $R^{3U}$ is $CF_2H$ and all remain variables have the same meaning as represented in each line of table 8.

Analog to the compounds numbered 8-01 to 8-0245 are the compounds numbered 8-1 to 8-245 wherein the variables have the same meaning except m being 1 instead of 0.

TABLE 9 describes examples with compounds number of the type 9-xxxx as represented in the following formula:

9-xxxx

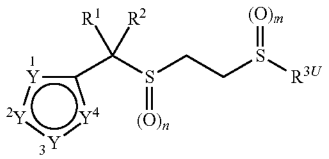

Compounds number 9-01 to 9-0205: m = 0

| No. | $Y^1$ | $Y^2$ | $Y^3$ | $Y^4$ | $R^1$ | $R^2$ | $R^{3U}$ | n |
|---|---|---|---|---|---|---|---|---|
| 9-01. | O | C—CF$_3$ | C—H | C—H | H | H | CF$_3$ | 0 |
| 9-02. | O | C—CF$_3$ | C—H | C—H | H | H | CF$_3$ | 1 |
| 9-03. | O | C—CF$_3$ | C—H | C—H | H | H | CF$_3$ | 2 |
| 9-04. | O | N | C—CF$_3$ | C—H | H | H | CF$_3$ | 0 |
| 9-05. | O | N | C—CF$_3$ | C—H | H | H | CF$_3$ | 1 |
| 9-06. | O | N | C—CF$_3$ | C—H | H | H | CF$_3$ | 2 |
| 9-07. | O | C—CF$_3$ | N | N | H | H | CF$_3$ | 0 |
| 9-08. | O | C—CF$_3$ | N | N | H | H | CF$_3$ | 1 |
| 9-09. | O | C—CF$_3$ | N | N | H | H | CF$_3$ | 2 |
| 9-010. | O | N | C—CF$_3$ | N | H | H | CF$_3$ | 0 |
| 9-011. | O | N | C—CF$_3$ | N | H | H | CF$_3$ | 1 |
| 9-012. | O | N | C—CF$_3$ | N | H | H | CF$_3$ | 2 |
| 9-013. | O | C—CF$_3$ | C—CN | N | H | H | CF$_3$ | 0 |
| 9-014. | O | C—CF$_3$ | C—CN | N | H | H | CF$_3$ | 1 |
| 9-015. | O | C—CF$_3$ | C—CN | N | H | H | CF$_3$ | 2 |
| 9-016. | S | C—Cl | C—H | C—H | H | H | CF$_3$ | 0 |
| 9-017. | S | C—Cl | C—H | C—H | H | H | CF$_3$ | 1 |
| 9-018. | S | C—Cl | C—H | C—H | H | H | CF$_3$ | 2 |
| 9-019. | S | C—Cl | C—H | C—H | Me | H | CF$_3$ | 0 |
| 9-020. | S | C—Cl | C—H | C—H | Me | H | CF$_3$ | 1 |
| 9-021. | S | C—Cl | C—H | C—H | Me | H | CF$_3$ | 2 |
| 9-022. | S | C—H | C—H | C—H | COOMe | H | CF$_3$ | 0 |
| 9-023. | S | C—H | C—H | C—H | COOMe | H | CF$_3$ | 1 |
| 9-024. | S | C—H | C—H | C—H | COOMe | H | CF$_3$ | 2 |
| 9-025. | S | C—H | C—H | C—H | COOH | H | CF$_3$ | 0 |
| 9-026. | S | C—H | C—H | C—H | CON(Me)$_2$ | H | CF$_3$ | 0 |
| 9-027. | O | C—CH═CH—CH═CH—C | | C—H | H | H | CF$_3$ | 0 |
| 9-028. | O | C—CH═CH—CH═CH—C | | C—H | H | H | CF$_3$ | 1 |
| 9-029. | O | C—CH═CH—CH═CH—C | | C—H | H | H | CF$_3$ | 2 |
| 9-030. | O | C—CH═CH—CH═CH—C | | C—H | Me | H | CF$_3$ | 0 |
| 9-031. | O | C—CH═CH—CH═CH—C | | C—H | Me | H | CF$_3$ | 1 |
| 9-032. | O | C—CH═CH—CH═CH—C | | C—H | Me | H | CF$_3$ | 2 |
| 9-033. | S | C—CH═CH—CH═CH—C | | C—H | H | H | CF$_3$ | 0 |
| 9-034. | S | C—CH═CH—CH═CH—C | | C—H | H | H | CF$_3$ | 1 |
| 9-035. | S | C—CH═CH—CH═CH—C | | C—H | H | H | CF$_3$ | 2 |
| 9-036. | S | C—CH═CH—CH═CH—C | | C—H | Me | H | CF$_3$ | 0 |
| 9-037. | S | C—CH═CH—CH═CH—C | | C—H | Me | H | CF$_3$ | 1 |
| 9-038. | S | C—CH═CH—CH═CH—C | | C—H | Me | H | CF$_3$ | 2 |
| 9-039. | N—H | C—CH═CH—CH═CH—C | | C—H | H | H | CF$_3$ | 0 |
| 9-040. | N—H | C—CH═CH—CH═CH—C | | C—H | H | H | CF$_3$ | 1 |
| 9-041. | N—H | C—CH═CH—CH═CH—C | | C—H | H | H | CF$_3$ | 2 |
| 9-042. | N—Me | C—CH═CH—CH═CH—C | | C—H | H | H | CF$_3$ | 0 |
| 9-043. | N—Me | C—CH═CH—CH═CH—C | | C—H | H | H | CF$_3$ | 1 |
| 9-044. | N—Me | C—CH═CH—CH═CH—C | | C—H | H | H | CF$_3$ | 2 |
| 9-045. | O | C—CH═CH—CH═CH—C | | N | H | H | CF$_3$ | 0 |
| 9-046. | O | C—CH═CH—CH═CH—C | | N | H | H | CF$_3$ | 1 |
| 9-047. | O | C—CH═CH—CH═CH—C | | N | H | H | CF$_3$ | 2 |
| 9-048. | S | C—CH═CH—CH═CH—C | | N | H | H | CF$_3$ | 0 |
| 9-049. | S | C—CH═CH—CH═CH—C | | N | H | H | CF$_3$ | 1 |
| 9-050. | S | C—CH═CH—CH═CH—C | | N | H | H | CF$_3$ | 2 |
| 9-051. | S | C—CH═CH—CH═CH—C | | N | Me | H | CF$_3$ | 0 |
| 9-052. | S | C—CH═CH—CH═CH—C | | N | Me | H | CF$_3$ | 1 |
| 9-053. | S | C—CH═CH—CH═CH—C | | N | Me | H | CF$_3$ | 2 |
| 9-054. | N—H | C—CH═CH—CH═CH—C | | N | H | H | CF$_3$ | 0 |
| 9-055. | N—H | C—CH═CH—CH═CH—C | | N | H | H | CF$_3$ | 1 |
| 9-056. | N—H | C—CH═CH—CH═CH—C | | N | H | H | CF$_3$ | 2 |
| 9-057. | N—Me | C—CH═CH—CH═CH—C | | N | H | H | CF$_3$ | 0 |
| 9-058. | N—Me | C—CH═CH—CH═CH—C | | N | H | H | CF$_3$ | 1 |
| 9-059. | N—Me | C—CH═CH—CH═CH—C | | N | H | H | CF$_3$ | 2 |
| 9-060. | S | C—Cl | N | C—CF$_3$ | H | H | CF$_3$ | 0 |
| 9-061. | S | C—Cl | N | C—CF$_3$ | H | H | CF$_3$ | 1 |
| 9-062. | S | C—Cl | N | C—CF$_3$ | H | H | CF$_3$ | 2 |

TABLE 9-continued describes examples with compounds number of the type 9-xxxx as represented in the following formula:

9-xxxx

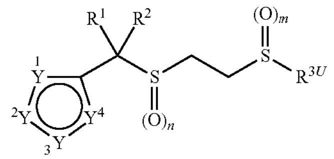

Compounds number 9-01 to 9-0205: m = 0

| No. | $Y^1$ | $Y^2$ | $Y^3$ | $Y^4$ | $R^1$ | $R^2$ | $R^{3U}$ | n |
|---|---|---|---|---|---|---|---|---|
| 9-063. | O | C—CH═CH—CH═CH—C | | N | Me | H | $CF_3$ | 0 |
| 9-064. | O | C—CH═CH—CH═CH—C | | N | Me | H | $CF_3$ | 1 |
| 9-065. | O | C—CH═CH—CH═CH—C | | N | Me | H | $CF_3$ | 2 |
| 9-066. | O | N | C—$CF_3$ | C—H | Me | H | $CF_3$ | 0 |
| 9-067. | O | N | C—$CF_3$ | C—H | Me | H | $CF_3$ | 1 |
| 9-068. | O | N | C—$CF_3$ | C—H | Me | H | $CF_3$ | 2 |
| 9-069. | O | N | C—t-Bu | C—H | Me | H | $CF_3$ | 0 |
| 9-070. | O | N | C—t-Bu | C—H | Me | H | $CF_3$ | 1 |
| 9-071. | O | N | C—t-Bu | C—H | Me | H | $CF_3$ | 2 |
| 9-072. | O | C—CH═CF—CH═CH—C | | N | Me | H | $CF_3$ | 0 |
| 9-073. | O | C—CH═CF—CH═CH—C | | N | Me | H | $CF_3$ | 1 |
| 9-074. | O | C—CH═CF—CH═CH—C | | N | Me | H | $CF_3$ | 2 |
| 9-075. | O | C—CH═CH—CF═CH—C | | N | Me | H | $CF_3$ | 0 |
| 9-076. | O | C—CH═CH—CF═CH—C | | N | Me | H | $CF_3$ | 1 |
| 9-077. | O | C—CH═CH—CF═CH—C | | N | Me | H | $CF_3$ | 2 |
| 9-078. | O | C—CH═CH—C($CF_3$)═CH—C | | N | Me | H | $CF_3$ | 0 |
| 9-079. | O | C—CH═CH—C($CF_3$)═CH—C | | N | Me | H | $CF_3$ | 1 |
| 9-080. | O | C—CH═CH—C($CF_3$)═CH—C | | N | Me | H | $CF_3$ | 2 |
| 9-081. | O | C—CF═CF—CF═CF—C | | N | Me | H | $CF_3$ | 0 |
| 9-082. | O | C—CF═CF—CF═CF—C | | N | Me | H | $CF_3$ | 1 |
| 9-083. | O | C—CF═CF—CF═CF—C | | N | Me | H | $CF_3$ | 2 |
| 9-084. | N | O | C—$CF_3$ | C—H | H | H | $CF_3$ | 0 |
| 9-085. | N | O | C—$CF_3$ | C—H | H | H | $CF_3$ | 1 |
| 9-086. | N | O | C—$CF_3$ | C—H | H | H | $CF_3$ | 2 |
| 9-087. | N | O | C—$CF_3$ | C—H | Me | H | $CF_3$ | 2 |
| 9-088. | C—H | O | C—Cl | N | H | H | $CF_3$ | 0 |
| 9-089. | C—H | O | C—Cl | N | H | H | $CF_3$ | 1 |
| 9-090. | C—H | O | C—Cl | N | H | H | $CF_3$ | 2 |
| 9-091. | C—H | O | C—Cl | N | Me | H | $CF_3$ | 2 |
| 9-092. | C—Cl | S | C—Cl | C—H | Me | H | $CF_3$ | 0 |
| 9-093. | C—Cl | S | C—Cl | C—H | Me | H | $CF_3$ | 1 |
| 9-094. | C—Cl | S | C—Cl | C—H | Me | H | $CF_3$ | 2 |
| 9-095. | C—H | N—t-Bu | N | N | H | H | $CF_3$ | 0 |
| 9-096. | C—H | N—t-Bu | N | N | H | H | $CF_3$ | 1 |
| 9-097. | C—H | N—t-Bu | N | N | H | H | $CF_3$ | 2 |
| 9-098. | N | N—CH═$CH_2$ | N | N | H | H | $CF_3$ | 0 |
| 9-099. | N | N—CH═$CH_2$ | N | N | H | H | $CF_3$ | 1 |
| 9-0100. | N | N—CH═$CH_2$ | N | N | H | H | $CF_3$ | 2 |
| 9-0101. | N | O | C—$CF_3$ | C—H | Me | H | $CF_3$ | 0 |
| 9-0102. | N | O | C—$CF_3$ | C—H | Me | H | $CF_3$ | 1 |

In analogy to the above table, further examples are the compounds numbered 9-0103 to 9-205 wherein $R^{3U}$ is $CF_2H$ and all remain variables have the same meaning as represented in each line of table 9.

Analog to the compounds numbered 9-01 to 9-205 are the compounds numbered 9-1 to 9-205 wherein the variables have the same meaning except m being 1 instead of 0.

In analogy to the above listed compounds numbered 1-01 to 9-205, further examples of compounds according to the present invention are when not explicitly listed in the table compounds wherein n is 0 or 1 instead of 2.

The compounds of formula (I) may be prepared by processes adapted from those described in WO 2009/075080, WO 2009/025397 or WO 2009/028727 which are hereby incorporated by reference in their entirety. The compounds according to the present invention, represented by general formula [I] may be manufactured according to the manufacturing processes given hereunder, but the present invention will not be limited by these processes. The variables used in the different structures for the different examples of synthesis if not explicitly defined are the same as in formula (I). It will be understood by those skilled in the art that certain functional groups in the compounds and intermediates may be unprotected or protected by suitable protecting groups, as taught by Greene et al. Protective Groups in Organic Synthesis, John Wiley and Sons, Inc., 3rd edition 1999. Further, it will be apparent to those skilled in the art that the compounds and intermediates may be isolated by standard aqueous work-up conditions and optionally purified. For example, the compounds or intermediates may be purified by chromatographic methods or crystallized to yield the desired product in suitable purity.

The compounds of the present invention may be also represented by the following formula (II)

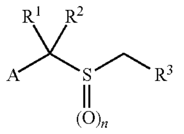

(II)

with $R^3$ = 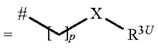 and A = U # is the bonding site in formula (II) and the other variables in formula (II) and $R^3$ having the same meaning as aforementioned.

The compounds of the type $R^3$ attached to a leaving group $Z^1$ can be prepared for example as follows and described e.g. in WO 2007/071609 and WO 2007/147888 for further use in the synthesis of compounds of formula (I).

In general, compounds ($IVR^{3u}$), if not commercially available, can be synthesized from alcohols ($IIIR^{3U}$) via conversion to the respective tosylates, mesylates or halides in analogy to methods mentioned in J. March, Advanced Organic Chemistry, $4^{th}$ edition, Wiley.

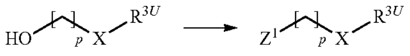

$IIIR^{3U}$ $IVR^{3U}$

Compounds ($IIIR^{3U}$) can be obtained via alkylation of compounds ($VR^{3u}$) where $Z^2$ is a suitable leaving group such as a halogen atom, methanesulfonate, trifluoromethanesulfonate or toluenesulfonate, with compounds (VI $R^{3u}$) which are suitably substituted thiols or alcohols or salts thereof in analogy to procedures described in Can. J. Chem. 1979, 57, p. 1958-1966 and J. Am. Chem. Soc. 1924, 46, p. 1503.

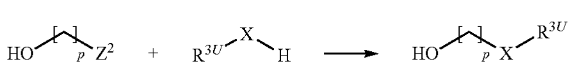

$VR^{3U}$ $VIR^{3U}$ $IVR^{3U}$

Specifically, compounds ($IVR^{3U}$) wherein p=2, $R^{3U}$ is $CF_3$, X is sulfur and $Z^1$ is halogen can also be obtained by reaction of $CF_3$—SH with vinyl halides $CH_2CH$—$Z^1$ as described in J. Am. Chem. Soc. 1962, 84, p. 3148-3153.

Compounds ($IIIR^{3u}$) wherein $R^{3U}$ is $CF_3$ and X is sulfur can be prepared for example by alkylation of mercapto alcohols HO—$(CH_2)_n$—SH under irradiation conditions as described in WO 2001/36410; p. 19.

Compounds ($IVR^{3U}$) wherein $R^{3U}$ is $CF_3$ and X is oxygen can be obtained as described in J. Fluorine Chemistry 1982, 21, p. 133-143 or J. Org. Chem. 2001, 66, p. 1061-1063.

Manufacturing Process 1

A compound represented by formula [Ia] may be manufactured according to the undermentioned process:

Scheme 1

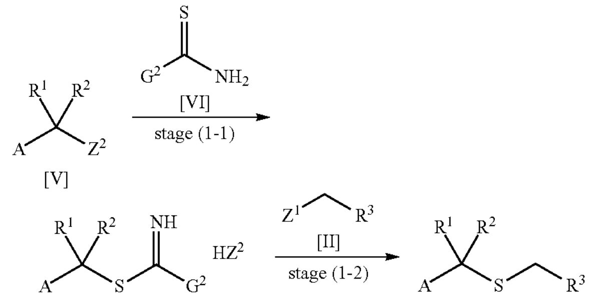

[VII] [Ia]

In the formulae, A, $R^1$, $R^2$, $R^3$, $Z^1$ and $Z^2$ represent the same meanings as the aforementioned, and $G^2$ represents a methyl group or an amino group.

Stage (1-1)

A compound [VII] may be manufactured by the reaction of a compound [V] and a compound [VI] in a solvent. The quantities to use of a compound [VI] may be appropriately selected from, normally the range 1 to 3 equivalents, preferably 1 to 2 equivalents, per 1 equivalent of a compound [V]. Examples of the solvents which may be used in this reaction: halogenated hydrocarbons such as dichloromethane and chloroform; and alcohols such as methanol, ethanol and propanol; or mixtures thereof. The quantities of the above-mentioned solvents are normally 0.1 to 10 liters, preferably 0.2 to 3.0 liters per 1 mole of a compound [V]. The reaction temperature is any temperature from 0° C. to reflux temperature in the reaction system, preferably in the temperature range 10° to 120° C. The reaction time will vary according to, for example, the reaction temperature, reaction substrate and quantities reacted, but is normally in the range 0.5 to 72 hours. After the reaction has been completed, the compound [VII] may be isolated by carrying out operations such as concentration. The isolated compound [VII] may be further purified by means of recrystallization, as required.

Stage (1-2)

A compound represented by formula [Ia] may be manufactured by the reaction of a compound [VII] and a compound [II] in a solvent, in the presence of a base. The quantities to use of a compound [II] used herein may be appropriately selected from, normally the range 0.8 to 5 equivalents, preferably 0.8 to 2 equivalents, per 1 equivalent of a compound [VII]. Examples of the solvents which may be used in this reaction are: ethers such as diethyl ether, 1,2-dimethoxyethane and tetrahydrofuran; amides such as N,N-dimethylacetamide, N,N-dimethylformamide, 1,3-dimethyl-2-imidazolidinone and N-methyl-2-pyrrolidinone; sulfur compounds such as dimethylsulfoxide and sulfolane; nitriles such as acetonitrile and propionitrile; alcohols such as methanol, ethanol and propanol; aliphatic hydrocarbons such as hexane and heptane; aromatic hydrocarbons such as benzene, toluene and xylene; halogenated hydrocarbons such as 1,2-dichloroethane and chlorobenzene; and water; or mixtures thereof. The quantities of the above-mentioned solvents are normally 0.1 to 50 liters, preferably 0.2 to 10 liters per 1 mole of a compound [VII]. Examples of bases which may be used in this reaction are inorganic bases such as: hydroxides of alkali metals, for instance, sodium hydroxide and potassium hydroxide; hydroxides of alkaline earth metals, for instance calcium hydroxide and magnesium hydroxide; or metal salts of alcohols, for instance, sodium methoxide, sodium ethoxide and potassium tert-butoxide. The quantities of a base to use may normally be appropriately selected from a range of 1 to 20 equivalents, preferably 1 to 10 equivalents, per 1 equivalent of a compound [VII].

The said reaction may be carried out using a phase transfer catalyst such as tetra-n-butylammonium bromide. The quantities of a phase transfer catalyst to use may be appropriately selected from a range of 0 to 1.0 equivalent, per 1 equivalent of a compound [VII]. The reaction temperature is any temperature from −50° C. to reflux temperature in the reaction system, preferably in the temperature range −10° to 100° C.

The reaction time will vary according to, for example, the reaction temperature, reaction substrate and quantities reacted, but is normally in the range 1 to 48 hours. After the reaction has been completed, compound [Ia] may be isolated by carrying out operations such as addition of the reaction mixture to water and extraction with an organic solvent, then concentration. The isolated compound [Ia] may be further purified by means of column chromatography and recrystallization, as required.

Manufacturing Process 2

A compound represented by formula [Ia] may be manufactured according to the undermentioned process.

Scheme 2

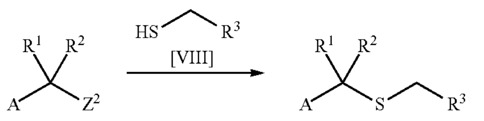

[V] [Ia]

In the formulae, A, $R^1$, $R^2$, $R^3$, and $Z^2$ represent the same meanings as the aforementioned. A compound represented by formula [Ia] may be manufactured by the reaction of a compound [V] and a compound [VIII] in a solvent, in the presence of a base. The quantities to use of a compound [VIII] used herein may be appropriately selected from, normally the range 0.8 to 5 equivalents, preferably 0.8 to 2 equivalents, per 1 equivalent of a compound [V]. The solvents which may be used in this reaction are the same as those in stage (1-2) of manufacturing process 1. The quantities of the above-mentioned solvents are normally 0.1 to 50 liters, preferably 0.2 to 10 liters per 1 mole of a compound [V]. Examples of bases which may be used in this reaction are: organic bases such as triethylamine and 1,8-diazabicyclo[5.4.0]-7-undecene; inorganic bases such as: hydroxides of alkali metals, for instance, sodium hydroxide and potassium hydroxide; hydroxides of alkaline earth metals, for instance calcium hydroxide and magnesium hydroxide; carbonates of alkali metals, for instance, sodium carbonate and potassium carbonate; and hydrogen carbonates of alkali metals, for instance, sodium hydrogen carbonate and potassium hydrogen carbonate; metal salts of alcohols, for instance, sodium methoxide, sodium ethoxide and potassium tert-butoxide; or hydrides of alkali metals, for instance sodium hydride. The quantities of a base may normally be appropriately selected from a range of 1 to 10 equivalents, preferably 1 to 5 equivalents, per 1 equivalent of a compound [V]. The reaction temperature is any temperature from −50° C. to reflux temperature in the reaction system, preferably in the temperature range −10° to 100° C. The reaction time will vary according to, for example, the reaction temperature, reaction substrate and quantities reacted, but is normally in the range 1 to 24 hours. After the reaction has been completed, the compound [Ia] may be isolated by carrying out operations such as addition of the reaction mixture to water and extraction with an organic solvent, then concentration. The isolated compound [Ia] may be further purified by means of column chromatography and recrystallization, as required.

Manufacturing Process 3

A compound represented by formula [Ia] may be manufactured according to the undermentioned process.

Scheme 3

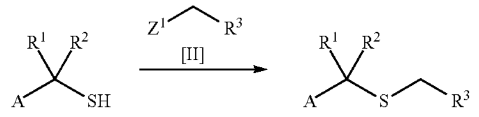

[IX] [Ia]

In the formulae, A, $R^1$, $R^2$, $R^3$, and $Z^1$ represent the same meanings as the aforementioned.

A compound represented by formula [Ia] may be manufactured by the reaction of a compound [IX] and a compound [II] in a solvent, in the presence of a base. The quantities to use of a compound [II] used herein may be appropriately selected from, normally the range 0.8 to 5 equivalents, preferably 0.8 to 2 equivalents, per 1 equivalent of a compound [IX]. The solvents which may be used in this reaction are the same as those in stage (1-2) of manufacturing process 1. The quantities of the above-mentioned solvents are normally 0.1 to 50 liters, preferably 0.2 to 10 liters per 1 mole of a compound [IX]. Examples of the bases which may be used in this reaction are the same as those in manufacturing process 2. The quantities of a base to use may normally be appropriately selected from a range of 1 to 10 equivalents, preferably 1 to 5 equivalents, per 1 equivalent of a compound [IX]. The reaction temperature is any temperature from −50° C. to reflux temperature in the reaction system, preferably in the temperature range −10° to 100° C. The reaction time will vary according to, for example, the reaction temperature, reaction substrate and quantities reacted, but is normally in the range 1 to 48 hours. After the reaction has been completed, compound [Ia] may be isolated by carrying out operations such as addition of the reaction mixture to water and extraction with an organic solvent, then concentration. The isolated compound [Ia] may be further purified by means of column chromatography and recrystallization, as required.

The aforementioned compound [VIII] and compound [IX] may also be manufactured according to the processes described in the Journal of Organic Chemistry, pages 93 to 95 (1962) and in Heterocycles pages 1331 to 1346 (1986).

Manufacturing Process 4 of the compounds represented by general formula [I], the compounds represented by formula [Ib], wherein n is 1 or 2, may be manufactured according to the undermentioned process:

Scheme 4

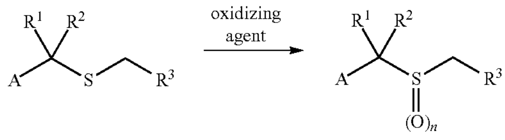

[Ia] [Ib]

In the formulae, A, $R^1$, $R^2$ and $R^3$ represent the same meanings as the aforementioned, and n represents 1 or 2.

A compound represented by formula [Ib] may be manufactured by the reaction of a compound represented by formula [Ia] and an oxidizing agent, in a solvent. Examples of the oxidizing agents which may be used in the reaction are: organic peroxides such as metachloroperoxybenzoic acid, performic acid or peracetic acid; oxone (DuPont trade name, 2 $KHSO_5.KHSO_4.K_2SO_4$); halogen-containing imides such as N-chlorosuccinimide; and inorganic peroxides such as hydrogen peroxide, potassium permanganate, or sodium periodate. The quantities to use of an oxidizing agent used herein may be appropriately selected from, normally the range 0.8 to 10 equivalents, preferably 0.8 to 5 equivalents, per 1 equivalent of a compound [Ia].

Examples of the solvents which may be used in this reaction are: halogenated hydrocarbons such as dichloromethane, chloroform, 1,2-dichloroethane and chlorobenzene; alcohols such as methanol, ethanol and propanol; aromatic hydrocarbons such as benzene, toluene and xylene; ketones such as acetone and 2-butanone; nitriles such as acetonitrile; esters such as ethyl acetate; aliphatic carboxylic acids such as acetic acid and trifluoroacetic acid; water; or mixtures thereof. The quantities of the above-mentioned solvents are normally 0.1 to 50 liters, preferably 0.2 to 10 liters per 1 mole of a compound [Ia]. The reaction temperature is any temperature from −50° C. to reflux temperature in the reaction system, preferably in the temperature range −10° to 60° C.

The reaction time will vary according to, for example, the reaction temperature, reaction substrate and quantities reacted, but is normally in the range 1 to 24 hours. After the reaction has been completed, a compound [Ib] may be isolated by carrying out operations such as addition of the reaction mixture to water and extraction with an organic solvent, then concentration. The isolated compound [Ib] may be further purified by means of column chromatography and recrystallization, as required.

Preferred methods for the selective conversion of sulfides (Ia) to sulfoxides (Ib), for which n is 1, are the use of hydrogen peroxide as the oxidant in the presence of hexafluoroisopropanol as described in Tetrahedron Lett. 1998, 39, 3141-3144, or the use of meta-chloroperbenzoic acid as the oxidizing agent in the presence or absence of a base in an aprotic solvent such as chloroform or dichloromethane at temperatures below ambient temperature.

Other methods for the oxidation of sulfide compounds to sulfoxides and to sulfone products are well known in the art, and any suitable procedure known in the art may be used (for example, for synthesis of sulfoxides see Varma et al., Org. Lett., 1999, 1, 189-191; Kim et al., Synthesis, 2002, 2484-2486; Qian et al., Synlett, 2006, 709-712; Matteucci et al., Org. Lett., 2003, 5, 235-237; Mba et al., Org. Lett., 2007, 9, 21-24; Karimi et al.; Org. Lett., 2005, 7, 625-628; for preparation of sulfones, see Varma et al., Org. Lett, 1999, 1, 189-191; Jana et al., Org. Lett., 2003, 5, 3787-3790; Karimi et al., Org. Lett., 2005, 7, 625-628; Shaabania et al, Tetrahedron, 2004, 60, 1 1415-1 1420).

Manufacturing Process 5

A compound represented by formula [Ic] may be manufactured according to the undermentioned process:

Scheme 5

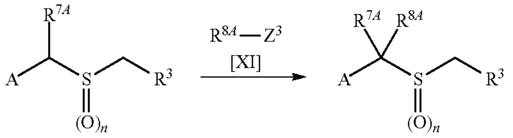

[X] [Ic]

In the formulae [X] and [Ic], A, $R^3$ and n represent the same meanings as the aforementioned and:

$R^{7A}$ in formulae [X] and [Ic] denotes halogen, $C_1$-$C_6$-alkyl which may be substituted by halogen, by $C_1$-$C_4$-alkoxy, by $C_1$-$C_4$-alkylthio, by $C_1$-$C_4$-alkylsulfinyl, by $C_1$-$C_6$-alkylsulfonyl, by CN, by C(═O)$R^9$A, or by di($C_1$-$C_3$-alkyl)amino, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_3$-alkyl which may be substituted with halogen atoms, CN, C(═O)$R^{10A}$;

$R^{8A}$ in formulae [X] and [Ic] denotes $C_1$-$C_6$-alkyl which may be substituted by halogen, by $C_1$-$C_4$-alkoxy, by $C_1$-$C_4$-alkylthio, by CN, by C(═O)R9A, or by hydroxyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_3$-alkyl which may be substituted by halogen atoms, or C(═O)$R^{11A}$;

$R^{9A}$ in formulae [X] and [Ic] denotes $C_1$-$C_6$-alkyl, $C_1$-$C_6$-haloalkyl, $C_1$-$C_6$-alkoxy, amino, mono-($C_1$-$C_6$-alkyl)amino, di-($C_1$-$C_4$-alkyl)amino, $C^2$-$C^5$-cyclic amino;

$R^{10A}$ in formula [X] and [Ic] denotes $C_1$-$C_6$-alkoxy, di-($C_1$-$C_4$-alkyl)amino, $C^2$-$C^5$-cyclic amino; $R^{11A}$ in formulae [X] and [Ic] denotes $C_1$-$C_6$-alkyl, $C_1$-$C_6$-haloalkyl, $C_1$-$C_6$-alkoxy, di-($C_1$-$C_4$-alkyl)amino, $C_2$-$C_5$-cyclic amino;

$Z^3$ represents a leaving group such as a chlorine atom, bromine atom, iodine atom, methanesulfonyloxy group, or trifluoromethanesulfonyloxy group.

A compound represented by formula [Ic] may be manufactured by the reaction of a compound [X] and a compound [XI] in a solvent, in the presence of a base. The quantities to use of a compound [XI] used herein may be appropriately selected from, normally the range 1 to 10 equivalents, preferably 1 to 5 equivalents, per 1 equivalent of a compound [X]. Examples of the solvents which may be used in this reaction are: ethers such as diethyl ether, 1,2-dimethoxyethane and tetrahydrofuran; amides such as N,N-dimethylacetamide, N,N-dimethylformamide, 1,3-dimethyl-2-imidazolidinone and N-methyl-2-pyrrolidinone; sulfur compounds such as dimethylsulfoxide and sulfolane; nitriles such as acetonitrile and propionitrile; and aromatic hydrocarbons such as benzene, toluene and xylene; or mixtures thereof. The quantities of the above-mentioned solvents are normally 0.1 to 50 liters, preferably 0.2 to 10 liters per 1 mole of a compound [X]. Examples of bases which may used in this reaction are: organic bases such as triethylamine and 1,8-diazabicyclo [5.4.0]-7-undecene; inorganic bases such as: hydroxides of alkali metals, for instance, sodium hydroxide and potassium hydroxide; hydroxides of alkaline earth metals, for instance calcium hydroxide and magnesium hydroxide; carbonates of alkali metals, for instance, sodium carbonate and potassium carbonate; and hydrogen carbonates of alkali metals, for instance, sodium hydrogen carbonate and potassium hydrogen carbonate; metal salts of alcohols, for instance, sodium methoxide, sodium ethoxide and potassium tert-butoxide; hydrides of alkali metals, for instance sodium hydride; or organolithium compounds such as n-butyllithium and lithium diisopropylamide. The quantities of a base to use may normally be appropriately selected from a range of 1 to 10 equivalents, preferably 1 to 5 equivalents, per 1 equivalent of a compound [X]. The reaction temperature is any temperature from −100° C. to reflux temperature in the reaction system, preferably in the temperature range −78° to 100° C. The reaction time will vary according to, for example, the reaction temperature, reaction substrate and quantities reacted, but is normally in the range 1 to 24 hours. After the reaction has been completed, the compound [Ic] may be isolated by carrying out operations such as addition of the reaction mixture to water and extraction with an organic solvent, then concentration. The isolated compound [Ic] may be further purified by means of column chromatography and recrystallization, as required.

Manufacturing Process 6

A compound represented by formula [Ie] may be manufactured according to the undermentioned process from a compound [X].

Scheme 6

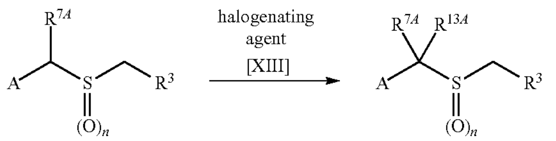

[X]

[Ie]

in the formulae [X] and [Ie], A, $R^3$, $R^{7A}$ and n represent the same meanings as the aforementioned; $R^{13A}$ in formula [Ie] represents a halogen atom.

A compound represented by formula [Ie] may be manufactured by the reaction of a compound [X] and a halogenating agent [XIII], in a solvent, in the presence of a base. Examples of the halogenating agents [XIII] which may be used in the reaction are: halogenated hydrocarbons such as carbon tetrachloride and hexachloroethane; halogen-containing imides such as N-fluorobenzenesulfonimide, N-chlorosuccinimide and N-bromosuccinimide; halogenated sulfur compounds such as sulfuryl chloride and thionyl chloride; halogenated phosphorus compounds such as phosphorus pentachloride and phosphorus oxychloride; N-fluoropyridinium salts such as 1-fluoro-2,4,6-trimethylpyridinium trifluoromethanesulfonate; 1-(chloromethyl)-4-fluoro-1,4-diazoniabicyclo[2.2.2]octane bis(tetrafluoroborate); halogens such as fluorine, chlorine, bromine and iodine; or copper halides such as copper(II) chloride and copper(II) bromide. The quantities to use of a halogenating agent [XIII] used herein may be appropriately selected from, normally the range 1 to 10 equivalents, preferably 1 to 5 equivalents, per 1 equivalent of a compound [X]. Examples of the solvents which may be used in this reaction are: ethers such as diethyl ether, 1,2-dimethoxyethane and tetrahydrofuran; amides such as N,N-dimethylacetamide, N,N-dimethylformamide, 1,3-dimethyl-2-imidazolidinone and N-methyl-2-pyrrolidinone; sulfur compounds such as dimethylsulfoxide and sulfolane; nitriles such as acetonitrile and propionitrile; aromatic hydrocarbons such as benzene, toluene and xylene; halogenated hydrocarbons such as dichloromethane, 1,2-dichloroethane and chlorobenzene; water; or mixtures thereof. The quantities of the above-mentioned solvents are normally 0.1 to 50 liters, preferably 0.2 to 20 liters per 1 mole of a compound [X]. Examples of the bases which may be used for this reaction are the same as those in manufacturing example 5. The quantities of a base to use may normally be appropriately selected from a range of 1 to 10 equivalents, preferably 1 to 5 equivalents, per 1 equivalent of a compound [X]. The reaction temperature is any temperature from −100° C. to reflux temperature in the reaction system, preferably in the temperature range −78° to 100° C. The reaction time will vary according to, for example, the reaction temperature, reaction substrate and quantities reacted, but is normally in the range 1 to 24 hours. After the reaction has been completed, the compound [Ie] may be isolated by carrying out operations such as addition of the reaction mixture to water and extraction with an organic solvent, then concentration. The isolated compound [Ie] may be further purified by means of column chromatography and recrystallization, as required.

Manufacturing Process 7

A compound represented by formula [Ig] may be manufactured according to the undermentioned process.

Scheme 7

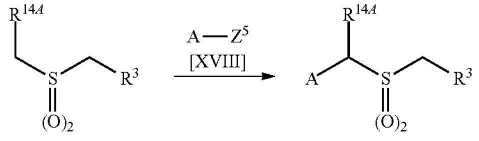

[XVII]

[Ig]

in the formulae [XVII] and [Ig], A and $R^3$ represent the same meanings as the aforementioned, $R^{14A}$ in the formulae in formula [XVII] and [Ig] denotes a cyano group or a C(=O)$R^{10A}$ group $R^{10A}$ represents the same meaning as the aforementioned in formula [X] and [Ic]

$Z^5$ represents a leaving group such as a chlorine atom, bromine atom, iodine atom, or a trifluoromethanesulfonyloxy group.

A compound represented by formula [Ig] may be manufactured by the reaction of a compound [XVII] and a compound [XVIII], in a solvent, in the presence of a base and a transition metal catalyst. This reaction may be carried out with the addition of a phosphine ligand such as triphenylphosphine or tri-tert-butylphosphine, as required.

The quantities to use of a compound [XVIII] used herein may be appropriately selected from, normally the range 1 to 5 equivalents, preferably 1 to 3 equivalents, per 1 equivalent of a compound [XVII]. Examples of the solvents which may be used in this reaction are: ethers such as tetrahydrofuran, 1,4-dioxan and 1,2-dimethoxyethane; nitriles such as acetonitrile and propionitrile; amides such as N,N-dimethylformamide and N,N-dimethylacetamide; and aromatic hydrocarbons such as benzene, toluene and xylene; or mixtures thereof. The quantities of a solvent in the above-mentioned are normally from 0.1 to 50 liters, preferably 0.2 to 20 liters, per 1 mole of a compound (XVII). Examples of bases which may used in this reaction are: organic bases such as triethylamine, diisopropylethylamine and 1,8-diazabicyclo[5.4.0]-7-undecene; inorganic bases such as: hydroxides of alkali metals, for instance, sodium hydroxide and potassium hydroxide; carbonates of alkali metals, for instance, sodium carbonate and potassium carbonate; and hydrogen carbonates of alkali metals, for instance, sodium hydrogen carbonate and potassium hydrogen carbonate; and phosphates such as potassium phosphate; metal salts of alcohols such as sodium methoxide, sodium tert-butoxide and potassium tertbutoxide; or hydrides of alkali metals such as sodium hydride. The quantities of a base to use may normally be appropriately selected from a range of 1 to 10 equivalents, preferably 1 to 5 equivalents, per 1 equivalent of a compound [XVII]. Examples of the transition metal compounds which may be used according to the present invention are palladium compounds such as palladium acetate, dichlorobis(triphenylphosphine) palladium, tetrakis(triphenylphosphine)palladium and tris(dibenzylideneacetone)dipalladium-chloroform. The quantities of a transition metal compound to use may be normally appropriately selected from the range 0.01 to 0.5 equivalents, preferably 0.02 to 0.2 equivalents, per 1 equivalent of a compound [XVII]. The quantities of a phosphine ligand to use may be appropriately selected from the range 0 to 1.5 equivalents per 1 equivalent of a compound [XVII]. The reaction temperature is any temperature from 0° C. to reflux temperature in the reaction system, preferably in the temperature range 20° to 120° C. The reaction time will vary according to, for example, the reaction temperature, reaction substrate and quantities reacted, but is normally in the range 1 to 48 hours. After the reaction has been completed, a compound [Ig] may be isolated by carrying out operations such as addition of the reaction mixture to water and extraction with an organic solvent, then concentration. The isolated compound [Ig] may be further purified by means of column chromatography, as required. A compound [XVII] may also be manufactured according to the processes described in manufacturing process 3 and manufacturing process 4.

Manufacturing Process 8

Of the compounds represented by formula [I], a compound [Ij] may be manufactured according to the undermentioned process.

$Z^7$ represents a halogen atom such as a chlorine atom or a bromine atom. $Z^8$ represents a leaving group such as a chlorine atom, bromine atom, or OC(=O)$R^{19A}$.

Stage (8-2a)

A compound [XXXI] may be manufactured by the reaction of a compound [XXVI] and a compound [XXVII] in a solvent, in the presence of a base. The quantities to use of a compound [XXVII] used herein may be appropriately selected from, normally the range 1 to 5 equivalents, preferably 1 to 2 equivalents, per 1 equivalent of a compound [XXVI]. Examples of the solvents which may be used in this reaction are: ethers such as diethyl ether, 1,2-dimethoxyethane and tetrahydrofuran; nitriles such as acetonitrile and propionitrile; aromatic hydrocarbons such as benzene, toluene and xylene; halogenated hydrocarbons such as dichloromethane, 1,2-dichloroethane and chlorobenzene; alcohols such as methanol, ethanol, or propanol; water; or mixtures thereof. The quantities of solvents in the above-mentioned are normally 0.1 to 50 liters, preferably 0 to 0.2 to 20 liters per 1 mole of a compound [XXVI]. Examples of bases which may be used in this reaction are: organic bases such as triethylamine and 1,8-diazabicyclo[5.4.0]-7-undecene; inorganic bases such as: hydroxides of alkali metals, for instance, sodium hydroxide and potassium hydroxide; hydroxides of alkaline earth metals, for instance calcium hydroxide and magnesium hydroxide; carbonates of alkali metals, for instance, sodium carbonate and potassium carbonate; and hydrogen carbonates of alkali metals, for instance, sodium hydrogen carbonate and potassium hydrogen carbonate. The quantities of a base to use may normally be appropriately Scheme 8

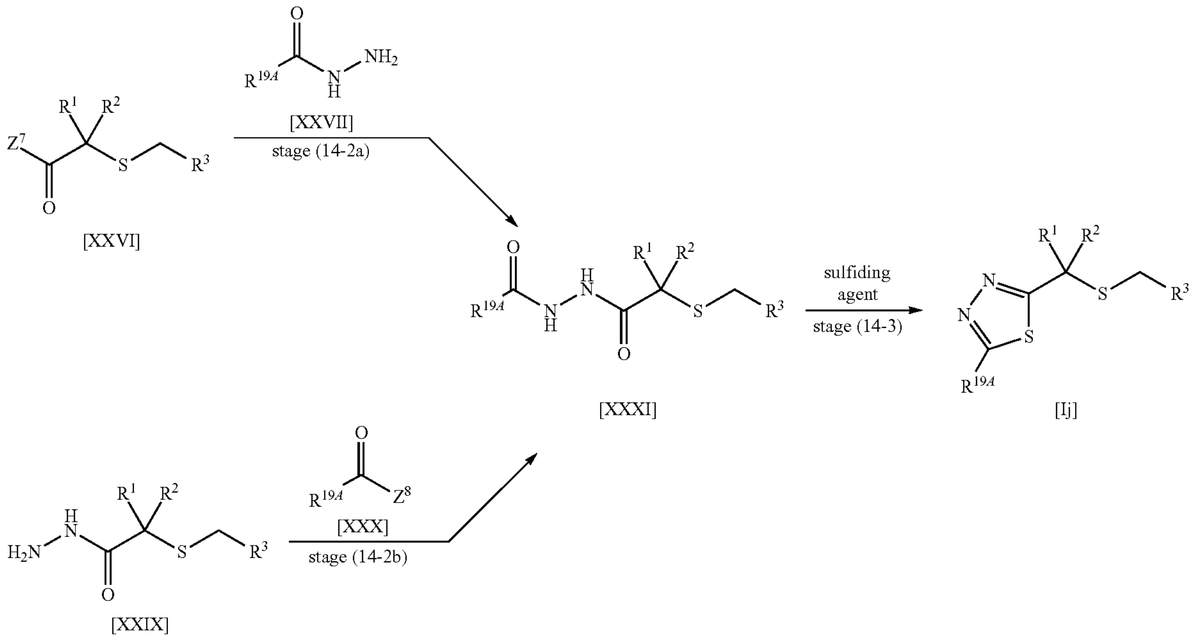

in the formulae in scheme 8, $R^1$, $R^2$ and $R^3$ represent the same meanings as the aforementioned, $R^{19A}$ represents $C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_3$-alkyl;

selected from a range of 1 to 10 equivalents, preferably 1 to 5 equivalents, per 1 equivalent of a compound [XXVI]. The reaction temperature is any temperature from −50° C. to reflux temperature in the reaction system, preferably in the temperature range −20° to 100° C. The reaction time will vary according to, for example, the reaction temperature, reaction substrate and quantities reacted, but is normally in the range 1 to 24 hours. After the reaction has been completed, a compound [XXXI] may be isolated by carrying out operations such as addition of the reaction mixture to water and extraction with an organic solvent, then concentration. The isolated compound [XXXI] may be further purified by means of column chromatography and recrystallization, as required.

Stage (8-2b)

A compound [XXXI] may be manufactured by the reaction of a compound [XXIX] and a compound [XXX] in a solvent, in the presence of a base. The quantities to use of a compound [XXX] used herein may be appropriately selected from, normally the range 1 to 5 equivalents, preferably 1 to 2-equivalents, per 1 equivalent of a compound [XXIX]. Examples of the solvents and bases which may be used in this reaction are the same as for Stage (8-2a). The quantities of solvents in the above-mentioned are normally 0.1 to 50 liters, preferably 0 to 0.2 to 20 liters per 1 mole of a compound [XXIX]. The quantities of a base to use may normally be appropriately selected from a range of 1 to 10 equivalents, preferably 1 to 5 equivalents, per 1 equivalent of a compound [XXIX]. The reaction temperature is any temperature from −50° C. to reflux temperature in the reaction system, preferably in the temperature range −20° to 100° C. The reaction time will vary according to, for example, the reaction temperature, reaction substrate and quantities reacted, but is normally in the range 1 to 24 hours. After the reaction has been completed, a compound [XXXI] may be isolated by carrying out operations such as addition of the reaction mixture to water and extraction with an organic solvent, then concentration. The isolated compound [XXXI] may be further purified by means of column chromatography and recrystallization, as required.

Stage (8-3)

A compound represented by formula [Ij] may be manufactured by the reaction of a compound [XXXI] and a sulfiding agent in a solvent. Examples of the solvents which may be used in this reaction are: ethers such as tetrahydrofuran and 1,4-dioxan; aromatic hydrocarbons such as benzene, toluene and xylene; halogenated hydrocarbons such as chloroform, 1,2-dichloroethane and chlorobenzene; nitriles such as acetonitrile and propionitrile; or mixtures thereof. The quantities of solvents in the above-mentioned are normally 0.1 to 50 liters, preferably 0.2 to 20 liters per 1 mole of a compound [XXXI]. Examples of the sulfiding agents which may be used in the reaction are 2,4-bis(4-methoxyphenyl)-1,3-dithia-2,4-diphosphetane-2,4-disulfide reagent, or phosphorus pentasulfide. The quantities to use of a sulfiding agent used herein may be appropriately selected from normally the range 0.5 to 10 equivalents, preferably 1 to 5 equivalents, per 1 equivalent of a compound [XXXI]. The reaction temperature is normally any temperature from 0° C. to reflux temperature in the reaction system, preferably in the temperature range 20° to 180° C. The reaction time will vary according to, for example, the reaction temperature, reaction substrate and quantities reacted, but is normally in the range 1 to 72 hours. After the reaction has been completed, a compound [Ij] may be isolated by filtering the reaction mixture, then carrying out an operation such as concentration. The isolated compound [Ij] may be further purified by means of column chromatography, as required.

Compound [XXVII] may be manufactured, for example, according to the process described in the Journal of Organic Chemistry pages 102 to 105 (1960).

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt or N-oxide thereof or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of formula I or an agriculturally acceptable salt or N-oxide thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects; arachnids and nematodes, and even more preferably from insects, acarids and nematodes. In the sense of the present invention, "invertebrate pests" are most preferably insects.

The invention further provides an agricultural composition for combating such invertebrate pests, which comprises such an amount of at least one compound of the general formula I or at least one agriculturally useful salt or N-oxide thereof and at least one inert liquid and/or solid agronomically acceptable carrier that has a pesticidal action and, if desired, at least one surfactant.

Such a composition may contain a single active compound of the formula I or a salt or N-oxide thereof or a mixture of several active compounds I or their salts according to the present invention. The composition according to the present invention may comprise an individual isomer or mixtures of isomers as well as individual tautomers or mixtures of tautomers.

The compounds of the formula I and the pestidicidal compositions comprising them are effective agents for controlling arthropod pests and nematodes. Invertebrate pests controlled by the compounds of formula I include for example insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana,*

*Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani and Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Criceris asparagi, Diabrotica longicornis, Diabrotica* 12 *punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribisnigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand*, and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei*, and Eriophyidae spp. such as *Aculus schlechtendali, Phyllocoptrata oleivora* and *Eriophyes sheldoni*; Tarsonemidae spp. such as *Phytonemus pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and *Tetranychus urticae, Panonychus ulmi, Panonychus citri*, and *oligonychus pratensis;* siphonatera, e.g. *Xenopsylla cheopsis, Ceratophyllus* spp.

The compositions and compounds of formula I are useful for the control of nematodes, especially plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formula I are used for controlling insects or arachnids, in particular insects of the orders Lepidoptera, Coleoptera, Thysanoptera and Homoptera and arachnids of the order Acarina. The compounds of the formula I according to the present invention are particularly useful for controlling insects of the order Thysanoptera and Homoptera.

The compounds of formula I or the pesticidal compositions comprising them may be used to protect growing plants and crops from attack or infestation by invertebrate pests, especially insects, acaridae or arachnids by contacting the plant/crop with a pesticidally effective amount of compounds of formula I. The term "crop" refers both to growing and harvested crops.

The compounds of formula I can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation tech-nology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, anti-foaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulphates, alkylsulfonates, fatty alcohol sulfates, fatty acids and sulphated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally color-ants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 1 12, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100 by weight, preferably 95% to 100% % by weight (according to NMR spectrum).

For seed treatment purposes, respective formulations can be diluted 2- to 10-fold leading to concentrations in the ready to use preparations of 0.01 to 60% by weight active compound by weight, preferably 0.1 to 40% by weight.

The compounds of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wetable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to %10, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetting agents or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetting agents and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetting agents and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formula I are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pre-germinated the latter.

In a preferred embodiment a FS formulation is used for seed treatment. Typically, a FS formulation may comprise 1 to 800 g/l of active ingredient, 1 to 200 g/l surfactant, 0 to 200 g/l antifreez-ing agent, 0 to 400 g/l of binder, 0 to 200 g/l of a pigment and up to 1 liter of a solvent, preferably water.

Other preferred FS formulations of compounds of formula I for seed treatment comprise from 0.5 to 80 wt of the active ingredient, from 0.05 to 5 wt of a wetting agent, from 0.5 to 15 wt of a dispersing agent, from 0.1 to 5 wt of a thickener, from 5 to 20 wt of an anti-freeze agent, from 0.1 to 2 wt of an anti-foam agent, from 1 to 20 wt of a pigment and/or a dye, from 0 to 15 wt of a sticker/adhesion agent, from 0 to 75 wt of a filler/vehicle, and from 0.01 to 1 wt of a preservative.

Various types of oils, wetting agents, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

For use against ants, termites, wasps, flies, mosquitoes, crickets, or cockroaches, corn-pounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spraying devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cock-roaches to eat it. The attractiveness can be manipulated by using feeding stimulants or sex pheromones. Food stimulants are chosen, for example, but not exclusively, from animal and/or plant proteins (meat, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g. in spray cans), oil sprays or pump sprays are highly suitable for the non-professional user for controlling pests such as flies, fleas, ticks, mosquitoes or cockroaches. Aerosol recipes are preferably corn-posed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethyl-formamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3 to 7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methyl neodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formula I or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formula I into contact with each other, and "seed dressing" to methods of seed treatment which provide the seeds with an amount of the compounds of formula I, i.e. which generate a seed comprising the compound of formula I. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "un-sown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formula I, or the enantiomers, diastereomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The present invention also provides a non-therapeutic method for treating, controlling, preventing and protecting animals against infestation and infection by parasites, which comprises applying to a locus a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises including a parasiticidally effective amount of a compound of formula I or the enantiomers or veterinarily acceptable salts thereof in a composition comprising it.

The invention relates further to the use of compounds of formula I for treating, controlling, preventing or protecting animals against infestation or infection by parasites.

The invention relates also to the use of a compound of formula I, or a composition comprising it, for the manufacture of a medicament for the therapeutic treatment of animals against infections or infections by parasites.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals. The compounds of formula I or the enantiomers or veterinarily acceptable salts thereof and compositions comprising them are suitable for systemic and/or non-systemic control of ecto- and/or endoparasites. They are active against all or some stages of development.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I are especially useful for combating ectoparasites.

The compounds of formula I are especially useful for combating endoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis,*

*Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., Psoroptes spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp., and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp. a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

Applications

The present invention relates to the therapeutic and the non-therapeutic use of compounds of formula I for controlling and/or combating parasites in and/or on animals.

The compounds of formula I may be used to protect the animals from attack or infestation by parasites by contacting them with a parasitically effective amount of compounds of formula I. As such, "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of compounds of formula I.

"Locus" as defined above means the habitat, food supply, breeding ground, area, material or environment in which a parasite is growing or may grow outside of the animal. The compounds of the invention can also be applied preventively to places at which occurrence of the pests or parasites is expected.

The compounds of formula I can be effective through both contact (via soil, glass, wall, bed net, carpet, blankets or animal parts) and ingestion (e.g. baits).

The administration can be carried out prophylactically, therapeutically or non-therapeutically.

Administration of the active compounds is carried out directly or in the form of suitable preparations, orally, topically/dermally or parenterally.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally it is favorable to apply the compounds of formula I in total amounts of 0.5 mg/kg to 100 mg/kg per day, preferably 1 mg/kg to 50 mg/kg per day.

Formulations

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable Preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable Hydrophobic Phases (Oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable Emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

The compositions which can be used in the invention can comprise generally from about 0.001 to 95% of the compound of formula I.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

The compositions comprising the compounds of formula I them can be applied orally, parenterally or topically, respectively dermally. For example, optionally the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The active compounds can be applied solely or in a mixture with synergists or with other active compounds which act against pathogenic endo- and ectoparasites.

For example, the active compounds of formula I can be applied in mixtures with synthetic coccidiosis compounds, polyetherantibiotics as Amprolium, Robenidin, Toltrazuril, Monensin, Salinomycin, Maduramicin, Lasalocid, Narasin or Semduramicin or with other pesticides which are described in the list M below.

Compositions to be used according to this invention for agricultural or veterinary purposes may also contain other active ingredients, for example other pesticides, insecticides, herbicides, fungicides, bactericides, fertilizers such as ammonium nitrate, urea, potash, and super-phosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formula I or the compositions comprising them in the use form as pesticides with other pesticides frequently results in a broader pesticidal spectrum of action.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphosethyl, azinphosmethyl, chlorethoxyfos, chlorfenvinphos, chlormephos, chlorpyrifos, chlorpyrifos-methyl, coumaphos, cyanophos, demeton-5-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, para-thion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cistrans allethrin, d-trans allethrin, bifenthrin, bioallethrin, bioallethrin S-cylclopentenyl, bioresmethrin, cycloprothrin, cyfluthrin, betacyfluthrin, cyhalothrin, lambda-cyhalothrin, gamma-cyhalothrin, cypermethrin, alphacypermethrin, betacypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultapsodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonists: amitraz;

M.21. Ryanodine receptor modulators: flubendiamide,(R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydroisoxazol-3-yl]-2-methyl-N-pyridin-2-ylmethyl-benzamide (M22.1), 4-[5-(3,5-Dichlorophenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoroethylcarbamoyl)-methyl]-amide (M22.4) and 4-[5-(3,5-Dichlorophenyl)-5-trifluoromethyl-4,5-dihydro-isoxazol-3-yl]-N—[(methoxyimino)methyl]-2-methylbenzamide (M22.5), 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6); 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole,

5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methylbenzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoropropyl)malononitrile (CF2H—CF2-CF2-CF2-CH2-C(CN)2-CH2-CH2-CF3) (M24.1) and 2-(2,2,3,3,4,4,5,5-octafluoropentyl)-2-(3,3,4,4,4-pentafluorobutyl)-malonodinitrile ($CF_2H—CF_2—CF_2—CF_2—CH_2—C(CN)_2—CH_2—CH_2—CF_2—CF_3$) (M24.2);

M.25. Microbial disruptors: *Bacillus thuringiensis* subsp. *Israelensi, Bacillus sphaericus, Bacillus thuringiensis* subsp. *Aizawai, Bacillus thuringiensis* subsp. *Kurstaki, Bacillus thuringiensis* subsp. *Tenebrionis;*

M.26. Aminofuranone Compounds:

4-{[(6-Bromopyrid-3-yl)methyl](2-fluoroethyl)amino}furan-2(5H)-on (M26.1),

4-{[(6-Fluoropyrid-3-yl)methyl](2,2-difluoroethyl)amino}furan-2(5H)-on (M26.2),

4-{[(2-Chlorol,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl](2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl)amino}furan-2(5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R''' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoropyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethylpyridazin-3-yl)-3-aza-bicyclo[3.2.1]octane (M27.3).

The commercially available compounds of the group M may be found in The Pesticide Manual, 14th Edition, British Crop Protection Council (2006).

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779. AKD 1022 and its preparation have been described in U.S. Pat. No. 6,300,348. The compounds (M22.6) and (M22.7) are known from WO 2009/126668 and the compound (M22.8) is known from WO 2009/051956. The anthranilamides M23.1 to M23.6 have been described in WO 2008/72743 and WO 2008/72783, those M23.7 to M23.12 in WO 2007/043677. The phthalamide M 21.1 is known from WO 2007/101540. The alkynylether compound M27.1 is described e.g. in JP 2006/131529. Organic sulfur compounds have been described in WO 2007/060839. The isoxazoline compounds M 22.1 to M 22.5 have been described in e.g. WO 2005/085216, WO 2007/079162 and WO 2007/026965. The aminofuranone compounds M 26.1 to M 26.10 have been described eg. in WO 2007/1 15644. The pyripyropene derivative M 27.2 has been described in WO 2008/66153 and WO 2008/108491. The pyridazin compound M 27.3 has been described in JP 2008/1 15155. Malononitrile compounds as those (M24.1) and (M24.2) have been described in WO 2002/089579, WO 2002/090320, WO 2002/090321, WO 2004/006677, WO 2005/068423, WO 2005/068432 and WO 2005/063694.

The following list of active substances, in conjunction with which the compounds according to the invention can be used, is intended to illustrate the possible combinations but does not limit them:

F.I) Respiration Inhibitors

F.I-1) Inhibitors of complex III at Qo site (e.g. strobilurins)

strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxy-imino-N methylacetamide;

oxazolidinediones and imidazolinones: famoxadone, fenamidone;

F.I-2) Inhibitors of complex II (e.g. carboxamides):

carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5'trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;

F.I-3) Inhibitors of complex III at Qi site: cyazofamid, amisulbrom;

F.I-4) Other respiration inhibitors (complex I, uncouplers)

diflumetorim; tecnazen; ferimzone; ametoctradin; silthiofam;

nitrophenyl derivates: binapacryl, dinobuton, dinocap, fluazinam, nitrthal-isopropyl, organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles)

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole;

imidazoles: imazalil, pefurazoate, oxpoconazole, prochloraz, triflumizole;

pyrimidines, pyridines and piperazines: fenarimol, nuarimol, pyrifenox, triforine;

F.II-2) Delta 14-reductase inhitors (Amines, e.g. morpholines, piperidines)

morpholines: aldimorph, dodemorph, dodemorph-acetate, fenpropimorph, tridemorph;

piperidines: fenpropidin, piperalin;

spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.III-2) DNA topisomerase inhibitors: oxolinic acid;

F.III-3) Nucleotide metabolism (e.g. adenosin-deaminase) hydroxy (2-amino)-pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;

triazolopyrimidines: 5-chloro-7(4-methylpiperidin-1-yl)-6-(2,4,6-trifluorophenyl)-[1,2,4]triazolo[1,5a]pyrimidine F.IV-2) Other cell division inhibitors benzamides and phenyl acetamides: diethofencarb, ethaboxam, pencycuron, fluopicolide, zoxamide;

F.IV-3) Actin inhibitors: benzophenones: metrafenone;

F.V) Inhibitors of amino acid and protein synthesis

F.V-1) Mmethionine synthesis inhibitors (anilino-pyrimidines)

anilino-pyrimidines: cyprodinil, mepanipyrim, nitrapyrin, pyrimethanil;

F.V-2) Protein synthesis inhibitors (anilino-pyrimidines) antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines)

dicarboximides: fluoroimid, iprodione, procymidone, vinclozolin;

phenylpyrroles: fenpiclonil, fludioxonil;

F.VI-2) G protein inhibitors: quinolines: quinoxyfen;

F.VI I) Lipid and membrane synthesis inhibitors

F.VI 1-1) Phospholipid biosynthesis inhibitors organophosphorus compounds: edifenphos, iprobenfos, pyrazophos;

dithiolanes: isoprothiolane;

F.VII-2) Lipid peroxidation aromatic hydrocarbons: dicloran, quintozene, tecnazene, tolclofos-methyl, biphenyl, chloroneb, etridiazole;

F.VII-3) Carboxyl acid amides (CAA fungicides)

cinnamic or mandelic acid amides: dimethomorph, flumorph, mandipropamid, pyrimorph;

valinamide carbamates: benthiavalicarb, iprovalicarb, pyribencarb, valifenalate and N-(1-(1-(4-cyano-phenyl) ethanesulfonyl)-but-2-yl) carbamic acid-(4-fluorophenyl) ester;

F.VII-4) Compounds affecting cell membrane permeability and fatty acides carbamates: propamocarb, propamocarb-hydrochlorid F.VI II) Inhibitors with Multi Site Action F.VI 11-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles):

anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitrophenyl)-N-ethyl-4-methyl-benzenesulfonamide;

F.VIII-4) Guanidines: guanidine, dodine, dodine free base, guazatine, guazatine-acetate, iminoctadine, iminoctadine-triacetate, iminoctadine-tris(albesilate);

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-S-methyl;

F.X-2) Others: probenazole, isotianil, tiadinil, prohexadione-calcium;

phosphonates: fosetyl, fosetyl-aluminum, phosphorous acid and its salts;

F.XI) Unknown mode of action:

bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)methyl)-2-phenylacetamide, N'-(4-(4-chloro-3-trifluoromethyl-phenoxy)-2,5-dimethyl-phenyl)N-ethyl-N methyl formamidine, N'(4-(4-fluoro-3-trifluoromethyl-phenoxy)-2,5-dimethylphenyl)-N-ethyl-N-methyl formamidine, N'-(2-methyl-5-trifluoromethyl-4-(3-trimethylsilanylpropoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)acetyl]piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl] piperidin-4-yl}-N-[(1R)-1,2,3,4-tetrahydronaphthalen-1-yl]-4-thiazolecarboxamide, 3-[5-(4-chloro-phenyl)-2,3-dimethylisoxazolidin-3yl]-pyridine (pyrisoxazole), 3-[5-(4-methyl-phenyl)-2,3-dimethyl-isoxazolidin-3-yl]-pyridine, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

F.XI) Growth regulators:
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodo-benzoic acid, trinexapac-ethyl and uniconazole;

F.XI I) Biological control agents antifungal biocontrol agents: *Bacillus substilis* strain with NRRL No. B-21661 (e.g. RHAPSODY®, SERENADE® MAX and SERENADE® ASO from AgraQuest, Inc., USA.), *Bacillus pumilus* strain with NRRL No. B-30087 (e.g. SONATA® and BALLAD® Plus from AgraQuest, Inc., USA), *Ulocladium oudemansii* (e.g. the product BOTRYZEN from BotriZen Ltd., New Zealand), Chitosan (e.g. ARMOUR-ZEN from BotriZen Ltd., New Zealand).

The invertebrate pest, i.e. arthropodes and nematodes, the plant, soil or water in which the plant is growing can be contacted with the compound(s) of formula I or composition(s) containing them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

Moreover, invertebrate pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

"Locus" in general means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and the compositions comprising said compounds can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formula I can also be applied preventively to places at which occurrence of the pests is expected.

The compounds of formula I may also be used to protect growing plants from attack or infestation by pests by contacting the plant with a pesticidally effective amount of compounds of formula I. As such, "contacting the plant" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 5 g to 600 g per hectare, more desirably from 10 g to 300 g per hectare.

In the treatment of seed, the application rates of the active ingredients are generally from 0.1 g to 10 kg per 100 kg of seed, preferably from 1 g to 1 kg per 100 kg of seed, in particular from 1 g to 250 g per 100 kg of seed, in particular from 50 g to 150 g per 100 kg of seed.

The present invention is now illustrated in further detail by the following examples which are not intended to limit the invention to them.

I. PREPARATION EXAMPLES

Products were characterized by HPLC-MS (High Performance Liquid Chromatography Mass Spectrometry). HPLC was carried out using an analytic RP-18e column (Chromolith Speed ROD from Merck KgaA, Germany) which was operated at 40° C. Acetonitrile with 0.1% by volume of a trifluoroacetic acid/water mixture and 0.1% by volume of trifluoroacetic acid served as mobile phase; flow rate: 1.8 mL/min and injection volume: 2 μl.

Following notations when used in the text are as follows defined:

n-BuLi n-butyllithium
m-CPBA m-chloroperoxybenzoic acid
DCM dichloromethane
DIPEA N,N-diisopropylethylamine
DME 1,2-dimethoxy ethane
DMP Dess-Martin periodinane DMSO dimethylsulfoxide
EtOAc ethyl acetate
EtOH ethanol
M molar
NCS N-chlorosuccinimide
TFAA trifluoroacetic anhydride
THF tetrahydrofuran
TLC thin layer chromatography
p-TsOH p-toluene sulfonic acid Scheme for the preparation of the representative examples 7, 8 and 9:

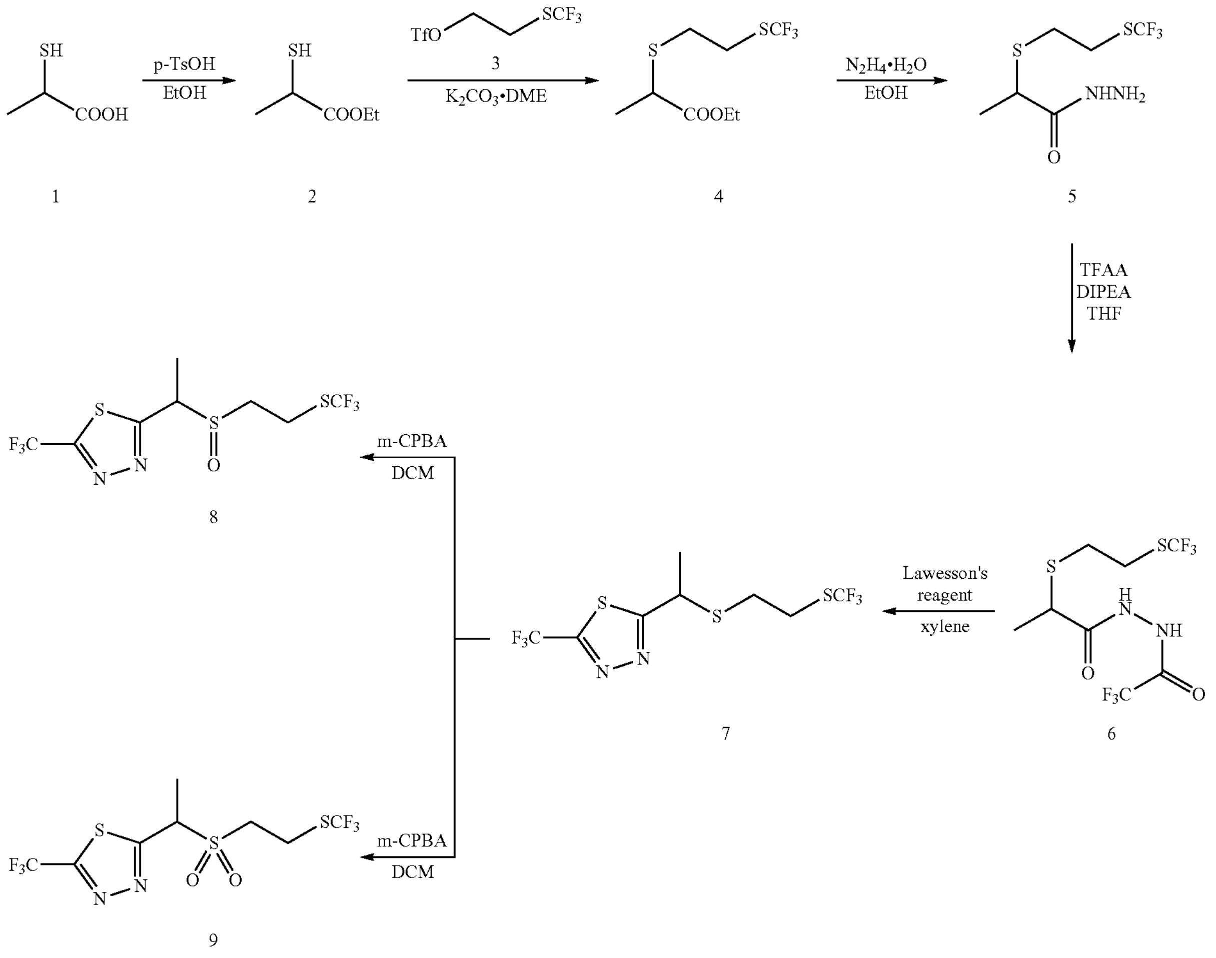

Preparation of 2-(Trifluoromethyl)-5-{1-[2-(trifluoromethylthio)ethylthio]ethyl}-1,3,4-thiadiazole (7, correspond to example 11-1)

To a stirred solution of hydrazide 6 (0.55 g, 1.59 mmol) in xylene (20 ml) was added Lawesson's reagent (0.64 g, 1.59 mmol) at room temperature. The mixture was then stirred and heated at 120° C. for 2 h and at reflux for 18 h. The solvent was removed in vacuum; the crude residue was purified by column chromatography (silica gel, eluent: hexanes/EtOAc, gradient 9:1 to 8:2) to afford the title compound (0.28 g, 51%) as yellow oil.

Preparation of 2-(Trifluoromethyl)-5-{1-[2-(trifluoromethylthio)ethylsulfinyl]ethyl}-1,3,4-thiadiazole (8, correspond to example 11-3)

To a stirred and chilled (0° C.) solution of thiadiazole 7 (0.50 g, 1.46 mmol) in anhydrous $CH_2Cl_2$ (10 ml) was added m-CPBA (77%, 0.39 g, 1.75 mmol), and the mixture was stirred at 0° C. for 30 min under nitrogen. Reaction mixture was quenched with $NaHCO_3$ (aq. sat., 50 ml) and extracted with EtOAc (2×100 ml). Combined organic layers were washed with $NaHCO_3$ (aq. sat., 3×50 ml), water (2×100 ml), brine (2×50 ml), dried over sodium sulfate and concentrated in vacuum. The residue was purified by column chromatography (silica gel, eluent: hexanes/EtOAc, gradient 1:1 to 3:7) to afford the title compound (0.32 g, 61%) as colorless oil.

Preparation of 2-(Trifluoromethyl)-5-{1-[2-(trifluoromethylthio)ethylsulfonyl]-ethyl}-1,3,4-thiadiazole (9, correspond to example 11-2)

To a stirred and chilled (0° C.) solution of thiadiazole 7 (0.50 g, 1.46 mmol) in anhydrous $CH_2Cl_2$ (15 ml) was added m-CPBA (77%, 0.98 g, 4.38 mmol), and the mixture was stirred at room temperature for 30 min under nitrogen. The reaction mixture was quenched with sat.NaHCOs (100 ml) and extracted with EtOAc (2×100 ml). Combined organic layers were washed with Na—$HCO_3$ (aq. sat., 2×150 ml), water (2×100 ml), brine (2×50 ml), dried over sodium sulfate and concentrated in vacuum. The residue was purified by column chromatography (silica gel, eluent: hexanes/EtOAc, gradient 4:1 to 1:1) to afford the title compound (0.36 g, 66%) as white solid

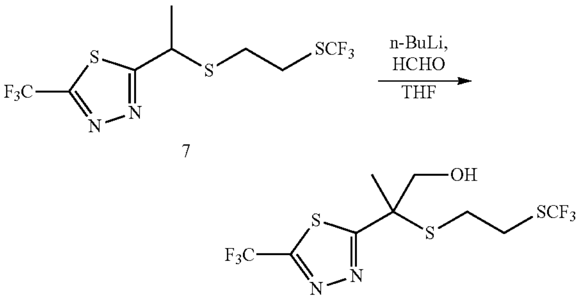

7

10

Preparation of 2-[5-(trifluoromethyl)-1,3,4-thiadiazol-2-yl]-2-[2-(trifluoromethylthio)ethylthio]propan-1-ol (10, correspond to example 11-4)

To a stirred and chilled (−78° C.) solution of thiadiazole 7 (2.0 g, 5.8 mmol) in THF (20 ml) was added n-BuLi (1.6 M in hexanes, 4.0 ml, 6.4 mmol) dropwise. The reaction mixture was stirred at this temperature for 30 min under nitrogen. Paraformaldehyde (0.52 g, 17.523 mmol) in THF (20 ml) was added dropwise and the reaction mixture was slowly warmed to room temperature. Stirring was continued for additional 2 h. The mixture was quenched with $NH_4Cl$ (aq. sat., 150 ml), and extracted with EtOAc (2×150 ml). Combined organic layers were washed with water (2×100 ml), brine (2×50 ml), dried over sodium sulfate and concentrated in vacuum. The residue was purified by column chromatography (silica gel, eluent: hexanes/EtOAc, gradient 7:3 to 3:2) to afford the title compound (1.3 g, 60%) as yellow oil.

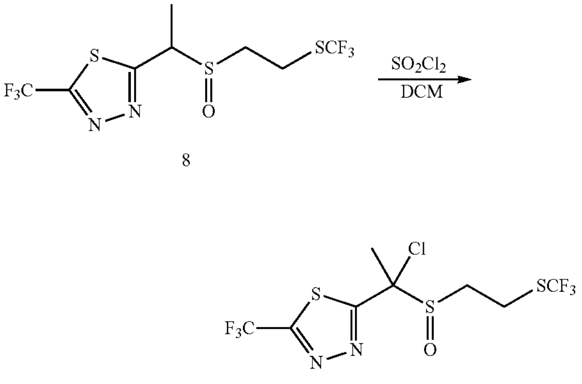

8

11

Preparation of 2-{1-Chloro-1-[2-(trifluoromethylthio)ethylsulfinyl]ethyl}-5-(trifluoromethyl)-1,3,4-thiadiazole (11, correspond to example 1-8)

To a stirred and chilled (0° C.) solution of thiadiazole 8 (0.50 g, 1.4 mmol) in anhydrous $CH_2Cl_2$ (5 ml) was added sulfuryl chloride (0.11 ml, 1.4 mmol) under nitrogen. Reaction mixture was quenched with $NaHCO_3$ (sat. aq., 30 ml) and extracted with EtOAc (2×50 ml). Combined organic layers were washed with brine (2×50 ml), dried over sodium sulfate and concentrated. The residue was purified by preparative TLC (silica gel, multiple runs; mobile phase: hexanes/EtOAc 9:1) to afford the title compound (0.130 g, 23%) as light yellow oil.

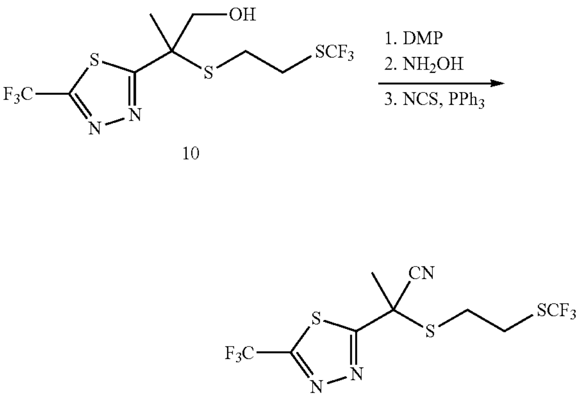

10

12

Preparation of 2-(5-(trifluoromethyl)-1,3,4-thiadiazol-2-yl)-2-(2-(trifluoromethylthio)ethylthio)propanenitrile; (12, correspond to example 11-9)

To a stirred and chilled (0° C.) solution of thiadiazole 10 (0.79 g, 2.1 mmol) in anhydrous $CH_2Cl_2$ (10 ml) was added Dess-Martin periodinane (1.08 g, 2.5 mmol) under nitrogen. Stirring continued at room temperature for 2 h, the reaction mixture was quenched with water (50 ml) and extracted with $CH_2Cl_2$ (3×50 ml). Combined organic layers were washed with $NaHCO_3$ (sat. aq., 3×50 ml), brine (2×50 ml), dried over sodium sulfate and concentrated in vacuum to afford the corresponding aldehyde (0.65 g, 82%) as yellow syrup.

To a stirred under nitrogen solution of the crude aldehyde (0.65 g, 1.8 mmol) in EtOH (7 ml) was added hydroxylamine hydrochloride (0.366 g, 5.3 mmol), followed by addition of sodium acetate (0.435 g, 5.3 mmol) at room temperature. After 12 h stirring and removal of the solvent, water (50 ml) was added to the residue, and the reaction mixture was extracted with EtOAc (3×50 ml). Combined organic layers were washed with brine (2×50 ml), dried over sodium sulfate and concentrated to yield the corresponding oxime (0.54 g, 80%) as beige solid.

To a stirred solution of triphenylphosphine (0.633 g, 2.4 mmol) and N-chlorosuccinimide (0.322 g, 2.4 mmol) in $CH_2Cl_2$ (15 ml) was added the crude oxime (0.71 g, 2.0 mmol) in $CH_2Cl_2$ (5 ml) at room temperature under nitrogen. After 30 min of stirring the organic layer was removed under reduced pressure, and the residue was purified by column chromatography (silica gel, eluent: hexanes/EtOAc 4:1) to afford the title compound (0.240 g, 35%) as light yellow oil.

The procedures described in the synthesis examples above were used to prepare further compounds by appropriate modification of the starting compounds. The compounds thus obtained are listed in the table below, together with physicochemical data.

Examples and Biology (I1-x)

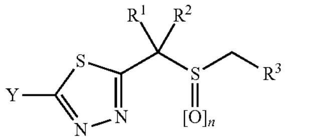

| Example | Y | $R^1$ | $R^2$ | $R^3$ | n | Phys.data: [min] r.t./ | m/z |
|---|---|---|---|---|---|---|---|
| I1-1 | $CF_3$ | H | Me | $CH_2SCF_3$ | 0 | 4.011 | 342.4 |
| I1-2 | $CF_3$ | H | Me | $CH_2SCF_3$ | 2 | 3.481 | 374.4 |
| I1-3 | $CF_3$ | H | Me | $CH_2SCF_3$ | 1 | 3.161 | 358.4 |
| I1-4 | $CF_3$ | $CH_2OH$ | Me | $CH_2SCF_3$ | 0 | 3.602 | 372.4 |
| I1-5 | $CF_3$ | $CH_2OH$ | Me | $CH_2SCF_3$ | 1 | 3.039 | 388.4 |
| I1-6 | $CF_3$ | Cl | Me | $CH_2SCF_3$ | 2 | 3.811 | 408.8 |
| I1-7 | $CF_3$ | $CH_2OH$ | Me | $CH_2SCF_3$ | 2 | 3.307 | 404.4 |
| I1-8 | $CF_3$ | Cl | Me | $CH_2SCF_3$ | 1 | 3.643 | 392.8 |
| I1-9 | $CF_3$ | CN | Me | $CH_2SCF_3$ | 0 | 3.864 | 367.4 |
| I1-10 | $C_2F_5$ | H | Me | $CH_2SCF_3$ | 0 | 4.273 | 392.4 |
| I1-11 | $C_2F_5$ | H | Me | $CH_2SCF_3$ | 1 | 3.523 | 408.4 |
| I1-12 | $C_2F_5$ | H | Me | $CH_2SCF_3$ | 2 | 3.781 | 424.4 |
| I1-13 | $CF_3$ | H | Me | $CH_2OCF_3$ | 0 | 3.807 | 327.0 |
| I1-14 | $CF_3$ | H | Me | $CH_2OCF_3$ | 1 | 2.959 | 342.9 |
| I1-15 | $CF_3$ | H | Me | $CH_2OCF_3$ | 2 | 3.249 | 358.9 |

r.t. is HPLC retention time in minutes
m/z of the [M+] peaks

II. EVALUATION OF PESTICIDAL ACTIVITY 11.1 Activity Against Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications. After application, 5 to 8 adult aphids were placed on the artificial membrane inside the microtiter plate wells. The aphids were then allowed to suck on the treated aphid diet and incubated at about 23+1° C. and about 50+5% relative humidity for 3 days. Aphid mortality and fecundity was then visually assessed.

In this test, compounds 11-7, 11-11 and 11-14, respectively at 2500 ppm showed 100% mortality in comparison with untreated controls.

II.2 Activity Against Cowpea Aphid (*Aphis craccivora*)

The active compounds were formulated in 50:50 (vohvol) acetone:water. The test solution was prepared at the day of use.

Potted cowpea plants colonized with 100-150 aphids of various stages were sprayed after the pest population had been recorded. Population reduction was assesed after 24, 72, and 120 hours.

In this test, the compounds 11-2, 11-3, 11-6, 11-10, 11-11 and 11-12, respectively, at 500 ppm showed a mortality of at least 75% in comparison with untreated controls.

11.3 Activity Against Vetch Aphid (*Megoura viciae*)

The active compounds were formulated in 1:3 (vol:vol) DMSO:water with different concentrations of formulated compounds.

Bean leaf disks were placed into microtiterplates filled with 0.8% agar-agar and 2.5 ppm OPUST™. The leaf disks were sprayed with 2.5 μl of the test solution and 5 to 8 adult aphids were placed into the microtiterplates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds 11-1, 11-2, 11-3, 11-6, 11-7, 11-11 and 11-12, respectively at a concentration of the test solution of 2500 mg/L showed 100% mortality in comparison with untreated controls.

11.4 Activity against Silverleaf Whitefly (*Bemisia argentifolii*, adult)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compound 11-2 at 500 ppm and the compound 11-11 at 300 ppm showed a mortality of at least 75% in comparison with untreated controls.

11.5 Activity Against Boll Weevil (*Anthonomus grandis*)

The compounds were formulated in 75:25 (vohvol) water: DMSO.

For evaluating control of boll weevil (*Anthonomus grandis*) the test unit consisted of 24-well-microtiter plates containing an insect diet and 20-30 *A. grandis* eggs. Different concentrations of formulated compounds were sprayed onto the insect diet at 20 μl, using a custom built micro atomizer, at two replications. After application, the microtiter plates were incubated at 23±1° C. and 50±5% relative humidity for 5 days. Egg and larval mortality was then visually assessed.

In this test, the compounds 11-1, 11-2, 11-3, 11-6, 11-7, 11-8, 11-10, 11-11 and 11-12, respectively at a concentration of the test solution of 2500 mg/L showed a mortality of 100% mortality in comparison with untreated controls.

11.6 Activity Against Vanda/Orchid *Thrips* (*Dichromothrips corbetti*)

The active compounds were formulated as a 50:50 (vohvol) acetone:water solution. Surfactant (Alkamuls® EL 620 from Rhodia) was added at the rate of 0.1% (vol/vol). Vanda orchids petals were cleaned, washed and air dried prior to dipping. Petals were dipped into the test solution for 3 seconds, air dried, placed inside a resealable plastic and inoculated with 20 adults. The treated petals were kept inside the holding room at 28-29° C. and relative humidity of 50-60%. Percent mortality was recorded after 72 hours.

In this test, compounds 11-2 and 11-3, respectively at 500 ppm and compound 11-11 at 300 ppm showed a mortality of at least 75% in comparison with untreated controls.

11.7 Activity Against Brown Planthopper (*Nilaparvata lugens*)

The active compounds were formulated as a 50:50 (vohvol) acetone:water solution. Surfactant (Alkamuls® EL 620 from Rhodia) was added at the rate of 0.1% (vol/vol).

Rice seedlings were cleaned and washed 24 h before spraying. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compounds 11-3, 11-8, 11-11 and 11-12, respectively at 500 ppm showed a mortality of at least 75% in comparison with untreated controls.

11.8 Activity Against Mediterranean Fruitfly (*Ceratitis capitata*)

The active compounds were formulated in 1:3 (vohvol) DMSO:water.

For evaluating control of Mediterranean fruitfly the test unit consisted of microtiter plates containing an insect diet and 50 to 80 *C. capitata* eggs.

Different concentrations of formulated compounds were sprayed onto the insect diet at 5 µl, using a custom built micro atomizer, at two replications. After application, microtiter plates were incubated at 28±1° C. and 80±5% relative humidity for 5 days. Egg and larval mortality was then visually assessed.

In this test the eggs which have been treated with 2500 ppm of compound 11-2, 11-9 and 11-11, respectively showed a mortality of at least 50%.

11.9 Activity Against Diamondback Moth (*Plutella xylostella*)

The active compounds were formulated in 50:50 acetone: water and 0.1% (vol/vol) Alkamuls® EL 620 surfactant. A 6 cm leaf disk of cabbage leaves was dipped in the test solution for 3 seconds and allowed to air dry in a Petri plate lined with moist filter paper. The leaf disk was inoculated with 10 third instar larvae and kept at 25-27° C. and 50-60% humidity for 3 days. Mortality was assessed after 72 h of treatment.

In this test, the compound 11-3 at a concentration of the test solution of 500 ppm showed a mortality of at least 75% in comparison with untreated controls.

We claim:

1. A compound of formula I, or a salt or N-oxide thereof:

(I)

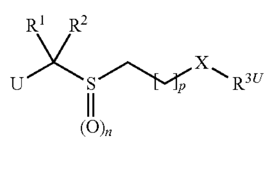

wherein

X is O or $S(=O)_m$;

m is 0, 1 or 2;

n is 0, 1 or 2;

p is 1 or 2

$R^{3U}$ is $C_1$-$C_{10}$-haloalkyl, $C_2$-$C_6$-haloalkenyl, $C_3$-$C_6$-haloalkynyl, $C_3$-$C_6$-halocycloalkyl or $C_3$-$C_6$-halocycloalkenyl, wherein at least one halogen in said $C_1$-$C_{10}$-haloalkyl, $C_2$-$C_6$-haloalkenyl, $C_3$-$C_6$-haloalkynyl, $C_3$-$C_6$-halocycloalkyl or $C_3$-$C_6$-halocycloalkenyl is fluorine;

U is a 5- to 12-membered monocyclic or bicyclic heteroaromatic ring-system which may contain 1 to 4 heteroatoms selected from O, S and N, wherein the heteroaromatic ring may be substituted by one to four substituents V;

V is independently halogen, $C_1$-$C_6$-alkyl, $C_1$-$C_6$-haloalkyl, $C_3$-$C_6$-cycloalkyl-$C_1$-$C_3$-alkyl which may be substituted with halogen atoms, $C_2$-$C_6$-alkenyl, $C_2$-$C_6$-haloalkenyl, $C_2$-$C_6$-alkynyl, $C_2$-$C_6$haloalkynyl, $C_3$-$C_6$-cycloalkyl, $C_3$-$C_6$-halocycloalkyl, $C_1$-$C_6$-alkoxy, $C_1$-$C_6$-haloalkoxy, $C(=O)R^4$, $C(=S)R^4$, $S(O)_oR^{10}$, CN, $NO_2$ or an amino group which may be substituted or disubstituted by $C_1$-$C_4$-alkyl or by $C_1$-$C_4$-acyl;

o is 0, 1 or 2;

$R^1$ and $R^2$ are independently of each other selected from the group consisting of hydrogen, halogen, $C_1$-$C_6$-alkyl which may be substituted by halogen, by $C_1$-$C_4$-alkoxy, by $C_1$-$C_4$-alkylthio, by $C_1$-$C_4$-alkylsulfinyl, by $C_1$-$C_6$-alkylsulfonyl, by CN, by $C(=O)R^4$, by $OC(=O)R^4$, by $N-(C_1$-$C_3$-alkyl$)_2$, or by OH, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_3$-alkyl which may be substituted by one or more halogen atom(s), CN, $C(=O)R^7$, $C(=S)R^7$, $C(R^{11})=NR^{12}$ and $C(R^{11})=N-OR^{12}$, or $R^1$ and $R^2$ may form together with the carbon atom whereto they are bonded $C_3$-$C_6$-cycloalkyl, $C=C(R^5)R^6$ or $C=N-OR^5$;

$R^4$ is hydrogen, hydroxyl, $C_1$-$C_6$-alkyl, $C_1$-$C_6$-haloalkyl, $C_1$-$C_6$-alkoxy or $NR^8R^9$;

$R^5$ is hydrogen or $C_1$-$C_4$-alkyl;

$R^6$ is $C_1$-$C_6$-alkoxy or $NR^8R^9$;

$R^7$ is hydrogen, $C_1$-$C_6$-alkyl, $C_1$-$C_6$-haloalkyl, OH, $C_1$-$C_6$-alkoxy which may be substituted by halogen, by $C_1$-$C_4$-alkoxy, by $C_1$-$C_4$-alkoxy-$C_1$-$C_4$-alkoxy, by $C_1$-$C_4$-alkylthio, by $C_1$-$C_4$-alkylsulfinyl, by $C_1$-$C_6$-alkylsulfonyl, by $C_3$-$C_6$-cycloalkyl, by tetrahydrofuryl, by phenyl, by pyridyl; wherein said phenyl or pyridyl may be substituted by halogen, by CN, by $C(=O)OR^{12}$ or by $C(=O)NR^{11}R^{12}$, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyloxy which may be substituted by halogen, $C_3$-$C_6$-cycloalkylthio which may be substituted by halogen, $NR^8R^9$, $C_1$-$C_6$-alkylthio, $N(R^{13})C(=O)N(R^{14})R^{15}$ or the following groups W to $W^5$:

$W^1$

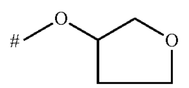

$W^2$

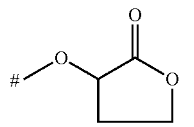

$W^3$

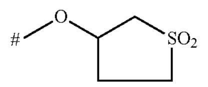

$W^4$

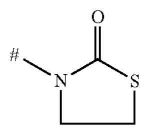

-continued

W5

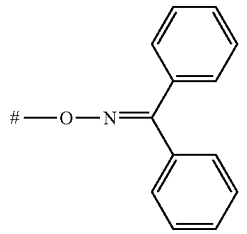

$R^8$ and $R^9$ form together with the nitrogen atom to which they are attached an amino, or mono-($C_1$-$C_6$-alkyl) amino or di-($C_1$-$C_4$-alkyl)amino or a $C_2$-$C_5$-cyclic amino group;

$R^{11}$, $R^{12}$, $R^{13}$, $R^{14}$ and $R^{15}$ are independently hydrogen or $C_1$-$C_6$-alkyl;

$R^{10}$ is $C_1$-$C_6$-alkyl which may be substituted by halogen, by $C_1$-$C_4$-alkoxy, by $C_1$-$C_4$-alkoxy-$C_1$-$C_4$-alkoxy, by $S(O)_0$—$C_1$-$C_6$-alkyl, by phenyl or by tetrahydrofuryl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl or $C_3$-$C_6$-cycloalkyl-$C_1$-$C_3$-alkyl which may be substituted with halogen atoms.

2. A compound according to claim 1, wherein

U is a 5- to 10-membered monocyclic or bicyclic heteroaromatic ring-system selected from the group consisting of pyridine, pyrimidine, pyrazine, pyridazine, 1,3,5-triazine, quinoline, 1H-indole, 1H-benzoimidazole, benzothiazole, benzooxazole, benzofuran, benzothiophene, 1H-pyrrole, 1H-pyrazole, 1H-1,2,4-triazole, 1H-imidazole, 1H-1,2,3-triazole, 1H-tetrazole, thiophene, thiazole, 1,3,4-thiadiazole, furan, oxazole, isoxazole, 1,2,4-oxadiazole and 1,3,4-oxadiazole, wherein the heteroaromatic ring may be substituted by V;

p is 1;

X is $S(=O)_m$ with m being 0, 1 or 2; and $R^{3U}$ is $C_1$-$C_3$-fluoroalkyl.

3. A compound according to claim 1 wherein

U is a 5-membered heteroaromatic ring selected from the group consisting of 1H-pyrrole, 1H-pyrazole, 1H-1,2,4-triazole, 1H-imidazole, 1H-1,2,3-triazole, 1H-tetrazole, thiophene, thiazole, 1,3,4-thiadiazole, furan, oxazole, isoxazole, 1,2,4-oxadiazole and 1,3,4-oxadiazole, wherein the heteroaromatic ring is substituted by V;

p is 1

X is $S(=O)_m$ with m being 0 or 1; and $R^{3U}$ is $C_1$-$C_3$-fluoroalkyl.

4. A compound according to claim 1, wherein:

U is a 5-membered heteroaromatic ring selected from the group consisting of 1H-pyrrole, 1H-pyrazole, 1H-1,2,4-triazole, 1H-imidazole, 1H-1,2,3-triazole, 1H-tetrazole, thiophene, thiazole, 1,3,4-thiadiazole, furan, oxazole, isoxazole, 1,2,4-oxadiazole and 1,3,4-oxadiazole, wherein the heteroaromatic ring is substituted by V; and $R^1$ and $R^2$ are independently from each other selected from the group consisting of H, $C_1$-$C_4$-alkyl, Cl, CN, C(O)—$C_1$-$C_4$-alkyl, C(O)—$C_1$-$C_4$-alkoxy, $C(O)NH_2$, C(O)NHMe, C(O)NHEt, $C(O)NMe_2$, C(O)NMeEt, $C(O)NEt_2$, $C(S)NH_2$, C(S)NHMe, C(S)NHEt, $C(S)NMe_2$, C(S)NMeEt and $C(S)NEt_2$.

5. A compound according to claim 1, wherein:

U is a 5-membered heteroaromatic ring selected from the group consisting of 1H-pyrrole, 1H-pyrazole, 1H-1,2,4-triazole, 1H-imidazole, 1H-1,2,3-triazole, 1H-tetrazole, thiophene, thiazole, 1,3,4-thiadiazole, furan, oxazole, isoxazole, 1,2,4-oxadiazole and 1,3,4-oxadiazole; wherein the heteroaromatic ring is substituted by at least one of the groups selected from halogen, CN, tert-butyl and $CF_3$.

6. A compound according to claim 1, wherein:

U is a 5-membered heteroaromatic ring selected from the group consisting of 1H-pyrazole, 1H-1,2,4-triazole and 1,3,4-thiadiazole; wherein the heteroaromatic ring is substituted by one of the groups selected from Cl, CN, tert-butyl and $CF_3$;

$R^1$ is selected from the group consisting of H, CN, C(=O)-Me, C(=O)-Et, C(=O)—$NH_2$, C(=O)—NMeH, C(=O)—NEtH, C(=O)—$NMe_2$, C(=O)—NMeEt, C(=O)—$NEt_2$, C(=S)—$NH_2$, C(=S)—NMeH, C(=S)—NEtH, C(=S)—$NMe_2$, C(=S)—NMeEt and C(=S)—$NEt_2$;

$R^2$ is selected from the group consisting of H, Cl, Me and Et;

p is 1;

X is $S(=O)_m$ with m being 0 or 1; and $R^{3U}$ is $CF_3$ or $CHF_2$.

7. A compound of claim 1, wherein:

U is 1,3,4-thiadiazole;

V is $CF_3$ or $CF_2CF_3$;

$R^1$ is H, CN or $CH_2OH$;

$R^2$ is $C_1$-$C_6$ alkyl which may be substituted by halogen;

X is $S(=O)_m$ with m being 0 or 1;

$R^{3U}$ is $C_1$-$C_3$-fluoroalkyl;

n is 1 or 2; and p is 1.

8. A compound of claim 7, wherein:

$R^1$ is H;

$R^2$ is methyl or ethyl;

$R^{3U}$ is $CF_3$; and n is 2.

9. A compound of claim 7, wherein:

$R^1$ is CN or $CH_2OH$;

$R^2$ is methyl;

X is $S(=O)_m$ with m being 0;

$R^{3U}$ is $CF_3$; and n is 2.

10. A compound according to claim 1, of formula 1-xxxx, selected from Table 1:

TABLE 1

1-xxxx

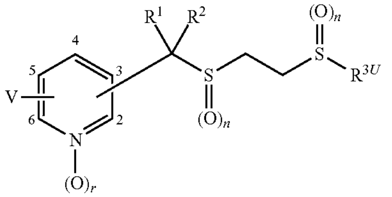

| No. | Position | V | r | $R^1$ | $R^2$ | $R^{3U}$ | n |
|---|---|---|---|---|---|---|---|
| 1-01. | 2 | 5-$CF_3$ | 0 | H | H | $CF_3$ | 2 |
| 1-02. | 2 | 5-$CF_3$ | 0 | H | H | $CF_2H$ | 2 |
| 1-03. | 2 | 5-$CF_3$ | 0 | CN | H | $CF_3$ | 2 |
| 1-04. | 2 | 5-$CF_3$ | 0 | CN | H | $CF_2H$ | 2 |
| 1-05. | 2 | 5-$CF_3$ | 0 | COOMe | H | $CF_3$ | 2 |
| 1-06. | 2 | 5-$CF_3$ | 0 | COOMe | H | $CF_2H$ | 2 |
| 1-07. | 2 | 5-$CF_3$ | 0 | COOEt | H | $CF_3$ | 2 |
| 1-08. | 2 | 5-$CF_3$ | 0 | COOEt | H | $CF_2H$ | 2 |

TABLE 1-continued 1-xxxx

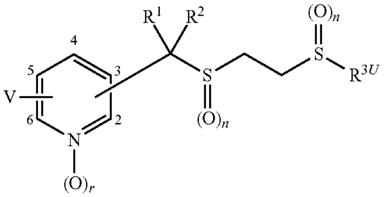

| No. | Position | V | r | $R^1$ | $R^2$ | $R^{3U}$ | n |
|---|---|---|---|---|---|---|---|
| 1-09. | 2 | 5-$CF_3$ | 0 | COO—i-Pr | H | $CF_3$ | 2 |
| 1-010. | 2 | 5-$CF_3$ | 0 | COO—i-Pr | H | $CF_2H$ | 2 |
| 1-011. | 2 | 5-$CF_3$ | 0 | COO—t-Bu | H | $CF_3$ | 2 |
| 1-012. | 2 | 5-$CF_3$ | 0 | COO—t-Bu | H | $CF_2H$ | 2 |
| 1-013. | 2 | 5-$CF_3$ | 0 | $CON(Me)_2$ | H | $CF_3$ | 2 |
| 1-014. | 2 | 5-$CF_3$ | 0 | $CON(Me)_2$ | H | $CF_2H$ | 2 |
| 1-015. | 2 | 5-$CF_3$ | 0 | 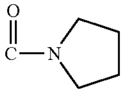 | H | $CF_3$ | 2 |
| 1-016. | 2 | 5-$CF_3$ | 0 | 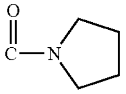 | H | $CF_2H$ | 2 |
| 1-017. | 2 | 5-$CF_3$ | 0 | COOMe | F | $CF_3$ | 2 |
| 1-018. | 2 | 5-$CF_3$ | 0 | COOMe | F | $CF_2H$ | 2 |
| 1-019. | 2 | 5-$CF_3$ | 0 | COOMe | Cl | $CF_3$ | 2 |
| 1-020. | 2 | 5-$CF_3$ | 0 | COOMe | Cl | $CF_2H$ | 2 |
| 1-021. | 2 | 5-$CF_3$ | 0 | COOMe | Me | $CF_3$ | 2 |
| 1-022. | 2 | 5-$CF_3$ | 0 | COOMe | Me | $CF_2H$ | 2 |
| 1-023. | 2 | 5-$CF_3$ | 0 | Me | H | $CF_3$ | 2 |
| 1-024. | 2 | 5-$CF_3$ | 0 | Me | H | $CF_2H$ | 2 |
| 1-025. | 2 | 3-Cl—5-$CF_3$ | 0 | H | H | $CF_3$ | 2 |
| 1-026. | 2 | 3-Cl—5-$CF_3$ | 0 | H | H | $CF_2H$ | 2 |
| 1-027. | 2 | 3-Cl—5-$CF_3$ | 0 | CN | H | $CF_3$ | 2 |
| 1-028. | 2 | 3-Cl—5-$CF_3$ | 0 | CN | H | $CF_2H$ | 2 |
| 1-029. | 2 | 3-Cl—5-$CF_3$ | 0 | COOMe | H | $CF_3$ | 2 |
| 1-030. | 2 | 3-Cl—5-$CF_3$ | 0 | COOMe | H | $CF_2H$ | 2 |
| 1-031. | 2 | 3-Cl—5-$CF_3$ | 0 | COOEt | H | $CF_3$ | 2 |
| 1-032. | 2 | 3-Cl—5-$CF_3$ | 0 | COOEt | H | $CF_2H$ | 2 |
| 1-033. | 2 | 5-CN | 0 | H | H | $CF_3$ | 2 |
| 1-034. | 2 | 5-CN | 0 | H | H | $CF_2H$ | 2 |
| 1-035. | 2 | 5-CN | 0 | CN | H | $CF_3$ | 2 |
| 1-036. | 2 | 5-CN | 0 | CN | H | $CF_2H$ | 2 |
| 1-037. | 3 | 6-Cl | 0 | H | H | $CF_3$ | 0 |
| 1-038. | 3 | 6-Cl | 0 | H | H | $CF_2H$ | 0 |
| 1-039. | 3 | 6-Cl | 0 | H | H | $CF_3$ | 1 |
| 1-040. | 3 | 6-Cl | 0 | H | H | $CF_2H$ | 1 |
| 1-041. | 3 | 6-Cl | 0 | H | H | $CF_3$ | 2 |
| 1-042. | 3 | 6-Cl | 0 | H | H | $CF_2H$ | 2 |
| 1-043. | 3 | 6-Cl | 1 | H | H | $CF_3$ | 2 |
| 1-044. | 3 | 6-Cl | 1 | H | H | $CF_2H$ | 2 |
| 1-045. | 3 | 6-Cl | 0 | Me | H | $CF_3$ | 2 |
| 1-046. | 3 | 6-Cl | 0 | Me | H | $CF_2H$ | 2 |
| 1-047. | 3 | 6-Cl | 0 | Me | Me | $CF_3$ | 2 |
| 1-048. | 3 | 6-Cl | 0 | Me | Me | $CF_2H$ | 2 |
| 1-049. | 3 | 6-Cl | 0 | H | H | $CF_3$ | 0 |
| 1-050. | 3 | 6-Cl | 0 | H | H | $CF_2H$ | 0 |
| 1-051. | 3 | 6-Cl | 0 | H | H | $CF_3$ | 1 |
| 1-052. | 3 | 6-Cl | 0 | H | H | $CF_2H$ | 1 |
| 1-053. | 3 | 6-Cl | 0 | H | H | $CF_3$ | 2 |
| 1-054. | 3 | 6-Cl | 0 | H | H | $(CF_2)CF_3$ | 0 |
| 1-055. | 3 | 6-Cl | 0 | H | H | $(CF_2)CF_3$ | 1 |
| 1-056. | 3 | 6-Cl | 0 | H | H | $(CF_2)CF_3$ | 2 |
| 1-057 . | 3 | 6-Cl | 0 | Me | H | $(CF_2)CF_3$ | 2 |
| 1-058. | 3 | 6-Cl | 0 | H | H | $CF_2H$ | 2 |
| 1-059. | 3 | 6-Cl | 0 | F | H | $CF_3$ | 2 |
| 1-060. | 3 | 6-Cl | 0 | F | H | $CF_2H$ | 2 |
| 1-061. | 3 | 6-Cl | 0 | F | F | $CF_3$ | 2 |
| 1-062. | 3 | 6-Cl | 0 | F | F | $CF_2H$ | 2 |
| 1-063. | 3 | 6-Cl | 0 | Cl | H | $CF_3$ | 2 |
| 1-064. | 3 | 6-Cl | 0 | Cl | H | $CF_2H$ | 2 |

TABLE 1-continued 1-xxxx

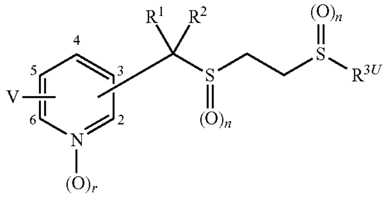

| No. | Position | V | r | $R^1$ | $R^2$ | $R^{3U}$ | n |
|---|---|---|---|---|---|---|---|
| 1-065. | 3 | 6-Cl | 0 | Cl | Cl | $CF_3$ | 2 |
| 1-066. | 3 | 6-Cl | 0 | Cl | Cl | $CF_2H$ | 2 |
| 1-067. | 3 | 6-$CF_3$ | 0 | H | H | $CF_3$ | 0 |
| 1-068. | 3 | 6-$CF_3$ | 0 | H | H | $CF_2H$ | 0 |
| 1-069. | 3 | 6-$CF_3$ | 0 | H | H | $CF_3$ | 1 |
| 1-070. | 3 | 6-$CF_3$ | 0 | H | H | $CF_2H$ | 1 |
| 1-071. | 3 | 6-$CF_3$ | 0 | H | H | $CF_3$ | 2 |
| 1-072. | 3 | 6-$CF_3$ | 0 | H | H | $CF_2H$ | 2 |
| 1-073. | 3 | 6-$CF_3$ | 0 | Me | H | $CF_3$ | 2 |
| 1-074. | 3 | 6-$CF_3$ | 0 | Me | H | $CF_2H$ | 2 |
| 1-075. | 3 | 6-$CF_3$ | 0 | Me | Me | $CF_3$ | 2 |
| 1-076. | 3 | 6-$CF_3$ | 0 | Me | Me | $CF_2H$ | 2 |
| 1-077. | 3 | 6-$CF_3$ | 0 | Et | H | $CF_3$ | 2 |
| 1-078. | 3 | 6-$CF_3$ | 0 | Et | H | $CF_2H$ | 2 |
| 1-079. | 3 | 6-$CF_3$ | 0 | i-Pr | H | $CF_3$ | 2 |
| 1-080. | 3 | 6-$CF_3$ | 0 | i-Pr | H | $CF_2H$ | 2 |
| 1-081. | 3 | 6-$CF_3$ | 0 | Pr | H | $CF_3$ | 2 |
| 1-082. | 3 | 6-$CF_3$ | 0 | Pr | H | $CF_2H$ | 2 |
| 1-083. | 3 | 6-$CF_3$ | 0 | s-Bu | H | $CF_3$ | 2 |
| 1-084. | 3 | 6-$CF_3$ | 0 | s-Bu | H | $CF_2H$ | 2 |
| 1-085. | 3 | 6-$CF_3$ | 0 | i-Bu | H | $CF_3$ | 2 |
| 1-086. | 3 | 6-$CF_3$ | 0 | i-Bu | H | $CF_2H$ | 2 |
| 1-087. | 3 | 6-$CF_3$ | 0 | Bu | H | $CF_3$ | 2 |
| 1-088. | 3 | 6-$CF_3$ | 0 | Bu | H | $CF_2H$ | 2 |
| 1-089. | 3 | 6-$CF_3$ | 0 | $CH_2$—c-Pr | H | $CF_3$ | 2 |
| 1-090. | 3 | 6-$CF_3$ | 0 | $CH_2$—c-Pr | H | $CF_2H$ | 2 |
| 1-091. | 3 | 6-$CF_3$ | 0 | $CH_2CH{=}CH_2$ | H | $CF_3$ | 2 |
| 1-092. | 3 | 6-$CF_3$ | 0 | $CH_2CH{=}CH_2$ | H | $CF_2H$ | 2 |
| 1-093. | 3 | 6-$CF_3$ | 0 | $CH_2C{\equiv}CH$ | H | $CF_3$ | 2 |
| 1-094. | 3 | 6-$CF_3$ | 0 | $CH_2C{\equiv}CH$ | H | $CF_2H$ | 2 |
| 1-095. | 3 | 6-$CF_3$ | 0 | COOMe | H | $CF_3$ | 2 |
| 1-096. | 3 | 6-$CF_3$ | 0 | COOMe | H | $CF_2H$ | 2 |
| 1-097. | 3 | 6-$CF_3$ | 0 | F | H | $CF_3$ | 2 |
| 1-098. | 3 | 6-$CF_3$ | 0 | F | H | $CF_2H$ | 2 |
| 1-099. | 3 | 6-$CF_3$ | 0 | F | F | $CF_3$ | 2 |
| 1-0100. | 3 | 6-$CF_3$ | 0 | F | F | $CF_2H$ | 2 |
| 1-0101. | 3 | 6-$CF_3$ | 0 | Cl | H | $CF_3$ | 2 |
| 1-0102. | 3 | 6-$CF_3$ | 0 | Cl | H | $CF_2H$ | 2 |
| 1-0103. | 3 | 6-$CF_3$ | 0 | Cl | Cl | $CF_3$ | 2 |
| 1-0104. | 3 | 6-$CF_3$ | 0 | Cl | Cl | $CF_2H$ | 2 |
| 1-0105. | 3 | 6-$CF_3$ | 0 | H | H | $CF_2CF_3$ | 0 |
| 1-0106. | 3 | 6-$CF_3$ | 0 | H | H | $CF_2CF_3$ | 1 |
| 1-0107. | 3 | 6-$CF_3$ | 0 | H | H | $CF_2CF_3$ | 2 |
| 1-0108. | 3 | 6-$OCH_2CF_3$ | 0 | H | H | $CF_3$ | 0 |
| 1-0109. | 3 | 6-$OCH_2CF_3$ | 0 | H | H | $CF_2H$ | 0 |
| 1-0110. | 3 | 6-$OCH_2CF_3$ | 0 | H | H | $CF_3$ | 1 |
| 1-0111. | 3 | 6-$OCH_2CF_3$ | 0 | H | H | $CF_2H$ | 1 |
| 1-0112. | 3 | 6-$OCH_2CF_3$ | 0 | H | H | $CF_3$ | 2 |
| 1-0113. | 3 | 6-$OCH_2CF_3$ | 0 | H | H | $CF_2H$ | 2 |
| 1-0114. | 3 | 6-$C{\equiv}CH$ | 0 | H | H | $CF_3$ | 0 |
| 1-0115. | 3 | 6-$C{\equiv}CH$ | 0 | H | H | $CF_2H$ | 0 |
| 1-0116. | 3 | 6-$C{\equiv}CH$ | 0 | H | H | $CF_3$ | 1 |
| 1-0117. | 3 | 6-$C{\equiv}CH$ | 0 | H | H | $CF_2H$ | 1 |
| 1-0118. | 3 | 6-$C{\equiv}CH$ | 0 | H | H | $CF_3$ | 2 |
| 1-0119. | 3 | 6-$C{\equiv}CH$ | 0 | H | H | $CF_2H$ | 2 |
| 1-0120. | 3 | 6-$C{\equiv}CH$ | 1 | H | H | $CF_3$ | 2 |
| 1-0121. | 3 | 6-$C{\equiv}CH$ | 1 | H | H | $CF_2H$ | 2 |
| 1-0122. | 3 | 6-$SCF_3$ | 0 | H | H | $CF_3$ | 0 |
| 1-0123. | 3 | 6-$SCF_3$ | 0 | H | H | $CF_2H$ | 1 |
| 1-0124. | 3 | 6-$SCF_3$ | 0 | H | H | $CF_3$ | 2 |
| 1-0125. | 3 | 6-$SCF_3$ | 0 | H | H | $CF_2H$ | 2 |
| 1-0126. | 3 | 6-SMe | 0 | H | H | $CF_3$ | 2 |
| 1-0127. | 3 | 6-SMe | 0 | H | H | $CF_2H$ | 2 |
| 1-0128. | 3 | 6-SOMe | 0 | H | H | $CF_3$ | 2 |
| 1-0129. | 3 | 6-SOMe | 0 | H | H | $CF_2H$ | 2 |

TABLE 1-continued 1-xxxx

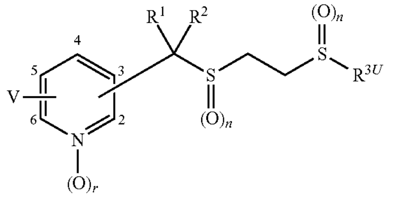

| No. | Position | V | r | $R^1$ | $R^2$ | $R^{3U}$ | n |
|---|---|---|---|---|---|---|---|
| 1-0130. | 3 | 6-$SO_2$Me | 0 | H | H | $CF_3$ | 2 |
| 1-0131. | 3 | 6-$SO_2$Me | 0 | H | H | $CF_2H$ | 2 |
| 1-0132. | 4 | 2,6-$(Cl)_2$ | 0 | H | H | $CF_3$ | 0 |
| 1-0133. | 4 | 2,6-$(Cl)_2$ | 0 | H | H | $CF_2H$ | 0 |
| 1-0134. | 4 | 2,6-$(Cl)_2$ | 0 | H | H | $CF_3$ | 1 |
| 1-0135. | 4 | 2,6-$(Cl)_2$ | 0 | H | H | $CF_2H$ | 1 |
| 1-0136. | 4 | 2,6-$(Cl)_2$ | 0 | H | H | $CF_3$ | 2 |
| 1-0137. | 4 | 2,6-$(Cl)_2$ | 0 | H | H | $CF_2H$ | 2 |
| 1-0138. | 4 | 2,6-$(Cl)_2$ | 0 | Me | H | $CF_3$ | 2 |
| 1-0139. | 4 | 2,6-$(Cl)_2$ | 0 | Me | H | $CF_2H$ | 2 |
| 1-0140. | 4 | 2,3,5,6-$(F)_4$ | 0 | H | H | $CF_3$ | 0 |
| 1-0141. | 4 | 2,3,5,6-$(F)_4$ | 0 | H | H | $CF_2H$ | 0 |
| 1-0142. | 4 | 2,3,5,6-$(F)_4$ | 0 | H | H | $CF_3$ | 1 |
| 1-0143. | 4 | 2,3,5,6-$(F)_4$ | 0 | H | H | $CF_2H$ | 1 |
| 1-0144. | 4 | 2,3,5,6-$(F)_4$ | 0 | H | H | $CF_3$ | 2 |
| 1-0145. | 4 | 2,3,5,6-$(F)_4$ | 0 | H | H | $CF_2H$ | 2 |

wherein m is 0 or 1;

Position in Table 1 is the position on the pyridyl group which is substituted by the moiety

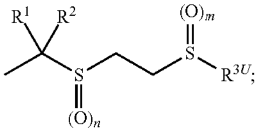

;

and

V, r, $R^1$, $R^2$, $R^{3U}$ and n are defined in Table 1.

11. A compound according to claim 1, of formula 2-xxxx, selected from Table 2:

TABLE 2

2-xxxx

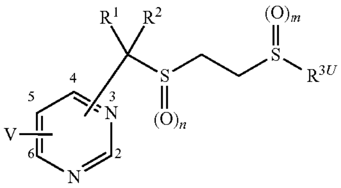

| No. | Position | V | $R^1$ | $R^2$ | $R^{3U}$ | n |
|---|---|---|---|---|---|---|
| 2-01. | 2 | 4,6-$(Cl)_2$ | H | H | $CF_3$ | 0 |
| 2-02. | 2 | 4,6-$(Cl)_2$ | H | H | $CF_2H$ | 0 |
| 2-03. | 2 | 4,6-$(Cl)_2$ | H | H | $CF_3$ | 1 |
| 2-04. | 2 | 4,6-$(Cl)_2$ | H | H | $CF_2H$ | 1 |
| 2-05. | 2 | 4,6-$(Cl)_2$ | H | H | $CF_3$ | 2 |
| 2-06. | 2 | 4,6-$(Cl)_2$ | H | H | $CF_2H$ | 2 |
| 2-07. | 2 | 4-$CF_3$ | H | H | $CF_3$ | 2 |
| 2-08. | 2 | 4-$CF_3$ | H | H | $CF_2H$ | 2 |
| 2-09. | 2 | 4-$CF_3$ | COOMe | H | $CF_3$ | 2 |
| 2-010. | 2 | 4-$CF_3$ | COOMe | H | $CF_2H$ | 2 |
| 2-011. | 2 | 4-$CF_3$ | COOEt | H | $CF_3$ | 2 |
| 2-012. | 2 | 4-$CF_3$ | COOEt | H | $CF_2H$ | 2 |

TABLE 2-continued 2-xxxx

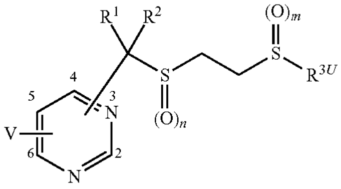

| No. | Position | V | $R^1$ | $R^2$ | $R^{3U}$ | n |
|---|---|---|---|---|---|---|
| 2-013. | 2 | 4-$CF_3$ | CN | H | $CF_3$ | 2 |
| 2-014. | 2 | 4-$CF_3$ | CN | H | $CF_2H$ | 2 |
| 2-015. | 4 | 2,6-$(Cl)_2$ | H | H | $CF_3$ | 0 |
| 2-016. | 4 | 2,6-$(Cl)_2$ | H | H | $CF_2H$ | 0 |
| 2-017. | 4 | 2,6-$(Cl)_2$ | H | H | $CF_3$ | 1 |
| 2-018. | 4 | 2,6-$(Cl)_2$ | H | H | $CF_2H$ | 1 |
| 2-019. | 4 | 2,6-$(Cl)_2$ | H | H | $CF_3$ | 2 |
| 2-020. | 4 | 2,6-$(Cl)_2$ | H | H | $CF_2H$ | 2 |
| 2-021. | 4 | 2-$CF_3$ | H | H | $CF_3$ | 2 |
| 2-022. | 4 | 2-$CF_3$ | H | H | $CF_2H$ | 2 |
| 2-023. | 4 | 2-$CF_3$ | COOMe | H | $CF_3$ | 2 |
| 2-024. | 4 | 2-$CF_3$ | COOMe | H | $CF_2H$ | 2 |
| 2-025. | 4 | 2-$CF_3$ | COOEt | H | $CF_3$ | 2 |
| 2-026. | 4 | 2-$CF_3$ | COOEt | H | $CF_2H$ | 2 |
| 2-027. | 4 | 2-$CF_3$ | CN | H | $CF_3$ | 2 |
| 2-028. | 4 | 2-$CF_3$ | CN | H | $CF_2H$ | 2 |
| 2-029. | 4 | 6-$CF_3$ | H | H | $CF_3$ | 2 |
| 2-030. | 4 | 6-$CF_3$ | H | H | $CF_2H$ | 2 |
| 2-031. | 4 | 6-$CF_3$ | COOMe | H | $CF_3$ | 2 |
| 2-032. | 4 | 6-$CF_3$ | COOMe | H | $CF_2H$ | 2 |
| 2-033. | 4 | 6-$CF_3$ | COOEt | H | $CF_3$ | 2 |
| 2-034. | 4 | 6-$CF_3$ | COOEt | H | $CF_2H$ | 2 |
| 2-035. | 4 | 6-$CF_3$ | CN | H | $CF_3$ | 2 |
| 2-036. | 4 | 6-$CF_3$ | CN | H | $CF_2H$ | 2 |
| 2-037. | 5 | 2-$CF_3$ | H | H | $CF_3$ | 0 |
| 2-038. | 5 | 2-$CF_3$ | H | H | $CF_2H$ | 0 |
| 2-039. | 5 | 2-$CF_3$ | H | H | $CF_3$ | 1 |
| 2-040. | 5 | 2-$CF_3$ | H | H | $CF_2H$ | 1 |
| 2-041. | 5 | 2-$CF_3$ | H | H | $CF_3$ | 2 |
| 2-042. | 5 | 2-$CF_3$ | H | H | $CF_2H$ | 2 |
| 2-043. | 5 | 2-$CF_3$ | Me | H | $CF_3$ | 2 |
| 2.044. | 5 | 2-$CF_3$ | Me | H | $CF_2H$ | 2 |
| 2-045. | 5 | 2-$CF_3$ | Me | Me | $CF_3$ | 2 |
| 2-046. | 5 | 2-$CF_3$ | Me | Me | $CF_2H$ | 2 |
| 2-047. | 5 | 2-$CF_3$ | Et | H | $CF_3$ | 2 |
| 2-048. | 5 | 2-$CF_3$ | Et | H | $CF_2H$ | 2 |
| 2-049. | 5 | 2-$CF_3$ | i-Pr | H | $CF_3$ | 2 |
| 2-050. | 5 | 2-$CF_3$ | i-Pr | H | $CF_2H$ | 2 |
| 2-051. | 5 | 2-$CF_3$ | Pr | H | $CF_3$ | 2 |
| 2-052. | 5 | 2-$CF_3$ | Pr | H | $CF_2H$ | 2 |
| 2-053. | 5 | 2-$CF_3$ | s-Bu | H | $CF_3$ | 2 |
| 2-054. | 5 | 2-$CF_3$ | s-Bu | H | $CF_2H$ | 2 |
| 2-055. | 5 | 2-$CF_3$ | i-Bu | H | $CF_3$ | 2 |
| 2-056. | 5 | 2-$CF_3$ | i-Bu | H | $CF_2H$ | 2 |
| 2-057. | 5 | 2-$CF_3$ | Bu | H | $CF_3$ | 2 |
| 2-058. | 5 | 2-$CF_3$ | Bu | H | $CF_2H$ | 2 |
| 2-059. | 5 | 2-$CF_3$ | $CH_2$-c-Pr | H | $CF_3$ | 2 |
| 2-060. | 5 | 2-$CF_3$ | $CH_2$-c-Pr | H | $CF_2H$ | 2 |
| 2-061. | 5 | 2-$CF_3$ | $CH_2CH{=}CH_2$ | H | $CF_3$ | 2 |
| 2-062. | 5 | 2-$CF_3$ | $CH_2CH{=}CH_2$ | H | $CF_2H$ | 2 |
| 2-063. | 5 | 2-$CF_3$ | $CH_2CH{=}CH$ | H | $CF_3$ | 2 |
| 2-064. | 5 | 2-$CF_3$ | $CH_2CH{=}CH$ | H | $CF_2H$ | 2 |
| 2-065. | 5 | 2-$CF_3$ | COOMe | H | $CF_3$ | 2 |
| 2-066. | 5 | 2-$CF_3$ | COOMe | H | $CF_2H$ | 2 |
| 2-067. | 5 | 2-$CF_3$ | CONHEt | H | $CF_3$ | 2 |
| 2-068. | 5 | 2-$CF_3$ | CONHEt | H | $CF_2H$ | 2 |
| 2-069. | 5 | 2-$CF_3$ | CSNHMe | H | $CF_3$ | 2 |
| 2-070. | 5 | 2-$CF_3$ | CSNHMe | H | $CF_2H$ | 2 |
| 2-071. | 5 | 2-$CF_3$ | F | H | $CF_3$ | 2 |
| 2-072. | 5 | 2-$CF_3$ | F | H | $CF_2H$ | 2 |
| 2-073. | 5 | 2-$CF_3$ | F | F | $CF_3$ | 2 |
| 2-074. | 5 | 2-$CF_3$ | F | F | $CF_2H$ | 2 |
| 2-075. | 5 | 2-$CF_3$ | Cl | H | $CF_3$ | 2 |
| 2-076. | 5 | 2-$CF_3$ | Cl | H | $CF_2H$ | 2 |
| 2-077. | 5 | 2-$CF_3$ | Cl | Cl | $CF_3$ | 2 |
| 2-078. | 5 | 2-$CF_3$ | Cl | Cl | $CF_2H$ | 2 |
| 2-079. | 5 | 2-$CF_3$ | H | H | $CF_2CF_3$ | 0 |

TABLE 2-continued 2-xxxx

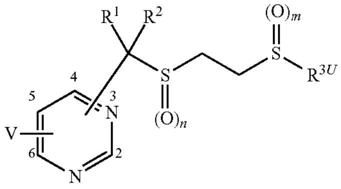

| No. | Position | V | $R^1$ | $R^2$ | $R^{3U}$ | n |
|---|---|---|---|---|---|---|
| 2-080. | 5 | 2-$CF_3$ | H | H | $CF_2CF_3$ | 1 |
| 2-081. | 5 | 2-$CF_3$ | H | H | $CF_2CF_3$ | 2 |
| 2-082. | 5 | 2-$CF_3$-4-Me | H | H | $CF_3$ | 0 |
| 2-083. | 5 | 2-$CF_3$-4-Me | H | H | $CF_2H$ | 0 |
| 2-084. | 5 | 2-$CF_3$-4-Me | H | H | $CF_3$ | 1 |
| 2-085. | 5 | 2-$CF_3$-4-Me | H | H | $CF_2H$ | 1 |
| 2-086. | 5 | 2-$CF_3$-4-Me | H | H | $CF_3$ | 2 |
| 2-087. | 5 | 2-$CF_3$-4-Me | H | H | $CF_2H$ | 2 |
| 2-088. | 5 | 2-$CF_3$-4-Me | Me | H | $CF_3$ | 2 |
| 2-089. | 5 | 2-$CF_3$-4-Me | Me | H | $CF_2H$ | 2 |
| 2-090. | 5 | 2-$SCF_3$-4-Me | H | H | $CF_3$ | 0 |
| 2-091. | 5 | 2-$SCF_3$-4-Me | H | H | $CF_2H$ | 0 |
| 2-092. | 5 | 2-$SCF_3$-4-Me | H | H | $CF_3$ | 1 |
| 2-093. | 5 | 2-$SCF_3$-4-Me | H | H | $CF_2H$ | 1 |
| 2-094. | 5 | 2-$SCF_3$-4-Me | H | H | $CF_3$ | 2 |
| 2-095. | 5 | 2-$SCF_3$-4-Me | H | H | $CF_2H$ | 2 |
| 2-096. | 5 | 2-$SCF_3$-4-Me | Me | H | $CF_3$ | 2 |
| 2-097. | 5 | 2-$SCF_3$-4-Me | Me | H | $CF_2H$ | 2 |
| 2-098. | 5 | 2-c-Pr | H | H | $CF_3$ | 0 |
| 2-099. | 5 | 2-c-Pr | H | H | $CF_2H$ | 0 |
| 2-0100. | 5 | 2-c-Pr | H | H | $CF_3$ | 1 |
| 2-0101. | 5 | 2-c-Pr | H | H | $CF_2H$ | 1 |
| 2-0102. | 5 | 2-c-Pr | H | H | $CF_3$ | 2 |
| 2-0103. | 5 | 2-c-Pr | H | H | $CF_2H$ | 2 |
| 2-0104. | 5 | 2-c-Pr | Me | H | $CF_3$ | 2 |
| 2-0105. | 5 | 2-c-Pr | Me | H | $CF_2H$ | 2 |
| 2-0106. | 5 | 2-t-Bu | H | H | $CF_3$ | 0 |

TABLE 2-continued 2-xxxx

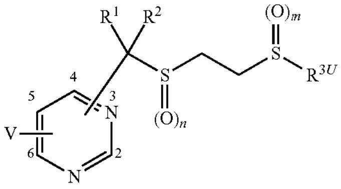

| No. | Position | V | $R^1$ | $R^2$ | $R^{3U}$ | n |
|---|---|---|---|---|---|---|
| 2-0107. | 5 | 2-t-Bu | H | H | $CF_2H$ | 0 |
| 2-0108. | 5 | 2-t-Bu | H | H | $CF_3$ | 1 |
| 2-0109. | 5 | 2-t-Bu | H | H | $CF_2H$ | 1 |
| 2-0110. | 5 | 2-t-Bu | H | H | $CF_3$ | 2 |
| 2-0111. | 5 | 2-t-Bu | H | H | $CF_2H$ | 2 |
| 2-0112. | 5 | 2-t-Bu | Me | H | $CF_3$ | 2 |
| 2-0113. | 5 | 2-t-Bu | Me | H | $CF_2H$ | 2 |

wherein m is 0 or 1;

Position in Table 2 is the position on the pyrimidyl group which is substituted by the moiety

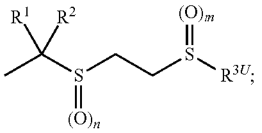

and

V, $R^1$, $R^2$, $R^{3U}$ and n are defined in Table 2.

12. A compound according to claim 1, of formula 3-xxxx, selected from Table 3:

TABLE 3

3-xxxx

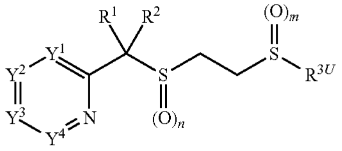

| No. | $Y^1$ | $Y^2$ | $Y^3$ | $Y^4$ | $R^1$ | $R^2$ | $R^{3U}$ | n |
|---|---|---|---|---|---|---|---|---|
| 3-01. | C—H | N | C—H | C—Cl | H | H | $CF_3$ | 2 |
| 3-02. | C—H | N | C—H | C—Cl | H | H | $CF_2H$ | 2 |
| 3-03. | C—H | N | C—H | C—Cl | COOMe | H | $CF_3$ | 2 |
| 3-04. | C—H | N | C—H | C—Cl | COOMe | H | $CF_2H$ | 2 |
| 3-05. | C—H | N | C—H | C—Cl | COOMe | H | $CF_3$ | 2 |
| 3-06. | C—H | N | C—H | C—Cl | COOMe | H | $CF_2H$ | 2 |
| 3-07. | C—H | N | C—H | C—Cl | CN | H | $CF_3$ | 2 |
| 3-08. | C—H | N | C—H | C—Cl | CN | H | $CF_2H$ | 2 |
| 3-09. | C—Cl | N | C—CN | C—CN | H | H | $CF_3$ | 2 |
| 3-010. | C—Cl | N | C—CN | C—CN | H | H | $CF_2H$ | 2 |
| 3-011. | C—Cl | N | C—CN | C—CN | COOMe | H | $CF_3$ | 2 |
| 3-012. | C—Cl | N | C—CN | C—CN | COOMe | H | $CF_2H$ | 2 |
| 3-013. | C—Cl | N | C—CN | C—CN | COOEt | H | $CF_3$ | 2 |
| 3-014. | C—Cl | N | C—CN | C—CN | COOEt | H | $CF_2H$ | 2 |
| 3-015. | C—Cl | N | C—CN | C—CN | CN | H | $CF_3$ | 2 |
| 3-016. | C—Cl | N | C—CN | C—CN | CN | H | $CF_2H$ | 2 |
| 3-017. | C—H | N | C—CN | C—CN | H | H | $CF_3$ | 2 |
| 3-018. | C—H | N | C—CN | C—CN | H | H | $CF_2H$ | 2 |
| 3-019. | C—H | N | C—CN | C—CN | COOMe | H | $CF_3$ | 2 |
| 3-020. | C—H | N | C—CN | C—CN | COOMe | H | $CF_2H$ | 2 |
| 3-021. | C—H | N | C—CN | C—CN | COOEt | H | $CF_3$ | 2 |
| 3-022. | C—H | N | C—CN | C—CN | COOEt | H | $CF_2H$ | 2 |
| 3-023. | C—H | N | C—CN | C—CN | CN | H | $CF_3$ | 2 |
| 3-024. | C—H | N | C—CN | C—CN | CN | H | $CF_2H$ | 2 |
| 3-025. | C—H | C—H | C—Cl | N | H | H | $CF_3$ | 2 |

TABLE 3-continued 3-xxxx

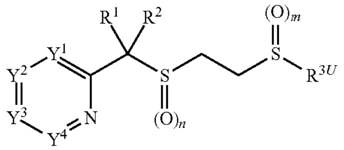

| No. | $Y^1$ | $Y^2$ | $Y^3$ | $Y^4$ | $R^1$ | $R^2$ | $R^{3U}$ | n |
|---|---|---|---|---|---|---|---|---|
| 3-026. | C—H | C—H | C—Cl | N | H | H | $CF_2H$ | 2 |
| 3-027. | C—H | C—H | C—Cl | N | COOMe | H | $CF_3$ | 2 |
| 3-028. | C—H | C—H | C—Cl | N | COOMe | H | $CF_2H$ | 2 |
| 3-029. | C—H | C—H | C—Cl | N | COOEt | H | $CF_3$ | 2 |
| 3-030. | C—H | C—H | C—Cl | N | COOEt | H | $CF_2H$ | 2 |
| 3-031. | C—H | C—H | C—Cl | N | CN | H | $CF_3$ | 2 |
| 3-032. | C—H | C—H | C—Cl | N | CN | H | $CF_2H$ | 2 |
| 3-033. | C—H | C—H | C—$CF_3$ | N | H | H | $CF_3$ | 2 |
| 3-034. | C—H | C—H | C—$CF_3$ | N | H | H | $CF_2H$ | 2 |
| 3-035. | C—H | C—H | C—$CF_3$ | N | COOMe | H | $CF_3$ | 2 |
| 3-036. | C—H | C—H | C—$CF_3$ | N | COOMe | H | $CF_2H$ | 2 |
| 3-037. | C—H | C—H | C—$CF_3$ | N | COOEt | H | $CF_3$ | 2 |
| 3-038. | C—H | C—H | C—$CF_3$ | N | COOEt | H | $CF_2H$ | 2 |
| 3-039. | C—H | C—H | C—$CF_3$ | N | CN | H | $CF_3$ | 2 |
| 3-040. | C—H | C—H | C—$CF_3$ | N | CN | H | $CF_2H$ | 2 |
| 3-041. | N | C—Cl | N | C—Cl | H | H | $CF_3$ | 2 |
| 3-042. | N | C—Cl | N | C—Cl | H | H | $CF_2H$ | 2 |
| 3-043. | N | C—Cl | N | C—Cl | COOMe | H | $CF_3$ | 2 |
| 3-044. | N | C—Cl | N | C—Cl | COOMe | H | $CF_2H$ | 2 |
| 3-045. | N | C—Cl | N | C—Cl | COOEt | H | $CF_3$ | 2 |
| 3-046. | N | C—Cl | N | C—Cl | COOEt | H | $CF_2H$ | 2 |
| 3-047. | N | C—Cl | N | C—Cl | CN | H | $CF_3$ | 2 |
| 3-048. | N | C—Cl | N | C—Cl | CN | H | $CF_2H$ | 2 |
| 3-049. | N | C—OMe | N | C—OMe | H | H | $CF_3$ | 2 |
| 3-050. | N | C—OMe | N | C—OMe | H | H | $CF_2H$ | 2 |
| 3-051. | N | C—OMe | N | C—OMe | COOMe | H | $CF_3$ | 2 |
| 3-052. | N | C—OMe | N | C—OMe | COOMe | H | $CF_2H$ | 2 |
| 3-053. | N | C—OMe | N | C—OMe | COOEt | H | $CF_3$ | 2 |
| 3-054. | N | C—OMe | N | C—OMe | COOEt | H | $CF_2H$ | 2 |
| 3-055. | N | C—OMe | N | C—OMe | CN | H | $CF_3$ | 2 |
| 3-056. | N | C—OMe | N | C—OMe | CN | H | $CF_2H$ | 2 |
| 3-057. | C—H | C—H | C—CH═CH—CH═CH—C | | H | H | $CF_3$ | 0 |
| 3-058. | C—H | C—H | C—CH═CH—CH═CH—C | | H | H | $CF_2H$ | 0 |
| 3-059. | C—H | C—H | C—CH═CH—CH═CH—C | | H | H | $CF_3$ | 1 |
| 3-060. | C—H | C—H | C—CH═CH—CH═CH—C | | H | H | $CF_2H$ | 1 |
| 3-061. | C—H | C—H | C—CH═CH—CH═CH—C | | H | H | $CF_3$ | 2 |
| 3-062. | C—H | C—H | C—CH═CH—CH═CH—C | | H | H | $CF_2H$ | 2 |

wherein m is 0 or 1; and $Y^1$, $Y^2$, $Y^3$, $Y^4$, $R^1$, $R^2$, $R^{3U}$ and n are defined in Table 3.

13. A compound according to claim 1, of formula 7-xxxx, selected from Table 7:

TABLE 7

7-xxxx

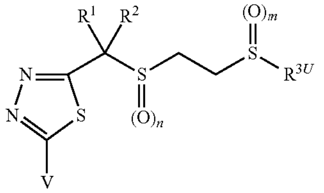

| No. | V | $R^1$ | $R^2$ | $R^{3U}$ | n |
|---|---|---|---|---|---|
| 7-01. | $CF_3$ | H | H | $CF_3$ | 0 |
| 7-02. | $CF_3$ | H | H | $CF_3$ | 1 |
| 7-03. | $CF_3$ | H | H | $CF_3$ | 2 |
| 7-04. | $CF_3$ | Me | H | $CF_3$ | 0 |
| 7-05. | $CF_3$ | Me | H | $CF_3$ | 1 |
| 7-06. | $CF_3$ | Me | H | $CF_3$ | 2 |
| 7-07. | $CF_3$ | Me | Me | $CF_3$ | 2 |

TABLE 7-continued 7-xxxx

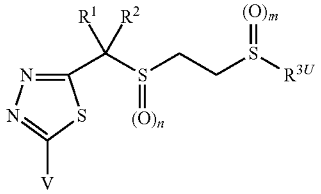

| No. | V | $R^1$ | $R^2$ | $R^{3U}$ | n |
|---|---|---|---|---|---|
| 7-08. | $CF_3$ | Me | F | $CF_3$ | 2 |
| 7-09. | $CF_3$ | Me | Cl | $CF_3$ | 2 |
| 7-10. | $CF_3$ | Me | $CH_2OMe$ | $CF_3$ | 2 |
| 7-11. | $CF_3$ | Me | $CH_2OH$ | $CF_3$ | 2 |
| 7-12. | $CF_3$ | Me | $CH_2F$ | $CF_3$ | 2 |
| 7-13. | $CF_3$ | Me | $CH_2N(Me)_2$ | $CF_3$ | 2 |
| 7-14. | $CF_3$ | Me | $CH_2CN$ | $CF_3$ | 2 |
| 7-15. | $CF_3$ | Et | H | $CF_3$ | 0 |
| 7-16. | $CF_3$ | Et | H | $CF_3$ | 1 |
| 7-17. | $CF_3$ | Et | H | $CF_3$ | 2 |
| 7-18. | $CF_3$ | i-Pr | H | $CF_3$ | 0 |
| 7-19. | $CF_3$ | i-Pr | H | $CF_3$ | 1 |
| 7-20. | $CF_3$ | i-Pr | H | $CF_3$ | 2 |

TABLE 7-continued 7-xxxx

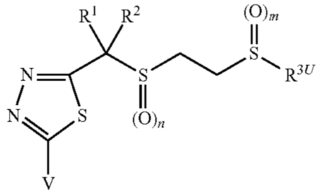

| No. | V | $R^1$ | $R^2$ | $R^{3U}$ | n |
|---|---|---|---|---|---|
| 7-21. | $CF_3$ | Pr | H | $CF_3$ | 2 |
| 7-22. | $CF_3$ | s-Bu | H | $CF_3$ | 2 |
| 7-23. | $CF_3$ | i-Bu | H | $CF_3$ | 2 |
| 7-24. | $CF_3$ | Bu | H | $CF_3$ | 2 |
| 7-25. | $CF_3$ | $CH_2$-c-Pr | H | $CF_3$ | 2 |
| 7-26. | $CF_3$ | $CH_2CH{=}CH_2$ | H | $CF_3$ | 2 |
| 7-27. | $CF_3$ | $CH_2CH{=}CH_2$ | $CH_2CH{=}CH_2$ | $CF_3$ | 2 |
| 7-28. | $CF_3$ | $CH_2CH{\equiv}CH$ | H | $CF_3$ | 2 |
| 7-29. | $CF_3$ | $CH_2CH{\equiv}CH$ | $CH_2C{\equiv}CH$ | $CF_3$ | 2 |
| 7-30. | $CF_3$ | COOMe | H | $CF_3$ | 2 |
| 7-31. | $CF_3$ | COOMe | Me | $CF_3$ | 2 |
| 7-32. | $CF_3$ | COOMe | F | $CF_3$ | 2 |
| 7-33. | $CF_3$ | COOMe | Cl | $CF_3$ | 2 |
| 7-34. | $CF_3$ | COOEt | H | $CF_3$ | 2 |
| 7-35. | $CF_3$ | CN | H | $CF_3$ | 2 |
| 7-36. | $CF_3$ | CHO | H | $CF_3$ | 2 |
| 7-37. | $CF_3$ | Ac | H | $CF_3$ | 2 |
| 7-38. | $CF_3$ | COEt | H | $CF_3$ | 2 |
| 7-39. | $CF_3$ | CO-i-Pr | H | $CF_3$ | 2 |
| 7-40. | $CF_3$ | $COCH_2Cl$ | H | $CF_3$ | 2 |
| 7-41. | $CF_3$ | $CON(Me)_2$ | H | $CF_3$ | 2 |
| 7-42. | $CF_3$ | F | H | $CF_3$ | 2 |
| 7-43. | $CF_3$ | F | F | $CF_3$ | 2 |
| 7-44. | $CF_3$ | Cl | H | $CF_3$ | 2 |
| 7-45. | $CF_3$ | Cl | Cl | $CF_3$ | 2 |
| 7-46. | $CF_3$ | =CH—OMe | | $CF_3$ | 2 |
| 7-47. | $CF_3$ | =CH—OEt | | $CF_3$ | 2 |
| 7-48. | $CF_3$ | =C(Me)—OEt | | $CF_3$ | 2 |
| 7-49. | $CF_3$ | =CH—$N(Me)_2$ | | $CF_3$ | 2 |
| 7-50. | $CF_3$ | =N—OH | | $CF_3$ | 0 |
| 7-51. | $CF_3$ | =N—OMe | | $CF_3$ | 0 |
| 7-52. | $CF_3$ | =N—OMe | | $CF_3$ | 1 |
| 7-53. | $CF_3$ | =N—OMe | | $CF_3$ | 2 |
| 7-54. | $CF_3$ | =N—OEt | | $CF_3$ | 0 |
| 7-55. | $CF_3$ | =N—OEt | | $CF_3$ | 1 |
| 7-56. | $CF_3$ | =N—OEt | | $CF_3$ | 2 |
| 7-57. | $CF_2CF_3$ | Me | H | $CF_3$ | 0 |
| 7-58. | $CF_2CF_3$ | Me | H | $CF_3$ | 1 |
| 7-59. | $CF_2CF_3$ | Me | H | $CF_3$ | 2 |
| 7-60. | $CF(CF_3)_2$ | Me | H | $CF_3$ | 0 |
| 7-61. | $CF(CF_3)_2$ | Me | H | $CF_3$ | 1 |
| 7-62. | $CF(CF_3)_2$ | Me | H | $CF_3$ | 2 |
| 7-63. | $C(Me)(CF_3)_2$ | Me | H | $CF_3$ | 0 |
| 7-64. | $C(Me)(CF_3)_2$ | Me | H | $CF_3$ | 1 |
| 7-65. | $C(Me)(CF_3)_2$ | Me | H | $CF_3$ | 2 |
| 7-66. | $NH_2$ | Me | H | $CF_3$ | 0 |
| 7-67. | Cl | Me | H | $CF_3$ | 0 |
| 7-68. | Cl | Me | H | $CF_3$ | 1 |
| 7-69. | Cl | Me | H | $CF_3$ | 2 |
| 7-70. | Br | Me | H | $CF_3$ | 0 |
| 7-71. | Br | Me | H | $CF_3$ | 1 |
| 7-72. | Br | Me | H | $CF_3$ | 2 |
| 7-73. | I | Me | H | $CF_3$ | 0 |
| 7-74. | I | Me | H | $CF_3$ | 1 |
| 7-75. | I | Me | H | $CF_3$ | 2 |
| 7-76. | Me | Me | H | $CF_3$ | 0 |
| 7-77. | Me | Me | H | $CF_3$ | 1 |
| 7-78. | Me | Me | H | $CF_3$ | 2 |
| 7-79. | Et | Me | H | $CF_3$ | 0 |
| 7-80. | Et | Me | H | $CF_3$ | 1 |
| 7-81. | Et | Me | H | $CF_3$ | 2 |
| 7-82. | i-Pr | Me | H | $CF_3$ | 0 |
| 7-83. | i-Pr | Me | H | $CF_3$ | 1 |
| 7-84. | i-Pr | Me | H | $CF_3$ | 2 |
| 7-85. | c-Pr | Me | H | $CF_3$ | 0 |
| 7-86. | c-Pr | Me | H | $CF_3$ | 1 |
| 7-87. | c-Pr | Me | H | $CF_3$ | 2 |

TABLE 7-continued 7-xxxx

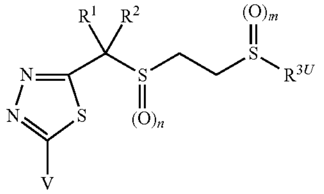

| No. | V | $R^1$ | $R^2$ | $R^{3U}$ | n |
|---|---|---|---|---|---|
| 7-88. | t-Bu | Me | H | $CF_3$ | 0 |
| 7-89. | t-Bu | Me | H | $CF_3$ | 1 |
| 7-90. | t-Bu | Me | H | $CF_3$ | 2 |
| 7-91. | $CF_3$ | Cl | H | $CF_3$ | 0 |
| 7-92. | $CF_3$ | Cl | H | $CF_3$ | 1 |
| 7-93. | $CF_3$ | COO-t-Bu | H | $CF_3$ | 2 |
| 7-94. | $CF_3$ | $CH_2Cl$ | Cl | $CF_3$ | 0 |
| 7-95. | $CF_3$ | Me | $CH_2OH$ | $CF_3$ | 0 |
| 7-96. | $CF_3$ | Me | $CH_2OH$ | $CF_3$ | 1 |
| 7-97. | $CF_3$ | Et | $CH_2OH$ | $CF_3$ | 0 |
| 7-98. | $CF_3$ | Et | $CH_2OH$ | $CF_3$ | 1 |
| 7-99. | $CF_3$ | Et | $CH_2OH$ | $CF_3$ | 2 |
| 7-100. | $CF_3$ | Et | $CH_2OMe$ | $CF_3$ | 2 |
| 7-101. | $CF_3$ | Et | F | $CF_3$ | 2 |
| 7-102. | $CF_3$ | Et | Cl | $CF_3$ | 2 |
| 7-103. | $CF_3$ | Et | $CH_2F$ | $CF_3$ | 2 |

wherein m is 0 or 1;

V, $R^1$, $R^2$, and n are defined in Table 7; and $R^{3U}$ is $CF_2H$ or $CF_3$.

14. A compound according to claim 1, of formula 8-xxxx, selected from Table 8:

TABLE 8

8-xxxx

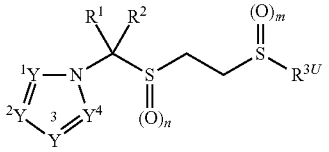

| No. | $Y^1$ | $Y^2$ | $Y^3$ | $Y^4$ | $R^1$ | $R^2$ | $R^{3U}$ | n |
|---|---|---|---|---|---|---|---|---|
| 8-01. | C—H | C—$NO_2$ | C—H | C—H | H | H | $CF_3$ | 0 |
| 8-02. | C—H | C—$NO_2$ | C—H | C—H | H | H | $CF_3$ | 1 |
| 8-03. | C—H | C—$NO_2$ | C—H | C—H | H | H | $CF_3$ | 2 |
| 8-04. | C—Me | C—Ac | C—Me | C—H | H | H | $CF_3$ | 0 |
| 8-05. | C—Me | C—Ac | C—Me | C—H | H | H | $CF_3$ | 1 |
| 8-06. | C—Me | C—Ac | C—Me | C—H | H | H | $CF_3$ | 2 |
| 8-07. | C—H | N | C—$CF_3$ | C—H | H | H | $CF_3$ | 0 |
| 8-08. | C—H | N | C—$CF_3$ | C—H | H | H | $CF_3$ | 1 |
| 8-09. | C—H | N | C—$CF_3$ | C—H | H | H | $CF_3$ | 2 |
| 8-010. | C—H | N | C—$CF_3$ | C—H | Me | H | $CF_3$ | 0 |
| 8-011. | C—H | N | C—$CF_3$ | C—H | Me | H | $CF_3$ | 1 |
| 8-012. | C—H | N | C—$CF_3$ | C—H | Me | H | $CF_3$ | 2 |
| 8-013. | C—H | N | C—$CF_3$ | C—H | Et | H | $CF_3$ | 0 |
| 8-014. | C—H | N | C—$CF_3$ | C—H | Et | H | $CF_3$ | 1 |
| 8-015. | C—H | N | C—$CF_3$ | C—H | Et | H | $CF_3$ | 2 |
| 8 016. | C—H | N | C—$CF_3$ | C—H | i-Pr | H | $CF_3$ | 0 |
| 8-017. | C—H | N | C—$CF_3$ | C—H | i-Pr | H | $CF_3$ | 1 |
| 8-018. | C—H | N | C—$CF_3$ | C—H | i-Pr | H | $CF_3$ | 2 |
| 8-019. | C—H | N | C—$CF_3$ | C—H | c-Pr | H | $CF_3$ | 0 |
| 8-020. | C—H | N | C—$CF_3$ | C—H | c-Pr | H | $CF_3$ | 1 |
| 8-021. | C—H | N | C—$CF_3$ | C—H | c-Pr | H | $CF_3$ | 2 |
| 8-022. | C—H | N | C—$CF_3$ | C—H | Pr | H | $CF_3$ | 0 |
| 8-023. | C—H | N | C—$CF_3$ | C—H | Pr | H | $CF_3$ | 1 |
| 8-024. | C—H | N | C—$CF_3$ | C—H | Pr | H | $CF_3$ | 2 |
| 8-025. | C—H | N | C—$CF_3$ | C—H | s-Bu | H | $CF_3$ | 0 |
| 8-026. | C—H | N | C—$CF_3$ | C—H | s-Bu | H | $CF_3$ | 1 |
| 8-027. | C—H | N | C—$CF_3$ | C—H | s-Bu | H | $CF_3$ | 2 |
| 8-028. | C—H | N | C—$CF_3$ | C—H | i-Bu | H | $CF_3$ | 0 |

TABLE 8-continued 8-xxxx

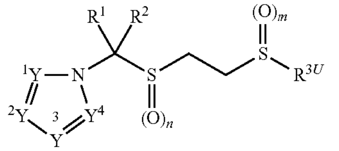

| No. | $Y^1$ | $Y^2$ | $Y^3$ | $Y^4$ | $R^1$ | $R^2$ | $R^{3U}$ | n |
|---|---|---|---|---|---|---|---|---|
| 8-029. | C—H | N | C—$CF_3$ | C—H | i-Bu | H | $CF_3$ | 1 |
| 8-030. | C—H | N | C—$CF_3$ | C—H | i-Bu | H | $CF_3$ | 2 |
| 8-031. | C—H | N | C—$CF_3$ | C—H | Bu | H | $CF_3$ | 0 |
| 8-032. | C—H | N | C—$CF_3$ | C—H | Bu | H | $CF_3$ | 1 |
| 8-033. | C—H | N | C—$CF_3$ | C—H | Bu | H | $CF_3$ | 2 |
| 8-034. | C—H | N | C—$CF_3$ | C—H | 2-Pen | H | $CF_3$ | 0 |
| 8-035. | C—H | N | C—$CF_3$ | C—H | 2-Pen | H | $CF_3$ | 1 |
| 8-036. | C—H | N | C—$CF_3$ | C—H | 2-Pen | H | $CF_3$ | 2 |
| 8-037. | C—H | N | C—$CF_3$ | C—H | 3-Pen | H | $CF_3$ | 0 |
| 8-038. | C—H | N | C—$CF_3$ | C—H | 3-Pen | H | $CF_3$ | 1 |
| 8-039. | C—H | N | C—$CF_3$ | C—H | 3-Pen | H | $CF_3$ | 2 |
| 8-040. | C—H | N | C—$CF_3$ | C—H | c-Pen | H | $CF_3$ | 0 |
| 8-041. | C—H | N | C—$CF_3$ | C—H | c-Pen | H | $CF_3$ | 1 |
| 8-042. | C—H | N | C—$CF_3$ | C—H | c-Pen | H | $CF_3$ | 2 |
| 8-043. | C—H | N | C—$CF_3$ | C—H | c-Hex | H | $CF_3$ | 0 |
| 8-044. | C—H | N | C—$CF_3$ | C—H | c-Hex | H | $CF_3$ | 1 |
| 8-045. | C—H | N | C—$CF_3$ | C—H | c-Hex | H | $CF_3$ | 2 |
| 8-046. | C—H | N | C—$CF_3$ | C—H | CN | H | $CF_3$ | 0 |
| 8-047. | C—H | N | C—$CF_3$ | C—H | CN | H | $CF_3$ | 1 |
| 8-048. | C—H | N | C—$CF_3$ | C—H | CN | H | $CF_3$ | 2 |
| 8-049. | C—H | N | C—$CF_3$ | C—H | COOMe | H | $CF_3$ | 0 |
| 8-050. | C—H | N | C—$CF_3$ | C—H | COOMe | H | $CF_3$ | 1 |
| 8-051. | C—H | N | C—$CF_3$ | C—H | COOMe | H | $CF_3$ | 2 |
| 8-052. | C—H | N | C—$CF_3$ | C—H | COOEt | H | $CF_3$ | 0 |
| 8-053. | C—H | N | C—$CF_3$ | C—H | COOEt | H | $CF_3$ | 1 |
| 8-054. | C—H | N | C—$CF_3$ | C—H | COOEt | H | $CF_3$ | 2 |
| 8-055. | N | N | C—$CF_3$ | C—H | H | H | $CF_3$ | 0 |
| 8-056. | N | N | C—$CF_3$ | C—H | H | H | $CF_3$ | 1 |
| 8-057. | N | N | C—$CF_3$ | C—H | H | H | $CF_3$ | 2 |
| 8-058. | N | N | C—$CF_3$ | N | H | H | $CF_3$ | 0 |
| 8-059. | N | N | C—$CF_3$ | N | H | H | $CF_3$ | 1 |
| 8-060. | N | N | C—$CF_3$ | N | H | H | $CF_3$ | 2 |
| 8-061. | N | N | C—$CF_3$ | N | Me | H | $CF_3$ | 0 |
| 8-062. | N | N | C—$CF_3$ | N | Me | H | $CF_3$ | 1 |
| 8-063. | N | N | C—$CF_3$ | N | Me | H | $CF_3$ | 2 |
| 8-064. | N | N | C—$CF_3$ | N | Et | H | $CF_3$ | 0 |
| 8-065. | N | N | C—$CF_3$ | N | Et | H | $CF_3$ | 1 |
| 8-066. | N | N | C—$CF_3$ | N | Et | H | $CF_3$ | 2 |
| 8-067. | N | N | C—$CF_3$ | N | i-Pr | H | $CF_3$ | 0 |
| 8-068. | N | N | C—$CF_3$ | N | i-Pr | H | $CF_3$ | 1 |
| 8-069. | N | N | C—$CF_3$ | N | i-Pr | H | $CF_3$ | 2 |
| 8-070. | N | N | C—$CF_3$ | N | c-Pr | H | $CF_3$ | 0 |
| 8-071. | N | N | C—$CF_3$ | N | c-Pr | H | $CF_3$ | 1 |
| 8-072. | N | N | C—$CF_3$ | N | c-Pr | H | $CF_3$ | 2 |
| 8-073. | N | N | C—$CF_3$ | N | Pr | H | $CF_3$ | 0 |
| 8-074. | N | N | C—$CF_3$ | N | Pr | H | $CF_3$ | 1 |
| 8-075. | N | N | C—$CF_3$ | N | Pr | H | $CF_3$ | 2 |
| 8-076. | N | N | C—$CF_3$ | N | s-Bu | H | $CF_3$ | 0 |
| 8-077. | N | N | C—$CF_3$ | N | s-Bu | H | $CF_3$ | 1 |
| 8-078. | N | N | C—$CF_3$ | N | s-Bu | H | $CF_3$ | 2 |

TABLE 8-continued 8-xxxx

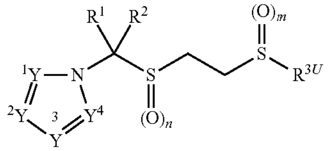

| No. | $Y^1$ | $Y^2$ | $Y^3$ | $Y^4$ | $R^1$ | $R^2$ | $R^{3U}$ | n |
|---|---|---|---|---|---|---|---|---|
| 8-079. | N | N | C—$CF_3$ | N | i-Bu | H | $CF_3$ | 0 |
| 8-080. | N | N | C—$CF_3$ | N | i-Bu | H | $CF_3$ | 1 |
| 8-081. | N | N | C—$CF_3$ | N | i-Bu | H | $CF_3$ | 2 |
| 8-082. | N | N | C—$CF_3$ | N | Bu | H | $CF_3$ | 0 |
| 8-083. | N | N | C—$CF_3$ | N | Bu | H | $CF_3$ | 1 |
| 8-084. | N | N | C—$CF_3$ | N | Bu | H | $CF_3$ | 2 |
| 8-085. | N | N | C—$CF_3$ | N | 2-Pen | H | $CF_3$ | 0 |
| 8-086. | N | N | C—$CF_3$ | N | 2-Pen | H | $CF_3$ | 1 |
| 8-087. | N | N | C—$CF_3$ | N | 2-Pen | H | $CF_3$ | 2 |
| 8-088. | N | N | C—$CF_3$ | N | 3-Pen | H | $CF_3$ | 0 |
| 8-089. | N | N | C—$CF_3$ | N | 3-Pen | H | $CF_3$ | 1 |
| 8-090. | N | N | C—$CF_3$ | N | 3-Pen | H | $CF_3$ | 2 |
| 8-091. | N | N | C—$CF_3$ | N | c-Pen | H | $CF_3$ | 0 |
| 8-092. | N | N | C—$CF_3$ | N | c-Pen | H | $CF_3$ | 1 |
| 8-093. | N | N | C—$CF_3$ | N | c-Pen | H | $CF_3$ | 2 |
| 8-094. | N | N | C—$CF_3$ | N | c-Hex | H | $CF_3$ | 0 |
| 8-095. | N | N | C—$CF_3$ | N | c-Hex | H | $CF_3$ | 1 |
| 8-096. | N | N | C—$CF_3$ | N | c-Hex | H | $CF_3$ | 2 |
| 8-097. | N | N | C—$CF_3$ | N | CN | H | $CF_3$ | 0 |
| 8-098. | N | N | C—$CF_3$ | N | CN | H | $CF_3$ | 1 |
| 8-099. | N | N | C—$CF_3$ | N | CN | H | $CF_3$ | 2 |
| 8-0100. | N | N | C—$CF_3$ | N | $CO_2$Me | H | $CF_3$ | 0 |
| 8-0101. | N | N | C—$CF_3$ | N | $CO_2$Me | H | $CF_3$ | 1 |
| 8-0102. | N | N | C—$CF_3$ | N | $CO_2$Me | H | $CF_3$ | 2 |
| 8-0103. | N | N | C—$CF_3$ | N | $CO_2$Et | H | $CF_3$ | 0 |
| 8-0104. | N | N | C—$CF_3$ | N | $CO_2$Et | H | $CF_3$ | 1 |
| 8-0105. | N | N | C—$CF_3$ | N | $CO_2$Et | H | $CF_3$ | 2 |
| 8-0106. | N | N | C—$CF_3$ | C—H | $CO_2$-t-Bu | H | $CF_3$ | 0 |
| 8-0107. | N | N | C—$CF_3$ | C—H | $CO_2$-t-Bu | H | $CF_3$ | 1 |
| 8-0108. | N | N | C—$CF_3$ | C—H | $CO_2$-t-Bu | H | $CF_3$ | 2 |
| 8-0109. | C—$CF_3$ | N | C—Et | C—H | $CO_2$Me | H | $CF_3$ | 2 |
| 8-0110. | C—H | N | C—H | C—$CF_3$ | Me | H | $CF_3$ | 2 |
| 8-0111. | C—Me | N | C—$CF_3$ | C—H | H | H | $CF_3$ | 0 |
| 8-0112. | C—Me | N | C—$CF_3$ | C—H | H | H | $CF_3$ | 1 |
| 8-0113. | C—Me | N | C—$CF_3$ | C—H | H | H | $CF_3$ | 2 |
| 8-0114. | C—$CF_3$ | N | C-t-Bu | C—H | $CO_2$-t-Bu | H | $CF_3$ | 0 |
| 8-0115. | C—$CF_3$ | N | C-t-Bu | C—H | $CO_2$-t-Bu | H | $CF_3$ | 1 |
| 8-0116. | C—$CF_3$ | N | C-t-Bu | C—H | $CO_2$-t-Bu | H | $CF_3$ | 2 |
| 8-0117. | C—H | N | C-t-Bu | C—H | $CO_2$-t-Bu | Me | $CF_3$ | 0 |
| 8-0118. | C—H | N | C-t-Bu | C—H | $CO_2$-t-Bu | Me | $CF_3$ | 1 |
| 8-0119. | C—H | N | C-t-Bu | C—H | $CO_2$-t-Bu | Me | $CF_3$ | 2 |
| 8-0120. | C—H | C—$NO_2$ | C—H | C—H | $CO_2$-t-Bu | H | $CF_3$ | 0 |
| 8-0121. | C—H | C—$NO_2$ | C—H | C—H | $CO_2$-t-Bu | Me | $CF_3$ | 0 |
| 8-0122. | C—H | C—$NO_2$ | C—H | C—H | $CO_2$-t-Bu | Me | $CF_3$ | 2 |

wherein m is 1 or 0;

$Y^1$, $Y^2$, $Y^3$, $Y^4$, R', $R^2$, and n are defined in Table 8; and $R^{3U}$ is $CF_2H$ or $CF_3$.

15. A compound according to claim 1, of formula 9-xxxx, selected from Table 9:

TABLE 9

9-xxxx

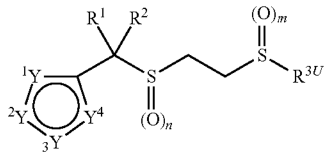

| No. | $Y^1$ | $Y^2$ | $Y^3$ | $Y^4$ | $R^1$ | $R^2$ | $R^{3U}$ |
|---|---|---|---|---|---|---|---|
| 9-01. | O | C—$CF_3$ | C—H | C—H | H | H | $CF_3$ |
| 9-02. | O | C—$CF_3$ | C—H | C—H | H | H | $CF_3$ |
| 9-03. | O | C—$CF_3$ | C—H | C—H | H | H | $CF_3$ |

TABLE 9-continued 9-xxxx

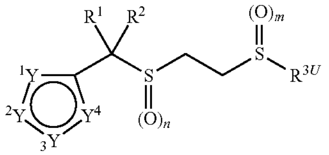

| No. | $Y^1$ | $Y^2$ | $Y^3$ | $Y^4$ | $R^1$ | $R^2$ | $R^{3U}$ |
|---|---|---|---|---|---|---|---|
| 9-04. | O | N | C—$CF_3$ | C—H | H | H | $CF_3$ |
| 9-05. | O | N | C—$CF_3$ | C—H | H | H | $CF_3$ |
| 9-06. | O | N | C—$CF_3$ | C—H | H | H | $CF_3$ |
| 9-07. | O | C—$CF_3$ | N | N | H | H | $CF_3$ |
| 9-08. | O | C—$CF_3$ | N | N | H | H | $CF_3$ |
| 9-09. | O | C—$CF_3$ | N | N | H | H | $CF_3$ |
| 9-010. | O | N | C—$CF_3$ | N | H | H | $CF_3$ |
| 9-011. | O | N | C—$CF_3$ | N | H | H | $CF_3$ |
| 9-012. | O | N | C—$CF_3$ | N | H | H | $CF_3$ |
| 9-013. | O | C—$CF_3$ | C—CN | N | H | H | $CF_3$ |
| 9-014. | O | C—$CF_3$ | C—CN | N | H | H | $CF_3$ |
| 9-015. | O | C—$CF_3$ | C—CN | N | H | H | $CF_3$ |
| 9-016. | S | C—Cl | C—H | C—H | H | H | $CF_3$ |
| 9-017. | S | C—Cl | C—H | C—H | H | H | $CF_3$ |
| 9-018. | S | C—Cl | C—H | C—H | H | H | $CF_3$ |
| 9-019. | S | C—Cl | C—H | C—H | Me | H | $CF_3$ |
| 9-020. | S | C—Cl | C—H | C—H | Me | H | $CF_3$ |
| 9-021. | S | C—Cl | C—H | C—H | Me | H | $CF_3$ |
| 9-022. | S | C—H | C—H | C—H | COOMe | H | $CF_3$ |
| 9-023. | S | C—H | C—H | C—H | COOMe | H | $CF_3$ |
| 9-024. | S | C—H | C—H | C—H | COOMe | H | $CF_3$ |
| 9-025. | S | C—H | C—H | C—H | COOH | H | $CF_3$ |
| 9-026. | S | C—H | C—H | C—H | CON(Me)$_2$ | H | $CF_3$ |
| 9-027. | O | C—CH═CH—CH═CH—C | | C—H | H | H | $CF_3$ |
| 9-028. | O | C—CH═CH—CH═CH—C | | C—H | H | H | $CF_3$ |
| 9-029. | O | C—CH═CH—CH═CH—C | | C—H | H | H | $CF_3$ |
| 9-030. | O | C—CH═CH—CH═CH—C | | C—H | Me | H | $CF_3$ |
| 9-031. | O | C—CH═CH—CH═CH—C | | C—H | Me | H | $CF_3$ |
| 9-032. | O | C—CH═CH—CH═CH—C | | C—H | Me | H | $CF_3$ |
| 9-033. | S | C—CH═CH—CH═CH—C | | C—H | H | H | $CF_3$ |
| 9-034. | S | C—CH═CH—CH═CH—C | | C—H | H | H | $CF_3$ |
| 9-035. | S | C—CH═CH—CH═CH—C | | C—H | H | H | $CF_3$ |
| 9-036. | S | C—CH═CH—CH═CH—C | | C—H | Me | H | $CF_3$ |
| 9-037. | S | C—CH═CH—CH═CH—C | | C—H | Me | H | $CF_3$ |
| 9-038. | S | C—CH═CH—CH═CH—C | | C—H | Me | H | $CF_3$ |
| 9-039. | N—H | C—CH═CH—CH═CH—C | | C—H | H | H | $CF_3$ |
| 9-040. | N—H | C—CH═CH—CH═CH—C | | C—H | H | H | $CF_3$ |
| 9-041. | N—H | C—CH═CH—CH═CH—C | | C—H | H | H | $CF_3$ |
| 9-042. | N—Me | C—CH═CH—CH═CH—C | | C—H | H | H | $CF_3$ |
| 9-043. | N—Me | C—CH═CH—CH═CH—C | | C—H | H | H | $CF_3$ |
| 9-044. | N—Me | C—CH═CH—CH═CH—C | | C—H | H | H | $CF_3$ |
| 9-045. | O | C—CH═CH—CH═CH—C | | N | H | H | $CF_3$ |
| 9-046. | O | C—CH═CH—CH═CH—C | | N | H | H | $CF_3$ |
| 9-047. | O | C—CH═CH—CH═CH—C | | N | H | H | $CF_3$ |
| 9-048. | S | C—CH═CH—CH═CH—C | | N | H | H | $CF_3$ |
| 9-049. | S | C—CH═CH—CH═CH—C | | N | H | H | $CF_3$ |
| 9-050. | S | C—CH═CH—CH═CH—C | | N | H | H | $CF_3$ |
| 9-051. | S | C—CH═CH—CH═CH—C | | N | Me | H | $CF_3$ |
| 9-052. | S | C—CH═CH—CH═CH—C | | N | Me | H | $CF_3$ |
| 9-053. | S | C—CH═CH—CH═CH—C | | N | Me | H | $CF_3$ |
| 9-054. | N—H | C—CH═CH—CH═CH—C | | N | H | H | $CF_3$ |
| 9-055. | N—H | C—CH═CH—CH═CH—C | | N | H | H | $CF_3$ |
| 9-056. | N—H | C—CH═CH—CH═CH—C | | N | H | H | $CF_3$ |
| 9-057. | N—Me | C—CH═CH—CH═CH—C | | N | H | H | $CF_3$ |
| 9-058. | N—Me | C—CH═CH—CH═CH—C | | N | H | H | $CF_3$ |
| 9-059. | N—Me | C—CH═CH—CH═CH—C | | N | H | H | $CF_3$ |
| 9-060. | S | C—Cl | N | C—$CF_3$ | H | H | $CF_3$ |
| 9-061. | S | C—Cl | N | C—$CF_3$ | H | H | $CF_3$ |
| 9-062. | S | C—Cl | N | C—$CF_3$ | H | H | $CF_3$ |
| 9-063. | O | C—CH═CH—CH═CH—C | | N | Me | H | $CF_3$ |
| 9-064. | O | C—CH═CH—CH═CH—C | | N | Me | H | $CF_3$ |
| 9-065. | O | C—CH═CH—CH═CH—C | | N | Me | H | $CF_3$ |
| 9-066. | O | N | C—$CF_3$ | C—H | Me | H | $CF_3$ |
| 9-067. | O | N | C—$CF_3$ | C—H | Me | H | $CF_3$ |
| 9-068. | O | N | C—$CF_3$ | C—H | Me | H | $CF_3$ |
| 9-069. | O | N | C-t-Bu | C—H | Me | H | $CF_3$ |
| 9-070. | O | N | C-t-Bu | C—H | Me | H | $CF_3$ |
| 9-071. | O | N | C-t-Bu | C—H | Me | H | $CF_3$ |

TABLE 9-continued 9-xxxx

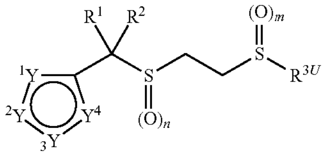

| No. | $Y^1$ | $Y^2$ | $Y^3$ | $Y^4$ | $R^1$ | $R^2$ | $R^{3U}$ |
|---|---|---|---|---|---|---|---|
| 9-072. | O | C—CH═CF—CH═CH—C | | N | Me | H | $CF_3$ |
| 9-073. | O | C—CH═CF—CH═CH—C | | N | Me | H | $CF_3$ |
| 9-074. | O | C—CH═CF—CH═CH—C | | N | Me | H | $CF_3$ |
| 9-075. | O | C—CH═CH—CF═CH—C | | N | Me | H | $CF_3$ |
| 9-076. | O | C—CH═CH—CF═CH—C | | N | Me | H | $CF_3$ |
| 9-077. | O | C—CH═CH—CF═CH—C | | N | Me | H | $CF_3$ |
| 9-078. | O | C—CH═CH—C($CF_3$)═CH—C | | N | Me | H | $CF_3$ |
| 9-079. | O | C—CH═CH—C($CF_3$)═CH—C | | N | Me | H | $CF_3$ |
| 9-080. | O | C—CH═CH—C($CF_3$)═CH—C | | N | Me | H | $CF_3$ |
| 9-081. | O | C—CF═CF—CF═CF—C | | N | Me | H | $CF_3$ |
| 9-082. | O | C—CF═CF—CF═CF—C | | N | Me | H | $CF_3$ |
| 9-083. | O | C—CF═CF—CF═CF—C | | N | Me | H | $CF_3$ |
| 9-084. | N | O | C—$CF_3$ | C—H | H | H | $CF_3$ |
| 9-085. | N | O | C—$CF_3$ | C—H | H | H | $CF_3$ |
| 9-086. | N | O | C—$CF_3$ | C—H | H | H | $CF_3$ |
| 9-087. | N | O | C—$CF_3$ | C—H | Me | H | $CF_3$ |
| 9-088. | C—H | O | C—Cl | N | H | H | $CF_3$ |
| 9-089. | C—H | O | C—Cl | N | H | H | $CF_3$ |
| 9-090. | C—H | O | C—Cl | N | H | H | $CF_3$ |
| 9-091. | C—H | O | C—Cl | N | Me | H | $CF_3$ |
| 9-092. | C—Cl | S | C—Cl | C—H | Me | H | $CF_3$ |
| 9-093. | C—Cl | S | C—Cl | C—H | Me | H | $CF_3$ |
| 9-094. | C—Cl | S | C—Cl | C—H | Me | H | $CF_3$ |
| 9-095. | C—H | N-t-Bu | N | N | H | H | $CF_3$ |
| 9-096. | C—H | N-t-Bu | N | N | H | H | $CF_3$ |
| 9-097. | C—H | N-t-Bu | N | N | H | H | $CF_3$ |
| 9-098. | N | N—CH═$CH_2$ | N | N | H | H | $CF_3$ |
| 9-099. | N | N—CH═$CH_2$ | N | N | H | H | $CF_3$ |
| 9-0100. | N | N—CH═$CH_2$ | N | N | H | H | $CF_3$ |
| 9-0101. | N | O | C—$CF_3$ | C—H | Me | H | $CF_3$ |
| 9-0102. | N | O | C—$CF_3$ | C—H | Me | H | $CF_3$ |

wherein m is 1 or 0;

n is 0, 1, or 2;

$Y^1$, $Y^2$, $Y^3$, $Y^4$, $R^1$, and $R^2$ are defined in Table 9; and $R^{3U}$ is $CF_2H$ or $CF_3$.

16. A compound of formula 4-xxxx, selected from Table 4:

TABLE 4

4-xxxx

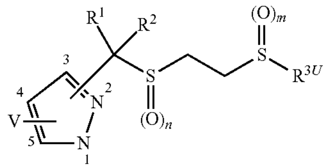

| No. | Position | V | $R^1$ | $R^2$ | $R^{3U}$ | n |
|---|---|---|---|---|---|---|
| 4-01. | 1 | 3-$CF_3$ | H | H | $CF_3$ | 0 |
| 4-02. | 1 | 3-$CF_3$ | H | H | $CF_2H$ | 0 |
| 4-03. | 1 | 3-$CF_3$ | H | H | $CF_3$ | 1 |
| 4-04. | 1 | 3-$CF_3$ | H | H | $CF_2H$ | 1 |
| 4-05. | 1 | 3-$CF_3$ | H | H | $CF_3$ | 2 |
| 4-06. | 1 | 3-$CF_3$ | H | H | $CF_2H$ | 2 |
| 4-07. | 1 | 3-$CF_3$ | Me | H | $CF_3$ | 0 |
| 4-08. | 1 | 3-$CF_3$ | Me | H | $CF_2H$ | 0 |
| 4-09. | 1 | 3-$CF_3$ | Me | H | $CF_3$ | 1 |
| 4-010. | 1 | 3-$CF_3$ | Me | H | $CF_2H$ | 1 |
| 4-011. | 1 | 3-$CF_3$ | Me | H | $CF_3$ | 2 |
| 4-012. | 1 | 3-$CF_3$ | Me | H | $CF_2H$ | 2 |
| 4-013. | 1 | 3-$CF_3$ | Et | H | $CF_3$ | 0 |
| 4-014. | 1 | 3-$CF_3$ | Et | H | $CF_2H$ | 0 |
| 4-015. | 1 | 3-$CF_3$ | Et | H | $CF_3$ | 1 |
| 4-016. | 1 | 3-$CF_3$ | Et | H | $CF_2H$ | 1 |

TABLE 4-continued 4-xxxx

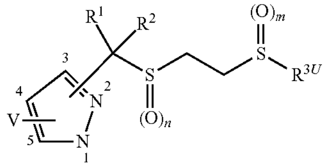

| No. | Position | V | $R^1$ | $R^2$ | $R^{3U}$ | n |
|---|---|---|---|---|---|---|
| 4-017. | 1 | 3-$CF_3$ | Et | H | $CF_3$ | 2 |
| 4-018. | 1 | 3-$CF_3$ | Et | H | $CF_2H$ | 2 |
| 4-019. | 1 | 3-$CF_3$ | i-Pr | H | $CF_3$ | 0 |
| 4-020. | 1 | 3-$CF_3$ | i-Pr | H | $CF_2H$ | 0 |
| 4-021. | 1 | 3-$CF_3$ | i-Pr | H | $CF_3$ | 1 |
| 4-022. | 1 | 3-$CF_3$ | i-Pr | H | $CF_2H$ | 1 |
| 4-023. | 1 | 3-$CF_3$ | i-Pr | H | $CF_3$ | 2 |
| 4-024. | 1 | 3-$CF_3$ | i-Pr | H | $CF_2H$ | 2 |
| 4-025. | 1 | 3-$CF_3$ | c-Pr | H | $CF_3$ | 0 |
| 4-026. | 1 | 3-$CF_3$ | c-Pr | H | $CF_2H$ | 0 |
| 4-027. | 1 | 3-$CF_3$ | c-Pr | H | $CF_3$ | 1 |
| 4-028. | 1 | 3-$CF_3$ | c-Pr | H | $CF_2H$ | 1 |
| 4-029. | 1 | 3-$CF_3$ | c-Pr | H | $CF_3$ | 2 |
| 4-030. | 1 | 3-$CF_3$ | c-Pr | H | $CF_2H$ | 2 |
| 4-031. | 1 | 3-$CF_3$ | Pr | H | $CF_3$ | 0 |
| 4-032. | 1 | 3-$CF_3$ | Pr | H | $CF_2H$ | 0 |
| 4-033. | 1 | 3-$CF_3$ | Pr | H | $CF_3$ | 1 |
| 4-034. | 1 | 3-$CF_3$ | Pr | H | $CF_2H$ | 1 |
| 4-035. | 1 | 3-$CF_3$ | Pr | H | $CF_3$ | 2 |
| 4-036. | 1 | 3-$CF_3$ | Pr | H | $CF_2H$ | 2 |
| 4-037. | 1 | 3-$CF_3$ | s-Bu | H | $CF_3$ | 0 |
| 4-038. | 1 | 3-$CF_3$ | s-Bu | H | $CF_2H$ | 0 |
| 4-039. | 1 | 3-$CF_3$ | s-Bu | H | $CF_3$ | 1 |
| 4-040. | 1 | 3-$CF_3$ | s-Bu | H | $CF_2H$ | 1 |
| 4-041. | 1 | 3-$CF_3$ | s-Bu | H | $CF_3$ | 2 |
| 4-042. | 1 | 3-$CF_3$ | s-Bu | H | $CF_2H$ | 2 |
| 4-043. | 1 | 3-$CF_3$ | i-Bu | H | $CF_3$ | 0 |
| 4-044. | 1 | 3-$CF_3$ | i-Bu | H | $CF_2H$ | 0 |
| 4-045. | 1 | 3-$CF_3$ | i-Bu | H | $CF_3$ | 1 |
| 4-046. | 1 | 3-$CF_3$ | i-Bu | H | $CF_2H$ | 1 |
| 4-047. | 1 | 3-$CF_3$ | i-Bu | H | $CF_3$ | 2 |
| 4-048. | 1 | 3-$CF_3$ | i-Bu | H | $CF_2H$ | 2 |
| 4-049. | 1 | 3-$CF_3$ | Bu | H | $CF_3$ | 0 |
| 4-050. | 1 | 3-$CF_3$ | Bu | H | $CF_2H$ | 0 |
| 4-051. | 1 | 3-$CF_3$ | Bu | H | $CF_3$ | 1 |
| 4-052. | 1 | 3-$CF_3$ | Bu | H | $CF_2H$ | 1 |
| 4-053. | 1 | 3-$CF_3$ | Bu | H | $CF_3$ | 2 |
| 4-054. | 1 | 3-$CF_3$ | Bu | H | $CF_2H$ | 2 |
| 4-055. | 1 | 3-$CF_3$ | 2-Pen | H | $CF_3$ | 0 |
| 4-056. | 1 | 3-$CF_3$ | 2-Pen | H | $CF_2H$ | 0 |
| 4-057. | 1 | 3-$CF_3$ | 2-Pen | H | $CF_3$ | 1 |
| 4-058. | 1 | 3-$CF_3$ | 2-Pen | H | $CF_2H$ | 1 |
| 4-059. | 1 | 3-$CF_3$ | 2-Pen | H | $CF_3$ | 2 |
| 4-060. | 1 | 3-$CF_3$ | 2-Pen | H | $CF_2H$ | 2 |
| 4-061. | 1 | 3-$CF_3$ | 3-Pen | H | $CF_3$ | 0 |
| 4-062. | 1 | 3-$CF_3$ | 3-Pen | H | $CF_2H$ | 0 |
| 4-063. | 1 | 3-$CF_3$ | 3-Pen | H | $CF_3$ | 1 |
| 4-064. | 1 | 3-$CF_3$ | 3-Pen | H | $CF_2H$ | 1 |
| 4-065. | 1 | 3-$CF_3$ | 3-Pen | H | $CF_3$ | 2 |
| 4-066. | 1 | 3-$CF_3$ | 3-Pen | H | $CF_2H$ | 2 |
| 4-067. | 1 | 3-$CF_3$ | c-Pen | H | $CF_3$ | 0 |
| 4-068. | 1 | 3-$CF_3$ | c-Pen | H | $CF_2H$ | 0 |
| 4-069. | 1 | 3-$CF_3$ | c-Pen | H | $CF_3$ | 1 |
| 4-070. | 1 | 3-$CF_3$ | c-Pen | H | $CF_2H$ | 1 |
| 4-071. | 1 | 3-$CF_3$ | c-Pen | H | $CF_3$ | 2 |
| 4-072. | 1 | 3-$CF_3$ | c-Pen | H | $CF_2H$ | 2 |
| 4-073. | 1 | 3-$CF_3$ | c-Hex | H | $CF_3$ | 0 |
| 4-074. | 1 | 3-$CF_3$ | c-Hex | H | $CF_2H$ | 0 |
| 4-075. | 1 | 3-$CF_3$ | c-Hex | H | $CF_3$ | 1 |
| 4-076. | 1 | 3-$CF_3$ | c-Hex | H | $CF_2H$ | 1 |
| 4-077. | 1 | 3-$CF_3$ | c-Hex | H | $CF_3$ | 2 |
| 4-078. | 1 | 3-$CF_3$ | c-Hex | H | $CF_2H$ | 2 |
| 4-079. | 1 | 3-$CF_3$ | CN | H | $CF_3$ | 0 |
| 4-080. | 1 | 3-$CF_3$ | CN | H | $CF_2H$ | 0 |
| 4-081. | 1 | 3-$CF_3$ | CN | H | $CF_3$ | 1 |
| 4-082. | 1 | 3-$CF_3$ | CN | H | $CF_2H$ | 1 |
| 4-083. | 1 | 3-$CF_3$ | CN | H | $CF_3$ | 2 |
| 4-084. | 1 | 3-$CF_3$ | CN | H | $CF_2H$ | 2 |

TABLE 4-continued 4-xxxx

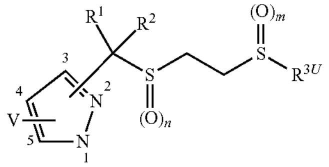

| No. | Position | V | $R^1$ | $R^2$ | $R^{3U}$ | n |
|---|---|---|---|---|---|---|
| 4-085. | 1 | 3-$CF_3$ | COOMe | H | $CF_3$ | 0 |
| 4-086. | 1 | 3-$CF_3$ | COOMe | H | $CF_2H$ | 0 |
| 4-087. | 1 | 3-$CF_3$ | COOMe | H | $CF_3$ | 1 |
| 4-088. | 1 | 3-$CF_3$ | COOMe | H | $CF_2H$ | 1 |
| 4-089. | 1 | 3-$CF_3$ | COOMe | H | $CF_3$ | 2 |
| 4-090. | 1 | 3-$CF_3$ | COOMe | H | $CF_2H$ | 2 |
| 4-091. | 1 | 3-$CF_3$ | COOEt | H | $CF_3$ | 0 |
| 4-092. | 1 | 3-$CF_3$ | COOEt | H | $CF_2H$ | 0 |
| 4-093. | 1 | 3-$CF_3$ | COOEt | H | $CF_3$ | 1 |
| 4-094. | 1 | 3-$CF_3$ | COOEt | H | $CF_2H$ | 1 |
| 4-095. | 1 | 3-$CF_3$ | COOEt | H | $CF_3$ | 2 |
| 4-096. | 1 | 3-$CF_3$ | COOEt | H | $CF_2H$ | 2 |
| 4-097. | 1 | 3-$CF_3$-5-Me | H | H | $CF_3$ | 0 |
| 4-098. | 1 | 3-$CF_3$-5-Me | H | H | $CF_2H$ | 0 |
| 4-099. | 1 | 3-$CF_3$-5-Me | H | H | $CF_3$ | 1 |
| 4-0100. | 1 | 3-$CF_3$-5-Me | H | H | $CF_2H$ | 1 |
| 4-0101. | 1 | 3-$CF_3$-5-Me | H | H | $CF_3$ | 2 |
| 4-0102. | 1 | 3-$CF_3$-5-Me | H | H | $CF_2H$ | 2 |
| 4-0103. | 1 | 3-$CF_3$-5-Me | Me | H | $CF_3$ | 0 |
| 4-0104. | 1 | 3-$CF_3$-5-Me | Me | H | $CF_2H$ | 0 |
| 4-0105. | 1 | 3-$CF_3$-5-Me | Me | H | $CF_3$ | 1 |
| 4-0106. | 1 | 3-$CF_3$-5-Me | Me | H | $CF_2H$ | 1 |
| 4-0107. | 1 | 3-$CF_3$-5-Me | Me | H | $CF_3$ | 2 |
| 4-0108. | 1 | 3-$CF_3$-5-Me | Me | H | $CF_2H$ | 2 |
| 4-0109. | 1 | 3-$CF_3$-5-Me | CN | H | $CF_3$ | 0 |
| 4-0110. | 1 | 3-$CF_3$-5-Me | CN | H | $CF_2H$ | 0 |
| 4-0111. | 1 | 3-$CF_3$-5-Me | CN | H | $CF_3$ | 1 |
| 4-0112. | 1 | 3-$CF_3$-5-Me | CN | H | $CF_2H$ | 1 |
| 4-0113. | 1 | 3-$CF_3$-5-Me | CN | H | $CF_3$ | 2 |
| 4-0114. | 1 | 3-$CF_3$-5-Me | CN | H | $CF_2H$ | 2 |
| 4-0115. | 1 | 3-$CF_3$-5-Me | COOMe | H | $CF_3$ | 0 |
| 4-0116. | 1 | 3-$CF_3$-5-Me | COOMe | H | $CF_2H$ | 0 |
| 4-0117. | 1 | 3-$CF_3$-5-Me | COOMe | H | $CF_3$ | 1 |
| 4-0118. | 1 | 3-$CF_3$-5-Me | COOMe | H | $CF_2H$ | 1 |
| 4-0119. | 1 | 3-$CF_3$-5-Me | COOMe | H | $CF_3$ | 2 |
| 4-0120. | 1 | 3-$CF_3$-5-Me | COOMe | H | $CF_2H$ | 2 |
| 4-0121. | 1 | 3-$CF_3$-5-Me | COOEt | H | $CF_3$ | 0 |
| 4-0122. | 1 | 3-$CF_3$-5-Me | COOEt | H | $CF_2H$ | 0 |
| 4-0123. | 1 | 3-$CF_3$-5-Me | COOEt | H | $CF_3$ | 1 |
| 4-0124. | 1 | 3-$CF_3$-5-Me | COOEt | H | $CF_2H$ | 1 |
| 4-0125. | 1 | 3-$CF_3$-5-Me | COOEt | H | $CF_3$ | 2 |
| 4-0126. | 1 | 3-$CF_3$-5-Me | COOEt | H | $CF_2H$ | 2 |
| 4-0127. | 1 | 3-$CF_3$-4-CN | H | H | $CF_3$ | 0 |
| 4-0128. | 1 | 3-$CF_3$-4-CN | H | H | $CF_2H$ | 0 |
| 4-0129. | 1 | 3-$CF_3$-4-CN | H | H | $CF_3$ | 1 |
| 4-0130. | 1 | 3-$CF_3$-4-CN | H | H | $CF_2H$ | 1 |
| 4-0131. | 1 | 3-$CF_3$-4-CN | H | H | $CF_3$ | 2 |
| 4-0132. | 1 | 3-$CF_3$-4-CN | H | H | $CF_2H$ | 2 |
| 4-0133. | 1 | 3-$CF_3$-4-CN | H | H | $CF_3$ | 2 |
| 4-0134. | 1 | 3-$CF_3$-4-CN | H | H | $CF_2H$ | 2 |
| 4-0135. | 1 | 3-$CF_3$-4-CN | Me | H | $CF_3$ | 0 |
| 4-0136. | 1 | 3-$CF_3$-4-CN | Me | H | $CF_2H$ | 0 |
| 4-0137. | 1 | 3-$CF_3$-4-CN | Me | H | $CF_3$ | 1 |
| 4-0138. | 1 | 3-$CF_3$-4-CN | Me | H | $CF_2H$ | 1 |
| 4-0139. | 1 | 3-$CF_3$-4-CN | Me | H | $CF_3$ | 2 |
| 4-0140. | 1 | 3-$CF_3$-4-CN | Me | H | $CF_2H$ | 2 |
| 4-0141. | 1 | 4-$CF_3$ | H | H | $CF_3$ | 0 |
| 4-0142. | 1 | 4-$CF_3$ | H | H | $CF_2H$ | 0 |
| 4-0143. | 1 | 4-$CF_3$ | H | H | $CF_3$ | 1 |
| 4-0144. | 1 | 4-$CF_3$ | H | H | $CF_2H$ | 1 |
| 4-0145. | 1 | 4-$CF_3$ | H | H | $CF_3$ | 2 |
| 4-0146. | 1 | 4-$CF_3$ | H | H | $CF_2H$ | 2 |
| 4-0147. | 1 | 4-$CF_3$ | Me | H | $CF_3$ | 0 |
| 4-0148. | 1 | 4-$CF_3$ | Me | H | $CF_2H$ | 0 |
| 4-0149. | 1 | 4-$CF_3$ | Me | H | $CF_3$ | 1 |
| 4-0150. | 1 | 4-$CF_3$ | Me | H | $CF_2H$ | 1 |
| 4-0151. | 1 | 4-$CF_3$ | Me | H | $CF_3$ | 2 |
| 4-0152. | 1 | 4-$CF_3$ | Me | H | $CF_2H$ | 2 |

TABLE 4-continued 4-xxxx

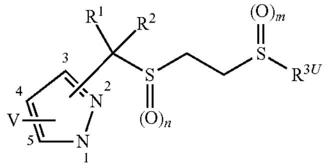

| No. | Position | V | $R^1$ | $R^2$ | $R^{3U}$ | n |
|---|---|---|---|---|---|---|
| 4-0153. | 1 | 4-$CF_3$ | Et | H | $CF_3$ | 0 |
| 4-0154. | 1 | 4-$CF_3$ | Et | H | $CF_2H$ | 0 |
| 4-0155. | 1 | 4-$CF_3$ | Et | H | $CF_3$ | 1 |
| 4-0156. | 1 | 4-$CF_3$ | Et | H | $CF_2H$ | 1 |
| 4-0157. | 1 | 4-$CF_3$ | Et | H | $CF_3$ | 2 |
| 4-0158. | 1 | 4-$CF_3$ | Et | H | $CF_2H$ | 2 |
| 4-0159. | 1 | 4-$CF_3$ | i-Pr | H | $CF_3$ | 0 |
| 4-0160. | 1 | 4-$CF_3$ | i-Pr | H | $CF_2H$ | 0 |
| 4-0161. | 1 | 4-$CF_3$ | i-Pr | H | $CF_3$ | 1 |
| 4-0162. | 1 | 4-$CF_3$ | i-Pr | H | $CF_2H$ | 1 |
| 4-0163. | 1 | 4-$CF_3$ | i-Pr | H | $CF_3$ | 2 |
| 4-0164. | 1 | 4-$CF_3$ | i-Pr | H | $CF_2H$ | 2 |
| 4-0165. | 1 | 4-$CF_3$ | c-Pr | H | $CF_3$ | 0 |
| 4-0166. | 1 | 4-$CF_3$ | c-Pr | H | $CF_2H$ | 0 |
| 4-0167. | 1 | 4-$CF_3$ | c-Pr | H | $CF_3$ | 1 |
| 4-0168. | 1 | 4-$CF_3$ | c-Pr | H | $CF_2H$ | 1 |
| 4-0169. | 1 | 4-$CF_3$ | c-Pr | H | $CF_3$ | 2 |
| 4-0170. | 1 | 4-$CF_3$ | c-Pr | H | $CF_2H$ | 2 |
| 4-0171. | 1 | 4-$CF_3$ | Pr | H | $CF_3$ | 0 |
| 4-0172. | 1 | 4-$CF_3$ | Pr | H | $CF_2H$ | 0 |
| 4-0173. | 1 | 4-$CF_3$ | Pr | H | $CF_3$ | 1 |
| 4-0174. | 1 | 4-$CF_3$ | Pr | H | $CF_2H$ | 1 |
| 4-0175. | 1 | 4-$CF_3$ | Pr | H | $CF_3$ | 2 |
| 4-0176. | 1 | 4-$CF_3$ | Pr | H | $CF_2H$ | 2 |
| 4-0177. | 1 | 4-$CF_3$ | s-Bu | H | $CF_3$ | 0 |
| 4-0178. | 1 | 4-$CF_3$ | s-Bu | H | $CF_2H$ | 0 |
| 4-0179. | 1 | 4-$CF_3$ | s-Bu | H | $CF_3$ | 1 |
| 4-0180. | 1 | 4-$CF_3$ | s-Bu | H | $CF_2H$ | 1 |
| 4-0181. | 1 | 4-$CF_3$ | s-Bu | H | $CF_3$ | 2 |
| 4-0182. | 1 | 4-$CF_3$ | s-Bu | H | $CF_2H$ | 2 |
| 4-0183. | 1 | 4-$CF_3$ | i-Bu | H | $CF_3$ | 0 |
| 4-0184. | 1 | 4-$CF_3$ | i-Bu | H | $CF_2H$ | 0 |
| 4-0185. | 1 | 4-$CF_3$ | i-Bu | H | $CF_3$ | 1 |
| 4-0186. | 1 | 4-$CF_3$ | i-Bu | H | $CF_2H$ | 1 |
| 4-0187. | 1 | 4-$CF_3$ | i-Bu | H | $CF_3$ | 2 |
| 4-0188. | 1 | 4-$CF_3$ | i-Bu | H | $CF_2H$ | 2 |
| 4-0189. | 1 | 4-$CF_3$ | Bu | H | $CF_3$ | 0 |
| 4-0190. | 1 | 4-$CF_3$ | Bu | H | $CF_2H$ | 0 |
| 4-0191. | 1 | 4-$CF_3$ | Bu | H | $CF_3$ | 1 |
| 4-0192. | 1 | 4-$CF_3$ | Bu | H | $CF_2H$ | 1 |
| 4-0193. | 1 | 4-$CF_3$ | Bu | H | $CF_3$ | 2 |
| 4-0194. | 1 | 4-$CF_3$ | Bu | H | $CF_2H$ | 2 |
| 4-0195. | 1 | 4-$CF_3$ | 2-Pen | H | $CF_3$ | 0 |
| 4-0196. | 1 | 4-$CF_3$ | 2-Pen | H | $CF_2H$ | 0 |
| 4-0197. | 1 | 4-$CF_3$ | 2-Pen | H | $CF_3$ | 1 |
| 4-0198. | 1 | 4-$CF_3$ | 2-Pen | H | $CF_2H$ | 1 |
| 4-0199. | 1 | 4-$CF_3$ | 2-Pen | H | $CF_3$ | 2 |
| 4-0200. | 1 | 4-$CF_3$ | 2-Pen | H | $CF_2H$ | 2 |
| 4-0201. | 1 | 4-$CF_3$ | 3-Pen | H | $CF_3$ | 0 |
| 4-0202. | 1 | 4-$CF_3$ | 3-Pen | H | $CF_2H$ | 0 |
| 4-0203. | 1 | 4-$CF_3$ | 3-Pen | H | $CF_3$ | 1 |
| 4-0204. | 1 | 4-$CF_3$ | 3-Pen | H | $CF_2H$ | 1 |
| 4-0205. | 1 | 4-$CF_3$ | 3-Pen | H | $CF_3$ | 2 |
| 4-0206. | 1 | 4-$CF_3$ | 3-Pen | H | $CF_2H$ | 2 |
| 4-0207. | 1 | 4-$CF_3$ | c-Pen | H | $CF_3$ | 0 |
| 4-0208. | 1 | 4-$CF_3$ | c-Pen | H | $CF_2H$ | 0 |
| 4-0209. | 1 | 4-$CF_3$ | c-Pen | H | $CF_3$ | 1 |
| 4-0210. | 1 | 4-$CF_3$ | c-Pen | H | $CF_2H$ | 1 |
| 4-0211. | 1 | 4-$CF_3$ | c-Pen | H | $CF_3$ | 2 |
| 4-0212. | 1 | 4-$CF_3$ | c-Pen | H | $CF_2H$ | 2 |
| 4-0213. | 1 | 4-$CF_3$ | c-Hex | H | $CF_3$ | 0 |
| 4-0214. | 1 | 4-$CF_3$ | c-Hex | H | $CF_2H$ | 0 |
| 4-0215. | 1 | 4-$CF_3$ | c-Hex | H | $CF_3$ | 1 |
| 4-0216. | 1 | 4-$CF_3$ | c-Hex | H | $CF_2H$ | 1 |
| 4-0217. | 1 | 4-$CF_3$ | c-Hex | H | $CF_3$ | 2 |
| 4-0218. | 1 | 4-$CF_3$ | c-Hex | H | $CF_2H$ | 2 |
| 4-0219. | 1 | 4-$CF_3$ | CN | H | $CF_3$ | 0 |
| 4-0220. | 1 | 4-$CF_3$ | CN | H | $CF_2H$ | 0 |

TABLE 4-continued 4-xxxx

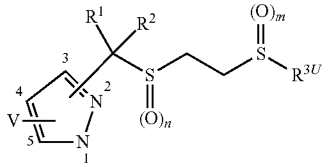

| No. | Position | V | $R^1$ | $R^2$ | $R^{3U}$ | n |
|---|---|---|---|---|---|---|
| 4-0221. | 1 | 4-$CF_3$ | CN | H | $CF_3$ | 1 |
| 4-0222. | 1 | 4-$CF_3$ | CN | H | $CF_2H$ | 1 |
| 4-0223. | 1 | 4-$CF_3$ | CN | H | $CF_3$ | 2 |
| 4-0224. | 1 | 4-$CF_3$ | CN | H | $CF_2H$ | 2 |
| 4-0225. | 1 | 4-$CF_3$ | COOMe | H | $CF_3$ | 0 |
| 4-0226. | 1 | 4-$CF_3$ | COOMe | H | $CF_2H$ | 0 |
| 4-0227. | 1 | 4-$CF_3$ | COOMe | H | $CF_3$ | 1 |
| 4-0228. | 1 | 4-$CF_3$ | COOMe | H | $CF_2H$ | 1 |
| 4-0229. | 1 | 4-$CF_3$ | COOMe | H | $CF_3$ | 2 |
| 4-0230. | 1 | 4-$CF_3$ | COOMe | H | $CF_2H$ | 2 |
| 4-0231. | 1 | 4-$CF_3$ | COOEt | H | $CF_3$ | 0 |
| 4-0232. | 1 | 4-$CF_3$ | COOEt | H | $CF_2H$ | 0 |
| 4-0233. | 1 | 4-$CF_3$ | COOEt | H | $CF_3$ | 1 |
| 4-0234. | 1 | 4-$CF_3$ | COOEt | H | $CF_2H$ | 1 |
| 4-0235. | 1 | 4-$CF_3$ | COOEt | H | $CF_3$ | 2 |
| 4-0236. | 1 | 4-$CF_3$ | COOEt | H | $CF_2H$ | 2 |
| 4-0237. | 3 | 1-Me-5-$OCHF_2$ | H | H | $CF_3$ | 0 |
| 4-0238. | 3 | 1-Me-5-$OCHF_2$ | H | H | $CF_2H$ | 0 |
| 4-0239. | 3 | 1-Me-5-$OCHF_2$ | H | H | $CF_3$ | 1 |
| 4-0240. | 3 | 1-Me-5-$OCHF_2$ | H | H | $CF_2H$ | 1 |
| 4-0241. | 3 | 1-Me-5-$OCHF_2$ | H | H | $CF_3$ | 2 |
| 4-0242. | 3 | 1-Me-5-$OCHF_2$ | H | H | $CF_2H$ | 2 |
| 4-0243. | 4 | 1-t-Bu | H | H | $CF_3$ | 0 |
| 4-0244. | 4 | 1-t-Bu | H | H | $CF_2H$ | 0 |
| 4-0245. | 4 | 1-t-Bu | H | H | $CF_3$ | 1 |
| 4-0246. | 4 | 1-t-Bu | H | H | $CF_2H$ | 1 |
| 4-0247. | 4 | 1-t-Bu | H | H | $CF_3$ | 2 |
| 4-0248. | 4 | 1-t-Bu | H | H | $CF_2H$ | 2 |
| 4-0249. | 4 | 1-$CHF_2$ | H | H | $CF_3$ | 0 |
| 4-0250. | 4 | 1-$CHF_2$ | H | H | $CF_2H$ | 0 |
| 4-0251. | 4 | 1-$CHF_2$ | H | H | $CF_3$ | 1 |
| 4-0252. | 4 | 1-$CHF_2$ | H | H | $CF_2H$ | 1 |
| 4-0253. | 4 | 1-$CHF_2$ | H | H | $CF_3$ | 2 |
| 4-0254. | 4 | 1-$CHF_2$ | H | H | $CF_2H$ | 2 |
| 4-0255. | 4 | 1-Me-3-$CF_3$-5-$OCHF_2$ | H | H | $CF_3$ | 0 |
| 4-0256. | 4 | 1-Me-3-$CF_3$-5-$OCHF_2$ | H | H | $CF_2H$ | 0 |
| 4-0257. | 4 | 1-Me-3-$CF_3$-5-$OCHF_2$ | H | H | $CF_3$ | 1 |
| 4-0258. | 4 | 1-Me-3-$CF_3$-5-$OCHF_2$ | H | H | $CF_2H$ | 1 |
| 4-0259. | 4 | 1-Me-3-$CF_3$-5-$OCHF_2$ | H | H | $CF_3$ | 2 |
| 4-0260. | 4 | 1-Me-3-$CF_3$-5-$OCHF_2$ | H | H | $CF_2H$ | 2 |
| 4-0261. | 5 | 1-Me-3-$OCHF_2$ | H | H | $CF_3$ | 0 |
| 4-0262. | 5 | 1-Me-3-$OCHF_2$ | H | H | $CF_2H$ | 0 |
| 4-0263. | 5 | 1-Me-3-$OCHF_2$ | H | H | $CF_3$ | 1 |
| 4-0264. | 5 | 1-Me-3-$OCHF_2$ | H | H | $CF_2H$ | 1 |
| 4-0265. | 5 | 1-Me-3-$OCHF_2$ | H | H | $CF_3$ | 2 |
| 4-0266. | 5 | 1-Me-3-$OCHF_2$ | H | H | $CF_2H$ | 2 |
| 4-0267. | 1 | 3-$CF_3$ | $CO_2Me$ | Me | $CF_3$ | 0 |
| 4-0268. | 1 | 3-$CF_3$ | $CO_2Me$ | Me | $CF_2H$ | 0 |
| 4-0269. | 1 | 3-$CF_3$ | $CO_2Me$ | Me | $CF_3$ | 1 |
| 4-0270. | 1 | 3-$CF_3$ | $CO_2Me$ | Me | $CF_2H$ | 1 |
| 4-0271. | 1 | 3-$CF_3$ | $CO_2Me$ | Me | $CF_3$ | 2 |
| 4-0272. | 1 | 3-$CF_3$ | $CO_2Me$ | Me | $CF_2H$ | 2 |
| 4-0273. | 1 | 3-$CF_3$ | $CO_2Et$ | Me | $CF_3$ | 0 |
| 4-0274. | 1 | 3-$CF_3$ | $CO_2Et$ | Me | $CF_2H$ | 0 |
| 4-0275. | 1 | 3-$CF_3$ | $CO_2Et$ | Me | $CF_3$ | 1 |
| 4-0276. | 1 | 3-$CF_3$ | $CO_2Et$ | Me | $CF_2H$ | 1 |
| 4-0277. | 1 | 3-$CF_3$ | $CO_2Et$ | Me | $CF_3$ | 2 |
| 4-0278. | 1 | 3-$CF_3$ | $CO_2Et$ | Me | $CF_2H$ | 2 |
| 4-0279. | 1 | 3-$CF_3$ | $CO_2$-i-Pr | Me | $CF_3$ | 0 |
| 4-0280. | 1 | 3-$CF_3$ | $CO_2$-i-Pr | Me | $CF_2H$ | 0 |
| 4-0281. | 1 | 3-$CF_3$ | $CO_2$-i-Pr | Me | $CF_3$ | 1 |
| 4-0282. | 1 | 3-$CF_3$ | $CO_2$-i-Pr | Me | $CF_2H$ | 1 |
| 4-0283. | 1 | 3-$CF_3$ | $CO_2$-i-Pr | Me | $CF_3$ | 2 |
| 4-0284. | 1 | 3-$CF_3$ | $CO_2$-i-Pr | Me | $CF_2H$ | 2 |
| 4-0285. | 1 | 3-$CF_3$ | $CO_2$-i-Pr | Me | $CF_3$ | 2 |
| 4-0286. | 1 | 3-$CF_3$ | $CO_2$-t-Bu | H | $CF_2H$ | 0 |
| 4-0287. | 1 | 3-$CF_3$ | $CO_2$-t-Bu | H | $CF_3$ | 0 |
| 4-0288. | 1 | 3-$CF_3$ | $CO_2$-t-Bu | H | $CF_2H$ | 1 |

TABLE 4-continued 4-xxxx

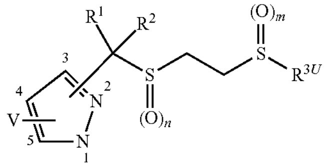

| No. | Position | V | $R^1$ | $R^2$ | $R^{3U}$ | n |
|---|---|---|---|---|---|---|
| 4-0289. | 1 | 3-$CF_3$ | $CO_2$-t-Bu | H | $CF_3$ | 1 |
| 4-0290. | 1 | 3-$CF_3$ | $CO_2$-t-Bu | H | $CF_2H$ | 2 |
| 4-0291. | 1 | 3-$CF_3$ | $CO_2$-t-Bu | H | $CF_3$ | 2 |
| 4-0292. | 1 | 3-$CF_3$ | $CO_2$-t-Bu | Me | $CF_2H$ | 0 |
| 4-0293. | 1 | 3-$CF_3$ | $CO_2$-t-Bu | Me | $CF_3$ | 0 |
| 4-0294. | 1 | 3-$CF_3$ | $CO_2$-t-Bu | Me | $CF_2H$ | 1 |
| 4-0295. | 1 | 3-$CF_3$ | $CO_2$-t-Bu | Me | $CF_3$ | 1 |
| 4-0296. | 1 | 3-$CF_3$ | $CO_2$-t-Bu | Me | $CF_2H$ | 2 |
| 4-0297. | 1 | 3-$CF_3$ | $CO_2$-t-Bu | Me | $CF_3$ | 2 |
| 4-0298. | 1 | 3-$CF_3$ | $CO_2$-c-Pen | Me | $CF_2H$ | 0 |
| 4-0299. | 1 | 3-$CF_3$ | $CO_2$-c-Pen | Me | $CF_3$ | 0 |
| 4-0300. | 1 | 3-$CF_3$ | $CO_2$-c-Pen | Me | $CF_2H$ | 1 |
| 4-0301. | 1 | 3-$CF_3$ | $CO_2$-c-Pen | Me | $CF_3$ | 1 |
| 4-0302. | 1 | 3-$CF_3$ | $CO_2$-c-Pen | Me | $CF_2H$ | 2 |
| 4-0303. | 1 | 3-$CF_3$ | $CO_2$-c-Pen | Me | $CF_3$ | 2 |
| 4-0304. | 1 | 3-$CF_3$ | $CO_2CH_2CF_3$ | Me | $CF_2H$ | 0 |
| 4-0305. | 1 | 3-$CF_3$ | $CO_2CH_2CF_3$ | Me | $CF_3$ | 0 |
| 4-0306. | 1 | 3-$CF_3$ | $CO_2CH_2CF_3$ | Me | $CF_2H$ | 1 |
| 4-0307. | 1 | 3-$CF_3$ | $CO_2CH_2CF_3$ | Me | $CF_3$ | 1 |
| 4-0308. | 1 | 3-$CF_3$ | $CO_2CH_2CF_3$ | Me | $CF_2H$ | 2 |
| 4-0309. | 1 | 3-$CF_3$ | $CO_2CH_2CF_3$ | Me | $CF_3$ | 2 |
| 4-0310. | 1 | 3-$CF_3$ | $CO_2(CH_2)_2OMe$ | Me | $CF_2H$ | 0 |
| 4-0311. | 1 | 3-$CF_3$ | $CO_2(CH_2)_2OMe$ | Me | $CF_3$ | 0 |
| 4-0312. | 1 | 3-$CF_3$ | $CO_2(CH_2)_2OMe$ | Me | $CF_2H$ | 1 |
| 4-0313. | 1 | 3-$CF_3$ | $CO_2(CH_2)_2OMe$ | Me | $CF_3$ | 1 |
| 4-0314. | 1 | 3-$CF_3$ | $CO_2(CH_2)_2OMe$ | Me | $CF_2H$ | 2 |
| 4-0315. | 1 | 3-$CF_3$ | $CO_2(CH_2)_2OMe$ | Me | $CF_3$ | 2 |
| 4-0316. | 1 | 3-$CF_3$ | $CO_2CH(Me)CH_2OMe$ | Me | $CF_2H$ | 0 |
| 4-0317. | 1 | 3-$CF_3$ | $CO_2CH(Me)CH_2OMe$ | Me | $CF_3$ | 0 |
| 4-0318. | 1 | 3-$CF_3$ | $CO_2CH(Me)CH_2OMe$ | Me | $CF_2H$ | 1 |
| 4-0319. | 1 | 3-$CF_3$ | $CO_2CH(Me)CH_2OMe$ | Me | $CF_3$ | 1 |
| 4-0320. | 1 | 3-$CF_3$ | $CO_2CH(Me)CH_2OMe$ | Me | $CF_2H$ | 2 |
| 4-0321. | 1 | 3-$CF_3$ | $CO_2CH(Me)CH_2OMe$ | Me | $CF_3$ | 2 |
| 4-0322. | 1 | 3-$CF_3$ | $CO_2(CH_2)_2O(CH_2)_2OMe$ | Me | $CF_2H$ | 0 |
| 4-0323. | 1 | 3-$CF_3$ | $CO_2(CH_2)_2O(CH_2)_2OMe$ | Me | $CF_3$ | 0 |
| 4-0324. | 1 | 3-$CF_3$ | $CO_2(CH_2)_2O(CH_2)_2OMe$ | Me | $CF_2H$ | 1 |
| 4-0325. | 1 | 3-$CF_3$ | $CO_2(CH_2)_2O(CH_2)_2OMe$ | Me | $CF_3$ | 1 |
| 4-0326. | 1 | 3-$CF_3$ | $CO_2CH(Me)CH_2OMe$ | Me | $CF_2H$ | 2 |
| 4-0327. | 1 | 3-$CF_3$ | $CO_2CH(Me)CH_2OMe$ | Me | $CF_3$ | 2 |
| 4-0328. | 1 | 3-$CF_3$ | $CO_2(CH_2)_2O(CH_2)_2OMe$ | Me | $CF_2H$ | 0 |
| 4-0329. | 1 | 3-$CF_3$ | $CO_2(CH_2)_2O(CH_2)_2OMe$ | Me | $CF_3$ | 0 |
| 4-0330. | 1 | 3-$CF_3$ | $CO_2(CH_2)_2O(CH_2)_2OMe$ | Me | $CF_2H$ | 1 |
| 4-0331. | 1 | 3-$CF_3$ | $CO_2(CH_2)_2O(CH_2)_2OMe$ | Me | $CF_3$ | 1 |
| 4-0332. | 1 | 3-$CF_3$ | $CO_2(CH_2)_2O(CH_2)_2OMe$ | Me | $CF_2H$ | 2 |
| 4-0333. | 1 | 3-$CF_3$ | $CO_2(CH_2)_2O(CH_2)_2OMe$ | Me | $CF_3$ | 2 |
| 4-0334. | 1 | 3-$CF_3$ | $CO_2(CH_2)_2SMe$ | Me | $CF_2H$ | 0 |
| 4-0335. | 1 | 3-$CF_3$ | $CO_2(CH_2)_2SMe$ | Me | $CF_3$ | 0 |
| 4-0336. | 1 | 3-$CF_3$ | $CO_2(CH_2)_2SO_2Me$ | Me | $CF_2H$ | 2 |
| 4-0337. | 1 | 3-$CF_3$ | $CO_2(CH_2)_2SO_2Me$ | Me | $CF_3$ | 2 |
| 4-0338. | 1 | 3-$CF_3$ | $CO_2CH_2CONH_2$ | Me | $CF_2H$ | 0 |
| 4-0339. | 1 | 3-$CF_3$ | $CO_2CH_2CONH_2$ | Me | $CF_3$ | 0 |
| 4-0340. | 1 | 3-$CF_3$ | $CO_2CH_2CONH_2$ | Me | $CF_2H$ | 1 |
| 4-0341. | 1 | 3-$CF_3$ | $CO_2CH_2CONH_2$ | Me | $CF_3$ | 1 |
| 4-0342. | 1 | 3-$CF_3$ | $CO_2CH_2CONH_2$ | Me | $CF_2H$ | 2 |
| 4-0343. | 1 | 3-$CF_3$ | $CO_2CH_2CONH_2$ | Me | $CF_3$ | 2 |
| 4-0344. | 1 | 3-$CF_3$ | $CO_2CH(Me)CONH_2$ | Me | $CF_2H$ | 0 |
| 4-0345. | 1 | 3-$CF_3$ | $CO_2CH(Me)CONH_2$ | Me | $CF_3$ | 0 |
| 4-0346. | 1 | 3-$CF_3$ | $CO_2CH(Me)CONH_2$ | Me | $CF_2H$ | 1 |
| 4-0347. | 1 | 3-$CF_3$ | $CO_2CH(Me)CONH_2$ | Me | $CF_3$ | 1 |
| 4-0348. | 1 | 3-$CF_3$ | $CO_2CH(Me)CONH_2$ | Me | $CF_2H$ | 2 |
| 4-0349. | 1 | 3-$CF_3$ | $CO_2CH(CH_3)CONH_2$ | Me | $CF_3$ | 2 |
| 4-0350. | 1 | 3-$CF_3$ | $CO_2CH(Me)CN$ | Me | $CF_2H$ | 0 |
| 4-0351. | 1 | 3-$CF_3$ | $CO_2CH(Me)CN$ | Me | $CF_3$ | 0 |
| 4-0352. | 1 | 3-$CF_3$ | $CO_2CH(Me)CN$ | Me | $CF_2H$ | 1 |
| 4-0353. | 1 | 3-$CF_3$ | $CO_2CH(Me)CN$ | Me | $CF_3$ | 1 |
| 4-0354. | 1 | 3-$CF_3$ | $CO_2CH(Me)CN$ | Me | $CF_3$ | 2 |
| 4-0355. | 1 | 3-$CF_3$ | $CO_2CH(Me)CN$ | Me | $CF_2H$ | 2 |
| 4-0356. | 1 | 3-$CF_3$ | $CO_2CH_2CH_2Cl$ | Me | $CF_3$ | 0 |

TABLE 4-continued

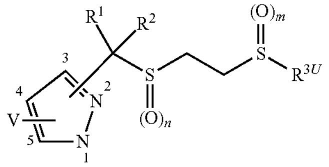

4-xxxx

| No. | Position | V | $R^1$ | $R^2$ | $R^{3U}$ | n |
|---|---|---|---|---|---|---|
| 4-0357. | 1 | $3-CF_3$ | $CO_2CH_2CH_2Cl$ | Me | $CF_2H$ | 0 |
| 4-0358. | 1 | $3-CF_3$ | $CO_2CH_2CH_2Cl$ | Me | $CF_3$ | 1 |
| 4-0359. | 1 | $3-CF_3$ | $CO_2CH_2CH_2Cl$ | Me | $CF_2H$ | 1 |
| 4-0360. | 1 | $3-CF_3$ | $CO_2CH_2CH_2Cl$ | Me | $CF_3$ | 2 |
| 4-0361. | 1 | $3-CF_3$ | $CO_2CH_2CH_2Cl$ | Me | $CF_2H$ | 2 |
| 4-0362. | 1 | $3-CF_3$ | $CO_2C(Me)_2CO_3Et$ | H | $CF_3$ | 0 |
| 4-0363. | 1 | $3-CF_3$ | $CO_2C(Me)_2CO_3Et$ | H | $CF_2H$ | 0 |
| 4-0364. | 1 | $3-CF_3$ | $CO_2C(Me)_2CO_3Et$ | H | $CF_3$ | 1 |
| 4-0365. | 1 | $3-CF_3$ | $CO_2C(Me)_2CO_3Et$ | H | $CF_2H$ | 1 |
| 4-0366. | 1 | $3-CF_3$ | $CO_2C(Me)_2CO_3Et$ | H | $CF_3$ | 2 |
| 4-0367. | 1 | $3-CF_3$ | $CO_2C(Me)_2CO_3Et$ | H | $CF_2H$ | 2 |
| 4-0368. | 1 | $3-CF_3$ | $CO_2C(Me)_2CO_3Et$ | Me | $CF_3$ | 0 |
| 4-0369. | 1 | $3-CF_3$ | $CO_2C(Me)_2CO_3Et$ | Me | $CF_2H$ | 0 |
| 4-0370. | 1 | $3-CF_3$ | $CO_2C(Me)_2CO_3Et$ | Me | $CF_3$ | 1 |
| 4-0371. | 1 | $3-CF_3$ | $CO_2C(Me)_2CO_3Et$ | Me | $CF_2H$ | 1 |
| 4-0372. | 1 | $3-CF_3$ | $CO_2C(Me)_2CO_3Et$ | Me | $CF_3$ | 2 |
| 4-0373. | 1 | $3-CF_3$ | $CO_2C(Me)_2CO_3Et$ | Me | $CF_2H$ | 2 |
| 4-0374. | 1 | $3-CF_3$ | $COO-E^2$ | Me | $CF_3$ | 0 |
| 4-0375. | 1 | $3-CF_3$ | $COO-E^2$ | Me | $CF_2H$ | 0 |
| 4-0376. | 1 | $3-CF_3$ | $COO-E^2$ | Me | $CF_3$ | 1 |
| 4-0377. | 1 | $3-CF_3$ | $COO-E^2$ | Me | $CF_2H$ | 1 |
| 4-0378. | 1 | $3-CF_3$ | $COO-E^2$ | Me | $CF_3$ | 2 |
| 4-0379. | 1 | $3-CF_3$ | $COO-E^2$ | Me | $CF_2H$ | 2 |
| 4-0380. | 1 | $3-CF_3$ | $COO-E^3$ | Me | $CF_3$ | 0 |
| 4-0381. | 1 | $3-CF_3$ | $COO-E^3$ | Me | $CF_2H$ | 0 |
| 4-0382. | 1 | $3-CF_3$ | $COO-E^3$ | Me | $CF_3$ | 1 |
| 4-0383. | 1 | $3-CF_3$ | $COO-E^3$ | Me | $CF_2H$ | 1 |
| 4-0384. | 1 | $3-CF_3$ | $COO-E^3$ | Me | $CF_3$ | 2 |
| 4-0385. | 1 | $3-CF_3$ | $COO-E^3$ | Me | $CF_2H$ | 2 |
| 4-0386. | 1 | $3-CF_3$ | $COO-E^4$ | Me | $CF_3$ | 0 |
| 4-0387. | 1 | $3-CF_3$ | $COO-E^4$ | Me | $CF_2H$ | 0 |
| 4-0388. | 1 | $3-CF_3$ | $COO-E^4$ | Me | $CF_3$ | 1 |
| 4-0389. | 1 | $3-CF_3$ | $COO-E^4$ | Me | $CF_2H$ | 1 |
| 4-0390. | 1 | $3-CF_3$ | $COO-E^4$ | Me | $CF_3$ | 2 |
| 4-0391. | 1 | $3-CF_3$ | $COO-E^4$ | Me | $CF_2H$ | 2 |
| 4-0392. | 1 | $3-CF_3$ | $COOCH_2-E^1$ | Me | $CF_3$ | 0 |
| 4-0393. | 1 | $3-CF_3$ | $COOCH_2-E^1$ | Me | $CF_2H$ | 0 |
| 4-0394. | 1 | $3-CF_3$ | $COOCH_2-E^1$ | Me | $CF_3$ | 1 |
| 4-0395. | 1 | $3-CF_3$ | $COOCH_2-E^1$ | Me | $CF_2H$ | 1 |
| 4-0396. | 1 | $3-CF_3$ | $COOCH_2-E^1$ | Me | $CF_3$ | 2 |
| 4-0397. | 1 | $3-CF_3$ | $COOCH_2-E^1$ | Me | $CF_2H$ | 2 |
| 4-0398. | 1 | $3-CF_3$ | $COOCH_2-E^2$ | Me | $CF_3$ | 0 |
| 4-0399. | 1 | $3-CF_3$ | $COOCH_2-E^2$ | Me | $CF_2H$ | 0 |
| 4-0400. | 1 | $3-CF_3$ | $COOCH_2-E^2$ | Me | $CF_3$ | 1 |
| 4-0401. | 1 | $3-CF_3$ | $COOCH_2-E^2$ | Me | $CF_2H$ | 1 |
| 4-0402. | 1 | $3-CF_3$ | $COOCH_2-E^2$ | Me | $CF_3$ | 2 |
| 4-0403. | 1 | $3-CF_3$ | $COOCH_2-E^2$ | Me | $CF_2H$ | 2 |
| 4-0404. | 1 | $3-CF_3$ | CONH-i-Pr | Me | $CF_3$ | 0 |
| 4-0405. | 1 | $3-CF_3$ | CONH-i-Pr | Me | $CF_2H$ | 0 |
| 4-0406. | 1 | $3-CF_3$ | CONH-i-Pr | Me | $CF_3$ | 1 |
| 4-0407. | 1 | $3-CF_3$ | CONH-i-Pr | Me | $CF_2H$ | 1 |
| 4-0408. | 1 | $3-CF_3$ | CONH-i-Pr | Me | $CF_3$ | 2 |
| 4-0409. | 1 | $3-CF_3$ | CONH-i-Pr | Me | $CF_2H$ | 2 |
| 4-0410. | 1 | $3-CF_3$ | Ac | H | $CF_3$ | 0 |
| 4-0411. | 1 | $3-CF_3$ | Ac | H | $CF_2H$ | 0 |
| 4-0412. | 1 | $3-CF_3$ | Ac | H | $CF_3$ | 1 |
| 4-0413. | 1 | $3-CF_3$ | Ac | H | $CF_2H$ | 1 |
| 4-0414. | 1 | $3-CF_3$ | Ac | H | $CF_3$ | 2 |
| 4-0415. | 1 | $3-CF_3$ | Ac | H | $CF_2H$ | 2 |
| 4-0416. | 1 | $3-CF_3$ | Ac | Me | $CF_3$ | 0 |
| 4-0417. | 1 | $3-CF_3$ | Ac | Me | $CF_2H$ | 0 |
| 4-0418. | 1 | $3-CF_3$ | Ac | Me | $CF_3$ | 1 |
| 4-0419. | 1 | $3-CF_3$ | Ac | Me | $CF_2H$ | 1 |
| 4-0420. | 1 | $3-CF_3$ | Ac | Me | $CF_3$ | 2 |
| 4-0421. | 1 | $3-CF_3$ | Ac | Me | $CF_2H$ | 2 |
| 4-0422. | 1 | $3-CF_3-4-Cl$ | COO-t-Bu | H | $CF_3$ | 0 |
| 4-0423. | 1 | $3-CF_3-4-Cl$ | COO-t-Bu | H | $CF_2H$ | 0 |
| 4-0424. | 1 | $3-CF_3-4-Cl$ | COO-t-Bu | H | $CF_3$ | 1 |

TABLE 4-continued 4-xxxx

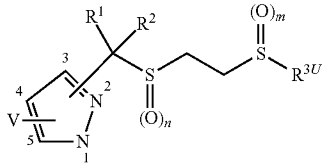

| No. | Position | V | $R^1$ | $R^2$ | $R^{3U}$ | n |
|---|---|---|---|---|---|---|
| 4-0425. | 1 | 3-$CF_3$-4-Cl | COO-t-Bu | H | $CF_2H$ | 1 |
| 4-0426. | 1 | 3-$CF_3$-4-Cl | COO-t-Bu | H | $CF_3$ | 2 |
| 4-0427. | 1 | 3-$CF_3$-4-Cl | COO-t-Bu | H | $CF_2H$ | 2 |
| 4-0428. | 1 | 3-$CF_3$-4-Cl | COO-t-Bu | Me | $CF_3$ | 0 |
| 4-0429. | 1 | 3-$CF_3$-4-Cl | COO-t-Bu | Me | $CF_2H$ | 0 |
| 4-0430. | 1 | 3-$CF_3$-4-Cl | COO-t-Bu | Me | $CF_3$ | 1 |
| 4-0431. | 1 | 3-$CF_3$-4-Cl | COO-t-Bu | Me | $CF_2H$ | 1 |
| 4-0432. | 1 | 3-$CF_3$-4-Cl | COO-t-Bu | Me | $CF_3$ | 2 |
| 4-0433. | 1 | 3-$CF_3$-4-Cl | COO-t-Bu | Me | $CF_2H$ | 2 |
| 4-0434. | 1 | 3-$CF_3$-4-$NO_2$ | COO-t-Bu | H | $CF_3$ | 0 |
| 4-0435. | 1 | 3-$CF_3$-4-$NO_2$ | COO-t-Bu | H | $CF_2H$ | 0 |
| 4-0436. | 1 | 3-$CF_3$-4-$NO_2$ | COO-t-Bu | H | $CF_3$ | 1 |
| 4-0437. | 1 | 3-$CF_3$-4-$NO_2$ | COO-t-Bu | H | $CF_2H$ | 1 |
| 4-0438. | 1 | 3-$CF_3$-4-$NO_2$ | COO-t-Bu | H | $CF_3$ | 2 |
| 4-0439. | 1 | 3-$CF_3$-4-$NO_2$ | COO-t-Bu | H | $CF_2H$ | 2 |
| 4-0440. | 1 | 3-$CF_3$-4-$NO_2$ | COO-t-Bu | Me | $CF_3$ | 0 |
| 4-0441. | 1 | 3-$CF_3$-4-$NO_2$ | COO-t-Bu | Me | $CF_2H$ | 0 |
| 4-0442. | 1 | 3-$CF_3$-4-$NO_2$ | COO-t-Bu | Me | $CF_3$ | 1 |
| 4-0443. | 1 | 3-$CF_3$-4-$NO_2$ | COO-t-Bu | Me | $CF_2H$ | 1 |
| 4-0444. | 1 | 3-$CF_3$-4-$NO_2$ | COO-t-Bu | Me | $CF_3$ | 2 |
| 4-0445. | 1 | 3-$CF_3$-4-$NO_2$ | COO-t-Bu | Me | $CF_2H$ | 2 |
| 4-0446. | 1 | 3-$CF_3$-5-Me | COO-t-Bu | H | $CF_3$ | 0 |
| 4-0447. | 1 | 3-$CF_3$-5-Me | COO-t-Bu | H | $CF_2H$ | 0 |
| 4-0448. | 1 | 3-$CF_3$-5-Me | COO-t-Bu | H | $CF_3$ | 1 |
| 4-0449. | 1 | 3-$CF_3$-5-Me | COO-t-Bu | H | $CF_2H$ | 1 |
| 4-0450. | 1 | 3-$CF_3$-5-Me | COO-t-Bu | H | $CF_3$ | 2 |
| 4-0451. | 1 | 3-$CF_3$-5-Me | COO-t-Bu | H | $CF_2H$ | 2 |
| 4-0452. | 1 | 3-$CF_3$-5-Me | COO-t-Bu | Me | $CF_3$ | 0 |
| 4-0453. | 1 | 3-$CF_3$-5-Me | COO-t-Bu | Me | $CF_2H$ | 0 |
| 4-0454. | 1 | 3-$CF_3$-5-Me | COO-t-Bu | Me | $CF_3$ | 1 |
| 4-0455. | 1 | 3-$CF_3$-5-Me | COO-t-Bu | Me | $CF_2H$ | 1 |
| 4-0456. | 1 | 3-$CF_3$-5-Me | COO-t-Bu | Me | $CF_3$ | 2 |
| 4-0457. | 1 | 3-$CF_3$-5-Me | COO-t-Bu | Me | $CF_2H$ | 2 |
| 4-0458. | 1 | 5-$CF_3$ | COOMe | H | $CF_3$ | 0 |
| 4-0459. | 1 | 5-$CF_3$ | COOMe | H | $CF_2H$ | 0 |
| 4-0460. | 1 | 5-$CF_3$ | COOMe | H | $CF_3$ | 1 |
| 4-0461. | 1 | 5-$CF_3$ | COOMe | H | $CF_2H$ | 1 |
| 4-0462. | 1 | 5-$CF_3$ | COOMe | H | $CF_3$ | 2 |
| 4-0463. | 1 | 5-$CF_3$ | COOMe | H | $CF_2H$ | 2 |
| 4-0464. | 1 | 3-t-Bu | COO-t-Bu | Me | $CF_3$ | 0 |
| 4-0465. | 1 | 3-t-Bu | COO-t-Bu | Me | $CF_2H$ | 0 |
| 4-0466. | 1 | 3-t-Bu | COO-t-Bu | Me | $CF_3$ | 1 |
| 4-0467. | 1 | 3-t-Bu | COO-t-Bu | Me | $CF_2H$ | 1 |
| 4-0468. | 1 | 3-t-Bu | COO-t-Bu | Me | $CF_3$ | 2 |
| 4-0469. | 1 | 3-t-Bu | COO-t-Bu | Me | $CF_2H$ | 2 |
| 4-0470. | 4 | 1-t-Bu-3-$CF_3$-5-Cl | H | H | $CF_3$ | 0 |
| 4-0471. | 4 | 1-t-Bu-3-$CF_3$-5-Cl | H | H | $CF_2H$ | 0 |
| 4-0472. | 4 | 1-t-Bu-3-$CF_3$-5-Cl | H | H | $CF_3$ | 1 |
| 4-0473. | 4 | 1-t-Bu-3-$CF_3$-5-Cl | H | H | $CF_2H$ | 1 |
| 4-0474. | 4 | 1-t-Bu-3-$CF_3$-5-Cl | H | H | $CF_3$ | 2 |
| 4-0475. | 4 | 1-t-Bu-3-$CF_3$-5-Cl | H | H | $CF_2H$ | 2 |
| 4-0476. | 4 | 1-t-Bu-3-$CF_3$-5-Cl | Me | H | $CF_3$ | 2 |
| 4-0477. | 4 | 1-t-Bu-3-$CF_3$-5-Cl | Me | H | $CF_2H$ | 2 |
| 4-0478. | 4 | 1-t-Bu-3-$CF_3$ | Me | H | $CF_3$ | 2 |
| 4-0479. | 4 | 1-t-Bu-3-$CF_3$ | Me | H | $CF_2H$ | 2 |
| 4-0480. | 1 | $CF_3$ | COO-i-Pr | H | $CF_3$ | 0 |
| 4-0481. | 1 | $CF_3$ | COO-i-Pr | H | $CF_2H$ | 0 |
| 4-0482. | 1 | $CF_3$ | COO-i-Pr | H | $CF_3$ | 1 |
| 4-0483. | 1 | $CF_3$ | COO-i-Pr | H | $CF_2H$ | 1 |
| 4-0484. | 1 | $CF_3$ | COO-i-Pr | H | $CF_3$ | 2 |
| 4-0485. | 1 | $CF_3$ | COO-i-Pr | H | $CF_2H$ | 2 |
| 4-0486. | 1 | $CF_3$ | COOH | Me | $CF_3$ | 0 |
| 4-0487. | 1 | $CF_3$ | COOH | Me | $CF_2H$ | 0 |

wherein m is 0 or 1;

Position in Table 4 is the position on the pyrazoyl group which is substituted by the moiety

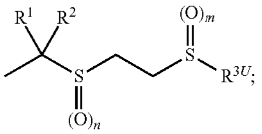

V, $R^1$, $R^2$, $R^{3U}$ and n are defined in Table 4; and $E^1$, $E^2$, $E_3$ and $E^4$ are the following structures:

$E^1$

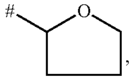

-continued $E^2$

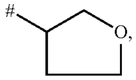

$E^3$

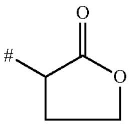

and $E^4$

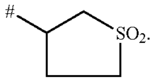

17. A compound of formula 5-xxxx, selected from Table 5:

TABLE 5

5-xxxx

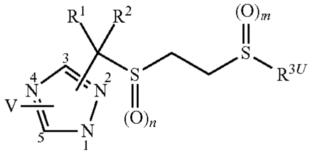

| No. | position | V | $R^1$ | $R^2$ | $R^{3U}$ | n |
|---|---|---|---|---|---|---|
| 5-01. | 1 | 3-$CF_3$ | H | H | $CF_3$ | 0 |
| 5-02. | 1 | 3-$CF_3$ | H | H | $CF_3$ | 1 |
| 5-03. | 1 | 3-$CF_3$ | H | H | $CF_3$ | 2 |
| 5-04. | 1 | 3-$CF_3$ | Me | H | $CF_3$ | 0 |
| 5-05. | 1 | 3-$CF_3$ | Me | H | $CF_3$ | 1 |
| 5-06. | 1 | 3-$CF_3$ | Me | H | $CF_3$ | 2 |
| 5-07. | 1 | 3-$CF_3$ | Me | Me | $CF_3$ | 2 |
| 5-08. | 1 | 3-$CF_3$ | Et | H | $CF_3$ | 0 |
| 5-09. | 1 | 3-$CF_3$ | Et | H | $CF_3$ | 1 |
| 5-010. | 1 | 3-$CF_3$ | Et | H | $CF_3$ | 2 |
| 5-011. | 1 | 3-$CF_3$ | i-Pr | H | $CF_3$ | 0 |
| 5-012. | 1 | 3-$CF_3$ | i-Pr | H | $CF_3$ | 1 |
| 5-013. | 1 | 3-$CF_3$ | i-Pr | H | $CF_3$ | 2 |
| 5-014. | 1 | 3-$CF_3$ | c-Pr | H | $CF_3$ | 0 |
| 5-015. | 1 | 3-$CF_3$ | c-Pr | H | $CF_3$ | 1 |
| 5-016. | 1 | 3-$CF_3$ | c-Pr | H | $CF_3$ | 2 |
| 5-017. | 1 | 3-$CF_3$ | Pr | H | $CF_3$ | 0 |
| 5-018. | 1 | 3-$CF_3$ | Pr | H | $CF_3$ | 1 |
| 5-019. | 1 | 3-$CF_3$ | Pr | H | $CF_3$ | 2 |
| 5-020. | 1 | 3-$CF_3$ | s-Bu | H | $CF_3$ | 0 |
| 5-021. | 1 | 3-$CF_3$ | s-Bu | H | $CF_3$ | 1 |
| 5-022. | 1 | 3-$CF_3$ | s-Bu | H | $CF_3$ | 2 |
| 5-023. | 1 | 3-$CF_3$ | i-Bu | H | $CF_3$ | 0 |
| 5-024. | 1 | 3-$CF_3$ | i-Bu | H | $CF_3$ | 1 |
| 5-025. | 1 | 3-$CF_3$ | i-Bu | H | $CF_3$ | 2 |
| 5-026. | 1 | 3-$CF_3$ | Bu | H | $CF_3$ | 0 |
| 5-027. | 1 | 3-$CF_3$ | Bu | H | $CF_3$ | 1 |
| 5-028. | 1 | 3-$CF_3$ | Bu | H | $CF_3$ | 2 |
| 5-029. | 1 | 3-$CF_3$ | 2-Pen | H | $CF_3$ | 0 |
| 5-030. | 1 | 3-$CF_3$ | 2-Pen | H | $CF_3$ | 1 |
| 5-031. | 1 | 3-$CF_3$ | 2-Pen | H | $CF_3$ | 2 |
| 5-032. | 1 | 3-$CF_3$ | 3-Pen | H | $CF_3$ | 0 |
| 5-033. | 1 | 3-$CF_3$ | 3-Pen | H | $CF_3$ | 1 |
| 5-034. | 1 | 3-$CF_3$ | 3-Pen | H | $CF_3$ | 2 |
| 5-035. | 1 | 3-$CF_3$ | c-Pen | H | $CF_3$ | 0 |
| 5-036. | 1 | 3-$CF_3$ | c-Pen | H | $CF_3$ | 1 |
| 5-037. | 1 | 3-$CF_3$ | c-Pen | H | $CF_3$ | 2 |
| 5-038. | 1 | 3-$CF_3$ | c-Hex | H | $CF_3$ | 0 |
| 5-039. | 1 | 3-$CF_3$ | c-Hex | H | $CF_3$ | 1 |
| 5-040. | 1 | 3-$CF_3$ | c-Hex | H | $CF_3$ | 2 |
| 5-041. | 1 | 3-$CF_3$ | CN | H | $CF_3$ | 0 |
| 5-042. | 1 | 3-$CF_3$ | CN | H | $CF_3$ | 1 |

TABLE 5-continued

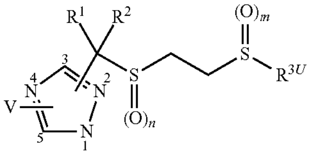

5-xxxx

| No. | position | V | $R^1$ | $R^2$ | $R^{3U}$ | n |
|---|---|---|---|---|---|---|
| 5-043. | 1 | 3-$CF_3$ | CN | H | $CF_3$ | 2 |
| 5-044. | 1 | 3-$CF_3$ | COOMe | H | $CF_3$ | 0 |
| 5-045. | 1 | 3-$CF_3$ | COOMe | H | $CF_3$ | 1 |
| 5-046. | 1 | 3-$CF_3$ | COOMe | H | $CF_3$ | 2 |
| 5-047. | 1 | 3-$CF_3$ | COOEt | H | $CF_3$ | 0 |
| 5-048. | 1 | 3-$CF_3$ | COOEt | H | $CF_3$ | 1 |
| 5-049. | 1 | 3-$CF_3$ | COOEt | H | $CF_3$ | 2 |
| 5-050. | 1 | 3-$SCF_3$ | H | H | $CF_3$ | 0 |
| 5-051. | 1 | 3-$SCF_3$ | H | H | $CF_3$ | 1 |
| 5-052. | 1 | 3-$SCF_3$ | H | H | $CF_3$ | 2 |
| 5-053. | 1 | 3-$SCF_3$ | Me | H | $CF_3$ | 0 |
| 5-054. | 1 | 3-$SCF_3$ | Me | H | $CF_3$ | 1 |
| 5-055. | 1 | 3-$SCF_3$ | Me | H | $CF_3$ | 2 |
| 5-056. | 1 | 3-$CF_3$-5-Me | H | H | $CF_3$ | 0 |
| 5-057. | 1 | 3-$CF_3$-5-Me | H | H | $CF_3$ | 1 |
| 5-058. | 1 | 3-$CF_3$-5-Me | H | H | $CF_3$ | 2 |
| 5-059. | 1 | 3-$CF_3$-5-Me | Me | H | $CF_3$ | 0 |
| 5-060. | 1 | 3-$CF_3$-5-Me | Me | H | $CF_3$ | 1 |
| 5-061. | 1 | 3-$CF_3$-5-Me | Me | H | $CF_3$ | 2 |
| 5-062. | 1 | 3-$CF_3$-5-Me | CN | H | $CF_3$ | 0 |
| 5-063. | 1 | 3-$CF_3$-5-Me | CN | H | $CF_3$ | 1 |
| 5-064. | 1 | 3-$CF_3$-5-Me | CN | H | $CF_3$ | 2 |
| 5-065. | 1 | 3-$CF_3$-5-Me | COOMe | H | $CF_3$ | 0 |
| 5-066. | 1 | 3-$CF_3$-5-Me | COOMe | H | $CF_3$ | 1 |
| 5-067. | 1 | 3-$CF_3$-5-Me | COOMe | H | $CF_3$ | 2 |
| 5-068. | 1 | 3-$CF_3$-5-Me | COOEt | H | $CF_3$ | 0 |
| 5-069. | 1 | 3-$CF_3$-5-Me | COOEt | H | $CF_3$ | 1 |
| 5-070. | 1 | 3-$CF_3$-5-Me | COOEt | H | $CF_3$ | 2 |
| 5-071. | 3 | — | H | H | $CF_3$ | 0 |
| 5-072. | 3 | 1-$CH_2CF_3$ | H | H | $CF_3$ | 0 |
| 5-073. | 3 | 1-$CH_2CF_3$ | H | H | $CF_3$ | 1 |
| 5-074. | 3 | 1-$CH_2CF_3$ | H | H | $CF_3$ | 2 |
| 5-075. | 3 | 1-$CBrF_2$ | H | H | $CF_3$ | 0 |
| 5-076. | 3 | 1-$CBrF_2$ | H | H | $CF_3$ | 1 |
| 5-077. | 3 | 1-$CBrF_2$ | H | H | $CF_3$ | 2 |
| 5-078. | 3 | 1-$CHF_2$ | H | H | $CF_3$ | 0 |
| 5-079. | 3 | 1-$CHF_2$ | H | H | $CF_3$ | 1 |
| 5-080. | 3 | 1-$CHF_2$ | H | H | $CF_3$ | 2 |
| 5-081. | 3 | 1-$CH_2$—c-Pr | H | H | $CF_3$ | 0 |
| 5-082. | 3 | 1-$CH_2$—c-Pr | H | H | $CF_3$ | 1 |
| 5-083. | 3 | 1-$CH_2$—c-Pr | H | H | $CF_3$ | 2 |
| 5-084. | 3 | 1-$CF_2CHF_2$ | H | H | $CF_3$ | 0 |
| 5-085. | 3 | 1-$CF_2CHF_2$ | H | H | $CF_3$ | 1 |
| 5-086. | 3 | 1-$CF_2CHF_2$ | H | H | $CF_3$ | 2 |
| 5-087. | 3 | 1-CF=$F_2$ | H | H | $CF_3$ | 0 |
| 5-088. | 3 | 1-CF=$F_2$ | H | H | $CF_3$ | 1 |
| 5-089. | 3 | 1-CF=$F_2$ | H | H | $CF_3$ | 2 |
| 5-090. | 5 | 1-$CBrF_2$ | H | H | $CF_3$ | 0 |
| 5-091. | 5 | 1-$CBrF_2$ | H | H | $CF_3$ | 1 |
| 5-092. | 5 | 1-$CBrF_2$ | H | H | $CF_3$ | 2 |
| 5-093. | 1 | 3-$CF_3$ | $CH_2OH$ | H | $CF_3$ | 0 |
| 5-094. | 1 | 3-$CF_3$ | $CH_2OH$ | H | $CF_3$ | 1 |
| 5-095. | 1 | 3-$CF_3$ | $CH_2OH$ | H | $CF_3$ | 2 |
| 5-096. | 1 | 3-$CF_3$ | $CH_2OH$ | Me | $CF_3$ | 0 |
| 5-097. | 1 | 3-$CF_3$ | $CH_2OH$ | Me | $CF_3$ | 1 |
| 5-098. | 1 | 3-$CF_3$ | $CH_2OH$ | Me | $CF_3$ | 2 |
| 5-099. | 1 | 3-$CF_3$ | $CH_2OMe$ | Me | $CF_3$ | 0 |
| 5-0100. | 1 | 3-$CF_3$ | $CH_2OMe$ | Me | $CF_3$ | 1 |
| 5-0101. | 1 | 3-$CF_3$ | $CH_2OMe$ | Me | $CF_3$ | 2 |
| 5-0102. | 1 | 3-$CF_3$ | $CH_2OAc$ | Me | $CF_3$ | 0 |
| 5-0103. | 1 | 3-$CF_3$ | $CH_2OAc$ | Me | $CF_3$ | 1 |
| 5-0104. | 1 | 3-$CF_3$ | $CH_2OAc$ | Me | $CF_3$ | 2 |
| 5-0105. | 1 | 3-$CF_3$ | $CH_2OCO$—t-Bu | Me | $CF_3$ | 0 |
| 5-0106. | 1 | 3-$CF_3$ | $CH_2OCO$—t-Bu | Me | $CF_3$ | 1 |
| 5-0107. | 1 | 3-$CF_3$ | $CH_2OCO$—t-Bu | Me | $CF_3$ | 2 |
| 5-0108. | 1 | 3-$CF_3$ | $CH_2OCONMe_2$ | Me | $CF_3$ | 0 |
| 5-0109. | 1 | 3-$CF_3$ | $CH_2OCONMe_2$ | Me | $CF_3$ | 1 |
| 5-0110. | 1 | 3-$CF_3$ | $CH_2OCONMe_2$ | Me | $CF_3$ | 2 |

TABLE 5-continued 5-xxxx

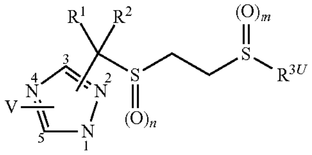

| No. | position | V | $R^1$ | $R^2$ | $R^{3U}$ | n |
|---|---|---|---|---|---|---|
| 5-0111. | 1 | 3-$CF_3$ | CH(Me)OH | Me | $CF_3$ | 0 |
| 5-0112. | 1 | 3-$CF_3$ | CH(Me)OH | Me | $CF_3$ | 2 |
| 5-0113. | 1 | 3-$CF_3$ | CH(Me)OMe | Me | $CF_3$ | 0 |
| 5-0114. | 1 | 3-$CF_3$ | CH(Me)OMe | Me | $CF_3$ | 2 |
| 5-0115. | 1 | 3-$CF_3$ | CH(OH)—t-Bu | Me | $CF_3$ | 0 |
| 5-0116. | 1 | 3-$CF_3$ | COOH | Me | $CF_3$ | 0 |
| 5-0117. | 1 | 3-$CF_3$ | COOMe | Me | $CF_3$ | 0 |
| 5-0118. | 1 | 3-$CF_3$ | COOMe | Me | $CF_3$ | 1 |
| 5-0119. | 1 | 3-$CF_3$ | COOMe | Me | $CF_3$ | 2 |
| 5-0120. | 1 | 3-$CF_3$ | COOEt | Me | $CF_3$ | 0 |
| 5-0121. | 1 | 3-$CF_3$ | COOEt | Me | $CF_3$ | 1 |
| 5-0122. | 1 | 3-$CF_3$ | COOEt | Me | $CF_3$ | 2 |
| 5-0123. | 1 | 3-$CF_3$ | COO—i-Pr | H | $CF_3$ | 0 |
| 5-0124. | 1 | 3-$CF_3$ | COO—i-Pr | H | $CF_3$ | 1 |
| 5-0125. | 1 | 3-$CF_3$ | COO—i-Pr | H | $CF_3$ | 2 |
| 5-0126. | 1 | 3-$CF_3$ | COO—i-Pr | Me | $CF_3$ | 0 |
| 5-0127. | 1 | 3-$CF_3$ | COO—i-Pr | Me | $CF_3$ | 1 |
| 5-0128. | 1 | 3-$CF_3$ | COO—i-Pr | Me | $CF_3$ | 2 |
| 5-0129. | 1 | 3-$CF_3$ | COO—t-Bu | H | $CF_3$ | 0 |
| 5-0130. | 1 | 3-$CF_3$ | COO—t-Bu | H | $CF_3$ | 1 |
| 5-0131. | 1 | 3-$CF_3$ | COO—t-Bu | H | $CF_3$ | 2 |
| 5-0132. | 1 | 3-$CF_3$ | COO—t-Bu | Me | $CF_3$ | 0 |
| 5-0133. | 1 | 3-$CF_3$ | COO—t-Bu | Me | $CF_3$ | 1 |
| 5-0134. | 1 | 3-$CF_3$ | COO—t-Bu | Me | $CF_3$ | 2 |
| 5-0135. | 1 | 3-$CF_3$ | COO—i-Bu | Me | $CF_3$ | 0 |
| 5-0136. | 1 | 3-$CF_3$ | COO—i-Bu | Me | $CF_3$ | 1 |
| 5-0137. | 1 | 3-$CF_3$ | COO—i-Bu | Me | $CF_3$ | 2 |
| 5-0138. | 1 | 3-$CF_3$ | COO—s-Bu | Me | $CF_3$ | 0 |
| 5-0139. | 1 | 3-$CF_3$ | COO—s-Bu | Me | $CF_3$ | 1 |
| 5-0140. | 1 | 3-$CF_3$ | COO—s-Bu | Me | $CF_3$ | 2 |
| 5-0141. | 1 | 3-$CF_3$ | COO—c-Pen | Me | $CF_3$ | 0 |
| 5-0142. | 1 | 3-$CF_3$ | COO—c-Pen | Me | $CF_3$ | 1 |
| 5-0143. | 1 | 3-$CF_3$ | COO—c-Pen | Me | $CF_3$ | 2 |
| 5-0144. | 1 | 3-$CF_3$ | $COOCH_2$—t-Bu | Me | $CF_3$ | 0 |
| 5-0145. | 1 | 3-$CF_3$ | $COOCH_2$—t-Bu | Me | $CF_3$ | 1 |
| 5-0146. | 1 | 3-$CF_3$ | $COOCH_2$—t-Bu | Me | $CF_3$ | 2 |
| 5-0147. | 1 | 3-$CF_3$ | $COOCH_2$—c-Pr | Me | $CF_3$ | 0 |
| 5-0148. | 1 | 3-$CF_3$ | $COOCH_2$—c-Pr | Me | $CF_3$ | 1 |
| 5-0149. | 1 | 3-$CF_3$ | $COOCH_2$—c-Pr | Me | $CF_3$ | 2 |
| 5-0150. | 1 | 3-$CF_3$ | $COOCH_2CF_3$ | Me | $CF_3$ | 0 |
| 5-0151. | 1 | 3-$CF_3$ | $COOCH_2CF_3$ | Me | $CF_3$ | 1 |
| 5-0152. | 1 | 3-$CF_3$ | $COOCH_2CF_3$ | Me | $CF_3$ | 2 |
| 5-0153. | 1 | 3-$CF_3$ | $CO_2CH_2C{\equiv}CH$ | Me | $CF_3$ | 0 |
| 5-0154. | 1 | 3-$CF_3$ | $CO_2CH_2C{\equiv}CH$ | Me | $CF_3$ | 1 |
| 5-0155. | 1 | 3-$CF_3$ | $CO_2CH_2C{\equiv}CH$ | Me | $CF_3$ | 2 |
| 5-0156. | 1 | 3-$CF_3$ | $CO_2CH_2CH{=}CH_2$ | Me | $CF_3$ | 0 |
| 5-0157. | 1 | 3-$CF_3$ | $CO_2CH_2CH{=}CH_2$ | Me | $CF_3$ | 1 |
| 5-0158. | 1 | 3-$CF_3$ | $CO_2CH_2CH{=}CH_2$ | Me | $CF_3$ | 2 |
| 5-0159. | 1 | 3-$CF_3$ | $CO_2CH_2CH_2OMe$ | Me | $CF_3$ | 0 |
| 5-0160. | 1 | 3-$CF_3$ | $CO_2CH_2CH_2OMe$ | Me | $CF_3$ | 1 |
| 5-0161. | 1 | 3-$CF_3$ | $CO_2CH_2CH_2OMe$ | Me | $CF_3$ | 2 |
| 5-0162. | 1 | 3-$CF_3$ | $CO_2CH_2CH_2SMe$ | Me | $CF_3$ | 0 |
| 5-0163. | 1 | 3-$CF_3$ | $CO_2CH_2CH_2SO_2Me$ | Me | $CF_3$ | 0 |
| 5-0164. | 1 | 3-$CF_3$ | $CO_2CH_2CH_2SO_2Me$ | Me | $CF_3$ | 1 |
| 5-0165. | 1 | 3-$CF_3$ | $CO_2CH_2CH_2SO_2Me$ | Me | $CF_3$ | 2 |
| 5-0166. | 1 | 3-$CF_3$ | $CO_2CH_2CONH_2$ | Me | $CF_3$ | 0 |
| 5-0167. | 1 | 3-$CF_3$ | $CO_2CH_2CONH_2$ | Me | $CF_3$ | 1 |
| 5-0168. | 1 | 3-$CF_3$ | $CO_2CH_2CONH_2$ | Me | $CF_3$ | 2 |
| 5-0169. | 1 | 3-$CF_3$ | $CO_2CH(Me)C{\equiv}CH$ | Me | $CF_3$ | 0 |
| 5-0170. | 1 | 3-$CF_3$ | $CO_2CH(Me)C{\equiv}CH$ | Me | $CF_3$ | 1 |
| 5-0171. | 1 | 3-$CF_3$ | $CO_2CH(Me)C{\equiv}CH$ | Me | $CF_3$ | 2 |
| 5-0172. | 1 | 3-$CF_3$ | $CO_2CH(Me)CN$ | Me | $CF_3$ | 0 |
| 5-0173. | 1 | 3-$CF_3$ | $CO_2CH(Me)CN$ | Me | $CF_3$ | 1 |
| 5-0174. | 1 | 3-$CF_3$ | $CO_2CH(Me)CN$ | Me | $CF_3$ | 2 |
| 5-0175. | 1 | 3-$CF_3$ | $CO_2CH(Me)CONH_2$ | Me | $CF_3$ | 0 |
| 5-0176. | 1 | 3-$CF_3$ | $CO_2CH(Me)CONH_2$ | Me | $CF_3$ | 1 |
| 5-0177. | 1 | 3-$CF_3$ | $CO_2CH(Me)CONH_2$ | Me | $CF_3$ | 2 |
| 5-0178. | 1 | 3-$CF_3$ | $CO_2C(Me)_2COOEt$ | H | $CF_3$ | 0 |

TABLE 5-continued 5-xxxx

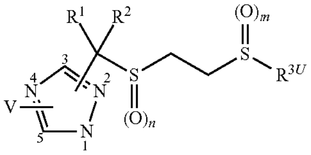

| No. | position | V | $R^1$ | $R^2$ | $R^{3U}$ | n |
|---|---|---|---|---|---|---|
| 5-0179. | 1 | 3-$CF_3$ | $CO_2C(Me)_2COOEt$ | H | $CF_3$ | 1 |
| 5-0180. | 1 | 3-$CF_3$ | $CO_2C(Me)_2COOEt$ | H | $CF_3$ | 2 |
| 5-0181. | 1 | 3-$CF_3$ | $CO_2C(Me)_2COOEt$ | Me | $CF_3$ | 0 |
| 5-0182. | 1 | 3-$CF_3$ | $CO_2C(Me)_2COOEt$ | Me | $CF_3$ | 1 |
| 5-0183. | 1 | 3-$CF_3$ | $CO_2C(Me)_2COOEt$ | Me | $CF_3$ | 2 |
| 5-0184. | 1 | 3-$CF_3$ | $COOCH_2$—$E^1$ | Me | $CF_3$ | 0 |
| 5-0185. | 1 | 3-$CF_3$ | $COOCH_2$—$E^1$ | Me | $CF_3$ | 1 |
| 5-0186. | 1 | 3-$CF_3$ | $COOCH_2$—$E^1$ | Me | $CF_3$ | 2 |
| 5-0187. | 1 | 3-$CF_3$ | COO—$E^2$ | Me | $CF_3$ | 0 |
| 5-0188. | 1 | 3-$CF_3$ | COO—$E^2$ | Me | $CF_3$ | 1 |
| 5-0189. | 1 | 3-$CF_3$ | COO—$E^2$ | Me | $CF_3$ | 2 |
| 5-0190. | 1 | 3-$CF_3$ | COO—$E^3$ | Me | $CF_3$ | 0 |
| 5-0191. | 1 | 3-$CF_3$ | COO—$E^3$ | Me | $CF_3$ | 1 |
| 5-0192. | 1 | 3-$CF_3$ | COO—$E^3$ | Me | $CF_3$ | 2 |
| 5-0193. | 1 | 3-$CF_3$ | COO—$E^4$ | Me | $CF_3$ | 0 |
| 5-0194. | 1 | 3-$CF_3$ | COO—$E^4$ | Me | $CF_3$ | 1 |
| 5-0195. | 1 | 3-$CF_3$ | COO—$E^4$ | Me | $CF_3$ | 2 |
| 5-0196. | 1 | 3-$CF_3$ | $COOCH_2Ph$ | Me | $CF_3$ | 0 |
| 5-0197. | 1 | 3-$CF_3$ | $COOCH_2Ph$ | Me | $CF_3$ | 1 |
| 5-0198. | 1 | 3-$CF_3$ | $COOCH_2Ph$ | Me | $CF_3$ | 2 |
| 5-0199. | 1 | 3-$CF_3$ | $CO_2CH(Me)$—$E^6$ | Me | $CF_3$ | 0 |
| 5-0200. | 1 | 3-$CF_3$ | $CO_2CH(Me)$—$E^6$ | Me | $CF_3$ | 1 |
| 5-0201. | 1 | 3-$CF_3$ | $CO_2CH(Me)$—$E^6$ | Me | $CF_3$ | 2 |
| 5-0202. | 1 | 3-$CF_3$ | COO—$E^7$ | Me | $CF_3$ | 0 |
| 5-0203. | 1 | 3-$CF_2$ | COO—$E^7$ | Me | $CF_3$ | 1 |
| 5-0204. | 1 | 3-$CF_3$ | COO—$E^7$ | Me | $CF_3$ | 2 |
| 5-0205. | 1 | 3-$CF_3$ | COS—i-Pr | Me | $CF_3$ | 0 |
| 5-0206. | 1 | 3-$CF_3$ | COS—i-Pr | Me | $CF_3$ | 1 |
| 5-0207. | 1 | 3-$CF_3$ | COS—i-Pr | Me | $CF_3$ | 2 |
| 5-0208. | 1 | 3-$CF_3$ | COS—t-Bu | Me | $CF_3$ | 0 |
| 5-0209. | 1 | 3-$CF_3$ | COS—t-Bu | Me | $CF_3$ | 1 |
| 5-0210. | 1 | 3-$CF_3$ | COS—t-Bu | Me | $CF_3$ | 2 |
| 5-0211. | 1 | 3-$CF_3$ | COS—c-Hex | Me | $CF_3$ | 0 |
| 5-0212. | 1 | 3-$CF_3$ | COS—c-Hex | Me | $CF_3$ | 1 |
| 5-0213. | 1 | 3-$CF_3$ | COS—c-Hex | Me | $CF_3$ | 2 |
| 5-0214. | 1 | 3-$CF_3$ | CONHMe | Me | $CF_3$ | 2 |
| 5-0215. | 1 | 3-$CF_3$ | CONH—i-Pr | Me | $CF_3$ | 2 |
| 5-0216. | 1 | 3-$CF_3$ | $CONHCONH_2$ | Me | $CF_3$ | 0 |
| 5-0217. | 1 | 3-$CF_3$ | $CONHCONH_2$ | Me | $CF_3$ | 1 |
| 5-0218. | 1 | 3-$CF_3$ | $CONHCONH_2$ | Me | $CF_3$ | 2 |
| 5-0219. | 1 | 3-$CF_3$ | CONHCONHMe | Me | $CF_3$ | 0 |
| 5-0220. | 1 | 3-$CF_3$ | $CON(Me)CONH_2$ | Me | $CF_3$ | 0 |
| 5-0221. | 1 | 3-$CF_3$ | $CON(Me)CONH_2$ | Me | $CF_3$ | 2 |
| 5-0222. | 1 | 3-$CF_3$ | CON(Me)CONHMe | Me | $CF_3$ | 0 |
| 5-0223. | 1 | 3-$CF_3$ | CON(Me)CONHMe | Me | $CF_3$ | 2 |
| 5-0224. | 1 | 3-$CF_3$ | CN | H | $CF_3$ | 0 |
| 5-0225. | 1 | 3-$CF_3$ | CN | Me | $CF_3$ | 0 |
| 5-0226. | 1 | 3-$CF_3$ | CN | Me | $CF_3$ | 1 |
| 5-0227. | 1 | 3-$CF_3$ | CN | Me | $CF_3$ | 2 |
| 5-0228. | 1 | 3-$CF_3$ | CHO | Me | $CF_3$ | 0 |
| 5-0229. | 1 | 3-$CF_3$ | Ac | H | $CF_3$ | 0 |
| 5-0230. | 1 | 3-$CF_3$ | Ac | Me | $CF_3$ | 0 |
| 5-0231. | 1 | 3-$CF_3$ | Ac | Me | $CF_3$ | 1 |
| 5-0232. | 1 | 3-$CF_3$ | Ac | Me | $CF_3$ | 2 |
| 5-0233. | 1 | 3-$CF_3$ | CO—i-Pr | Me | $CF_3$ | 0 |
| 5-0234. | 1 | 3-$CF_3$ | CO—t-Bu | Me | $CF_3$ | 0 |
| 5-0235. | 1 | 3-$CF_3$ | CO—t-Bu | Me | $CF_3$ | 1 |
| 5-0236. | 1 | 3-$CF_3$ | CO—t-Bu | Me | $CF_3$ | 2 |
| 5-0237. | 1 | 3-$CF_3$ | CH═N—OH | Me | $CF_3$ | 0 |
| 5-0238. | 1 | 3-$CF_3$ | CH═N—OH | Me | $CF_3$ | 1 |
| 5-0239. | 1 | 3-$CF_3$ | CH═N—OH | Me | $CF_3$ | 2 |
| 5-0240. | 1 | 3-$CF_3$ | CH═N—OMe | Me | $CF_3$ | 0 |
| 5-0241. | 1 | 3-$CF_3$ | CH═N—OMe | Me | $CF_3$ | 1 |
| 5-0242. | 1 | 3-$CF_3$ | CH═N—OMe | Me | $CF_3$ | 2 |
| 5-0243. | 1 | 3-$CF_3$ | C(Me)═N—OH | Me | $CF_3$ | 0 |
| 5-0244. | 1 | 3-$CF_3$ | C(Me)═N—OH | Me | $CF_3$ | 1 |
| 5-0245. | 1 | 3-$CF_3$ | C(Me)═N—OH | Me | $CF_3$ | 2 |
| 5-0246. | 1 | 3-$CF_3$ | C(Me)═N—OMe | H | $CF_3$ | 0 |

TABLE 5-continued 5-xxxx

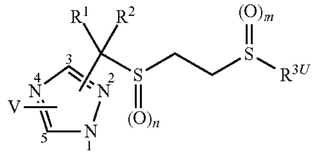

| No. | position | V | $R^1$ | $R^2$ | $R^{3U}$ | n |
|---|---|---|---|---|---|---|
| 5-0247. | 1 | 3-$CF_3$ | C(Me)═N—OMe | H | $CF_3$ | 1 |
| 5-0248. | 1 | 3-$CF_3$ | C(Me)═N—OMe | H | $CF_3$ | 2 |
| 5-0249. | 1 | 3-$CF_3$ | C(Me)═N—i-Pr | Me | $CF_3$ | 0 |
| 5-0250. | 1 | 3-$CF_3$-5-Me | COO—t-Bu | H | $CF_3$ | 0 |
| 5-0251. | 1 | 3-$CF_3$-5-Me | COO—t-Bu | H | $CF_3$ | 1 |
| 5-0252. | 1 | 3-$CF_3$-5-Me | COO—t-Bu | H | $CF_3$ | 2 |
| 5-0253. | 1 | 3-$CF_3$-5-Me | COO—t-Bu | Me | $CF_3$ | 0 |
| 5-0254. | 1 | 3-$CF_3$-5-Me | COO—t-Bu | Me | $CF_3$ | 1 |
| 5-0255. | 1 | 3-$CF_3$-5-Me | COO—t-Bu | Me | $CF_3$ | 2 |
| 5-0256. | 1 | 3-$CF_3$-5-$CF_3$ | COO—t-Bu | H | $CF_3$ | 0 |
| 5-0257. | 1 | 3-$CF_3$-5-$CF_3$ | COO—t-Bu | H | $CF_3$ | 1 |
| 5-0258. | 1 | 3-$CF_3$-5-$CF_3$ | COO—t-Bu | H | $CF_3$ | 2 |
| 5-0259. | 1 | 3-$CF_3$-5-$CF_3$ | COO—t-Bu | Me | $CF_3$ | 0 |
| 5-0260. | 1 | 3-$CF_3$-5-$CF_3$ | COO—t-Bu | Me | $CF_3$ | 1 |
| 5-0261. | 1 | 3-$CF_3$-5-$CF_3$ | COO—t-Bu | Me | $CF_3$ | 2 |
| 5-0262. | 1 | 3-$CF_3$-5-$NH_2$ | COO—t-Bu | H | $CF_3$ | 0 |
| 5-0253. | 1 | 3-$CF_3$-5-$NH_2$ | COO—t-Bu | H | $CF_3$ | 2 |
| 5-0264. | 1 | 3-$CF_3$-5-$NH_2$ | COO—t-Bu | Me | $CF_3$ | 0 |
| 5-0265. | 1 | 3-$CF_3$-5-$NH_2$ | COO—t-Bu | Me | $CF_3$ | 2 |
| 5-0266. | 1 | 3-$CF_3$-5-$NMe_2$ | COO—t-Bu | Me | $CF_3$ | 0 |
| 5-0267. | 1 | 3-$CF_3$-5-$NMe_2$ | COO—t-Bu | Me | $CF_3$ | 2 |
| 5-0268. | 1 | 3-$CF_3$-5-NHAc | COO—t-Bu | Me | $CF_3$ | 0 |
| 5-0269. | 1 | 3-$CF_3$-5-NHAc | COO—t-Bu | Me | $CF_3$ | 2 |
| 5-0270. | 1 | 3-$CF_3$-5-SMe | COOEt | H | $CF_3$ | 0 |
| 5-0271. | 1 | 3-$CF_3$-5-SMe | COOEt | H | $CF_3$ | 1 |
| 5-0272. | 1 | 3-$CF_3$-5-SMe | COOEt | Me | $CF_3$ | 0 |
| 5-0273. | 1 | 3-$CF_3$-5-SMe | COOEt | Me | $CF_3$ | 1 |
| 5-0274. | 1 | 3-$CF_3$-5-$SO_2$Me | COOEt | Me | $CF_3$ | 2 |
| 5-0275. | 1 | 3-$CF_3$-5-SMe | COO—i-Pr | Me | $CF_3$ | 0 |
| 5-0276. | 1 | 3-$CF_3$-5-$SO_2$Me | COO—i-Pr | Me | $CF_3$ | 2 |
| 5-0277. | 1 | 3-$CF_3$-5-SMe | COO—t-Bu | H | $CF_3$ | 0 |
| 5-0278. | 1 | 3-$CF_3$-5-$SO_2$Me | COO—t-Bu | H | $CF_3$ | 2 |
| 5-0279. | 1 | 3-$CF_3$-5-SMe | COO—i-Bu | Me | $CF_3$ | 0 |
| 5-0280. | 1 | 3-$CF_3$-5-$SO_2$Me | COO—i-Bu | Me | $CF_3$ | 2 |
| 5-0281. | 1 | 3-$CF_3$-5-SMe | COO—s-Bu | Me | $CF_3$ | 0 |
| 5-0282. | 1 | 3-$CF_3$-5-$SO_2$Me | COO—s-Bu | Me | $CF_3$ | 2 |
| 5-0283. | 1 | 3-$CF_3$-5-SMe | $CO_2CH_2CH_2OMe$ | H | $CF_3$ | 0 |
| 5-0284. | 1 | 3-$CF_3$-5-SMe | $CO_2CH_2CH_2OMe$ | Me | $CF_3$ | 0 |
| 5-0285. | 1 | 3-$CF_3$-5-$SO_2$Me | $CO_2CH_2CH_2OMe$ | Me | $CF_3$ | 2 |
| 5-0286. | 1 | 3-$CF_3$-5-SMe | $CO_2CH_2CONH_2$ | H | $CF_3$ | 0 |
| 5-0287. | 1 | 3-$CF_3$-5-SMe | $CO_2CH_2CONH_2$ | Me | $CF_3$ | 0 |
| 5-0288. | 1 | 3-$CF_3$-5-$SO_2$Me | $CO_2CH_2CONH_2$ | Me | $CF_3$ | 2 |
| 5-0289. | 1 | 3-$CF_3$-5-$SO_2$Me | Me | H | $CF_3$ | 2 |
| 5-0290. | 1 | 3-$CF_3$-5-SMe | Ac | H | $CF_3$ | 0 |
| 5-0291. | 1 | 3-$CF_3$-5-SMe | Ac | Me | $CF_3$ | 0 |
| 5-0292. | 1 | 3-$CF_3$-5-$SO_2$Me | Ac | Me | $CF_3$ | 2 |
| 5-0293. | 1 | 3-$CF_3$-5-SEt | COO—t-Bu | H | $CF_3$ | 0 |
| 5-0294. | 1 | 3-$CF_3$-5-SEt | COO—t-Bu | Me | $CF_3$ | 0 |
| 5-0295. | 1 | 3-$CF_3$-5-$SO_2$Et | COO—t-Bu | Me | $CF_3$ | 2 |
| 5-0296. | 1 | 3-$CF_3$-5-S—Pr | COOEt | H | $CF_3$ | 0 |
| 5-0297. | 1 | 3-$CF_3$-5-S—Pr | COOEt | Me | $CF_3$ | 0 |
| 5-0298. | 1 | 3-$CF_3$-5-$SO_2$—Pr | COOEt | Me | $CF_3$ | 2 |
| 5-0299. | 1 | 3-$CF_3$-5-$SO_2$—Pr | Me | H | $CF_3$ | 2 |
| 5-0300. | 1 | 3-$CF_3$-5-S—i-Pr | COOEt | H | $CF_3$ | 0 |
| 5-0301. | 1 | 3-$CF_3$-5-S—i-Pr | COOEt | Me | $CF_3$ | 0 |
| 5-0302. | 1 | 3-$CF_3$-5-$SO_2$—i-Pr | COOEt | Me | $CF_3$ | 2 |
| 5-0303. | 1 | 3-$CF_3$-5-$SO_2$—i-Pr | Me | H | $CF_3$ | 2 |
| 5-0304. | 1 | 3-$CF_3$-5-S—Bu | COOMe | H | $CF_3$ | 0 |
| 5-0305. | 1 | 3-$CF_3$-5-S—Bu | COOMe | Me | $CF_3$ | 0 |
| 5-0306. | 1 | 3-$CF_3$-5-$SO_2$—Bu | COOMe | Me | $CF_3$ | 2 |
| 5-0307. | 1 | 3-$CF_3$-5-S—i-Bu | COOMe | H | $CF_3$ | 0 |
| 5-0308. | 1 | 3-$CF_3$-5-S—i-Bu | COOMe | Me | $CF_3$ | 0 |
| 5-0309. | 1 | 3-$CF_3$-5-$SO_2$—i-Bu | COOMe | Me | $CF_3$ | 2 |
| 5-0310. | 1 | 3-$CF_3$-5-S—s-Bu | COOMe | H | $CF_3$ | 0 |
| 5-0311. | 1 | 3-$CF_3$-5-S—s-Bu | COOMe | Me | $CF_3$ | 0 |
| 5-0312. | 1 | 3-$CF_3$-5-$SO_2$—s-Bu | COOMe | Me | $CF_3$ | 2 |
| 5-0313. | 1 | 3-$CF_3$-5-S—c-Pen | COOMe | H | $CF_3$ | 0 |
| 5-0314. | 1 | 3-$CF_3$-5-S—c-Pen | COOMe | Me | $CF_3$ | 0 |

TABLE 5-continued 5-xxxx

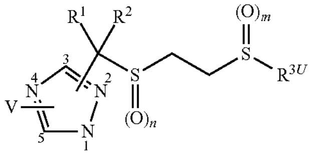

| No. | position | V | $R^1$ | $R^2$ | $R^{3U}$ | n |
|---|---|---|---|---|---|---|
| 5-0315. | 1 | $3-CF_3-5-SO_2$—c-Pen | COOMe | Me | $CF_3$ | 2 |
| 5-0316. | 1 | $3-CF_3-5-SCH_2$—c-Pr | COOMe | H | $CF_3$ | 0 |
| 5-0317. | 1 | $3-CF_3-5-SCH_2$—c-Pr | COOMe | Me | $CF_3$ | 0 |
| 5-0318. | 1 | $3-CF_3-5-SO_2CH_2$—c-Pr | COOMe | Me | $CF_3$ | 2 |
| 5-0319. | 1 | $3-CF_3-5-SCH_2CF_3$ | COOEt | H | $CF_3$ | 0 |
| 5-0320. | 1 | $3-CF_3-5-SCH_2CF_3$ | COOEt | Me | $CF_3$ | 0 |
| 5-0321. | 1 | $3-CF_3-5-SCH_2CF_3$ | COOEt | Me | $CF_3$ | 1 |
| 5-0322. | 1 | $3-CF_3-5-SOCH_2CF_3$ | COOEt | Me | $CF_3$ | 2 |
| 5-0323. | 1 | $3-CF_3-5-S(CH_2)_2CF_3$ | COOMe | Me | $CF_3$ | 0 |
| 5-0324. | 1 | $3-CF_3-5-SO_2(CH_2)_2CF_3$ | COOMe | Me | $CF_3$ | 2 |
| 5-0325. | 1 | $3-CF_3-5-S(CH_2)_2OMe$ | COOEt | H | $CF_3$ | 0 |
| 5-0326. | 1 | $3-CF_3-5-SO_2(CH_2)_2OMe$ | COOEt | H | $CF_3$ | 2 |
| 5-0327. | 1 | $3-CF_3-5-S(CH_2)_2OMe$ | COOEt | Me | $CF_3$ | 0 |
| 5-0328. | 1 | $3-CF_3-5-SO_2(CH_2)_2OMe$ | COOEt | Me | $CF_3$ | 2 |
| 5-0329. | 1 | $3-CF_3-5-S(CH_2)_2OEt$ | COOMe | H | $CF_3$ | 0 |
| 5-0330. | 1 | $3-CF_3-5-S(CH_2)_2OEt$ | COOMe | Me | $CF_3$ | 0 |
| 5-0331. | 1 | $3-CF_3-5-SO_2(CH_2)_2OEt$ | COOMe | Me | $CF_3$ | 2 |
| 5-0332. | 1 | $3-CF_3-5-S(CH_2)_2O(CH_2)_2OMe$ | COOEt | H | $CF_3$ | 0 |
| 5-0333. | 1 | $3-CF_3-5-S(CH_2)_2O(CH_2)_2OMe$ | COOEt | Me | $CF_3$ | 0 |
| 5-0334. | 1 | $3-CF_3-5-SO_2(CH_2)_2O(CH_2)_2OMe$ | COOEt | Me | $CF_3$ | 2 |
| 5-0335. | 1 | $3-CF_3-5-SCH_2$—$E^1$ | COOEt | H | $CF_3$ | 0 |
| 5-0336. | 1 | $3-CF_3-5-SCH_2$—$E^1$ | COOEt | Me | $CF_3$ | 0 |
| 5-0337. | 1 | $3-CF_2-5-SO_2CH_2$—$E^1$ | COOEt | Me | $CF_3$ | 2 |
| 5-0338. | 1 | $3-CF_3-5-SCH_2Ph$ | COOEt | H | $CF_3$ | 0 |
| 5-0339. | 1 | $3-CF_3-5-SO_2CH_2Ph$ | COOEt | H | $CF_3$ | 2 |
| 5-0340. | 1 | $3-CF_2-5-SCH_2Ph$ | COOEt | Me | $CF_3$ | 0 |
| 5-0341. | 1 | $3-CF_2-5-SO_2CH_2Ph$ | COOEt | Me | $CF_3$ | 2 |
| 5-0342. | 1 | $3-CF_3-5-F$ | COOMe | H | $CF_3$ | 0 |
| 5-0343. | 1 | $3-CF_3-5-F$ | COOMe | H | $CF_3$ | 2 |
| 5-0344. | 1 | $3-CF_3-5-F$ | COOMe | Me | $CF_3$ | 0 |
| 5-0345. | 1 | $3-CF_3-5-F$ | COOMe | Me | $CF_3$ | 2 |
| 5-0346. | 1 | $3-CF_3-5-Cl$ | COOMe | H | $CF_3$ | 0 |
| 5-0347. | 1 | $3-CF_3-5-Cl$ | COOMe | H | $CF_3$ | 2 |
| 5-0348. | 1 | $3-CF_3-5-Cl$ | COOMe | Me | $CF_3$ | 0 |
| 5-0349. | 1 | $3-CF_3-5-Cl$ | COOMe | Me | $CF_3$ | 2 |
| 5-0350. | 1 | $3-CF_3-5-Br$ | COOMe | H | $CF_3$ | 0 |
| 5-0351. | 1 | $3-CF_3-5-Br$ | COOMe | H | $CF_3$ | 2 |
| 5-0352. | 1 | $3-CF_3-5-Br$ | COOMe | Me | $CF_3$ | 0 |
| 5-0353. | 1 | $3-CF_3-5-Br$ | COOMe | Me | $CF_3$ | 2 |
| 5-0354. | 1 | $3-CF_3-5-COOEt$ | COO—t-Bu | H | $CF_3$ | 0 |
| 5-0355. | 1 | $3-CF_3-5-COOEt$ | COO—t-Bu | Me | $CF_3$ | 0 |
| 5-0356. | 1 | $3-CF_3-5-COOEt$ | COO—t-Bu | Me | $CF_3$ | 2 |
| 5-0357. | 1 | $3-CF_3-5-CN$ | COO—t-Bu | H | $CF_3$ | 0 |
| 5-0358. | 1 | $3-CF_3-5-CN$ | COO—t-Bu | Me | $CF_3$ | 0 |
| 5-0359. | 1 | $3-CF_3-5-CN$ | COO—t-Bu | Me | $CF_3$ | 2 |
| 5-0360. | 1 | 3-t-Bu | Me | H | $CF_3$ | 0 |
| 5-0361. | 1 | 3-t-Bu | Me | H | $CF_3$ | 1 |
| 5-0362. | 1 | 3-t-Bu | Me | H | $CF_3$ | 2 |
| 5-0363. | 1 | 3-t-Bu | COOH | Me | $CF_3$ | 0 |
| 5-0364. | 1 | 3-t-Bu | COOMe | H | $CF_3$ | 0 |
| 5-0365. | 1 | 3-t-Bu | COOMe | Me | $CF_3$ | 0 |
| 5-0366. | 1 | 3-t-Bu | COOMe | Me | $CF_3$ | 2 |
| 5-0367. | 1 | 3-t-Bu | COOEt | Me | $CF_3$ | 0 |
| 5-0368. | 1 | 3-t-Bu | COOEt | Me | $CF_3$ | 2 |
| 5-0369. | 1 | 3-t-Bu | COO—i-Pr | Me | $CF_3$ | 0 |
| 5-0370. | 1 | 3-t-Bu | COO—i-Pr | Me | $CF_3$ | 2 |
| 5-0371. | 1 | 3-t-Bu | $COOCH_2CH_2OMe$ | Me | $CF_3$ | 0 |
| 5-0372. | 1 | 3-t-Bu | $COOCH_2CH_2OMe$ | Me | $CF_3$ | 2 |
| 5-0373. | 1 | 3-t-Bu | $COOCH_2CONH_2$ | Me | $CF_3$ | 0 |
| 5-0374. | 1 | 3-t-Bu | $COOCH_2CONH_2$ | Me | $CF_3$ | 2 |
| 5-0375. | 1 | 3-t-Bu | COO—t-Bu | H | $CF_3$ | 0 |
| 5-0376. | 1 | 3-t-Bu | COO—t-Bu | H | $CF_3$ | 1 |
| 5-0377. | 1 | 3-t-Bu | COO—t-Bu | H | $CF_3$ | 2 |
| 5-0378. | 1 | 3-t-Bu | COO—t-Bu | Me | $CF_3$ | 0 |
| 5-0379. | 1 | 3-t-Bu | COO—t-Bu | Me | $CF_3$ | 1 |
| 5-0380. | 1 | 3-t-Bu | COO—t-Bu | Me | $CF_3$ | 2 |
| 5-0381. | 1 | 3-t-Bu-5-SMe | COO—t-Bu | Me | $CF_3$ | 0 |
| 5-0382. | 1 | $3-t-Bu-5-SO_2Me$ | COO—t-Bu | Me | $CF_3$ | 2 |

TABLE 5-continued 5-xxxx

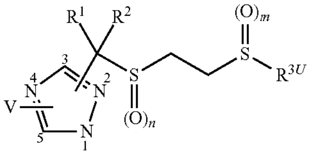

| No. | position | V | $R^1$ | $R^2$ | $R^{3U}$ | n |
|---|---|---|---|---|---|---|
| 5-0383. | 1 | 3-t-Bu-5-F | COOEt | H | $CF_3$ | 0 |
| 5-0384. | 1 | 3-t-Bu-5-F | COOEt | H | $CF_3$ | 2 |
| 5-0385. | 1 | 3-t-Bu-5-F | COOEt | Me | $CF_3$ | 0 |
| 5-0386. | 1 | 3-t-Bu-5-F | COOEt | Me | $CF_3$ | 2 |
| 5-0387. | 1 | 3-t-Bu-5-Cl | COOEt | H | $CF_3$ | 0 |
| 5-0388. | 1 | 3-t-Bu-5-Cl | COOEt | H | $CF_3$ | 2 |
| 5-0389. | 1 | 3-t-Bu-5-Cl | COOEt | Me | $CF_3$ | 0 |
| 5-0390. | 1 | 3-t-Bu-5-Cl | COOEt | Me | $CF_3$ | 2 |
| 5-0391. | 1 | 3-t-Bu-5-Br | COOEt | H | $CF_3$ | 0 |
| 5-0392. | 1 | 3-t-Bu-5-Br | COOEt | H | $CF_3$ | 2 |
| 5-0393. | 1 | 3-t-Bu-5-Br | COOEt | Me | $CF_3$ | 0 |
| 5-0394. | 1 | 3-t-Bu-5-Br | COOEt | Me | $CF_3$ | 2 |
| 5-0395. | 1 | 3-c-Pr | COO—t-Bu | H | $CF_3$ | 0 |
| 5-0396. | 1 | 3-c-Pr | COO—t-Bu | H | $CF_3$ | 1 |
| 5-0397. | 1 | 3-c-Pr | COO—t-Bu | H | $CF_3$ | 2 |
| 5-0398. | 1 | 3-c-Pr | COO—t-Bu | Me | $CF_3$ | 0 |
| 5-0399. | 1 | 3-c-Pr | COO—t-Bu | Me | $CF_3$ | 1 |
| 5-0400. | 1 | 3-c-Pr | COO—t-Bu | Me | $CF_3$ | 2 |
| 5-0401. | 1 | 5-c-Pr | COO—t-Bu | Me | $CF_3$ | 2 |
| 5-0402. | 1 | 3-$CHF_2$ | COOEt | H | $CF_3$ | 0 |
| 5-0403. | 1 | 3-$CHF_2$ | COOEt | H | $CF_3$ | 1 |
| 5-0404. | 1 | 3-$CHF_2$ | COOEt | H | $CF_3$ | 2 |
| 5-0405. | 1 | 3-$CHF_2$ | COOEt | Me | $CF_3$ | 0 |
| 5-0406. | 1 | 3-$CHF_2$ | COOEt | Me | $CF_3$ | 1 |
| 5-0407. | 1 | 3-$CHF_2$ | COOEt | Me | $CF_3$ | 2 |
| 5-0408. | 1 | 3-$CF_2CF_3$ | COO—t-Bu | H | $CF_3$ | 0 |
| 5-0409. | 1 | 3-$CF_2CF_3$ | COO—t-Bu | H | $CF_3$ | 1 |
| 5-0410. | 1 | 3-$CF_2CF_3$ | COO—t-Bu | H | $CF_3$ | 2 |
| 5-0411. | 1 | 3-$CF_2CF_3$ | COO—t-Bu | Me | $CF_3$ | 0 |
| 5-0412. | 1 | S-$CF_2CF_3$ | COO—t-Bu | Me | $CF_3$ | 1 |
| 5-0413. | 1 | 3-$CF_2CF_3$ | COO—t-Bu | Me | $CF_3$ | 2 |
| 5-0414. | 1 | 3-$CF_2CF_3$ | Me | H | $CF_3$ | 0 |
| 5-0415. | 1 | S-$CF_2CF_3$ | Me | H | $CF_3$ | 1 |
| 5-0416. | 1 | 3-$CF_2CF_3$ | Me | H | $CF_3$ | 2 |
| 5-0417. | 1 | 3-$CH(CF_3)_2$ | COO—t-Bu | H | $CF_3$ | 0 |
| 5-0418. | 1 | 3-$CH(CF_3)_2$ | COO—t-Bu | H | $CF_3$ | 1 |
| 5-0419. | 1 | 3-$CH(CF_3)_2$ | COO—t-Bu | H | $CF_3$ | 2 |
| 5-0420. | 1 | 3-$CH(CF_3)_2$ | COO—t-Bu | Me | $CF_3$ | 0 |
| 5-0421. | 1 | 3-$CH(CF_3)_2$ | COO—t-Bu | Me | $CF_3$ | 1 |
| 5-0422. | 1 | 3-$CH(CF_3)_2$ | COO—t-Bu | Me | $CF_3$ | 2 |
| 5-0423. | 1 | 3-$CH(CF_3)_2$ | Me | H | $CF_3$ | 0 |
| 5-0424. | 1 | 3-$CH(CF_3)_2$ | Me | H | $CF_3$ | 1 |
| 5-0425. | 1 | 3-$CH(CF_3)_2$ | Me | H | $CF_3$ | 2 |
| 5-0426. | 1 | — | COO—t-Bu | H | $CF_3$ | 0 |
| 5-0427. | 1 | — | COO—t-Bu | H | $CF_3$ | 1 |
| 5-0428. | 1 | — | COO—t-Bu | H | $CF_3$ | 2 |
| 5-0429. | 1 | — | COO—t-Bu | Me | $CF_3$ | 0 |
| 5-0430. | 1 | — | COO—t-Bu | Me | $CF_3$ | 1 |
| 5-0431. | 1 | — | COO—t-Bu | Me | $CF_3$ | 2 |
| 5-0432. | 1 | 3-$NO_2$ | COO—t-Bu | Me | $CF_3$ | 0 |
| 5-0433. | 1 | 3-$NO_2$ | COO—t-Bu | Me | $CF_3$ | 1 |
| 5-0434. | 1 | 3-$NO_2$ | COO—t-Bu | Me | $CF_3$ | 2 |
| 5-0435. | 1 | 3-NHAc | COO—t-Bu | Me | $CF_3$ | 0 |
| 5-0436. | 1 | 3-NHAc | COO—t-Bu | Me | $CF_3$ | 1 |
| 5-0437. | 1 | 3-NHAc | COO—t-Bu | Me | $CF_3$ | 2 |
| 5-0438. | 1 | 3-$SCF_3$ | COO—t-Bu | H | $CF_3$ | 0 |
| 5-0439. | 1 | 3-$SCF_3$ | COO—t-Bu | Me | $CF_3$ | 0 |
| 5-0440. | 1 | 3-$SOCF_3$ | COO—t-Bu | Me | $CF_3$ | 2 |
| 5-0441. | 1 | 3-SMe | COO—t-Bu | H | $CF_3$ | 0 |
| 5-0442. | 1 | 3-SMe | COO—t-Bu | Me | $CF_3$ | 0 |
| 5-0443. | 1 | 3-$SO_2Me$ | Me | H | $CF_3$ | 2 |
| 5-0444. | 1 | 3,5-$(SMe)_2$ | COO—t-Bu | H | $CF_3$ | 0 |
| 5-0445. | 1 | 3,5-$(SO_2Me)_2$ | COO—t-Bu | H | $CF_3$ | 2 |
| 5-0446. | 1 | 3,5-$(SMe)_2$ | COO—t-Bu | Me | $CF_3$ | 0 |
| 5-0447. | 1 | 3,5-$(SO_2Me)_2$ | COO—t-Bu | Me | $CF_3$ | 2 |
| 5-0448. | 1 | 3-SMe-5-$CF_2$ | COOEt | H | $CF_3$ | 0 |
| 5-0449. | 1 | 3-SMe-5-$CF_3$ | COOEt | Me | $CF_3$ | 0 |
| 5-0450. | 1 | 3-$SO_2Me$-5-$CF_3$ | COOEt | Me | $CF_3$ | 2 |

TABLE 5-continued 5-xxxx

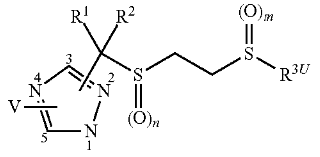

| No. | position | V | $R^1$ | $R^2$ | $R^{3U}$ | n |
|---|---|---|---|---|---|---|
| 5-0451. | 1 | 3-$SO_2$Me-5-$CF_3$ | Me | H | $CF_3$ | 2 |
| 5-0452. | 1 | 3-SEt-5-$CF_3$ | COO—t-Bu | Me | $CF_3$ | 0 |
| 5-0453. | 1 | 3-$SO_2$Et-5-$CF_3$ | COO—t-Bu | Me | $CF_3$ | 2 |
| 5-0454. | 1 | 3-$SO_2$Et-5-$CF_3$ | Me | H | $CF_3$ | 2 |
| 5-0455. | 1 | 3-S—Pr-5-$CF_3$ | COO—t-Bu | Me | $CF_3$ | 0 |
| 5-0456. | 1 | 3-$SO_2$—Pr-5-$CF_3$ | COO—t-Bu | Me | $CF_3$ | 2 |
| 5-0457. | 1 | 3-$SO_2$—Pr-5-$CF_3$ | Me | H | $CF_3$ | 2 |
| 5-0458. | 1 | 3-$SO_2(CH_2)_2CF_3$-5-$CF_3$ | COOMe | Me | $CF_3$ | 2 |
| 5-0459. | 1 | 3-$SO_2(CH_2)_2CF_3$-5-$CF_3$ | Me | H | $CF_3$ | 2 |
| 5-0460. | 1 | 3-COOEt-5-$CF_3$ | COO—t-Bu | H | $CF_3$ | 0 |
| 5-0461. | 1 | 3-COOEt-5-$CF_3$ | COO—t-Bu | H | $CF_3$ | 2 |
| 5-0462. | 1 | 3-COOEt-5-$CF_3$ | COO—t-Bu | Me | $CF_3$ | 0 |
| 5-0463. | 1 | 3-COOEt-5-$CF_3$ | COO—t-Bu | Me | $CF_3$ | 2 |
| 5-0464. | 3 | 1-Me-5-$CF_3$ | H | H | $CF_3$ | 0 |
| 5-0465. | 3 | 1-Me-5-$CF_3$ | H | H | $CF_3$ | 1 |
| 5-0466. | 3 | 1-Me-5-$CF_3$ | H | H | $CF_3$ | 2 |
| 5-0467. | 3 | 1-Me-5-$CF_3$ | Me | H | $CF_3$ | 0 |
| 5-0468. | 3 | 1-Me-5-$CF_3$ | Me | H | $CF_3$ | 1 |
| 5-0469. | 3 | 1-Me-5-$CF_3$ | Me | H | $CF_3$ | 2 |
| 5-0470. | 5 | 1-Me-3-$CF_3$ | H | H | $CF_3$ | 0 |
| 5-0471. | 5 | 1-Me-3-$CF_3$ | H | H | $CF_3$ | 1 |
| 5-0472. | 5 | 1-Me-5-$CF_3$ | H | H | $CF_3$ | 2 |
| 5-0473. | 5 | 1-Me-5-$CF_3$ | Me | H | $CF_3$ | 0 |
| 5-0474. | 5 | 1-Me-3-$CF_3$ | Me | H | $CF_3$ | 1 |
| 5-0475. | 5 | 1-Me-3-$CF_3$ | Me | H | $CF_3$ | 2 |
| 5-0476. | 5 | 1-Me-3-$CF_3$ | Me | Me | $CF_3$ | 2 |
| 5-0477. | 1 | 3-$CF_3$-5-COOEt | COO—t-Bu | H | $CF_3$ | 2 |
| 5-0478. | 1 | 3-$CF_3$-5-$SCH_2CH{=}CH_2$ | COOMe | H | $CF_3$ | 0 |
| 5-0479. | 1 | 3-$CF_3$-5-$SCH_2CH{=}CH_2$ | COOMe | Me | $CF_3$ | 0 |
| 5-0480. | 1 | 3-$CF_3$-5-$SO_2CH_2CH{=}CH_2$ | COOMe | Me | $CF_3$ | 2 |
| 5-0481. | 1 | 3-$CF_3$-5-$SCH_2CH{=}CHCl$ | COOMe | H | $CF_3$ | 0 |
| 5-0482. | 1 | 3-$CF_3$-5-$SCH_2CH{=}CHCl$ | COOMe | Me | $CF_3$ | 0 |
| 5-0483. | 1 | 3-$CF_3$-5-$SO_2CH_2CH{=}CHCl$ | COOMe | Me | $CF_3$ | 2 |
| 5-0484. | 1 | 3-$CF_3$-5-$SCH_2CH{=}CH$ | COOMe | H | $CF_3$ | 0 |
| 5-0485. | 1 | 3-$CF_3$-5-$SCH_2CH{=}CH$ | COOMe | Me | $CF_3$ | 0 |
| 5-0486. | 1 | 3-$CF_3$-5-$SO_2CH_2CH{=}CH$ | COOMe | Me | $CF_3$ | 2 |

wherein m is 0 or 1;

Position in Table 5 is the position on the 1,2,4-triazolyl group which is substituted by the moiety

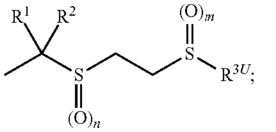

V, $R^1$, $R^2$, and n are defined in Table 5;

$R^{3U}$ is $CF_3$ or $CF_2H$; and $E^1$, $E^2$, $E^3$, $E^4$, $E^6$ and $E^7$ are the following structures:

$E^1$

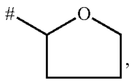

-continued $E^2$

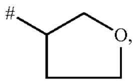

$E^3$

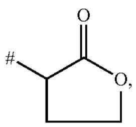

$E^4$

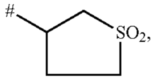

$E^6$

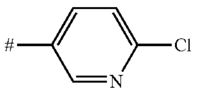

and

-continued

E7

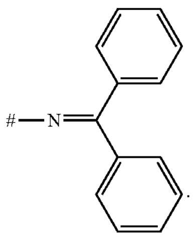

18. A compound of formula 6-xxxx, selected from Table 6:

TABLE 6

6-xxxx

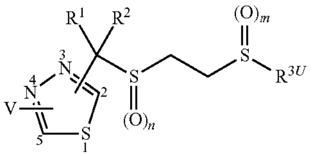

| No. | Position | V | $R^1$ | $R^2$ | $R^{3U}$ | n |
|---|---|---|---|---|---|---|
| 6-01. | 2 | 4-$CF_3$ | H | H | $CF_3$ | 0 |
| 6-02. | 2 | 4-$CF_3$ | H | H | $CF_3$ | 1 |
| 6-03. | 2 | 4-$CF_3$ | H | H | $CF_3$ | 2 |
| 6-04. | 2 | 4-$CF_3$ | Me | H | $CF_3$ | 0 |
| 6-05. | 2 | 4-$CF_3$ | Me | H | $CF_3$ | 1 |
| 6-06. | 2 | 4-$CF_3$ | Me | H | $CF_3$ | 2 |
| 6-07. | 2 | 4-$CF_3$ | Me | F | $CF_3$ | 2 |
| 6-08. | 2 | 4-$CF_3$ | Me | Cl | $CF_3$ | 2 |
| 6-09. | 2 | 4-$CF_3$ | Me | $CH_2CH_2Cl$ | $CF_3$ | 2 |
| 6-010. | 2 | 4-$CF_3$ | Me | $CH_2OMe$ | $CF_3$ | 2 |
| 6-011. | 2 | 4-$CF_3$ | Me | $CH_2CH_2OMe$ | $CF_3$ | 2 |
| 6-012. | 2 | 4-$CF_3$ | Me | $CH_2OH$ | $CF_3$ | 2 |
| 6-013. | 2 | 4-$CF_3$ | Me | $CH_2F$ | $CF_3$ | 2 |
| 6-048. | 5 | 2-$CF_3$ | Me | H | $CF_3$ | 2 |
| 6-049. | 5 | 2-$CF_3$ | Me | Me | $CF_3$ | 2 |
| 6-050. | 5 | 2-$CF_3$ | Et | H | $CF_3$ | 2 |
| 6-051. | 5 | 2-$CF_3$ | Et | Et | $CF_3$ | 2 |
| 6-052. | 5 | 2-$CF_3$ | i-Pr | H | $CF_3$ | 2 |
| 6-053. | 5 | 2-$CF_3$ | Pr | H | $CF_3$ | 2 |
| 6-054. | 5 | 2-$CF_3$ | Pr | Pr | $CF_3$ | 2 |
| 6-065. | 5 | 2-$CF_3$ | s-Bu | H | $CF_3$ | 2 |
| 6-056. | 5 | 2-$CF_3$ | i-Bu | H | $CF_3$ | 2 |
| 6-057. | 5 | 2-$CF_3$ | Bu | H | $CF_3$ | 2 |
| 6-058. | 5 | 2-$CF_3$ | $CH_2$—c-Pr | H | $CF_3$ | 2 |
| 6-059. | 5 | 2-$CF_3$ | $CH_2CH{=}CH_2$ | H | $CF_3$ | 2 |
| 6-060. | 5 | 2-$CF_3$ | $CH_2CH{=}CH_2$ | $CH_2CH{=}CH_2$ | $CF_3$ | 2 |
| 6-061. | 5 | 2-$CF_3$ | $CH_2C{\equiv}CH$ | H | $CF_3$ | 2 |
| 6-062. | 5 | 2-$CF_3$ | $CH_2C{\equiv}CH$ | $CH_2C{\equiv}CH$ | $CF_3$ | 2 |
| 6-063. | 5 | 2-$CF_3$ | $CH_2C(Cl){=}CH_2$ | H | $CF_3$ | 2 |
| 6-064. | 5 | 2-$CF_3$ | F | H | $CF_3$ | 2 |
| 6-065. | 5 | 2-$CF_3$ | F | F | $CF_3$ | 2 |
| 6-066. | 5 | 2-$CF_3$ | Cl | H | $CF_3$ | 2 |
| 6-067. | 5 | 2-$CF_3$ | Cl | Cl | $CF_3$ | 2 |
| 6-068. | 5 | 2-$CF_3$ | COOMe | H | $CF_3$ | 2 |
| 6-069. | 5 | 2-$CF_3$ | COOEt | H | $CF_3$ | 2 |
| 6-070. | 5 | 2-$CF_3$ | $CH_2CN$ | H | $CF_3$ | 2 |
| 6-071. | 5 | 2-$CF_3$ | $CH_2COOMe$ | H | $CF_3$ | 2 |
| 6-072. | 5 | 2-$CF_3$ | $CONH_2$ | H | $CF_3$ | 2 |
| 6-073. | 5 | 2-$CF_3$ | CONHEt | H | $CF_3$ | 2 |
| 6-074. | 5 | 2-$CF_3$ | CSNHMe | H | $CF_3$ | 2 |
| 6-075. | 5 | 2-$CF_3$ | $CON(Me)_2$ | H | $CF_3$ | 2 |
| 6-076. | 5 | 2-$CF_3$ | CHO | H | $CF_3$ | 2 |
| 6-077. | 5 | 2-$CF_3$ | Ac | H | $CF_3$ | 2 |
| 6-078. | 5 | 2-$CF_3$ | COEt | H | $CF_3$ | 2 |
| 6-079. | 5 | 2-$CF_3$ | CO—i-Pr | H | $CF_3$ | 2 |
| 6-080. | 5 | 2-$CF_3$ | $COCH_2Cl$ | H | $CF_3$ | 2 |
| 6-081. | 5 | 2-$CF_3$ | —$CH_2$—$CH_2$— | | $CF_3$ | 2 |
| 6-082. | 5 | 2-$CF_3$ | —$CH_2$—$CH_2$—$CH_2$— | | $CF_3$ | 2 |
| 6-083. | 5 | 2-$CF_3$ | —$CH_2$—$CH_2$—$CH_2$—$CH_2$— | | $CF_3$ | 2 |

TABLE 6-continued 6-xxxx

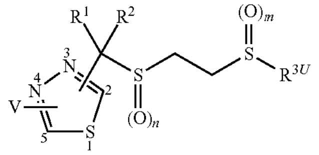

| No. | Position | V | $R^1$ | $R^2$ | $R^{3U}$ | n |
|---|---|---|---|---|---|---|
| 6-084. | 5 | 2-$CF_3$ | =CH—N(Me)$_2$ | | $CF_3$ | 2 |
| 6-085. | 5 | 2-$CF_3$ | =CH—NHMe | | $CF_3$ | 2 |
| 6-086. | 5 | 2-$CF_3$ | =CH—$NH_2$ | | $CF_3$ | 2 |
| 6-087. | 5 | 2-$CF_3$ | 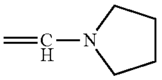 | | $CF_3$ | 2 |
| 6-088. | 5 | 2-$CF_3$ | =CH—OMe | | $CF_3$ | 2 |
| 6-089. | 5 | 2-$CF_3$ | =CH—OEt | | $CF_3$ | 2 |
| 6-090. | 5 | 2-$CF_3$ | =C(Me)—OEt | | $CF_3$ | 2 |
| 6-091. | 5 | 2-$CF_3$ | =N—OH | | 2-$CF_3$ | 0 |
| 6-092. | 5 | 2-$CF_3$ | =N—OMe | | 2-$CF_3$ | 0 |
| 6-093. | 5 | 2-$CF_3$ | =N—OMe | | 2-$CF_3$ | 1 |
| 6-094. | 5 | 2-$CF_3$ | =N—OMe | | 2-$CF_3$ | 2 |
| 6-095. | 5 | 2-$CF_3$ | =N—OEt | | 2-$CF_3$ | 0 |
| 6-096. | 5 | 2-$CF_3$ | =N—OEt | | 2-$CF_3$ | 1 |
| 6-097. | 5 | 2-$CF_3$ | =N—OEt | | 2-$CF_3$ | 2 |
| 6-098. | 5 | 2-$CF_3$ | H | H | $CF_2CF_3$ | 0 |
| 6-099. | 5 | 2-$CF_3$ | H | H | $CF_2CF_3$ | 1 |
| 6-0100. | 5 | 2-$CF_3$ | H | H | $CF_2CF_3$ | 2 |
| 6-0101. | 5 | 2-$CF_3$ | H | H | $CF_2CF_2CF_3$ | 0 |
| 6-0102. | 5 | 2-$CF_3$ | H | H | $CF_2CF_2CF_3$ | 1 |
| 6-0103. | 5 | 2-$CF_3$ | H | H | $CF_2CF_2CF_3$ | 2 |
| 6-0104. | 5 | 2-$CF_3$-4-Me | H | H | $CF_3$ | 0 |
| 6-0105. | 5 | 2-$CF_3$-4-Me | H | H | $CF_3$ | 1 |
| 6-0106. | 5 | 2-$CF_3$-4-Me | H | H | $CF_3$ | 2 |
| 6-0107. | 5 | 2-$CF_3$-4-Me | Me | H | $CF_3$ | 2 |
| 6-0108. | 5 | 2-Cl | H | H | $CF_3$ | 0 |
| 6-0109. | 5 | 2-Cl | H | H | $CF_3$ | 1 |
| 6-0110. | 5 | 2-Cl | H | H | $CF_3$ | 2 |
| 6-0111. | 5 | 2-Cl | Me | H | $CF_3$ | 2 |
| 6-0112. | 5 | 2-Cl | H | H | $CF_3$ | 0 |
| 6-0113. | 5 | 2-Cl | H | H | $CF_3$ | 1 |
| 6-0114. | 5 | 2-Cl | H | H | $CF_3$ | 2 |
| 6-0115. | 5 | 2-Cl | H | H | $CF_2CF_2CF_3$ | 0 |
| 6-0116. | 5 | 2-Cl | H | H | $CF_2CF_2CF_3$ | 1 |
| 6-0117. | 5 | 2-Cl | H | H | $CF_2CF_2CF_3$ | 2 |
| 6-0118. | 5 | 2-Me | H | H | $CF_3$ | 0 |
| 6-0119. | 5 | 2-Me | H | H | $CF_3$ | 1 |
| 6-0120. | 5 | 2-Me | H | H | $CF_3$ | 2 |
| 6-0121. | 5 | 2-Et | H | H | $CF_3$ | 0 |
| 6-0122. | 5 | 2-Et | H | H | $CF_3$ | 1 |
| 6-0123. | 5 | 2-Et | H | H | $CF_3$ | 2 |
| 6-0124. | 5 | 2-i-Pr | H | H | $CF_3$ | 0 |
| 6-0125. | 5 | 2-i-Pr | H | H | $CF_3$ | 1 |
| 6-0126. | 5 | 2-i-Pr | H | H | $CF_3$ | 2 |
| 6-0127. | 5 | 2-c-Pr | H | H | $CF_3$ | 0 |
| 6-0128. | 5 | 2-c-Pr | H | H | $CF_3$ | 1 |
| 6-0129. | 5 | 2-c-Pr | H | H | $CF_3$ | 2 |
| 6-0130. | 5 | 2-t-Bu | H | H | $CF_3$ | 0 |
| 6-0131. | 5 | 2-t-Bu | H | H | $CF_3$ | 1 |
| 6-0132. | 5 | 2-t-Bu | H | H | $CF_3$ | 2 |
| 6-0133. | 4 | 2-$CF_3$ | Me | H | $CF_3$ | 2 |

wherein m is 0 or 1;

Position in Table 6 is the position on the thiazolyl group which is substituted by the moiety

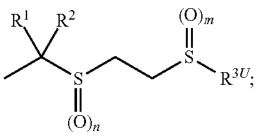

V, $R^1$, $R^2$, and n are defined in Table 6; and $R^{3U}$ is as defined in Table 6 or $CF_2H$.

19. An agricultural composition comprising at least one compound of any one of claims 1, 16, 17 or 18 and at least one agriculturally acceptable carrier.

20. A veterinary composition comprising at least one compound of any one of claim 1, 16, 17 or 18 and at least one veterinarily acceptable carrier.

21. A method for controlling invertebrate pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of at least one compound of any one of claim 1, 16, 17 or 18.

22. A method for protecting plants from attack or infestation by invertebrate pests, which method comprises treating the plants with a pesticidally effective amount of at least one compound of any one of claim 1, 16, 17 or 18.

23. A method for protecting plant propagation material or the plants which grow therefrom from attack or infestation by invertebrate pests, which method comprises treating the plant propagation material with a pesticidally effective amount of at least one compound of any one of claim 1, 16, 17 or 18.

24. Plant propagation material, comprising at least one compound of any one of claim 1, 16, 17 or 18.

25. A method for treating, controlling, preventing or protecting an animal from infestation or infection by invertebrate pests which comprises bringing the animal in contact with a pesticidally effective amount of at least one compound of any one of claim 1, 16, 17 or 18.

* * * * *